US009328150B2

(12) United States Patent
Savarino

(10) Patent No.: US 9,328,150 B2
(45) Date of Patent: May 3, 2016

(54) RECOMBINANT POLYPEPTIDE CONSTRUCT COMPRISING MULTIPLE ENTEROTOXIGENIC ESCHERICHIA COLI FIMBRIAL SUBUNITS

(71) Applicant: Stephen Savarino, Kensington, MD (US)

(72) Inventor: Stephen Savarino, Kensington, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/048,264

(22) Filed: Oct. 8, 2013

(65) Prior Publication Data
US 2015/0098961 A1    Apr. 9, 2015
US 2016/0052975 A9    Feb. 25, 2016

Related U.S. Application Data

(63) Continuation-in-part of application No. 11/340,003, filed on Jan. 10, 2006, now Pat. No. 9,079,945.

(60) Provisional application No. 60/642,771, filed on Jan. 11, 2005, provisional application No. 61/727,943, filed on Nov. 19, 2012.

(51) Int. Cl.
*A61K 39/02* (2006.01)
*C07K 14/245* (2006.01)
*A61K 39/108* (2006.01)
*A61K 39/00* (2006.01)

(52) U.S. Cl.
CPC ........... *C07K 14/245* (2013.01); *A61K 39/0258* (2013.01); *A61K 2039/523* (2013.01); *A61K 2039/543* (2013.01); *A61K 2039/545* (2013.01); *A61K 2039/55544* (2013.01); *A61K 2039/627* (2013.01); *A61K 2039/70* (2013.01)

(58) Field of Classification Search
None
See application file for complete search history.

(56) References Cited

U.S. PATENT DOCUMENTS

| | | |
|---|---|---|
| 4,761,283 A | 8/1988 | Anderson |
| 2002/0086037 A1 | 7/2002 | Hultgren |
| 2002/0150587 A1 | 10/2002 | Langermann |
| 2003/0021803 A1 | 1/2003 | Langridge |
| 2003/0099665 A1 | 5/2003 | Langermann |
| 2003/0138449 A1 | 7/2003 | Langermann |
| 2003/0199071 A1 | 10/2003 | Langermann |
| 2004/0156829 A1 | 8/2004 | Wolf et al. |
| 2004/0253710 A1 | 12/2004 | Turner et al. |
| 2005/0136070 A1 | 6/2005 | Altboum |
| 2005/0241024 A1 | 10/2005 | Langridge |
| 2006/0153878 A1 | 7/2006 | Savarino |
| 2006/0269560 A1* | 11/2006 | Savarino .................... 424/169.1 |
| 2009/0136567 A1 | 5/2009 | Savarino et al. |
| 2010/0136059 A1 | 6/2010 | Lebens et al. |
| 2010/0297141 A1 | 11/2010 | Savarino |
| 2011/0189236 A1 | 8/2011 | Scott et al. |

FOREIGN PATENT DOCUMENTS

WO    2005/113827 A2    12/2005
WO    WO 2007/148229 A2    12/2007

OTHER PUBLICATIONS

Jordi et al. ( Journal of Bacteriology vol. 175, No. 24, 1993.*
B3HIR3, UniProtKB/TrEMBL Accession No. B3HIR3_ECOLX, Sep. 2, 2008 [online]. [Retrieved on Jan. 8, 2014]. Retrieved from the Internet: <URL: http://www.uniprot.org/uniprot/B3HIR3.txt?version=1> Entire document; Relevant to Claim 17.
CP000795, GenBank Accession No. CP000795, *Escherichia coli* E24377A plasmid pETEC_80, complete sequence, Sep. 11, 2007 [online]. [Retrieved on Jan. 8, 2014]. Retrieved from the Internet: <URL: http://www.ncbi.nlm.nih.gov/nuccore/CP000795> Entire document; Relevant to Claim 20.
Ravi P. Anantha, Annette L. McVeigh, Lanfong H. Lee, Mary K. Agnew, Frederick J. Cassels, Daniel A. Scott, Thomas S. Whittam, Stephen J. Savarino, Evolutionary and functional relationships of colonization factor antigen 1 and other class 5 adhesive fimbriae of enterotoxigenic *Escherichia coli*, Infection and Immunity, vol. 72, No. 12, Dec. 2004, p. 7190-7201, DOI: 101128/IAI.72.12.7190-7201.2004.
Gerald O. Aspinall, Armando G. McDonald, Henrianna Pang, Structures of the O chains from ipopolysaccharides of Campylobacter jejuni serotypes O:23 and O:36, Carbohydrate Research, vol. 231 (1992), p. 13-3-, Elsevier Science Publishers B.V., Amsterdam.
Jin-Yong Lee, Jie Yu, David Henderson, William H.R. Langridge, Plant-synthesized *E. coli* CFA/I fimbrial protein protects Caco-2 cells from bacterial attachment, Vaccine 23 (2004) 222-231), available online at www.sciencedirect.com, www.elsevier.com/locate/vaccine.
Saumendra P. Roy, Mohammad M. Rahman, Xiao Di Yu, Minna Tuittila, Stefan D. Knight, Anton V. Zavlalov, Crystal structure of enterotoxigenic *Escherichia coli* colonization factor CS6 reveals a novel type of functional assembly, Molecular Microbiology (2012), 2012 Blackwell Publishing Ltd., DOI: 10.1111/mmi.12044.
Harry Sakellaris, George P. Munson, June R. Scott, A conserved residue in the tip proteins of CS1 and CFA/I pili of enterotoxigenic *Escherichia coli* that is essential for adherence, PNAS, Oct. 26, 1999, vol. 96, No. 22, 12828-12832.
Gabriel E. Soto, Scott J. Hultgren, Bacterial Adhesions: Common Themes and Variations in Architecture and Assembly, Journal of Bacteriology, vol. 181, No. 4, Feb. 1999, p. 1059-1071.
Jie Yu, Takeshi Arakawa, D.K.X. Chong, William H.R. Langridge, Assembly of Cholera Toxin-Antigen Fusion Proteins in Transgenic Potato, Transgenics, 2001, vol. 3(2-4), pp. 153-162, 2001 taylor and Francis, Inc.

* cited by examiner

*Primary Examiner* — J. Hines
*Assistant Examiner* — Khatol Shahnan Shah
(74) *Attorney, Agent, or Firm* — Albert M. Churilla; Ning Yang; Diane P. Tso

(57) ABSTRACT

The inventive subject matter relates to a recombinant polypeptide construct comprising enterotoxigenic *Escherichia coli* fimbrial subunits. The recombinant polypeptide constructs comprise multiple subunits to the same or different ETEC fimbrial types. The constructs are useful for inclusion in immunogenic formulations for the inductin of immunity against entertoxigenic *Escherichia coli*. The inventive subject matter also relates to the use of the recombinant polypeptide constructs in induce anti-enterotoxigenic *Escherichia coli*.

22 Claims, 20 Drawing Sheets

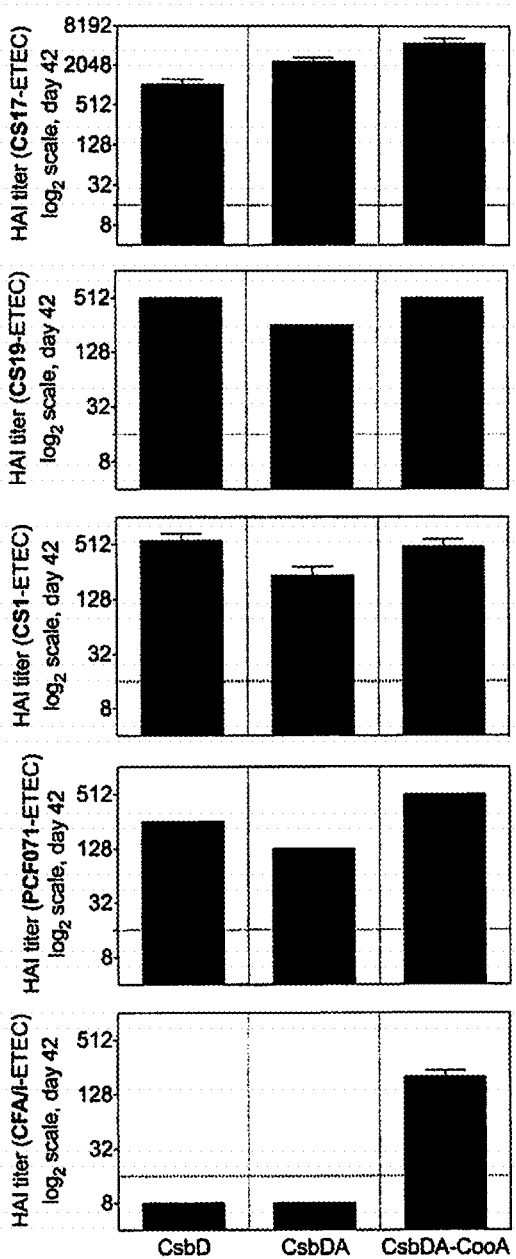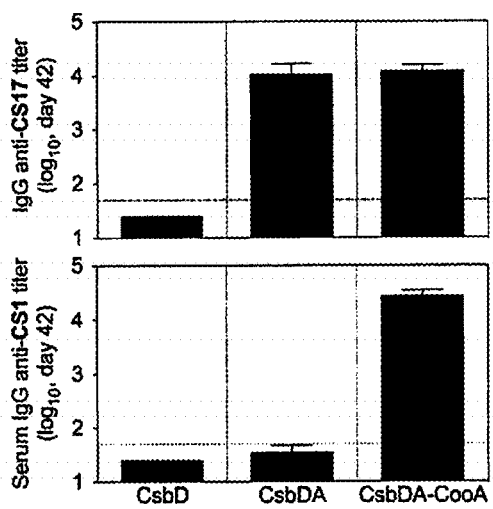
FIG. 6

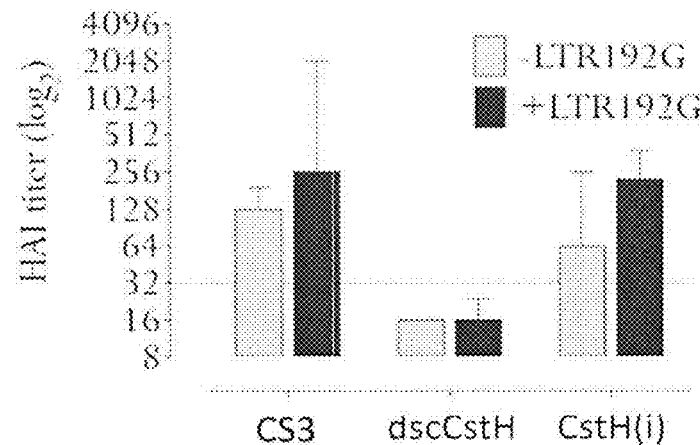
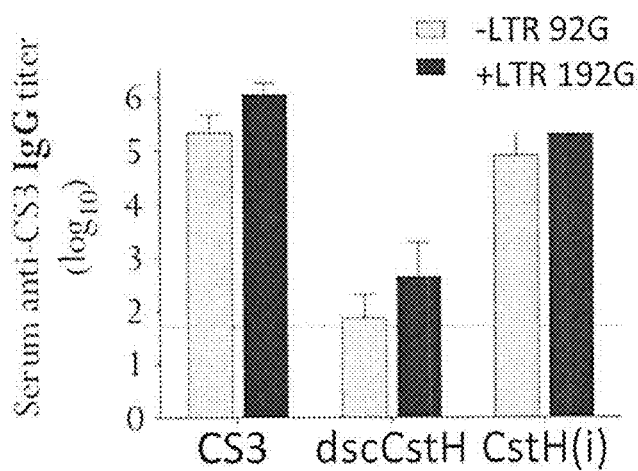
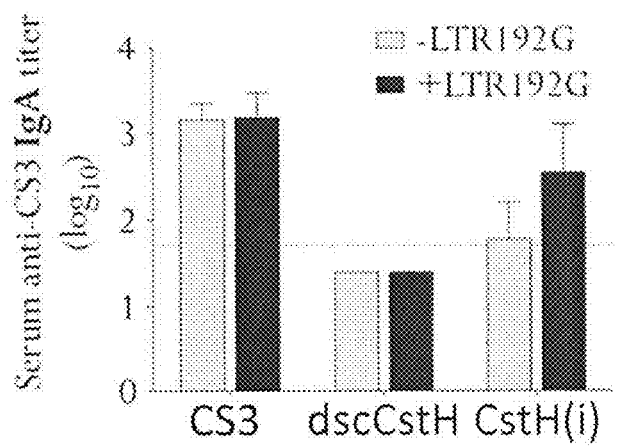
FIG. 9

$dsc_{14CfaB}$-CfaE-CfaB-(G)-$ntd_{18}dsc_{16CstH}$CstG-CstH
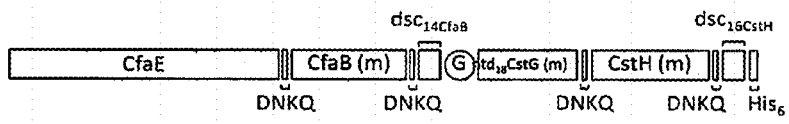
$dsc_{14CsfA}$CfaE-CfaB-CsuA2-CsfA-(G)-$ntd_{18}dsc_{16CstH}$CstG-CstH
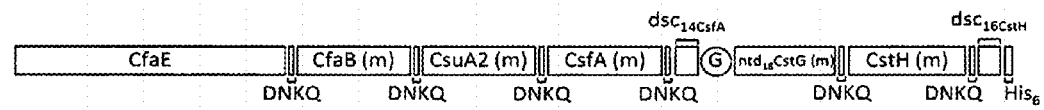
$dsc_{14CsbA}$CsbD-CsbA-$ntd_{15}dsc_{14CooA}$CooA-(G)-$ntd_{18}dsc_{16CstH}$ CstG-CstH
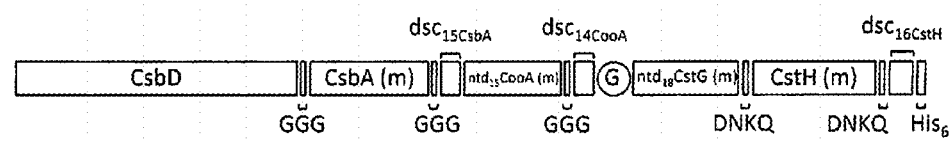
$dsc_{14CotA}$CotD-CotA-(G)-$ntd_{18}$ $dsc_{16CstH}$CstG-CstH
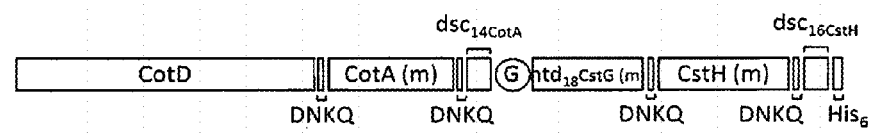
$dsc_{16CssA}$CssA-CssB-(G)-$ntd_{18}dsc_{16CstH}$CstG-CstH
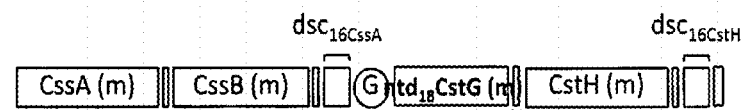
$dsc_{16CstH}$CstG-CstH-(G)-$ntd_{18}dsc_{16CssA}$-CssA-CssB
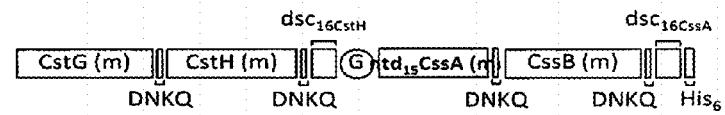
$dsc_{16}$CstG-CstH-sCTA2/LTB5
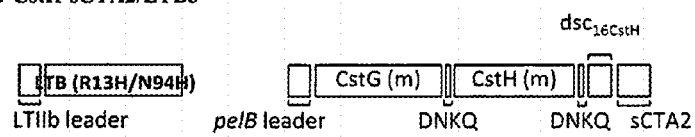
FIG. 13 dsc₁₄CfaE-CfaB-(G)-ntd₁₆dsc₁₆CssACssB-CssA

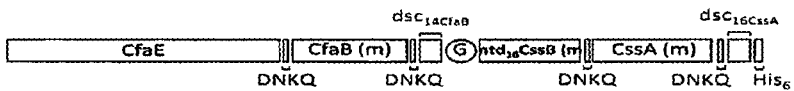

dsc₁₄CfaBCfaE-CfaB-(G)-ntd₁₆dsc₁₆CssBCssA-CssB

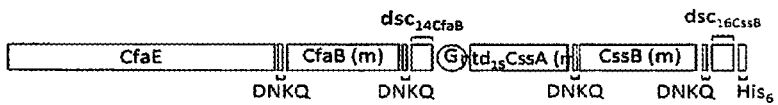

(with/without spd₂₂) dsc₁₄CsfACfaE-CfaB-CsuA2-CsfA-(G)-ntd₁₄dscCssB-CssA

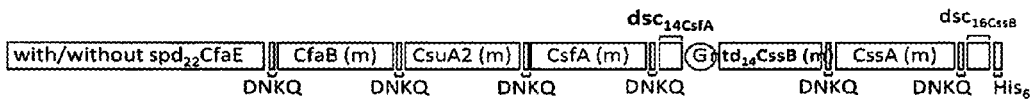

(with/without spd₁₉) dsc₁₄CotACotD-CotA-(G)-ntd₁₄dsc₁₆CssB-CssB-CssA

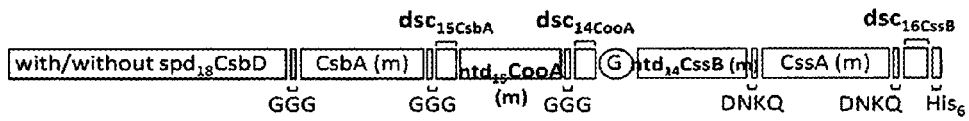

(with/without spd₁₉) dsc₁₄CotACotD-CotA-(G)-ntd₁₄dsc₁₆CssB-CssB-CssA

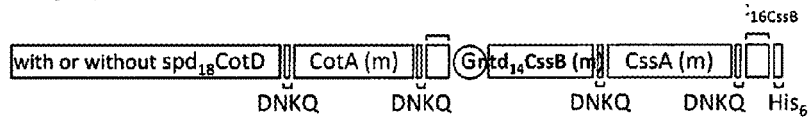

dsc₁₆HCstG-CstH-(G)-ntd₁₄dsc₁₆CssBCssB-CssA

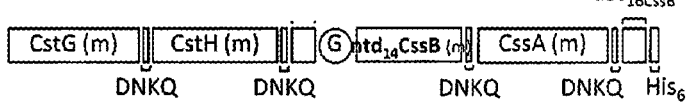

ntd₁₄dsc₁₆CssBCssB-CssA-(G)-ntd₁₈dsc₁₆CstHCstG-CstH

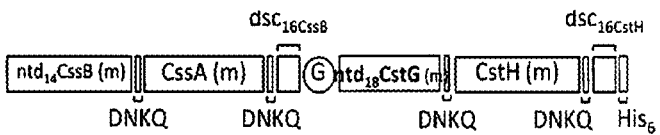

ntd14dsc16BCssBA-sCTA2/LTB5 or
ntd15dsc16ACssAB-sCTA2/LTB5

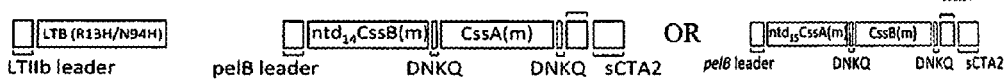

FIG. 14

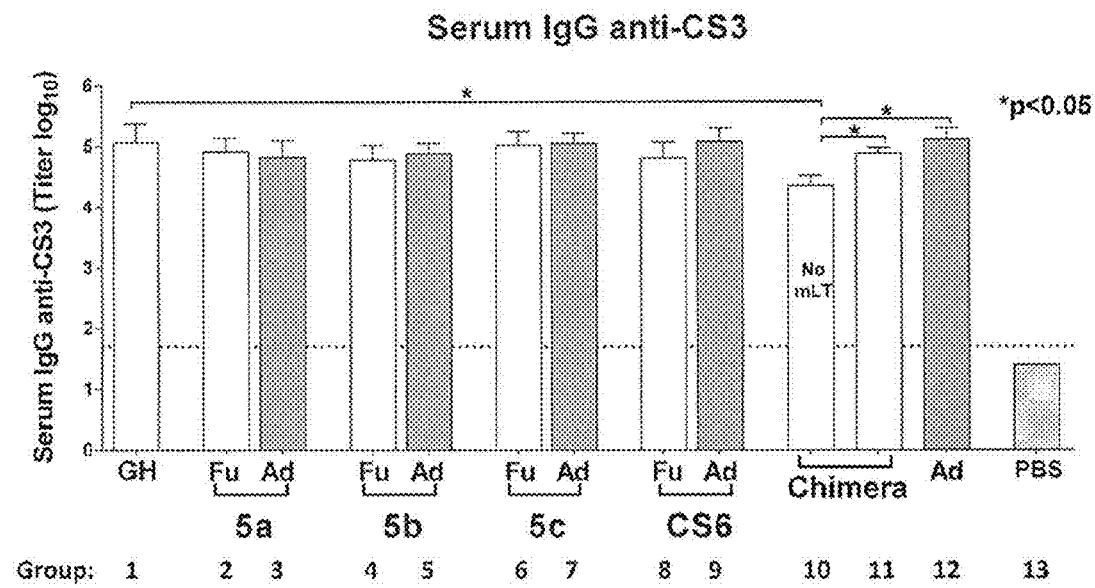
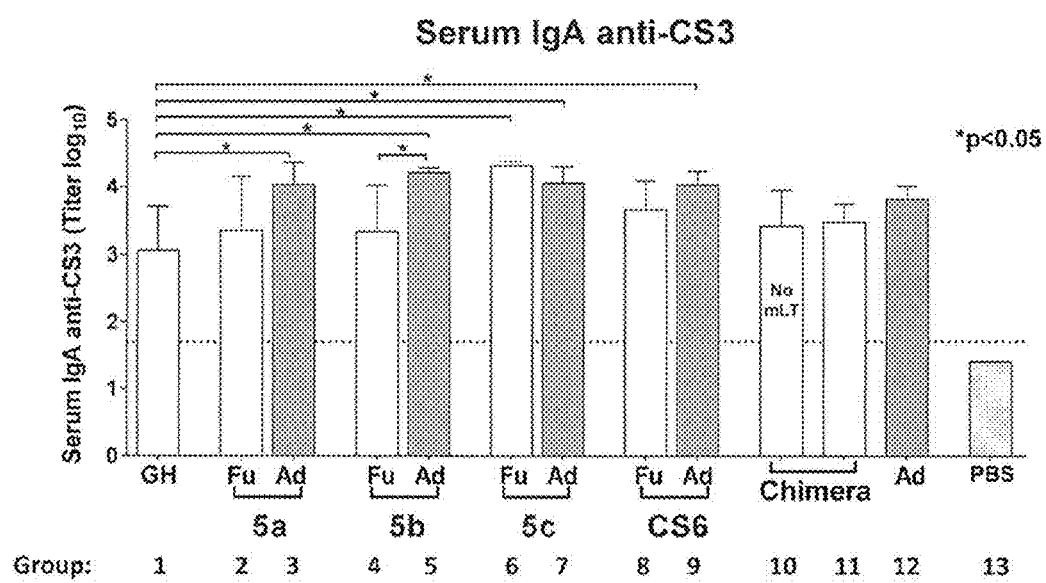
FIG. 16

A.
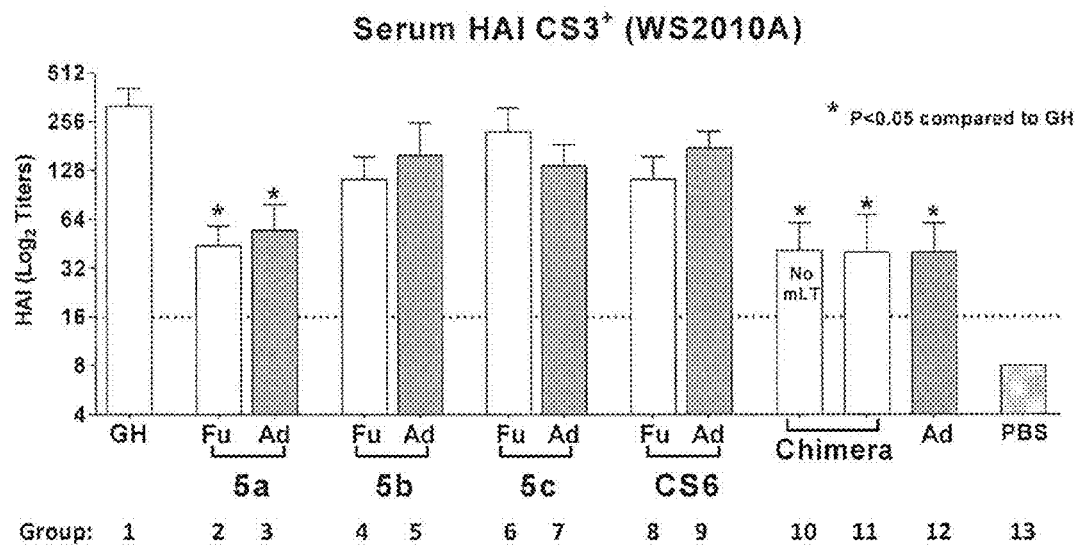
B.
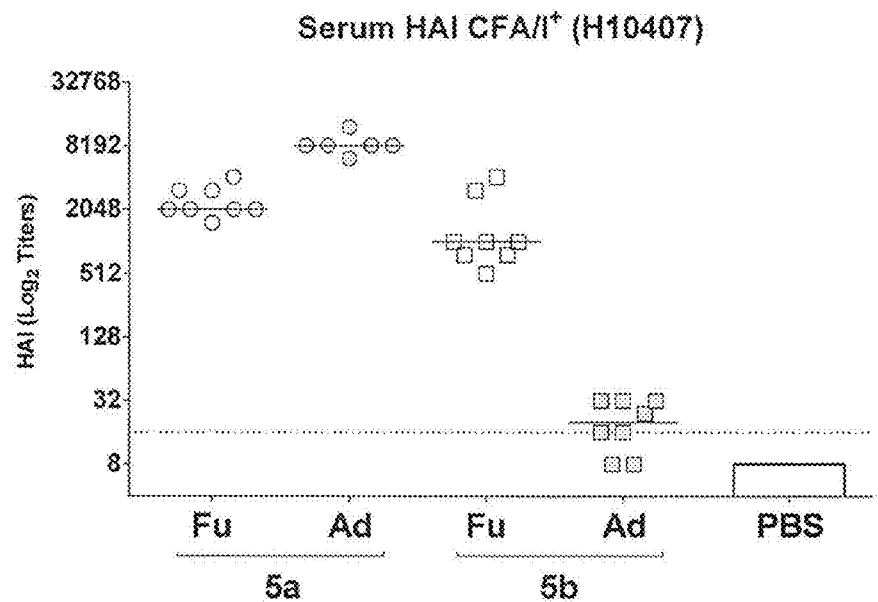
FIG. 17

A
CfaEB-CssBA = recombinant, multipartite fusion protein of Class 5a and CS6 fimbrial components.
CfaEB+CssBA = admixture of CfaEB (Class 5 adhesin-pilin) plus CssBA (CS6 subunit heterodimer)
B
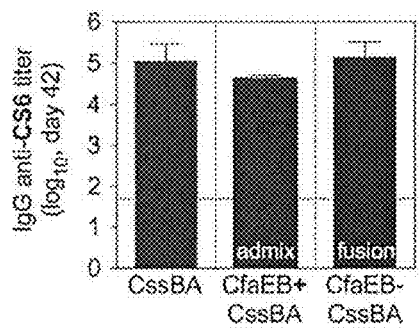
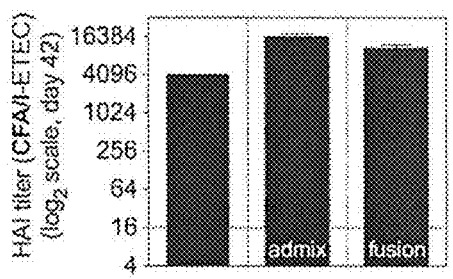
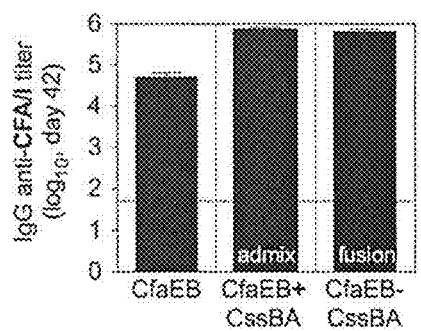
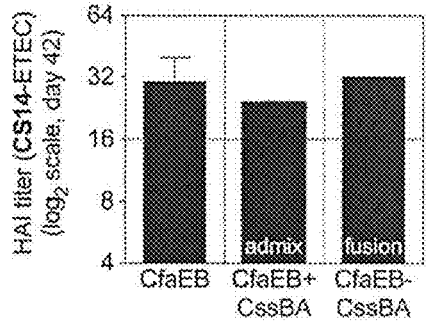
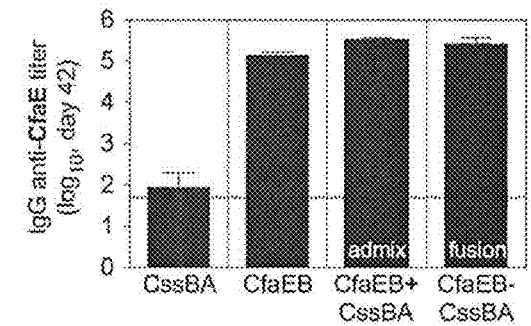
FIG. 18

RECOMBINANT POLYPEPTIDE CONSTRUCT COMPRISING MULTIPLE ENTEROTOXIGENIC *ESCHERICHIA COLI* FIMBRIAL SUBUNITS

CROSS-REFERENCES TO RELATED APPLICATIONS

This application is a Continuation-in-Part to U.S. Nonprovisional application Ser. No. 11/340,003, filed Jan. 10, 2006, which claims priority to U.S. Provisional application 60/642,771 filed Jan. 11, 2005, and a Continuation-in-Part to National Stage of International Application No. PCT/US2007/000712, filed Jan. 11, 2007, which claims priority to provisional application 60/758,099 filed Jan. 11, 2006, the contents herein are incorporated by reference. This application also claims priority to U.S. Provisional application 61/727,943, filed Nov. 19, 2012, the contents herein are incorporated by reference.

BACKGROUND OF INVENTION

1. Field of the Invention

The inventive subject matter relates to a method of inducing an immune response against enterotoxigenic *Escherichia coli* using bacterial fimbrial components. The method contemplates using enterotoxigenic *Escherichia coli* major and minor fimbrial subunits, incorporated into a stabilizing construct, as immunogens.

2. Description of Related Art

Enterotoxigenic *Escherichia coli* (ETEC) are a principal cause of diarrhea in young children in resource-limited countries and in travelers to these areas (Black, R. E. Rev. Infect. Dis. 12 (Suppl. 1): S73-79 (1990); Huilan, et al., Bull. World Health Organ. 69: 549-55 (1991)). ETEC-associated diarrheal disease is mediated by bacterial adherence to small intestinal epithelial cells and expression of a heat-labile (LT) and/or heat-stable (ST) enterotoxin (Nataro and Kaper, Clin. Microbiol. Rev. 11: 142-201 (1998)). ETEC typically attach to host cells via filamentous bacterial surface structures known as colonization factors (CFs). More than 20 different CFs have been described, a minority of which have been unequivocally incriminated in pathogenesis (Gaastra and Svennerholm, Trends Microbiol., 4: 444-452 (1996)).

Evidence for a pathogenic role exists for colonization factor antigen I (CFA/I), the first human-specific ETEC CF to be described. CFA/I is the archetype of a family of eight ETEC fimbriae that share genetic and biochemical features (Evans, et al., Infect. Immun., 12: 656-667 (1975); Gaastr and Svennerholm, Trends Microbiol., 4: 444-452 (1996); Grewal, et al., Infect. Immun., 65: 507-513 (1997)). This family includes coli surface antigen 1 (CS1), CS2, CS4, CS14, CS17, CS19 and putative colonization factor 071 (PCFO71). The complete DNA sequences of the gene clusters encoding CFA/I, CS1 and CS2 have been published (Froehlich, et al., Mol. Microbiol., 12: 387-401 (1994); Froehlich, et al., Infect. Immun., 63: 4849-56 (1995); Perez-Casal, et al., Infect. Immun. 58: 3594-3600 (1990); Scott, et al., Mol. Microbiol. 6: 293-300 (1992); Anantha, et al., Inf. And Imm., 72: 7190-7201 (2004)). The genes for the major subunit of two of the other related fimbriae have also been reported (Gaastra, et al., Int. J. Med. Microbiol. 292: 43-50 (2002); Grewal, et al., Infect. Immun. 65: 507-513 (1997). The four-gene bioassembly operons of CFA/I, CS1, and CS2 are similarly organized, encoding (in order) a periplasmic chaperone, major fimbrial subunit, outer membrane usher protein, and minor fimbrial subunit. CFA/I assembly takes place through the alternate chaperone pathway, distinct from the classic chaperone-usher pathway of type I fimbrial formation and that of other filamentous structures such as type IV pili (Ramer, et al., J. Bacteriol., 184: 3457-65 (2002); Soto and Hultgren., J. Bacteriol., 181: 1059-1071 (1999). Based on the primary sequence of the major fimbrial subunit, CFA/I and related fimbriae have been grouped as class 5 fimbriae.

Distinct from class 5 fimbriae, coli surface antigen 3 (CS3) represents the common adhesive fibrilla of the ETEC colonization factor antigen II (CFA/II) complex. ETEC expressing these antigens are prevalent in many parts of the world. Although the conformational nature of CS3 containing fibrillae are less understood than class 5 fimbriae, it is anticipated that these structures are important for eliciting anti-ETEC immune protection. Similarly, coli surface antigen 6 (CS6) (Tobias, et al., Vaccine., 26: 5373-5380 (2008)) has also been described and associated with ETEC mediated diarrheal disease (Gaastra and Svennerholm., Trends Microbiol., 4: 444-452 (1996); Qadri, et al., Clin. Microbiol., Rev. 18: 465-483 (2005); Sack, et al., Vaccine, 25: 4392-4400 (2007); Al-Gallas, et al., Am. J. Trop. Med. Hyg. 77: 571-582 (2007)).

Studies of CS1 have yielded details on the composition and functional features of Class 5 fimbriae Sakellaris and Scott, Mol. Microbiol. 30: 681-687 (1998). The CS1 fimbrial stalk consists of repeating CooA major subunits. The CooD minor subunit is allegedly localized to the fimbrial tip, comprises an extremely small proportion of the fimbrial mass, and is required for initiation of fimbrial formation (Sakellaris, et al., J. Bacteriol., 181: 1694-1697 (1999). Contrary to earlier evidence suggesting that the major subunit mediates binding (Buhler, et al., Infect. Immun. 59: 3876-3882 (1991), findings have implicated the minor subunit as the adhesin and identified specific amino acid residues required for in vitro adhesion of CS1 and CFA/I fimbriae Sakellaris, et al., PNAS (USA) 96: 12828-12832 (1999). The inferred primary amino acid structure of those major subunits that have been sequenced share extensive similarity. Serologic cross-reactivity of native fimbriae is, however, limited, and the pattern of cross-reactivity correlates with phylogenetically defined subtaxons of the major subunits (Gaastra, et al., Int. J. Med. Microbiol., 292: 43-50 (2002).

Studies to examine the evolutionary relationships of the minor and major subunits of Class 5 ETEC fimbriae as well as the two assembly proteins have been conducted (Anantha, et al., Inf. Imm., 72: 7190-7201 (2004)). The results demonstrated that evolutionary distinctions exist between the Class 5 major and minor fimbrial subunits and that the minor subunits function as adhesins.

The major subunit alleles of CS4, CS14, CS17 and CS19 gene clusters each showed 99-100% nucleotide sequence identity with corresponding gene sequence(s) previously deposited in GenBank, with no more than four nucleotide differences per allele. Each locus has four open reading frames that encoded proteins with homology to the CFA/I class chaperones, major subunits, ushers and minor subunits. As previously reported Gaastra, et al., Int. J. Med. Microbiol., 292: 43-50 (2002), the one exception was for the CS14 gene cluster, which contained two tandem open reading frames downstream of the chaperone gene. Their predicted protein sequences share 94% amino acid identity with one another and are both homologous to other Class 5 fimbriae major subunits.

Examination of the inferred amino acid sequences of all the protein homologs involved in Class 5 fimbrial biogenesis reveals many basic similarities. Across genera, each set of homologs generally share similar physicochemical properties in terms of polypeptide length, mass, and theoretical isoelectric point. All of the involved proteins contain an amino-terminal signal peptide that facilitates translocation to the periplasm via the type II secretion pathway. None of the major subunit proteins contain any cysteine residues, while the number and location of six cysteine residues are conserved for all of the minor subunits except that of the *Y. pestis* homolog 3802, which contains only four of these six residues.

Type 1 and P fimbriae have been useful models in elucidating the genetic and structural details of fimbriae assembled by the classical chaperone-usher pathway (23, 24, 25). An outcome of work with type 1 and P fimbriae (Kuehn, et al., Nature, 356: 252-255 (1992); Sauer, et al., Science, 285: 1058-1061 (1999); Choudhury, et al., Science, 285: 1061-1066 (1999)) has led to the development of the principle of donor strand complementation, a process in which fimbrial subunits non-covalently interlock with adjoining subunits by iterative intersubunit sharing of a critical, missing β-strand (Barnhart, et al, PNAS (USA), 97: 7709-7714 (2000); Viboud, et al., Microb. Athogen, 21: 139-147 (1996)).

The eight ETEC Class 5 fimbriae clustered into three subclasses of three (CFA/I, CS4, and CS14), four (CS1, PCFO71, CS17 and CS19), and one (CS2) member(s) (referred to as subclasses 5a, 5b, and 5c, respectively) (21). Previous reports demonstrated that ETEC bearing CFA/I, CS2, CS4, CS14 and CS19 manifest adherence to cultured Caco-2 cells (6, 22). However, conflicting data have been published regarding which of the component subunits of CFA/I and CS1 mediate adherence (19, 20).

SUMMARY OF THE INVENTION

The invention relates to a recombinant polypeptide construct expressing enterotoxigenic *Escherichia coli* (ETEC) fimbrial subunits. The composition is useful as an immunogenic composition against ETEC strains.

In a preferred embodiment, the composition comprises a recombinant polypeptide construct design wherein major or minor subunits, derived from the same ETEC fimbrial type, are connected, via polypeptide linkers, and stabilized by donor strand complementation. The C-terminal most ETEC major subunit is connected, via a linker, to a donor strand region from an ETEC major subunit, which can be either homologous or heterologous to the C-terminal major subunit. The immunogenic composition can comprise a whole or an immunogenic fragment, containing a donor β strand region, of the ETEC fimbrial major or minor subunits. In some construct examples, in order to avoid inadvertent association of subunits, especially in CS6 subunits to each other, major ETEC fimbrial subunits can contain an N-terminal deletion of 14 to 18 amino acids.

In another embodiment one or more of the above constructs are connected, via a polypeptide linker, to form a multipartite fusion construct, wherein the subunits derived from multiple fimbrial types are expressed. In this embodiment, the fimbrial subunits can be derived from any ETEC fimbrial types, including, but not limited to: ETEC class 5 fimbriae type, including class 5a, 5b or 5c; ETEC CS3; and ETEC CS6.

The embodied multipartite construct can contain a deletion of the N-terminal region of one or more fimbrial subunits to avoid undesirable associations with other monomers or multimers and to remove reduce amino acid sequence length between polypeptides to reduce the protease cleavage.

DNA encoding the recombinant polypeptide construct can be used to express a polypeptide for inclusion into immunogenic compositions, such as a subunit vaccine or the DNA encoding the recombinant polypeptide construct can be inserted into a suitable expression system such as a DNA plasmid, viral expression or bacterial vector. As such, an object of the invention also includes a use of the construct for immunizing mammals, including humans, against ETEC strains. The embodied use comprises one or more priming administrations of one or more of the immunogenic compositions, either as a subunit vaccine or expressed from a molecular construct inserted into an appropriate expression system, such as a live vaccine. The priming dose can be subsequently followed by one or more boosting doses of construct expressed as a subunit vaccine or as a recombinant construct inserted in a DNA plasmid, viral or bacterial expression vector.

BRIEF DESCRIPTION OF THE DRAWINGS

FIG. 6. Enhanced immunogenicity of Class 5b adhesin-pilin fusion compared to the prototype dscCsbD (CsbD) adhesin. Panel (A) shows HAI titer. Panel (B) shows anti-CS1 or anti-CS17 IgG responses.

FIG. 9. Hemaglutination-inhibition (HAI) titer and serum reactivity of dscCstH compared to non-cvalently linked oligomer (3-14 subunits) of CstH (denoted as CstH(i)). CstH(i) was isolated by capture of attached intein ("i"), which was cleaved from the intein-CstH fusion product.

FIG. 13. Examples of CS3 multipartite protein construct using construct design of FIG. 1.

FIG. 14. Examples of CS6 multipartite protein constructs using construct design of FIG. 1.

FIG. 16. Comparison of immunogenicity of CS3 fusion constructs against admixture of constructs. The groups listed on the x-axis are described in Table 9. In the figure, "Fu"=fusion; "Ad"=admixture; filled bars equate to administration with 100 ng of mLT; open bars equates to giving vaccine without mLT.

FIG. 17. Comparison of HAI titer of CS3 fusion construct examples against admixture of constructs. The groups listed on the x-axis are described in Table 9.

FIG. 18. Summary of data illustrating that a multipartite fusion, CfaEB-CssBA, comprising subunits from a Class 5 ETEC fimbrial type, i.e., CfaEB and a CS6 fimbrial type, i.e., CssBA, retains the immunogenic effects of the fimbrial types. Panel (A) shows the HAI titer for CFA/I and CS14. Panel (B) shows the IgG titer for CFA/I, CS6 and CfaE. The shorthand protein names shown in the graph labels and corresponding full names are as follows: CfaEB, dsc$_{19}$CfaEB[His]$_6$; CssBA, dsc$_{16.4}$CssBA(His)$_6$; CfaEB+CssBA, an admixture of CfaEB and CssBA; CfaEB-CssBA, the multipartite fusion dsc$_{14}$CfaEB-G-dsc$_{16.4}$CssBA(His)$_6$.

DETAILED DESCRIPTION OF PREFERRED EMBODIMENTS

Figure 1:
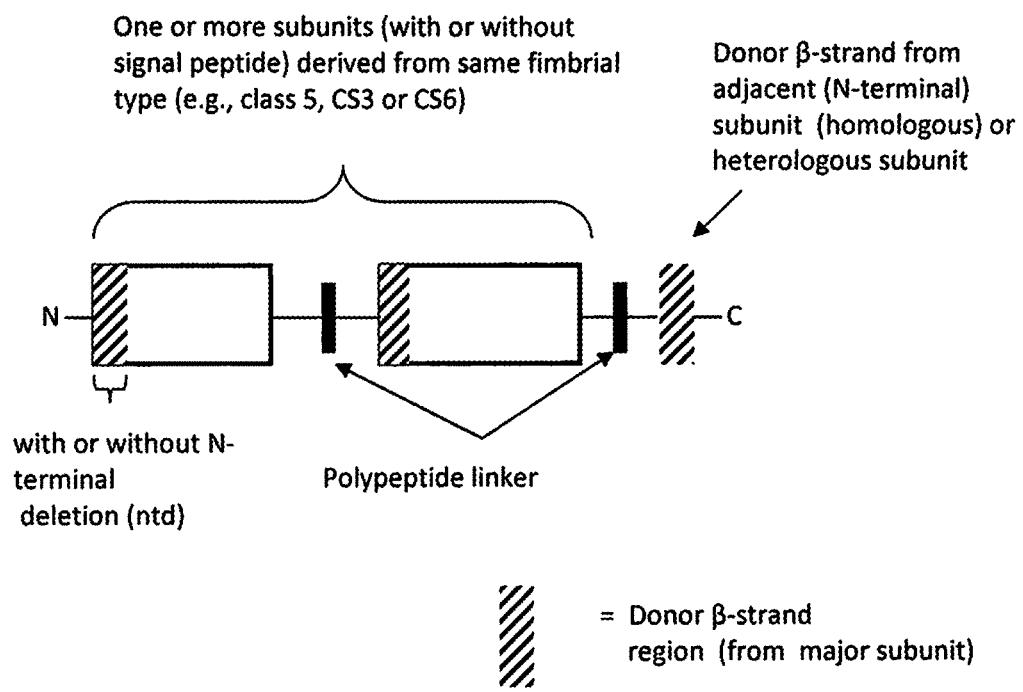
FIG. 1. Illustration of inventive construct design wherein major or minor subunits, derived from the same ETEC fimbrial type are connected, via polypeptide linkers and stabilized by donor strand complementation. The construct can contain a deletion of the N-terminal region of the N-terminal subunit. This feature prevents undesirable association with other monomers or multimers. The deletion also reduces amino acid sequence length between polypeptides, that are not involved in domain folding and precludes or reduces the likelihood of inter-subunit protease cleavage. The C-terminal subunit is stabilized by a donor β strand, connected to the subunit via a polypeptide linker, wherein the donor β strand is either derived from a homolgous subunit, which is defined as a subunit that is the same as the subunit the donor strand is stabilizing or from a heterologous subunit, defined as derived from a subunit that is different still from the same fimbrial type.

The terms "polypeptide," "peptide," and "protein" as used herein can be interchangeably used, and refer to a polymer formed of two or more amino acid residues, wherein one or more amino acid residues are naturally occurring amino acids. The term "amino acid sequence" refers to the order of the amino acids within a polypeptide. As used, herein, "oligomer" are polypeptides sequences comprising relatively few amino acids.

The term "recombinant polypeptide", "recombinant polypeptide construct", or "recombinant protein", as used herein, refers to polypeptides or proteins produced by recombinant DNA techniques, i.e., produced from cells transformed by an exogenous DNA construct encoding the desired polypeptide or the desired protein. The term "recombinant construct" refers to the DNA encoding the recombinant polypeptide, recombinant polypeptide construct or recombinant protein.

The term "donor strand" or "donor β strand" refers to the N-terminal region of an ETEC fimbrial subunit that associates with another ETEC fimbrial subunit in donor strand complementation.

The term "immunogenic composition" refers to a formulation containing proteins or polypeptides and other constitutions that induce a humoral and/or cellular immune response. The term "immunogenic coverage" or "spectrum of coverage" refers to the induction of humoral and/or cellular immune response against specific strains of bacteria under the "coverage." The term "immunogenic fragment" refers to a polypeptide containing one or more B- or T-cell epitopes and is of sufficient length to induce an immune response or to be recognized by T- or B-cells. The term "derivative" refers to a polypeptide or nucleic acid sequence with at least 80% identity with sequence of the identified gene. In this context, "identity" refers to two or more sequences or subsequences that are the same or have a specified percentage of amino acid residues that are the same, when aligned for maximum correspondence. Where some sequences differ in conservative substitutions, i.e., substitution of residues with identical properties, the percent sequence identity may be adjusted upwards to correct for the conservative nature of the substitution. Percent similarity refers to proportion of identical and similar (conserved change) residues.

"Fimbriae" are defined as projections or filaments on ETEC bacteria and are composed of major subunits, as in the case of CS3 and CS6 fimbriae or major and minor subunits, as in the case of class 5a, 5b and 5c ETEC. "Fibrillae" are narrow projections from a bacteria. CS3 and CS6 fimbriae can also be termed fibrillae due to their narrow characteristic. The term "fimbrial subunit" refers to the proteins that comprise ETEC fimbriae and is used interchangeably with "pilin." "Pilin", therefore, can refer to a "major" or "minor" "fimbrial subunit" that comprise ETEC fimbriae. A "minor fimbrial subunit" refers to the adhesin protein at the tip of class 5 ETEC fimbriae and is expressed in stoichiometrically low amounts compared to "major" subunits. The "minor fimbrial subunits" include, but are not limited to, CfaE, CsfD, CsuD, CooD, CosD, CsdD, CsbD and CotD. "Major fimbrial subunits" refers to the ETEC fimbrial proteins represented in stoichiometrially larger amounts in ETEC fimbriae, compared to "minor fimbrial subunits." "Major fimbrial subunits" include the ETEC class 5 proteins: CfaB, CsfA, CsuA2, CsuA1, CooA, CosA, CsdA, CsbA, CotA; the ETEC CS3 proteins: CstH, CstG; and the ETEC CS6 proteins: CssA, and CssB. A "fusion" is defined herein as two molecules covalently connected. Therefore, an "adhesin-pilin" fusion is a major or minor ETEC fimbrial subunit connected, covalently, to a Class 5 adhesin.

The term "fimbrial type" refers to fimbrial proteins derived from fimbriae of different ETEC types. The different "fimbrial types", as used in this application include, but are not limited to, CS6, which include CssA and CssB; CS3, which include CstH and CstG; ETEC Class 5a; ETEC Class 5b and ETEC Class 5c fimbriae.

The term "homologous subunit" is defined as a subunit that is an identical type to the subunit to which it is connected. The term "heterologous subunit" refers to a subunit that is a different type from the subunit to, which it is connected but that is derived from the same ETEC fimbrial type.

The present invention relates to recombinant polypeptide constructs for use in an immunogenic composition and to a method for using the composition to induce an immune response against enterotoxigenic *Escherichia coli*. The inventive composition utilizes a construct design that incorporates ETEC fimbrial subunits from multiple ETEC fimbrial types. Fimbrial types include, but are not limited to Class 5a, 5b, and 5c, as well as CS3, and CS6, in order to obtain broad anti-ETEC immunity. The construct also enables association of subunits, such as in CS3 and CS6 and stabilization of the subunits from proteolytic degradation, through donor strand complementation.

FIG. 1 illustrates the basic recombinant polypeptide construct design. As diagrammed in FIG. 1 the construct design comprises major or minor subunits, derived from the same ETEC fimbrial type, which are connected, via polypeptide linkers and stabilized by donor strand complementation. The construct can contain a deletion of the N-terminal region ("ntd") of the N-terminal subunit. This feature prevents undesirable associations with other monomers or multimers. The size of the deletion of the N-terminal region is 14 to 18 amino acids.

The C-terminal subunit is connected to and stabilized by a donor β strand, connected to the subunit via a polypeptide linker, wherein the donor β strand is either derived from the adjacent subunit (i.e., homologous) or from a different subunit of the same fimbrial type (i.e., heterologous). The size of the N-terminal donor strand depends on the fimbrial type and stabilized subunit. In preferred embodiments, for class 5 fimbrial subunits, the donor β strand, derived from the N-terminal region of the class 5 subunit stabilized, is 12 to 16 amino acids. In a preferred embodiment, for CS3 and CS6 subunits, the donor β strand is 14 to 16 amino acids.

Figure 2:
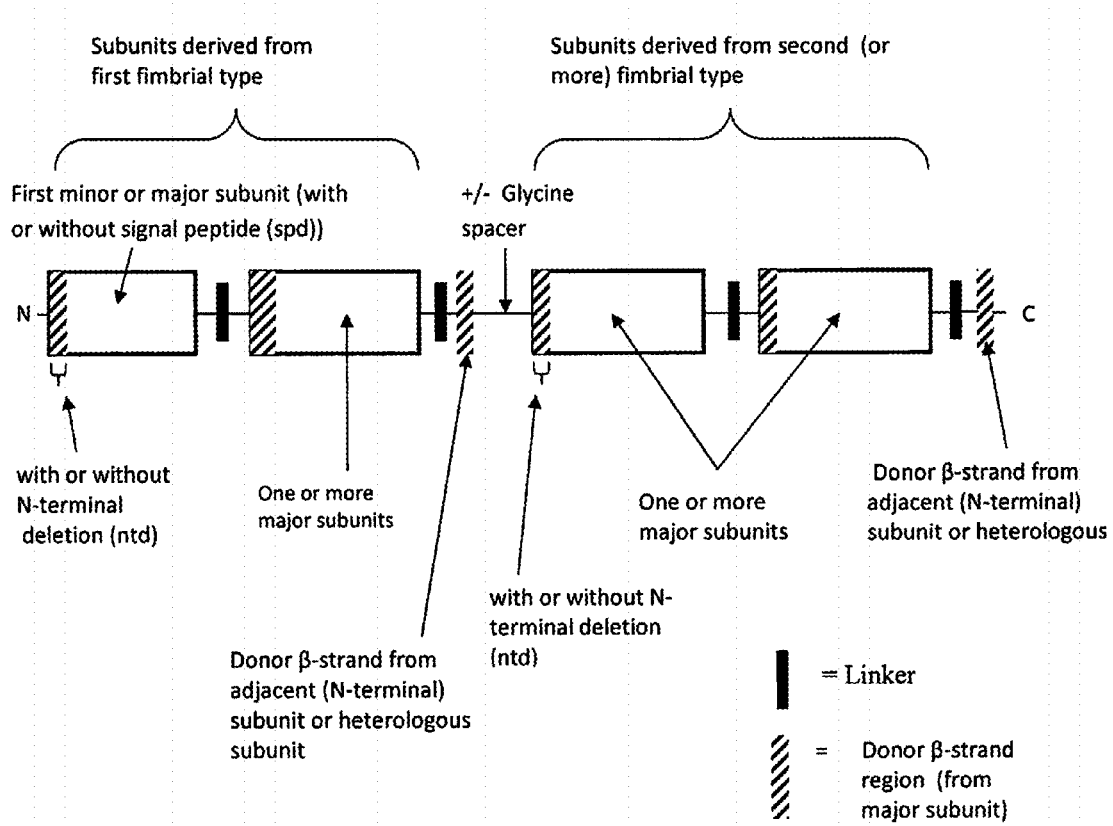
FIG. 2. Illustration of multipartite construct design wherein multiple compositions, illustrated in FIG. 1, are connected via a polypeptide linker. The first subunit, is a major or minor (e.g., ETEC class 5 adhesin) ETEC fimbrial subunit. One or more major ETEC fimbrial subunits are then connected to the first subunit and to each other via a linker, wherein the subunits are stabilized by donor strand complementation. The C-terminal most ETEC major subunit is connected, via a linker, to a donor strand region from an ETEC major subunit, which can be either homologous or heterologous to the terminal major subunit. In some construct examples, in order to avoid inadvertent association of subunits, especially in CS6 subunits, to each other, major ETEC fimbrial subunits can contain an N-terminal deletion of 14 to 18 amino acids. Deletion of amino acid sequence length, not involved in folding, also reduces the likelihood of proteolytic degradation.

FIG. 2 illustrates the basic multipartite construct, wherein multiple constructs as in FIG. 1, are connected forming a recombinant polypeptide construct comprising two or more fimbrial types. As illustrated in FIG. 1, major or minor subunits from the same fimbrial type are connected via a polypeptide linker sequence. In the multipartite construct, two or more constructs, as in FIG. 1, are connected, via a linker polypeptide.

In the multipartitie construct design, as in the basic design (compare FIG. 1 with FIG. 2), the first subunit (N-terminal) is a major or minor ETEC fimbrial subunit. Each additional subunit is connected to adjacent subunits via a polypeptide linker that enables rotary freedom of the molecular components. The subunits are associated with and stabilized via a donor strand complementation from a C-terminally adjacent subunit via a donor β strand, connected via a linker polypeptide, to the C-terminus of the stabilized subunit. In some embodiments, subunits can contain a deletion of 14 to 18 amino acids from its N-terminal end. Additionally, specific constructs can be constructed with or without signal peptides of 18 to 22 amino acids and with or without histidine tags at the C-terminus.

In the multipartite construct, subunits from the same fimbrial type are directly connected. Groupings of subunits from the same fimbrial type are then connected to other groupings of subunits from other fimbrial types. Fimbrial types include, but are not limited to ETEC class 5a, 5b, 5c, CS3 and CS6. For example a single construct can include subunits derived from any two or more of class 5a, 5b, 5c, CS3 and CS6 fimbrial types.

Figure 3:
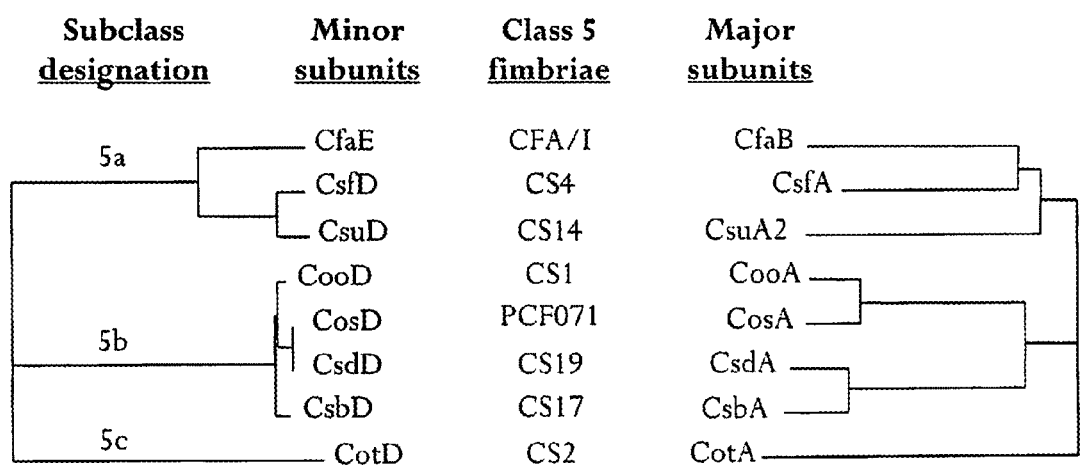
FIG. 3. Diagram of phylogenetic relationship of strains used.

Multiple linker sequences can be utilized in connecting the individual subunits. Examples of specific linkers include the tetrapeptide of SEQ ID No. 5. Another example is a triglycine linker (i.e., G-G-G). In the inventive construct, in cis donor strand complementation is used to stabilize adhesins and adhesin-pilin fusions for representative Class 5a, 5b, and 5c adhesins. A summary of the phylogenetic relationships of Class 5 minor (i.e., adhesins) and major subunits is illustrated in FIG. 3.

The contemplated composition is designed to enable as wide a range of coverage of ETEC strains as possible. As such, in one embodiment, the contemplated composition and use is aimed at inducing immunogenic response against class 5a, 5b, 5c ETEC, as well as ETEC strains expressing CS3 or CS6 fimbrial components.

Example 1

Recombinant Anti-ETEC Construct

Immunity to ETEC adhesin is important in reducing colonization of ETEC bacteria. However, the minor subunits (i.e., adhesin), the contact site of ETEC bacteria to the intestinal lumen, of ETEC Class 5 fimbriae are stoichiometrically represented in very low numbers relative to the major subunit. Therefore, in immunogenic compositions, it is important to enhance the immune recognition of the minor subunit over that not normally found in natural fimbriae.

Since fimbrial subunits, such as CfaE, are relatively susceptible to proteolytic degradation outside of the fimbrial structure, stabilization of the adhesin is also important. Therefore, constructs are designed to express ETEC subunits stabilized from misfolding and degradation by donor strand complementation. The donor β strand is provided by the major fimbrial subunit. For example, in the case of CfaE, stabilization is provided by the N-terminal region of CfaB. Engineering of dscCfaE by incorporation of a donor peptide strand from the N-terminus of the CFA/I major subunit CfaB at its C-terminus transformed an insoluble, unwieldy native, recombinant protein into a stable immunogenic composition (Savarino, U.S. Patent application publication no. 20060153878 (13 Jul. 2006)), which is incorporated by reference, herein.

Based on its atomic structure, dscCfaE is folded into a native, β-sandwich conformation, consisting of two half-barrels, comprising the N-terminal adhesin domain (CfaEad) a short α-helical connector, and the C-terminal pilin domain (CfaEpd). The molecule is functional in that it directly mediates MRHA of bovine and human erythrocytes, and generates neutralizing antibodies that act to inhibit MRHA and decorate the tips of CFA/I fimbriae on immunoelectron microscopy.

A fusion protein was engineered by genetic insertion of the coding sequence for mature major structural subunit of ETEC adhesin, such as CfaB, to the 3'-end of the minor subunit, such as CfaE. This concept was disclosed in Savarino, U.S. patent application (Ser. No. 11/340,003, filed Jan. 10, 2006), which is incorporated, herein. This molecule contains all three domains of the CFA/I fimbriae (i.e., ad, pd, and major subunit) in a ratio of 1:1:1, rather than that found in native fimbriae (ca. 1:1:1000).

A number of observations indicate the suitability of dscCfaE (cloned from ETEC strain E7473) as a vaccine antigen. First, sequencing of 31 different wild type alleles of cfaE from ETEC isolates of varying geographic origin and serotypes, show that the gene and predicted polypeptide sequence are nearly invariant, with three different nonsynonymous nucleotide changes at one site each in only five of these 31 alleles (Chattopadhyay, et al., J. Biol. Chem., 287(9): 6150-6158 (2012)). Hence, the target protein shows uniformity in natural ETEC bacterial populations.

Additionally, CfaE, a Class 5a fimbrial adhesin, is 80-81% identical with the other Class 5a minor subunits proteins adhesins CsuD of CS14 fimbriae and CsfD of CS4 fimbriae. CsuD and CsfD share 94% identity. This is considerably higher than the average identity with other Class 5b and 5c fimbrial adhesins (mean 50% identity).

Moreover, rabbit anti-dscCfaE serum cross-neutralizes CS4- and CS14-ETEC in the hemagglutination assay (HAI). A number of vaccination studies have been performed in small (rabbit and mice) and large (monkeys and cows) animals with various routes of administration and adjuvant combinations showing that dscCfaE is a potent immunogen that can elicit systemic and mucosal antibodies which recognize dscCfaE and CFA/I and are neutralizing (as measured by HAI assay).

An embodiment includes anti-class 5 ETEC constructs based on the construct design illustrated in FIG. 1, whereby the N-terminal subunit is an ETEC class 5 minor (i.e., adhesin) subunit, listed in Table 1, including CfaE, CsfD, CsuD, CooD, CsdD, CosD, CsbD and CotD, connected, via a polypeptide linker, to one or more ETEC major subunits, from the same ETEC class 5 type, listed in Table 1. The polypeptide linker can be any of a number of polypeptide sizes. In a preferred embodiment, the linker is a tetrapeptide with the polypeptide sequence of SEQ ID No. 5. The C-terminal class 5 subunit is connected to a donor β strand, derived from a homologous subunit and is typically 12-19 amino acids. In alternative embodiments, one or more major subunit can include a deletion of 12 to 16 amino acids from the N-terminal region of the subunit.

The design in FIG. 1, utilizes the concepts disclosed in Savarino, U.S. patent application (Ser. No. 11/340,003, filed Jan. 10, 2006)), including donor strand complementation to provide stabilized class 5 ETEC adhesin. Due to the homology of ETEC class 5 minor subunits and major subunits, FIG. 1 further contemplates multiple constructs incorporating the fimbrial subunits of Table 1, or deriviates of these polypeptides or DNA sequences.

TABLE 1

| Immune coverage | Subunit | SEQ ID No. (DNA of mature length (except as indicated) | SEQ ID No. (Full length polypeptide including spd[1]) | SEQ ID No. (Mature polypeptide) |
| --- | --- | --- | --- | --- |
| Class 5a | CfaE | 56 | 57 | 58 |
| | CfaB | 59 | 60 | 61 |
| | CsfD | 64 | 65 | 88 |
| | CsfA | 62 | 63 | 89 |
| | CsuD | 70 | 71 | 90 |
| | CsuA2 | 68 | 69 | 91 |
| | CsuA1 | 66 | 67 | 92 |
| Class 5b | CooD | 74 | 75 | 93 |
| | CooA | 72 | 73 | 94 |
| | CsdD | 78 | 79 | 95 |
| | CsdA | 76 | 77 | 96 |
| | Cos D | 82 | 83 | 97 |
| | CosA | 80 | 81 | 98 |
| | CsbD | 44 | 45 | 46 |
| | CsbA | 47 | 48 | 49 |
| Class 5c | CotD | 50 | 51 | 52 |
| | CotA | 53 | 54 | 55 |

The construct design, illustrated in FIG. 1, incorporates the donor strand complementation stabilization features of Savarino (U.S. patent application (Ser. No. 11/340,003, filed Jan. 10, 2006)), and furthers it by incorporating multiple major subunits, from a specific ETEC type, into a single adhesin-pilin construct. For example, multiple class 5b major subunits can be connected to a class 5b adhesin (i.e, minor subunit). Embodiments include adhesin-pilin constructs containing Csb D (ETEC Class 5b fimbrial adhesin) and Cot D (ETEC Class 5c fimbrial adhesin). Examples, for illustration, of embodiments of adhesin-pilin ETEC class 5 adhesin-pilin constructs, representing Class 5a, 5b and 5c are shown in Table 2.

TABLE 2

| Fimbriae class represented | Construct (adhesin-pilin) example[1] | SEQ ID No. (Protein/DNA)[3] |
| --- | --- | --- |
| Class 5a | $dsc_{14CsfA}$CfaE-CfaB-CsuA2-CsfA | 103/104 |
| Class 5b | $dsc_{14CsbA}$CsbD-CsbA-ntd$_{15}$dsc$_{14CooA}$CooA[2] | 105/106 |
| Class 5b | $dsc_{15CooA}$CsbD-CsbA-CooA[2] | 107/108 |
| Class 5c | $dsc_{14CotA}$CotD-CotA | 109/110 |

[1]dsc refers to donor strand complementation. The number and subunit refers to the N-terminal amino acids of length represented by the number from the subunit indicated that is connected at the C-terminus of the construct and is serving to stabilize the C-terminal construct. For example, "$dsc_{14CsfA}$" refers to the N-terminal 14 amino acids of CsfA connect to the C-terminus of the construct.
[2]Linkers polypeptides are GGG rather than DNKQ.
[3]Sequence in example contains a Leu-Glu-His6 at the C-terminus.

Examination of immunogenicity of the class 5 constructs (i.e., adhesin-pilin listed in Table 2) were conducted. The results of these studies show an enhanced immunogenicity of adhesin-pilin fusions compared to prototype dscCfaE (CfaE) adhesin, the results of which are shown in FIG. 4.

In these studies, groups of five BALB/c mice were vaccinated intradermally with each protein at molar equivalent doses (doses normalized to contain 5 μg of each pilin subunit) co-administered with the adjuvant LTR192G (i.e., mLT, 100 ng). Mice were vaccinated three times at 0, 14, and 28 days. The displayed titers are from serum collected at day 42.

Figure 4:
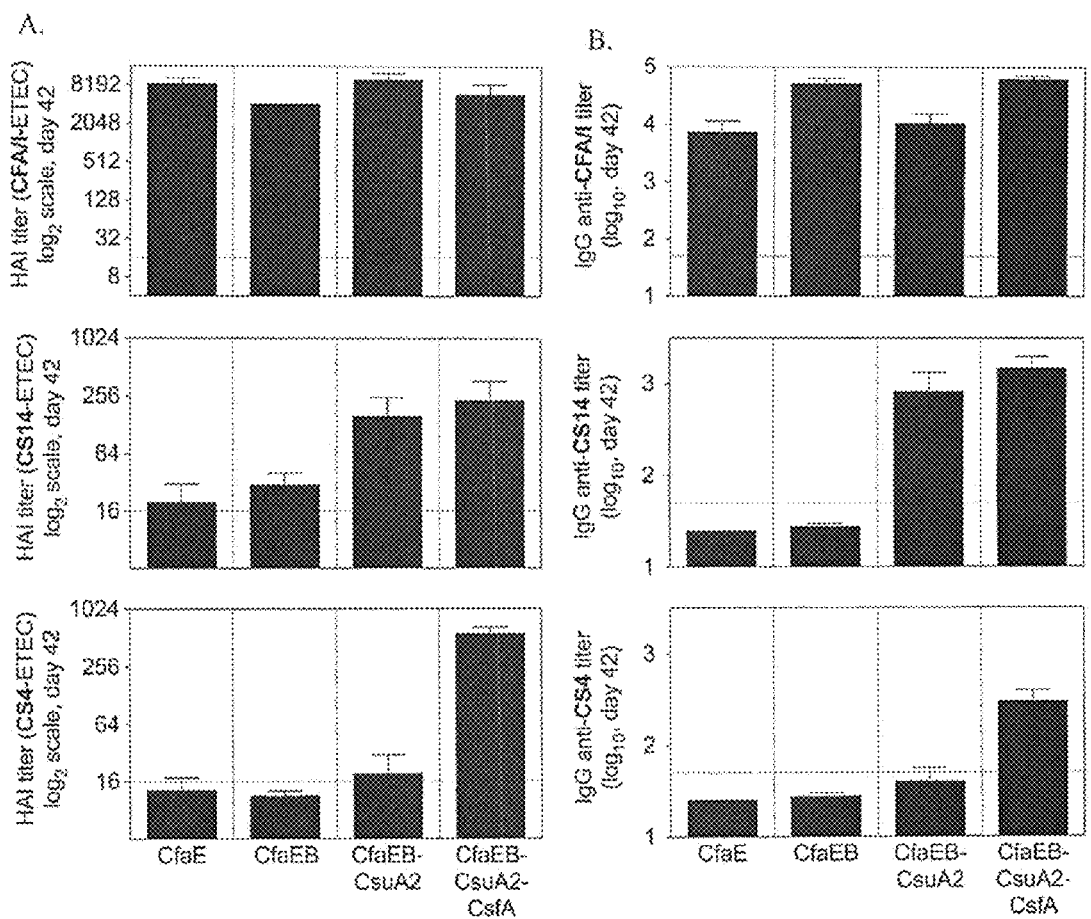
FIG. 4. Enhanced immunogenicity of adhesin-pilin fusions compared to the prototype dscCfaE (CfaE) adhesin. Panel A shows hemagglutination inhibition (HAI) titers against CFA/1-ETEC (upper), CS14-ETEC (middle), and CS4-ETEC (lower graph). Panel B shows serum IgG titers against CFA/I (upper), CS14 (middle) and CS4 (lower) fimbriae. Note that the middle and lower graphs in each panel display a different y-axis scale to that of the corresponding upper graphs. The shorthand protein names shown in the graph labels and corresponding full names are as follows: CfaE, $dsc_{19}CfaE(His)_6$; CfaEB, $dsc_{19}CfaE$-$CfaB[His]_6$; CfaEB-CsuA2, $dsc_{15}CfaEB$-CsuA2-$[His]_6$; and CfaEB-CsuA2-CsfA, $dsc_{15}CfaEB$-CsuA2-$CsfA[His]_6$; mLT, LTR192G.

As illustrated in FIG. 4, Panel A shows the hemagglutination inhibition (HAI) titers against CFA/1-ETEC (upper), CS14-ETEC (middle), and CS4-ETEC (lower graph). Elevated HAI titers against CS14-ETEC and CS4-ETEC coincide with the addition of CS14 (CsuA2) and CS4 (CsfA) pilins, respectively. Panel B shows serum IgG titers against CFA/I (upper), CS14 (middle) and CS4 (lower) fimbriae. Augmented serum anti-fimbrial titers to CFA/I, CS14, and CS4 coincide with the addition of CFA/I (CfaB), CS14 (CsuA2) and CS4 (CsfA) pilins, respectively. Each recombinant protein was stabilized by in cis donor strand complementation.

Figure 5:
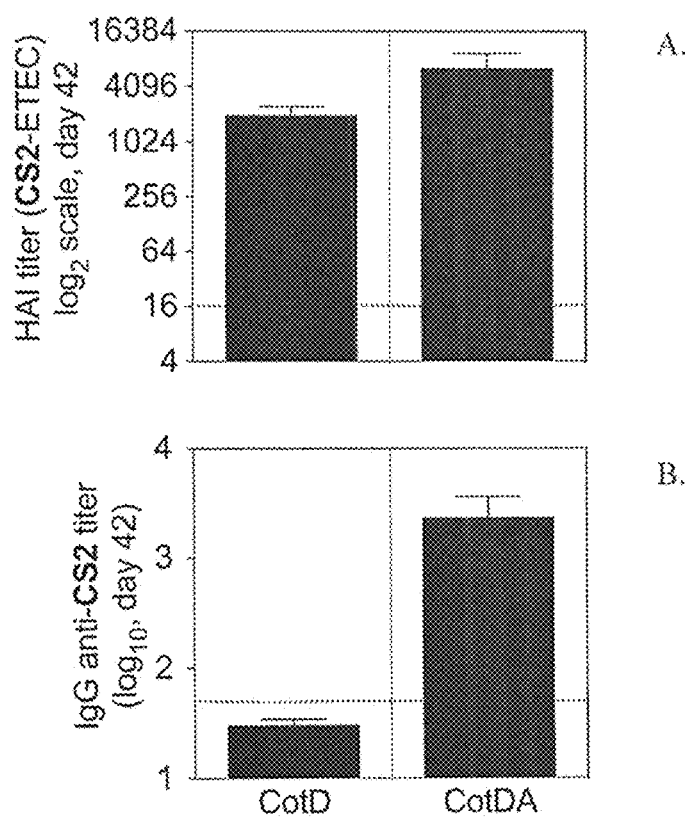
FIG. 5. Enhanced immunogenicity of a Class 5c adhesion-pilin fusion compared to dscCotD (CotD) adhesin. Panel (A) shows HAI titer. Panel (B) shows anti-CS2 IgG response.

Similar results are illustrated for CsbD and CotD adhesin, the results of which are shown in FIG. 5. FIG. 5 illustrates the enhanced immunogenicity of a Class 5c adhesin-pilin fusion compared to the prototype dscCotD (CotD) adhesin. In the adhesin-pilin protein shown in FIG. 5, the CS2 pilin (CotA) is fused to the C-terminus of dscCotD, wherein each component protein is stabilized by in cis donor strand complementation. Groups of ten BALB/c mice were vaccinated intranasally with 25 µg of each protein, co-administered with the adjuvant LTR192G (1.5 µg). Mice were vaccinated three times at 0, 14, and 28 days. The displayed titers are from serum collected at day 42. Panel A displays serum hemagglutination inhibition (HAI) titers against CS2-ETEC. Addition of the CS2 pilin is associated with an elicitation of higher homologous HAI titers. Panel B shows serum IgG titers against CS2 fimbriae. Illustrated in FIG. 5 is an augmentation of serum anti-fimbrial IgG titers, coinciding with the addition of the CS2 (CotA) pilin. Data is displayed as the geometric mean titer plus standard error of the mean. The horizontal dotted line in each graph shows the limit of assay detection. The shorthand protein names shown in the graph labels and corresponding full names are as follows: CotD, $dsc_{19}CotD(His)_6$; and CotDA, $dsc_{15}CotD\text{-}CotA[His]_6$.

FIG. 6 illustrates the response of the construct example "$dsc_{14CsbA}CsbD\text{-}CsbA\text{-}ntd_{15}dsc_{14CooA}CooA$", shown in Table 2. Similar to that in FIG. 5, FIG. 6 shows enhanced immunogenicity of Class 5b adhesin-pilin fusions compared to the prototype dscCsbD (CsbD) adhesin. In the two Class 5b adhesin-pilin proteins, the following Class 5b pilin components were successively fused to dscCsbD: CS17 pilin (CsbA), and CS1 pilin (CooA). Groups of ten BALB/c mice were vaccinated intranasally with 25 µg of each protein, co-administered with the adjuvant LTR192G (1.5 µg). Mice were vaccinated three times at 0, 14, and 28 days. The displayed titers are from serum collected at day 42. Panel A displays hemagglutination inhibition (HAI) titers against (from upper to lower panels) CS17-ETEC, CS19-ETEC, and CS1-ETEC, PCFO71-ETEC, and CFA/1-ETEC. Similarly elevated HAI titers against all of ETEC expressing each of the four Class 5b fimbriae were elicited, while the largest fusion, dscCsbDA-CooA also elicited elevated HAI to ETEC expressing the heterologous Class 5a fimbriae CFA/I. Panel B shows serum IgG titers against CS17 fimbriae (upper) and CS1 fimbriae (lower). Augmented serum anti-fimbrial titers to CS17 and CS1 coincide with the addition of CS17 (CsbA) and CS1 (CooA) pilins, respectively. Data is displayed as the geometric mean titer+standard error of the mean, with the exception of CS19-ETEC and PCFO71-ETEC HAI, for which a single value was derived (average of duplicate runs) from group pooled sera. The horizontal dotted line in each graph shows the limit of assay detection. The shorthand protein names shown in the graph labels and corresponding full names are as follows: CsbD, $dsc_{19}CsbD(His)_6$; CsbDA, $dsc_{15}CsbD\text{-}CsbA[His]_6$; and CsbDA-CooA, $dsc_{15}CsbDA\text{-}CooA\ [His]_6$. Each recombinant protein has been stabilized by in cis donor strand complementation.

Example 2

CS6 and CS3

Rabbit model (RITARD) studies suggest the colonization factor CS6 and CS3 has immune-protective potential (Svennerholm, et al., Infect. Immun. 56: 523-528 (1988); Svennerholm, et al., Infect. Immun. 58: 341-346 (1990)). As such, an important technical goal is to reproduce a stabilized CS6 expressing recombinant structure expressing CS6 antigens that maximally elicits antibody responses inhibitory to CS6-directed adhesion.

Unlike class 5 ETEC fimbriae, the fimbrial structures may function as polyadhesins rather than monadhesins (Zavialov, et al., FEMS Microbiol. Rev. 31: 478-514 (2007)). Extrapolation from related fimbriae, assembly of ETEC CS6 and CS3 may be mediated by a donor strand complementation mediated process through association of a CS6 or CS3 subunit with the N-terminal donor strand region of an adjacent subunit. Additionally, protection against misfolding and proteolytic degradation may also be afforded through donor strand complementation.

Association of monomers of CS3 and CS6 was evaluated by visualization of the subunit proteins under denaturing and non-denaturing conditions in polyacrylamide gel electrophoresis (PAGE). For both CS3 and CS6 monomers, under denaturing conditions the proteins migrating at the expected sizes. Under non-denaturing conditions multiple size (i.e., ladders) are seen formed by multimeric association of the subunits.

CS6 Fimbriae

CS6 fimbriae comprise CssA and CssB. Whereas the two CS3 major subunits show little to no variation in polypeptide sequences, modest variation in CS6 proteins is observed. For example, greater than 90% identity is found in CS6 protein CssA and greater than 95% identity is found in CssB allotypes. Both CS6 structural proteins exhibit a relatively low level of variation (i.e., greater than 90% amino acid conservation), with greater variation in CssA and the mutations randomly distributed along the CssA polypeptide.

In order to design an effective immunogenic composition that would be suitable for inclusion in a vaccine formulation a number of criteria were devised for determination of suitable constructs. These included the ability to maintain a structure without unwanted self-association or assembly; thermostability; and ability to generate anti-CS6 IgG and IgA antibody levels similar to those elicited by immunization with CS6.

Monomeric CS6 subunit assembly appears to be mediated by donor strands from adjacent CS6 subunits, as discussed above. It is hypothesized that interaction to form these stable structures is mediated by inter-subunit interaction through donor strand complementation. Donor strand complementation also affords protection against misfolding and proteolytic degradation. Therefore, in a preferred embodiment, multimeric CS6 constructs were developed to take advantage of these attributes of donor strand complementation. Additionally, multimeric expression provides more efficient manufacture over production of monomers.

CssA and CssB monomers exhibit similar thermal stability, as illustrated in Table 3. However, as also illustrated in Table 3, dimers of CssA or CssB are generally more thermally stable over larger structures. Additionally, multimers comprising both CssA and CssB were generally more thermally stable than homo-multimers (i.e., comprising only CssA or CssB). Furthermore, multimer constructs with CssB subunit that is N-terminal to CssA were generally more thermally stable over construct containing CssA N-terminal to CssB.

TABLE 3

| Antigen | Purity | Tm, ° C. (CD Spec) |
|---|---|---|
| dscCssA | 95.3% | 54 |
| dscCssB | 95.5% | 58 |
| dscCssAA | 95.4% | 46 |
| dscCssBB | >99% | 58 |
| dscCssAB | 98.1% | 58 |
| dscCssBA | 91.5% | 72 |

From the results illustrated in Table 3, an embodied construct comprises a multimeric CS6 with one or more of the CS6 subunits, CssA and CssB, or allelic variation or derivatives, with the construct design configuration illustrated in FIG. 1. In a preferred embodiment, the construct comprises a dimer of CssB and CssA with CssB N-terminal to CssA (i.e., CssB-CssA).

As illustrated in FIG. 1, or FIG. 2, CS6 subunit association is stabilized by in cis donor β strand complementation. Donor strand complementation is afforded by linking a CS6 subunit at its C-terminus, to the donor β strand region of another CS6 subunit, via a tetrapeptide linker. The linker can be any of a number of polypeptide regions. However, in a preferred embodiment, the linker is either as in SEQ ID No. 5 or a triglyicine linker. In the case of a terminal CS6 subunit, stabilization is provided by donor β strand, connected at its C-terminus, from a homologous or heterologous CS6 subunit. Homologous subunit is defined as two subunits of the same form (e.g., CssA OR CssB). Heteterologous subunits are of different forms (e.g., one is derived from CssA the other from CssB. The CS6 donor β strand is typically the N-terminal 14-16 amino acid region of CS6 subunit. The recombinant protein can be constructed with or without hexahistidine affinity tags, which are typically on the C-terminus.

Additionally, to prevent recombinant polypeptide constructs forming molecular associations resulting in un-desirable non-covalent oligomer formation, in a preferred embodiment, the N-terminal 14-16 amino acids of the N-terminal CS6 subunit is deleted. As an illustration, "dsc$_{B14}$CssBA" would contain a heterologous donor strand (i.e., "dsc"), from CS6 CssB, inserted at the C-terminus of the construct. In this case, the donor strand is 14 amino acids in length, as indicated by the "14." Similarly, a constructed designated "ntd$_{15}$dsc$_A$CssBA" would contain a homologous donor strand at the C-terminus of the construct and also comprises a deletion of the N-terminal amino acid region (termed "ntd").

Examples of constructs comprise one or more CS6 subunits with amino acid sequences selected from the group consisting of SEQ ID No. 2 (CssA) or SEQ ID No. 4 (CssB), or derivatives of these polypeptides. The DNA sequence for CssA is SEQ ID No. 1 and for CssB, SEQ ID No. 3. The subunits are connected by a polypeptide linker sequences. In a preferred embodiment, the linker is a tetrapeptide with the amino acid sequence of SEQ ID No. 5.

Figure 7:
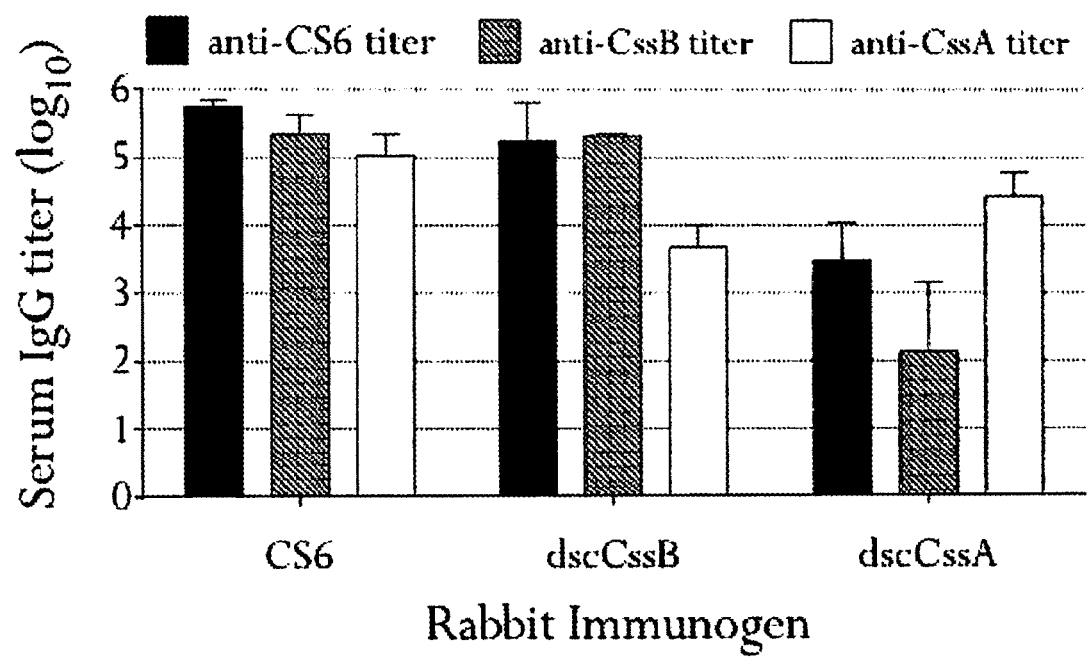
FIG. 7. Immunity of CS6 constructs, in rabbits. Shown are the serum IgG titers following administration of CS6; dscCssB or dscCssA antigen.

The evaluation of immune responses by various monomer (FIG. 7) and dimer (FIG. 8) CS6 constructs was conducted. In FIG. 7, rabbits were immunized every 28 days over an 84 day period, with two rabbits per group. The animals were primed with 400 μg and boost three times with 200 μg of either CS6, dscCssA or dscCssB, in Freund's adjuvant. The animals were bled at days 0, 14, 42, 70, 98 and 105. As shown in FIG. 7, CS6 elicits high homologous antibody titer, as well as high anti-CS6 (i.e., CssA or B) subunit titer. Immunization of rabbits with donor strand stabilized CssB (dscCssB) yielded high anti-CS6 and anti-CssB titers. However, immunization with dscCssA elicited somewhat lower anti-CS6 titers and intermediate levels of anti-CssA titers of IgG.

Figure 8:
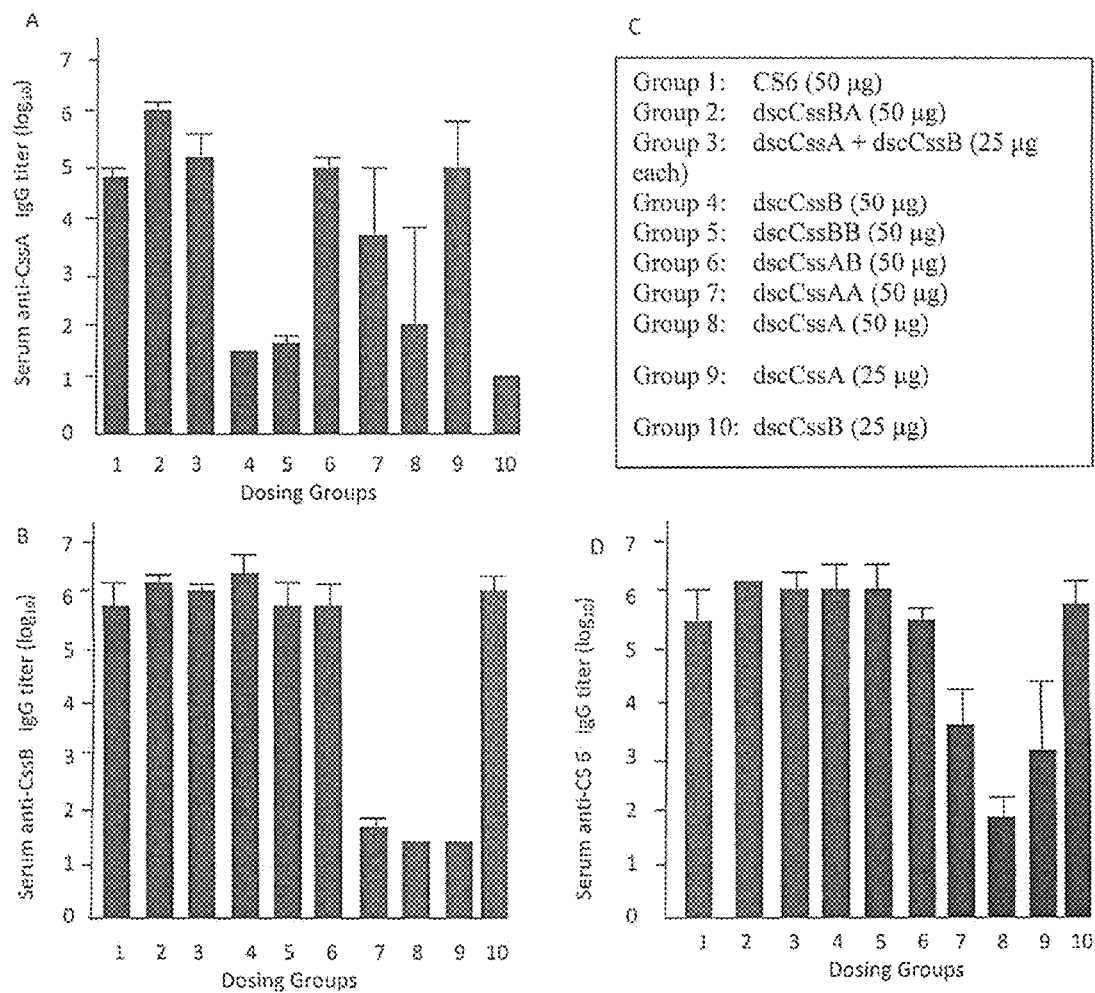
FIG. 8. Comparison of immunity in mice following administration of CS6 monomers, heterodimers and homodimers.

In FIG. 8, heterodimers, homodimers or monomers of CssA and CssB major subunits were used to immunize groups (n=4) of mice. All of the constructs, except CssA and CssAA elicited high IgG anti-CS6 serum antibody titers (FIG. 8D). FIG. 8A shows anti-CssA IgG titer and FIG. 8B shows anti-CssB IgG titer, in response to different CS6 antigens administered (FIG. 8C). As shown in FIG. 8, the dimeric constructs, comprising dscCssB-CssA elicited a somewhat better immune response than either dscCssA-CssB or when both dscCssA or dscCssB were both administered together at 25 μg dose for each monomer. In fact, administration of dscCssBA elicited a similar anti-CssB response as administration of dscCssB (at 25 or 50 μg) and a significantly greater anti-CssA response than when dscCssA was administered at 25 μg or 50 μg. This result is highly advantageous in providing broad anti-CS6 immune coverage while maximizing manufacturing efficiency and cost, over that associated with production of multiple monomers.

The ratio of fold-rise in anti-CS6 IgG serum titer elicited by each construct over that elicited by native CS6 is shown in Table 4. All constructs elicited an immune response at least as good as native CS6. These results illustrate that heterologous donor strand complementation provided the greatest increase in titer.

TABLE 4

| | dsc$_{16B}$ CssAB | dsc$_{16A}$ CssAB | ntd$_{15}$dsc$_{16B}$ CssAB | ntd$_{15}$dsc$_{16A}$ CssAB | dsc$_{16A}$ CssBA | Dsc$_{16B}$ CssBA | ntd$_{15}$dsc$_{16A}$ CssBA | ntd$_{15}$dsc$_{16B}$ CssBA |
|---|---|---|---|---|---|---|---|---|
| Fold Increase IgG | 1.16 | 1.14 | 1.20 | 1.18 | 1.20 | 1.20 | 1.16 | 1.22 |
| Fold Increase IgA | 0.79 | 0.86 | 1.02 | 0.71 | 1.00 | 0.99 | 1.24 | 1.23 |

As shown in Table 4, the highest ratio was associated with "ntd$_{15}$dsc$_B$CssBA." This construct contains a 16 amino acid donor strand region of CssB at the C-terminus of the construct, which is heterologous to the C-terminal subunit (i.e., CssA). The "ntd" illustrates that the construct also has the N-terminal region of CssB deleted in order to prevent self-association.

Also shown in Table 4 is the fold increase of IgA over titers observed in animals vaccinated with CS6 for a number of constructs. For the case of IgA, both ntd$_{15}$dsc$_{16B}$CssBA, and ntd$_{15}$dsc$_A$CssBA, yielded similar titer. However, as discussed above, ntd$_{15}$dsc$_{16A}$CssBA, which contains the homologous donor strand on CssA, is likely less stable.

A summary of results of CS6 constructs is shown in Table 5, comparing CssBA against CssAB constructs.

TABLE 5

| | CssA-CssB | | | | CssB-CssA | | | |
|---|---|---|---|---|---|---|---|---|
| | Original[1] | Het[2] | ntd[3] | Both | Original | Het | ntd | Both[4] |
| No. peaks, SE-HPLC (score: 1 peak = 1, >1 peaks = 0) | 2 | 1 | 1 | 1 | 2 | 1 | 1 | 1 |
| Tm, °C. (DSC) (Score: <61 = 0, 61-65 = 1, 66-70 = 2, >70 = 3) | 58 (0) | 70 (2) | 59 (0) | 60 (1) | 68 (2) | 74 (3) | 74 (3) | 75 (3) |
| IgG anti-CS6 Log$_{10}$ Titer (Score: Fold rise over CS6 Titer) | 5.15 (5.5) | 5.05 (8.3) | 5.34 (6.8) | 5.23 (8.4) | 5.33 (5.6) | 5.37 (9.4) | 5.16 (5.6) | 5.44 (9.5) |
| IgA anti-CS6 Log$_{10}$ Titer (Score: Fold rise over CS6 Titer) | 2.87 (0.2) | 3.10 (1.2) | 3.71 (0.1) | 2.56 (1.0) | 3.62 (0.3) | 3.59 (0.9) | 4.51 (7.6) | 4.47 (6.9) |

[1]Original is dsc$_{16B}$CssA-CssB.
[2]Het (heterologous) refers to the donor strand origination for the terminal (i.e., C-terminal) subunit. For CssA-CssB, "Het" construct contains a donor strand of 16 amino acids connected at the C-terminus derived from CssA. For CssB-CssA, "Het" construct contains a donor strand of 16 amino acids connected at the C-terminus derived from CssB.
[3]ntd refers to N-terminal deletion. For CssA-CssB, CssA contains a deletion of 15 amino acids from its N-terminus. For CssB-CssA, CssB contains a deletion of 14 amino acids its N-terminus.
[4]"Both" refers to constructs having both "ntd" and heterologous donor strand complementation of the C-terminal subunit.

CS3 Fimbriae

Savarino, U.S. patent application Ser. No. 11/340,003 (2006) claims donor strand complementation stabilized ETEC constructs. Embodiments of this application incorporate the donor strand stabilization of CstH and adds the second CS3 subunit, CstG. Embodiments herein add additional features found to be important for stabilization of the CS3 subunits and immunogenicity against CS3. CS3 comprises CstH and CstG. The CS3 structural protein CstH is invariant. CstG is also highly conserved, showing 99-100% identity in polypeptide sequence for 39 wildtype CS3 genes sequenced. Similiarly, although some variation CstG is observed, it is also relatively invariant, with 99-100% amino acid conservation.

Figure 10:
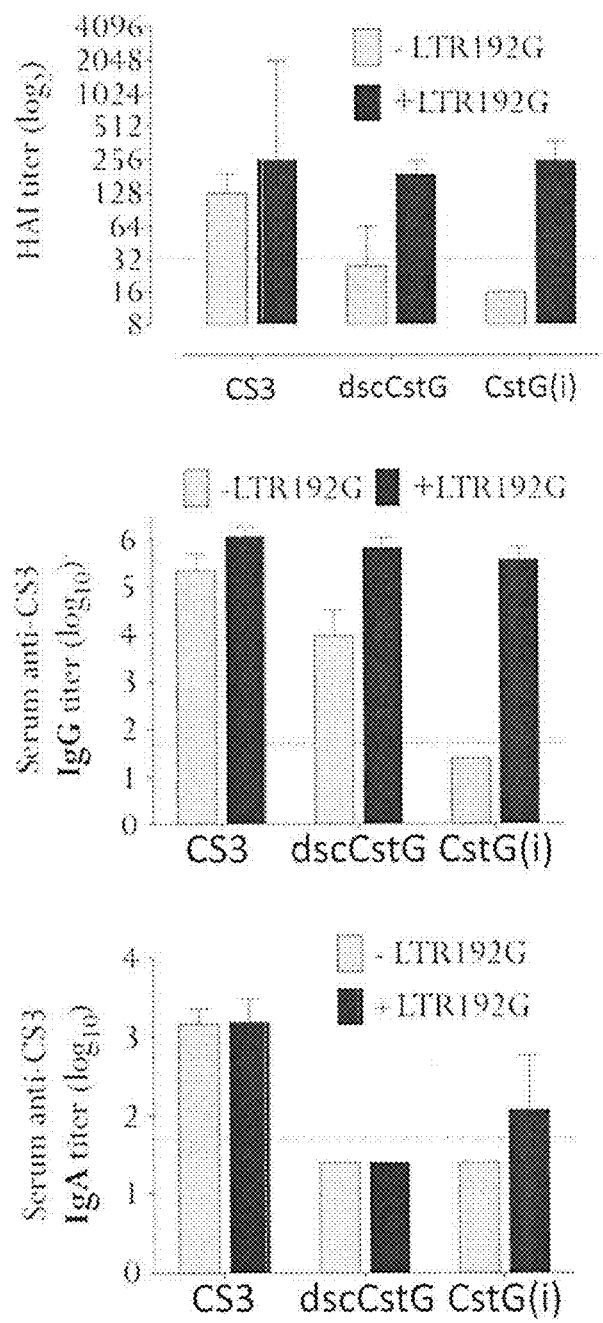
FIG. 10. Hemaglutining inhibition (HAI) and serum reactivity of dscCstG compared to oligommer (3-14 subunits) of CstG (denoted as CstG(i).

Evaluation of the immunogenicity of CS3 type fimbrial subunits was evaluated. Mice (BALB/c) were immunized intranasally, with 150 μg per dose in a 3 dose series at two week intervals with either oligomeric CstG or CstH, containing 3-14 subunits or donor strand complemented monomeric CstH or CstG, with or without adjuvant (LTR192G). The response was observed by serum anti-CS3 IgA or IgG and by hemaglutinination inhibition. The results are shown in FIGS. 9 and 10.

As shown in FIG. 9, monomeric donor strand complemented CstH was poorly immunogenic compared to noncovalently linked oligomers of multimeric CstH (denoted as CstH(i)), possibly due to presentation of linked repeating domains of CstH. In FIG. 9, "i" refers to intein, used in isolation of the oligomer. In contrast, both dscCstG and noncovalently linked oligomers of CstG were immunogenic (FIG. 10), however less so than CS3.

Figure 11:
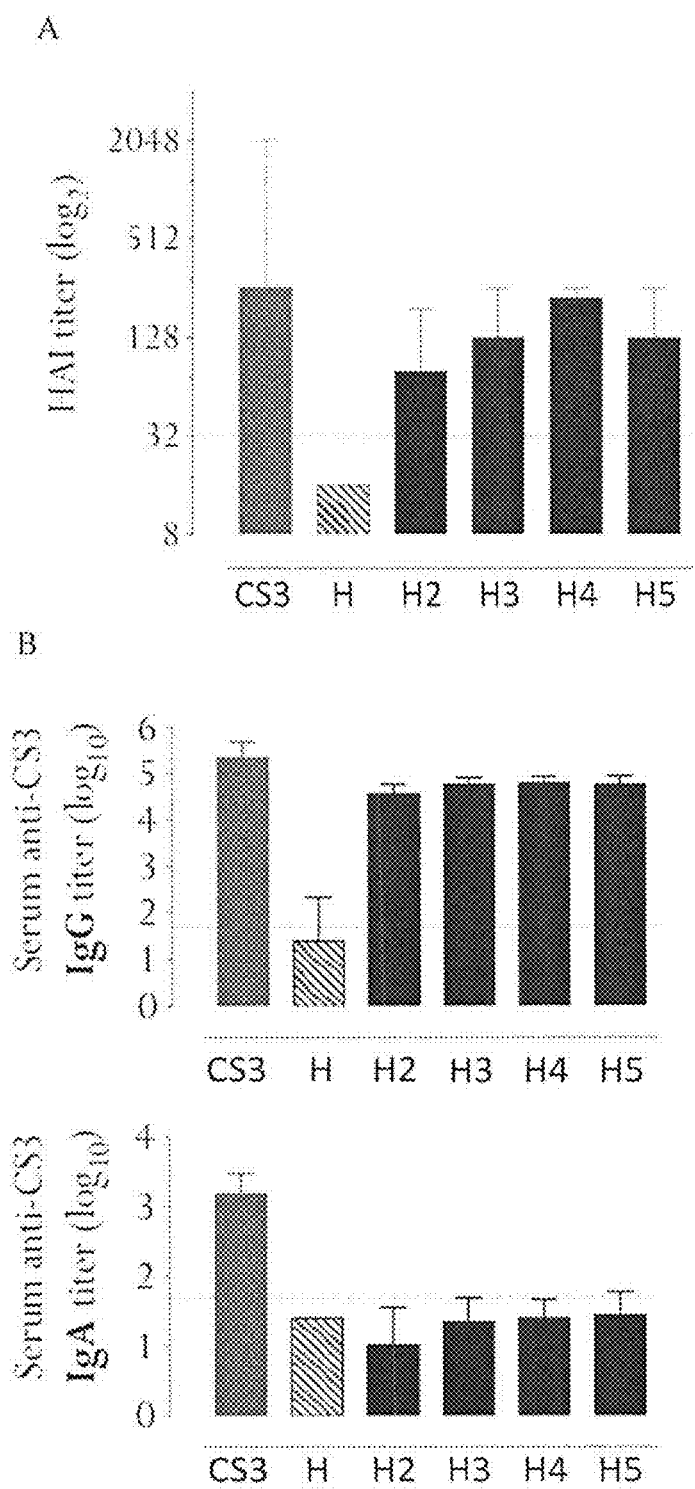
FIG. 11. Immune and HAI responses of multimeric donor strand complemented CstH. In the figure, H=dscCstH; H2=dscCstH2; H3=dscCstH3; H4=dscCstH4; H5=dscCstH5.

Due to the low immunogenicity of monomeric CstH, studies were conducted to evaluate larger donor strand complemented covalently-linked oligomers. The results of this study are shown in FIG. 11. In FIG. 9, "H" refers to dsc$_{16}$CstH (His)$_6$, whereby the construct is in cis donor strand complemented at its C-terminus with a tetrapeptide linker, connected to a 16 amino acide polypeptide sequence of the N-terminal beta strand of CstH. The construct also contains a string of six (6) histidine (His)$_6$ at its C-terminus. Similarly, H2 refers to dsc$_{16}$CstH2, whereby the construct comprises two CstH fimbrial subunits linked by a tetrapeptide linker and where the C-terminal CstH is connected, via a tetrapeptide linker, and in cis donor complemented at its C-terminus, to a 16 amino acide polypeptide sequence of the N-terminal beta strand of CstH. Similar constructs are referred to for H3 (but with three tandemly linked CstH fimbrial subunits), H4 (four tandemly linked CstH subunits) and H5 (five tandemly linked CstH subunits).

As illustrated in FIG. 11, increasing the number of tandem CstH subunits was associated with increasing HAI titer. However, dimeric dscCstH elicited a similar HAI titer as the higher size oligomers. Monomeric dscCstH did not elicit a demonstrable HAI titer.

Figure 12:
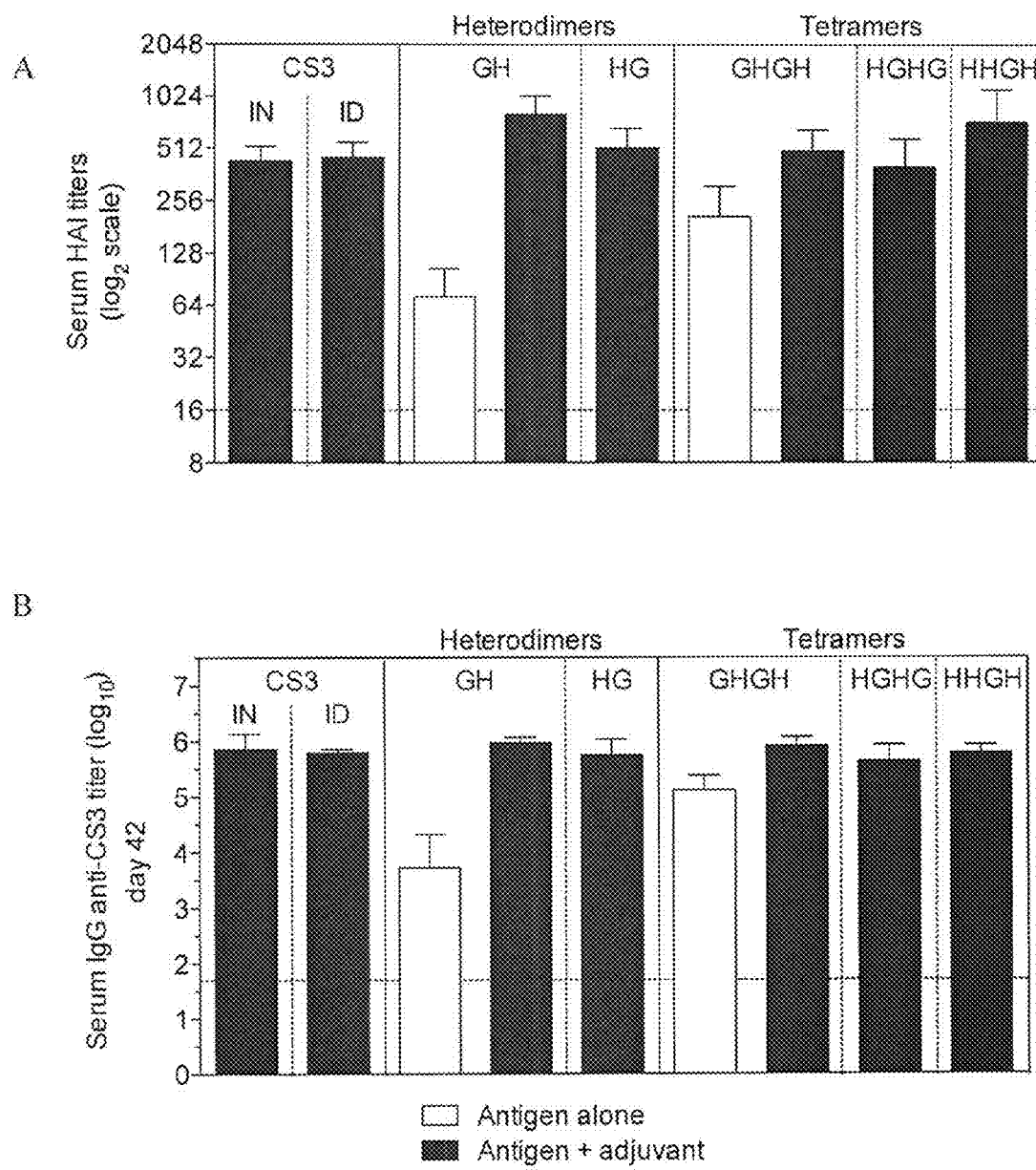
FIG. 12. Immune response to stabilized CS3-based heterodimers and tetramers. Immune responses, as measured by hemagglutination inhibition (HAI) against CS3-ETEC (Panel A), and serum IgG anti-CS3 titers (Panel B) are shown for serum drawn two weeks after the last dose (day 42). Abbreviations: GH, dsc$_{16}$CstGH; HG, dsc$_{16}$CstHG; GHGH, dsc$_{16}$CstGHGH; HGHG, dsc$_{16}$CstHGHG; and HHGH, dsc$_{16}$CstHHGH. All recombinant oligomers were engineered using in cis donor strand complementation.

In light of above, since CS3 contains both CstG and CstH, in near equal amounts, dimeric constructs were devised incorporating CstG and CstH, according to the template construct design of FIG. 1. A summary of the results of the analysis of these constructs is illustrated in FIG. 12. In FIG. 12, groups of 8 mice each were vaccinated with 25 μg of the denoted vaccine±LTR 192G adjuvant (100 ng, ID; 1.5 μg, IN) by the intradermal (ID) route in a 3-dose schedule (days 0, 14, 28); with CS3 intranasal (IN) vaccinated group serving as a mucosal vaccination control. Immune responses, as measured by hemagglutination inhibition (HAI) against CS3-ETEC (Panel (A)), and serum IgG anti-CS3 titers (Panel (B)) are shown for serum drawn two weeks after the last dose (day 42). Abbreviations: GH, dsc$_{16}$CstGH; HG, dsc$_{16}$CstHG; GHGH, dsc$_{16}$CstGHGH; HGHG, dsc$_{16}$CstHGHG; and HHGH, dsc$_{16}$CstHHGH, where dsc$_{16}$ refers to a 16 amino acid donor β strand, connected to the C-terminal fimbrial subunit via a tetrapeptide linker. All recombinant fusions were engineered using in cis donor strand complementation.

As illustrated in FIG. 12, the simple molecules "GH" and "HG" elicited similar responses and were both similar to CS3. However, "GH" elicited a somewhat higher response than "HG." Little response was demonstrable against either CstG or H monomers (data not shown). Therefore, the immune response to dimers was significantly higher than for monomers of CstH or CstG. Furthermore, response to heterodimers is comparable or greater than that observed against tetramers.

Based on these studies, a preferred embodiment for a polypeptide construct that can be used to elicit an immune response against CS3 comprises constructs designed according to FIG. 1. In FIG. 1, CS3 constructs comprise one or more CS3 fimbrial subunits connected via a polypeptide linker. The C-terminal fimbrial subunit is connected, via a polypeptide linker, to a donor β strand region of a CS3 fimbrial subunit. The C-terminal donor β strand can be derived from the same CS3 subunit to which it is connect (i.e., homologous) or derived from a different subunit (i.e., heterologous). The polypeptide linker can be any number of polypeptide regions, however, in a preferred embodiment, the linker is a tetrapeptide of the sequence of SEQ ID No. 5, or a triglycine (i.e., G-G-G). The donor β strand region is the N-terminal 14-16 amino acids of the mature CstH or CstG protein. In alternatives of this embodiment, the first 14-18 amino acids of the N-terminal region of the N-terminal most subunit is deleted to avoid undesirable associations.

In a preferred embodiment, the CS3 construct is a dimer. Although other examples are contemplated using the design of FIG. 1, as an illustrative example, the recombinant polypeptide construct can be configured as "dsc$_{16CstH}$CstG-(linker)-CstH". In this example, the mature CstG polypeptide (SEQ ID No. 101) or full length polypeptide sequence (SEQ ID No. 87) is connected at its C-terminus to CstH polypeptide (SEQ ID No. 99), via a polypeptide linker. In this example, the CstH polypeptide, is connected, at its C-terminus, to a donor β strand region of 16 amino acids derived from CstH via a polypeptide linker.

Other examples can include constructs, according to FIG. 1. In other examples, the C-terminal donor β strand can be either homologous (derived from the same subunit) or heterologous (derived from a different subunit) to the C-terminal most CS3 fimbrial subunit.

Example 4

Construction of Multipartite Fusion Constructs

Immunity to multiple strains of ETEC is important to obtain the greatest extent of anti-ETEC immunity. Toward this goal, recombinant polypeptide constructs were developed comprising two or more subunits derived from different ETEC fimbrial types according to the design illustrated in FIG. 2 to form multipartite fusion constructs. As used, herein, multipartite fusion or multipartite fusion constructs are recombinant polypeptide constructs according to FIG. 2. In this design, different ETEC fimbrial types are defined as fimbrial proteins derived from fimbriae of different strain ETEC types, as listed in Table 6, or deriviates of these polypeptides or DNA sequences. For example, the fimbrial type "CS3" comprises CstH and CstG. The fimbrial type "C56" comprises CssA and CssB. The fimbrial types of Class 5 ETEC include the fimbrial types Class 5a, Class 5b and Class 5c.

In a preferred embodiment, major and/or minor subunits, derived from the same ETEC fimbrial type are connected, via polypeptide linkers, and stabilized by donor β strand complementation, as illustrated in FIG. 1 and Examples 1-4. A multipartite fusion comprises one or more fimbrial subunits of the same fimbrial type, as in FIG. 1, connected to one or more fimbrial subunits derived from a different fimbrial type as illustrated in FIG. 2.

In one embodiment, the multipartite fusion construct can include a deletion of the N-terminal region of one or more fimbrial subunits, but is preferably on the N-terminal most fimbrial subunit for a given ETEC fimbrial type, as illustrated in FIG. 2. This feature prevents undesirable associations with other monomers or multimers. The size of the deletion of the N-terminal region is 14 to 18 amino acids. In other embodiments, multipartite fusion constructs comprising Class 5 adhesins do not contain a deletion of the N-terminal region.

As illustrated in FIG. 2, the C-terminal subunit, for an ETEC fimbrial type, is connected to and stabilized by a donor β strand, connected to the subunit via a polypeptide linker, wherein the donor β strand is either that derived from the adjacent subunit (i.e., homologous) or from a different subunit of the same fimbrial type (i.e., heterologous). The size of the N-terminal donor strand depends on the fimbrial type and subunit stabilized. In preferred embodiments, for class 5 fimbrial subunits, the donor β strand, derived from the N-terminal region of the class 5 subunit stabilized, is 12 to 16 amino acids. For CS3 and CS6 subunits, the donor β strand is 14 to 16 amino acids. As mentioned above, the construct can contain a deletion of the N-terminal region of the N-terminal subunit. This feature prevents undesirable associations with other monomers or multimers. The size of the deletion of the N-terminal region is 14 to 18 amino acids.

As illustrated in FIG. 2 multiple constructs as in FIG. 1 are connected forming a recombinant polypeptide construct comprising two or more ETEC fimbrial types. In this way, one or more major or minor subunits, derived from the same ETEC fimbrial type, are connected via polypeptide linkers and stabilized by donor strand complementation. In another embodiment, one or more glycine residues separates different ETEC fimbrial types, acting as a "swivel" means between the ETEC types. The glycine residue, due to its small, unbranched molecular characteristics, enables rotary freedom of the molecular components. Subunits derived from the same fimbrial type (as in FIG. 1) are connected by a polypeptide linker, with the subunits stabilized by donor strand complementation. As shown in FIG. 2, the C-terminal subunit of each ETEC fimbrial type is stabilized by a donor β strand that is homologous or heterologous to the C-terminal subunit of that fimbrial type.

In other embodiments, the construct can contain an N-terminal deletion at the N-terminus of the entire construct as well as an additional deletion, of 14 to 18 amino acids, at the N-terminus of the first "internal" subunit that is of a different fimbrial type. This is illustrated in FIG. 2. In the case of the deletion on the N-terminus of the "internal" subunit, the deletion serves to shorten the length between subunits, thus reducing the likelihood of misfolding and proteolytic cleavage. In another embodiment, a donor strand, derived from a homologous or heterologous subunit, is inserted at the C-terminus of the C-terminal CS6 or CS3 subunit. For class 5 fimbrial subunits, the donor β strand, derived from the N-terminal region of the class 5 subunit that is stabilized, is 12 to 16 amino acids. For example, in preferred embodiments, CfaB is stabilized by a 14 amino acid donor β strand; CsfA by a 14 amino acid donor β strand; CsbA by a 15 amino acid donor β strand, CooA by a 14 amino acid donor β strand and CotA by a 14 amino acid donor β strand. For CS3 and CS6 subunits, the donor β strand is 14 to 16 amino acids, with preferred embodiments of CS3 fimbrial subunits (i.e., CstH or CstG) stabilized by a 16 amino acid donor β strand derived from CstH or CstG; and CS6 fimbrial subunits (i.e., CssA or CssB) stabilized with a 16 amino acid donor β strand derived from CssA or CssB. However, other donor β strand lengths are envisioned.

The inventive compositions can utilize different linker sequences. In a preferred embodiment, the linker contains the amino acid sequence of SEQ ID No. 5. In another embodiment, the linker is a tri-glycine linker. In other embodiments, the C-terminal end of the construct contains a histidine tag for purification of the construct.

In the inventive construct, in cis donor strand complementation is used to stabilize adhesins and adhesin-pilin fusions for representative Class 5a, 5b, and 5c adhesins. For each adhesin target group, in a preferred embodiment, the compositions are constructed with the intent of eliciting anti-adhesive immune responses. Further towards this goal, Class 5 multipartite fusions comprising Class 5 adhesin minor subunits are typically construct such that the adhesin (i.e., minor fimbrial subunit) is located at the N-terminus of the constructed with the minor fimbrial subunit linked at its C-terminus to one or more major subunits, followed at the terminal end of the construct with the donor β-strand of the last major subunit.

Other embodiments include constructs comprising Class 5a adhesin CfaE tandemly linked at its C-terminus to one or more of CfaB (CFA/I major subunit), CsuA2 (CS14 major subunit) and CsfA (CS4 major subunit); Class 5b adhesin CsbD tandemly linked at its C-terminus to one or more of CsbA (CS17 major subunit), which shares high identity to the CS19 pilin subunit CsdA, and CooA (CS1 major subunit), which shares high identity to the PCFO71 pilin subunit CosA; and Class 5c adhesin CotD tandemly linked at its C-terminus to CotA (CS2 major subunit).

Embodiments of ETEC multipartite fusion constructs are illustrated in Table 7 and 8. In this embodiment, constructs comprise any major or minor ETEC fimbrial subunit from Table 6 in multiple combinations, connected by linker polypeptides and stabilized from proteolytic degradation by donor strand complementation utilizing the design illustrated in FIG. 2. Table 6 lists the ETEC fimbrial subunits (major and minor subunits) than can be used and incorporated into the multipartite fusion construct design of FIG. 2. Any subunit, therefore, is combined with one or more other ETEC major subunits from any ETEC fimbrial phenotypic type, including Class 5a, 5b, 5c, CS3 and CS6.

The recombinant polypeptide construct motif comprises a whole or immunogenic fragment of a minor or major ETEC fimbrial subunit connected at its C-terminal end to a linker. The linker is connected at its C-terminus to a whole major ETEC fimbrial subunit or a polypeptide donor strand of an ETEC major structural subunit, derived from the same fimbrial type. The whole ETEC major subunit or donor strand polypeptide is then connected, via a linker at its C-terminal end, to one or more additional major structural fimbrial subunits, derived from the same fimbrial type, from Table 6.

TABLE 6

| Immune coverage fimbria/ types) | Subunit | SEQ ID No. Full length sequences including spd[1] (DNA/polypeptide)) | SEQ ID No. Mature sequences (DNA/polypeptide)[2] |
|---|---|---|---|
| Class 5a | CfaE | 56/57 | 115/58 |
|  | CfaB | 59/60 | 116/61 |
|  | CsfD | 64/65 | 117/88 |
|  | CsfA | 62/63 | 118/89 |
|  | CsuD | 70/71 | 119/90 |
|  | CsuA2 | 68/69 | 120/91 |
|  | CsuA1 | 66/67 | 121/92 |

TABLE 6-continued

| Immune coverage fimbria/ types) | Subunit | SEQ ID No. Full length sequences including spd[1] (DNA/polypeptide)) | SEQ ID No. Mature sequences (DNA/polypeptide)[2] |
|---|---|---|---|
| Class 5b | CooD | 74/75 | 122/93 |
|  | CooA | 72/73 | 123/94 |
|  | CsdD | 78/79 | 124/95 |
|  | CsdA | 76/77 | 125/96 |
|  | Cos D | 82/83 | 133/97 |
|  | CosA | 80/81 | 126/98 |
|  | CsbD | 44/45 | 127/46 |
|  | CsbA | 47/48 | 128/49 |
| Class 5c | CotD | 50/51 | 129/52 |
|  | CotA | 53/54 | 130/55 |
| CS3 | CstH | 84/85 | 131/99 |
|  | CstG | 86/87 | 132/101 |
| CS6 | CssA | 134/135 | 1/2 |
|  | CssB | 136/137 | 3/4 |

[1]"spd" refers to signal peptide. The mature polypeptide sequence, therefore, would be the full length minus the signal peptide.
[2]DNA sequence encodes mature protein.

The strategy for selecting and developing specific genetic fusion constructs is guided, in part, by the phylogenetic and antigenic relatedness of subunits. For example, constructs containing Class 5a, 5b and 5c pilin subunits are selected based on the relatedness of minor and major subunits within a particular ETEC fimbrial class (i.e., class 5a, 5b or 5c), as illustrated in FIG. 3. As such, adhesin (i.e., minor fimbrial subunit) from a specific fimbrial type (e.g., Class 5a) are linked to Class 5a major subunits. Further selection of subunits is guided and based on epidemiological study analysis in order to achieve optimum immunogenic coverage of ETEC strains.

The examples of multipartite constructs listed in Table 7 and 8 are further illustrated in FIG. 13 (for CS3 constructs) and FIG. 14 (for CS6 constructs). In these figures, the linker polypeptide, depending on the example construct, can comprise a four (4) amino acid sequence (tetrapeptide) or a tri-glycine. Also, as illustrated in FIG. 2, the subunits are interconnected and stabilized by donor strand complementation, which is denoted, as in Table 7 and 8, by "dsc". In this nomenclature, the fimbrial subunit derivation is also indicated. For example, in the construct "dsc$_{16CstH}$ CstG-CstH-(G)-ntd$_{15}$dsc$_{16CssA}$CssA-CssB", the N-terminal CS3 subunit "CstG" is connected, via a linker, to the CS3 subunit "CstH", which is connected, via a linker, to a donor strand of 16 amino acids derived from "CstH." Similarly, the N-terminal CS6 subunit "CssB" is connected, via a linker, as illustrated in FIG. 2, to a 16 amino acid donor strand derived from "CssA." In this example, donor strand complementation of the "CssB" subunit is via a heterologous donor strand (i.e., derived from "CssA.").

Figure 15:
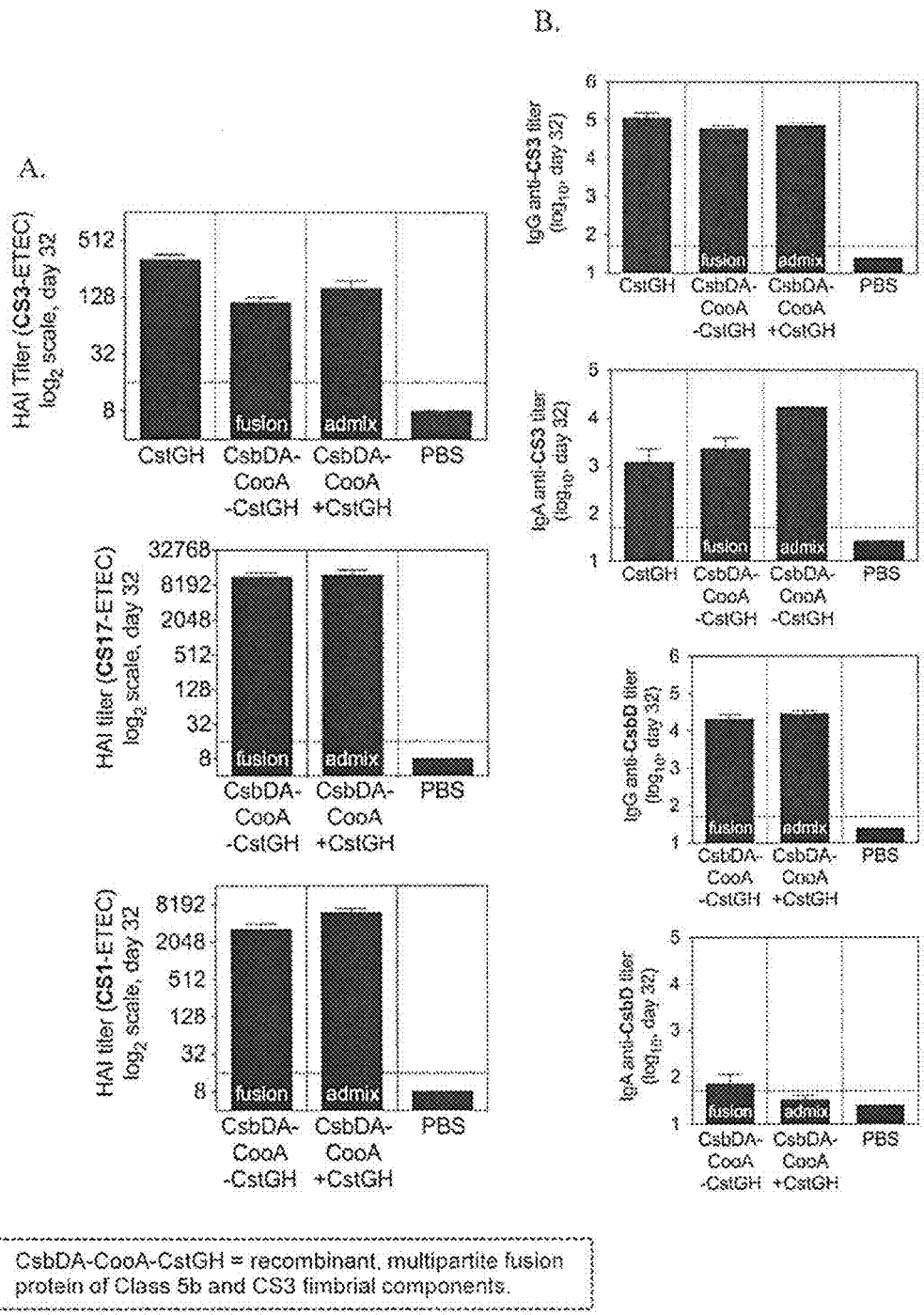
FIG. 15. Summary of data illustrating that that a multipartite fusion, CsbDA-CooA-CstGH, comprising subunits from a Class 5 ETEC fimbrial type, i.e., CsbDA-CooA and a CS3 fimbrial type, i.e., CstGH, retains the immunogenic effects of the fimbrial types. The shorthand protein names shown in the graph labels and corresponding full names are as follows: CsbDA-CooA, dsc$_{15}$CsbDA-CooA [His]$_6$; CstGH, dsc$_{16}$CstGH(His)$_6$; CsbDA-CooA+CstGH, an admixture of CsbDA-CooA and CstGH; CsbDA-CooA-CstGH, the multipartite fusion dsc$_{14}$CsbDA-CooA-ntd$_{18}$dsc$_{16}$CstGH(His)$_6$.
Figure 19:
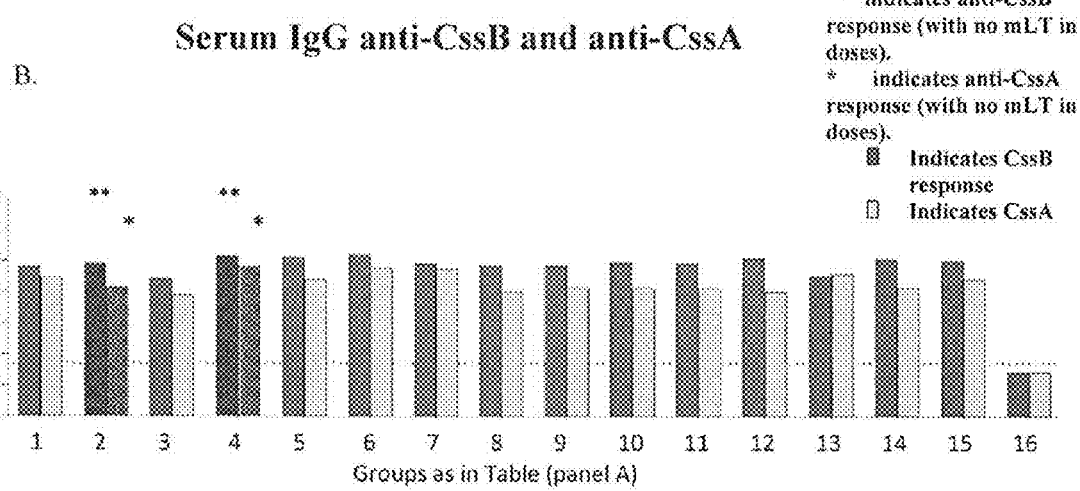
FIG. 19. Anti-CS6 fimbrial subunit IgG immune responses. The x-axis represents the antigens administered as in the table in FIG. 19. The darkly shaded bars represent response to CssB and the lightly shaded bars indicate response to CssA antigen. Therefore, the bars indicate the IgG response to the component CS6 fimbrial subunits CssB or CssA. In the figure, all mice received doses containing 100 ng of mLT, as in FIG. 19, with the exception of some mice receiving a CfaEB-CssBA (or CssAB) constructs, as indicated in the figure.
Figure 20:
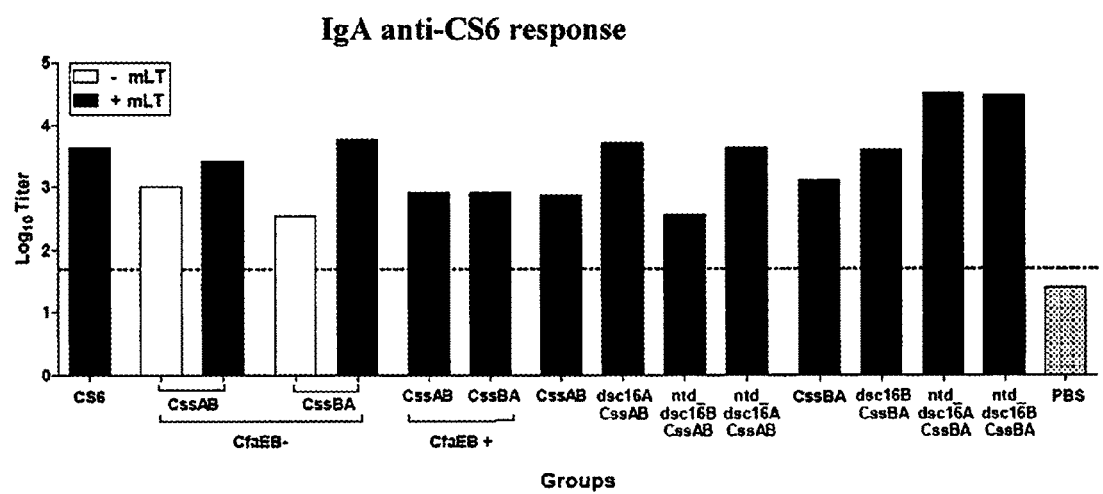
FIG. 20. Anti-CS6 fimbrial subunit IgA immune responses. Each bar represents the pooling of murine serum from mice immunized as in FIG. 19. The mice received doses containing 100 ng of mLT with the exception of the bars, indicated in all white.

In Table 7 and 8 and FIGS. 14 and 15, the examples contain a "G" (i.e., glycine) to provide a "swivel." Also, in some examples, the N-terminal region of N-terminal CS6 subunit is deleted (delineated by "ntd") to avoid undesirable association with other CS6 subunits, as described above. It should be noted that, in addition to the examples illustrated in Table 7 or 8, other combinations of major and minor subunits are contemplated utilizing the construct design illustrated in FIG. 2 and the fimbrial subunits of Table 6. In some sequences listed, a six (6) histidine (i.e., His$_6$) tag is inserted. The constructs can be designed to include the histidine (i.e., His$_6$) tag or designed without this tag region. Additionally, some sequences contain the signal peptide (designated "spd" in Table 2 and 3) region. Constructs can be constructed with or without this region, as well, which may be added to improve manufacturing efficiency of the multipartite fusion construct.

TABLE 7

| Fimbrial type (SEQ ID No. DNA/Protein) | Examples of CS3 containing constructs[1,2,4,5] |
|---|---|
| Class 5a/CS3 (6/7) | $dsc_{14CfaB}$-CfaE-CfaB-($G^3$)-$ntd_{18}dsc_{16CstH}$CstG-CstH |
| Class 5a/CS3 (8/9) | $dsc_{14CsfA}$CfaE-CfaB-CsuA2-CsfA-(G)-$ntd_{18}dsc_{16CstH}$CstG-CstH |
| Class 5b/CS3 (10/11) | $dsc_{14csbA}$CsbD-CsbA-$ntd_{15}dsc_{14CooA}$CooA-(G)-$ntd_{18}dsc_{16CstH}$CstG-CstH |
| Class 5c/CS3 (12/13) | $dsc_{14CotA}$CotD-CotA-(G)-$ntd_{18}dsc_{16CstH}$CstG-CstH |
| CS3/toxin fusion (36/37) | $dsc_{16CstH}$CstG-CstH-sCTA2 |
| LTB multimeric composition (38/39) | $LTB_5$ |
| CS3/CS6 (14/15) | $dsc_{16CstH}$CstG-CstH-(G)-$ntd_{15}dsc_{16CssA}$CssA-CssB |
| CS6/CS3 (34/35) | $ntd_{14}dsc_{16CssB}$CssB-CssA-(G)-$ntd_{18}dsc_{16CstH}$CstG-CstH |

[1]All combinations can include a histidine (i.e., $His_6$) at the C-terminal end.
[2]Subunits can be linked via either DNKQ or tri-glycine linker.
[3](G) refers to glycine residue introduced to provide a "swivel."
[4]"ntd" refers to N-terminal deletion (excised from mature protein) with extent of deletion (i.e., amino acids) indicated.
[5]"dsc" refers to span of N-terminal residues from donor β-strand, its amino acid length and its source.

Example 5

ETEC Fimbrial Subunit—Toxin Chimeric Constructs

In another embodiment, recombinant polypeptide constructs can contain a C-terminal toxin A subunit, such as cholera toxin A2 (CTA) to form a chimeric molecule. In this embodiment, a full-length or truncated CTA2 is connected to CS6 or CS3 multimeric recombinant polypeptide construct, such as a CS6 or CS3 dimer.

Examples of these toxin constructs are illustrated in FIG. 13 and FIG. 14 (and in Table 7 and 8). In these constructs, the LTB gene and the CS3 or CS6—toxin chimera are separately expressed. LTB, once expressed, would self assemble to form a pentameric structure. The ensuing LTB multimeric composition (i.e., $LTB_5$) and CS3 or CS6—toxin chimera then non-covalently associate to form a holotoxin-like heterohexamer.

Although other examples are contemplated, the sequences of examples of illustrative chimeric constructs, containing a C-terminal toxin component, are illustrated in Table 7 (for CS3) and 8 (for CS6).

For CS3-chimeric molecules, one or more CS3 fimbrial subunits are connected, as in FIG. 1, via a polypeptide linker, preferably a tetrapeptide or triglycine. The C-terminal most CS3 fimbrial subunit is then connected to a donor β strand, via a polypeptide linker. The donor strand can be homologous or heterologous to the C-terminal fimbrial subunit. The donor

TABLE 8

| Fimbrial type (SEQ ID No. DNA/Protein) | Examples of CS6 containing constructs |
|---|---|
| CS6/CS3 (34/35) | $ntd_{14}dsc_{16CssB}$CssB-CssA-(G)-$ntd_{18}dsc_{16CstH}$CstG-CstH |
| CS3/CS6 (32/33) | $dsc_{16}$CstG-CstH-(G)-$ntd_{14}dsc_{16CssB}$CssB-CssA |
| Class 5b/CS6 (28/29) | $spd_{19}$ $dsc_{14CotA}$CotD-CotA-(G)-$ntd_{14}dsc_{16CssB}$-CssB-CssA |
| Class 5b/CS6 (30/31) | $dsc_{14CotA}$CotD-CotA-(G)-$ntd_{14}dsc_{16CssB}$-CssB-CssA |
| Class5b/CS6 (24/25) | $spd_{19}dsc_{15CsbA}$CsbD-(GGG)-CsbA-(GGG)-$ntd_{14}dsc_{14cooA}$CooA-(G)-(GGG)-$ntd_{14}dsc_{16CssB}$CssB-CssA |
| Class 5b/CS6 (26/27) | $dsc_{15CsbA}$CsbD-(GGG)-CsbA-(GGG)-$ntd_{14}dsc_{14CooA}$CooA-(G)-(GGG)-$ntd_{14}dsc_{16CssB}$CssB-CssA |
| Class 5a/CS6 (16/17) | $dsc_{14CfaB}$CfaE-CfaB-(G)-$ntd_{16}dsc_{16CssA}$CssB-CssA |
| Class 5a/CS6 (113/114) | $dsc_{14CfaB}$CfaE-CfaB-(G)-$ntd_{16}dsc_{16CssB}$CssB-CssA |
| Class 5a/CS6 (18/19) | $dsc_{14CfaB}$CfaE-CfaB-(G)-$ntd_{16}dsc_{16CssB}$CssA-CssB |
| Class 5a/CS6 (111/112) | $dsc_{14CfaB}$CfaE-CfaB-(G)-$ntd_{16}dsc_{16CssA}$CssA-CssB |
| CS3/CS6 (101/102) | $dsc_{16CssA}$CssA-CssB-(G)-$ntd_{18}dsc_{16CstH}$CstG-CstH |
| Class 5a/CS6 (22/23) | $dsc_{14CsfA}$CfaE-CfaB-CsuA2-CsfA-(G)-$ntd_{14}$dscCssB-CssA |
| Class 5a/CS6 (20/21) | $spd_{22}dsc_{14CsfA}$CfaE-CfaB-CsuA2-CsfA-(G)-$ntd_{14}$dscCssB-CssA |
| CS6-chimera (40/41) | $ntd_{14}dsc16_{CssB}$CssB-CssA-sCTA2 |
| CS6-chimera (42/43) | $ntd_{15}dsc16_{CssA}$CssA-CssB-sCTA2 |

[1]All combinations can include a histidine (i.e., $His_6$) at the C-terminal end.
[2]Subunits can be linked via either DNKQ or tri-glycine (GGG) linker. In preferred embodiments, DNKQ is used, except where indicated with (GGG).
[3](G) refers to glycine residue introduced to provide a swivel.
[4]"spd" refers signal peptide. Number indicates number of amino acids.
[5]"ntd" refers to N-terminal deletion (excised from mature protein) with extent of deletion (i.e., amino acids) indicated.
[6]"dsc" refers to span of N-terminal residues from donor β-strand, its amino acid length and its source.

strand is then connected to a toxin fragment, such as CTA2. The CS3-chimera example shown in Table 7, comprise the polypeptide sequence of SEQ ID No. 37, which is encoded by the DNA sequence of SEQ ID No. 36. In this example, the N-terminal fimbrial subunit is CstG with a pelB leader (22 amino acids) connected at its N-terminal end (see FIG. 13). However, different ordering of CS3 fimbrial subunit units is contemplated. Also, in this example, the CstH is connected, via a polypeptide linker, to a 16 amino acid donor strand derived from the N-terminal 16 amino acids of CstH, which is connected to an A2 toxin fragment (i.e., CTA2). In a preferred embodiment, LTB is also expressed. LTB comprises the amino acid sequence of SEQ ID No. 39 and is encoded by the nucleotide sequence of SEQ ID No. 38. Once expressed, the LTB sequence would self assemble into a pentamer and associate, non-covalently, with the CS3-chimera to form a heterohexameric holotoxin-like structure.

CS6 toxin chimera examples are also illustrated in Table 8 and FIG. 14. For CS6 chimeras, as in CS3, one or more CS6 fimbrial subunits are connected via a polypeptide linker, preferably a tetrapeptide or triglycine. The C-terminal most CS6 fimbrial subunit is then connected to a donor β strand, via a polypeptide linker. The donor strand can be homologous or heterologous to the C-terminal fimbrial subunit. The donor strand is then connected to a toxin component (e.g., CTA2). In a preferred embodiment, like for CS3, the chimera is co-expressed, with LTB, which self assembles into a pentamer to form a non-covalent association with the chimeric adhesion-toxoid fusion molecule.

Although many additional combinations are possible, in the examples shown in Table 8, the constructs are dimers of CS6 subunits, connected via a tetrapeptide linker, with the C-terminal fimbrial subunit connected, via a tetrapeptide linker to a donor β strand. The donor β strand can be homologous or heterologous to the C-terminal most fimbrial subunit. However, in the examples in Table 8 the donor strands are heterologous to the C-terminal fimbrial subunit. The donor strand is then connected to a cholera toxin A2 (CTA2) subunit. The polypeptide sequences of one of the examples is as in SEQ ID No. 43, which is encoded by the nucleotide sequence of SEQ ID Nos. 42. In this example, the N-terminal subunit is CssA, with the N-terminal 15 amino acids of the mature CssA sequence deleted. In this example, a pelB leader sequence (22 amino acids) was also added, which is illustrated in FIG. 14.

Example 6

Anti-CS3 and anti-CS6 Immune Response of Multipartite Recombinant Polypeptide Construct In a preferred embodiment, in order to obtain broad anti-ETEC immunity, recombinant polypeptide constructs comprising fimbrial subunits derived from multiple ETEC fimbrial types were constructed, as described in Example 5. As mentioned above, broad immunogenicity in a single construct is highly advantageous due to ease of manufacture and standardization of administration, compared to compositions comprising multiple individual components.

The multipartite examples listed in Table 7 and 8 maintained immunity to each of its fimbrial components. As an illustrative example, the recombinant, multipartite fusion CsbDA-CooA-CstGH retains immunogenicity against the fimbrial subunits of the multiple fimbrial types, i.e., Class 5b and CS3. FIG. 15 illustrates the immunogenicity of the multiple fimbrial components of the construct CsbDA-CooA-CstGH, comprising fimbrial subunits derived from ETEC Class 5b, and CS3.

In FIG. 15, CsbDA-CooA-CstGH, comprises a tandem fusion (from N- to C-terminus) of CsbD, CsbA (adhesin and pilin subunits of CS17 fimbriae, respectively), CooA (pilin subunit of CS1 fimbriae), CstG and CstH (two major subunits of CS3), wherein each subunit is stabilized by in cis donor strand complementation.

In the study, groups of 5-8 BALB/c mice were vaccinated intradermally with the multipartite fusion or an admixture of CsbDA-CooA and CstGH ('CsbDA-CooA+CstGH'), the individual component proteins at molar equivalent doses (all matched to a 25 μg dose of CsbDA-CooA-CstGH), and co-administered with the adjuvant LTR192G (100 ng). Mice were vaccinated two times at 0 and 21 days. The displayed titers are from serum collected at day 32.

Panel A shows hemagglutination inhibition (HAI) titers against CS3-ETEC (upper), CS17-ETEC (middle), and CS1-ETEC (lower graph). As illustrated in FIG. 15, significant elevation of CS3-ETEC HAI titers were elicited by all preparations, with modestly higher titers observed with CstGH alone. Both the multipartite fusion and admixture preparations elicited similarly elevated HAI titers against CS17-ETEC and CS1-ETEC. Panel B shows serum IgG and IgA titers against CS3 (upper two graphs), and IgG and IgA anti-CsbD titers (lower two graphs). Similarly high serum anti-CS3 titers were elicited by all preparations containing CstGH, including the multipartite fusion. Both the multipartite fusion and admixture preparations elicited high anti-CsbD IgG titers, while only the fusion elicited detectable IgA anti-CsbD titers. Data is displayed as the geometric mean titer plus standard error of the mean. The horizontal dotted line in each graph shows the limit of assay detection.

The immune response of the CS3 component in several examples, described in FIG. 13, is summarized in FIG. 16. The immune induction following the administration of CS3 or CS3 donor strand complementation stabilized constructs was evaluated. In this study, mice were immunized intradermally on day 0 and day 21 and bled on day 28. The IgG and IgA antibody titer induced by a representative number of ETEC constructs, listed in Table 9, was determined by enzyme-linked immunosorbant assay (ELISA). As illustrated in FIG. 16, similar levels of IgG and IgA anti-CS3 immune responses were elicited by each of the multipartite fusion constructs. Also shown in FIG. 16 is the induction of an anti-CS3 response by a dscCsGH-CTA2/LTB adhesion-toxoid chimera (see Example 5).

TABLE 9

| Group # | Family/ Class | Antigen 1* | Antigen 2 | Adj. (100 ng) | Role | Legend |
|---|---|---|---|---|---|---|
| 1 | CS3 | dscCstGH | — | mLT | Pos. control | GH |
| 2 | 5a | dscCfaEB-CsuA2-CsfA-CstGH | — | mLT | Test | Fusion |
| 3 | 5a | dscCfaEB-CsuA2-CsfA | dscCstGH | mLT | Test | Admix |
| 4 | 5b | dscCsbDA-CooA-CstGH | — | mLT | Test | Fusion |

TABLE 9-continued

| Group # | Family/ Class | Antigen 1* | Antigen 2 | Adj. (100 ng) | Role | Legend |
|---|---|---|---|---|---|---|
| 5 | 5b | dscCsbDA-CooA | dscCstGH | mLT | Test | Admix |
| 6 | 5c | CotDA-CstGH | — | mLT | Test | Fusion |
| 7 | 5c | CotDA | dscCstGH | mLT | Test | Admix |
| 8 | CS6 | dscCssAB-CstGH | — | mLT | Test | Fusion |
| 9 | CS6 | dscCssAB | dscCstGH | mLT | Test | Admix |
| 10 | CS3 | dscCstGH-sCTA2/LTB$_5$ | — | — | Test | Chimera |
| 11 | CS3 | dscCstGH-sCTA2/LTB$_5$ | — | mLT | Test | Chimera |
| 12 | CS3 | dscCstGH | LTB | mLT | Test | Admix |
| 13 | — | 20 µL PBS | — | — | Neg. control | PBS |

*molar-matched to 7 µL of dscCstGH

FIG. 17 summarizes the results of studies evaluating the ability of different ETEC multipartite fusion constructs to inhibit mannose resistant hemagglutination in hemagglutination inhibition assays (HAI). The constructs evaluated are listed in Table 9.

In determining HAI, the bacterial strain (CS3$^+$ ETEC strain WS2010A) was used at a concentration corresponding to two times the minimal hemagglutination titer (2×MHT). The MHT was determined at the start of the HAI assay by making serial two-fold dilutions of the bacterial suspension. A total of 25 μL of each dilution was added to equal volumes of 3% erythrocyte suspension and PBS with a 0.5% D-mannose and rocked on ice. The MHT was defined as the reciprocal of the lowest concentration of bacterial showing at least $1^+$ MRHA.

To determine the HAI titer of each antiserum preparation, a two-fold dilution series of antibody was made. A 25 μL volume of each dilution was add to an equal volume of 2×MHT bacterial suspension and pre-incubated at room temperature with rocking for 20 minutes. An equal volume of erythrocyte suspension (3%) was then added to each well and rocked on ice for 20 minutes, after which the MRHA was scored. The HAI titer is expressed as the reciprocal of the highest dilution of antiserum that completely inhibited MRHA.

As illustrated in FIG. 17(A), no inhibition was exhibited by PBS. However, dscCstG-CstH (dscCstGH) and CstGH multipartite fusion constructs exhibited significant HAI. Interestingly, similar HAI was exhibited whether CstGH was a component of a fusion construct or was part of an admixture of the two components. This is graphically illustrated in Panel B in FIG. 17.

The results collectively illustrate that inclusion of fimbrial subunits from different fimbrial types as a multipartite construct generates a strong immune response against the component fimbrial subunits. As mentioned, a single fusion construct comprising multiple dimers from strains affords a broader spectrum of immunity, with greater standardization of administration. Furthermore, manufacture of a single construct is preferred over multiple constructs.

Multipartite constructs of comprising class 5 and CS6 subunits were also prepared and evaluated for reactivity for anti-CS6 immunogenicity. In these studies mice were immunized against different constructs, containing ETEC Class 5, and CS6 subunits, with or without the adjuvant mLT (genetically modified heat-labile enterotoxin).

As an illustrative example, the results of the immune response to components of the multipartite fusion construct CfaEB-CssBA is shown in FIG. 18. In FIG. 18, CfaEB-CssBA, comprises a tandem fusion (from N- to C-terminus) of CfaE, CfaB (minor and major subunits of CFA/I fimbriae, respectively), CssB and CssA (two major subunits of CS6), wherein each subunit is stabilized by in cis donor strand complementation.

In FIG. 18, Groups of eight BALB/c mice were vaccinated intradermally with the multipartite fusion or an admixture of CfaEB and CssBA ('CfaEB+CssBA'), the individual component proteins at molar equivalent doses (all matched to a 25 μg dose of CfaEB-CssBA), and co-administered with the adjuvant LTR192G (100 ng). Mice were vaccinated three times at 0, 14, and 28 days. The displayed titers are from serum collected at day 42.

Panel A displays hemagglutination inhibition (HAI) titers against CFA/1-ETEC (upper), and CS14-ETEC (lower graph). Similarly elevated homologous (CFA/1-ETEC) and within subclass heterologous (CS14-ETEC) HAI titers were observed after vaccination with the multipartite fusion, the admixture, and CfaEB alone (historical control).

Panel B shows serum IgG titers against CS6 (upper), CFA/I fimbriae (middle) and dscCfaE (lower) adhesin. Similarly high serum anti-CS6 titers were elicited by all preparations containing CssBA, including the multipartite fusion. Likewise, all preparations containing CfaEB, including the multipartite fusion, elicited high anti-CFA/I and anti-CfaE (i.e., anti-adhesin) IgG titers, while CssBA predictably did not elicit anti-CfaE IgG titers. Data is displayed as the geometric mean titer+standard error of the mean. The horizontal dotted line in each graph shows the limit of assay detection.

The results summarized in FIG. 18 illustrate that the construct (i.e., multipartite fusion) retains the ability to elicit an immune response to its multiple fimbrial components, specifically fimbrial subunits derived from ETEC Class 5a, and CS6.

Collectively, the results with CS6 multipartite constructs shows that no interference from the multiple construct components (i.e., each derived from different fimbrial types) resulted in interference.

As shown in FIG. 19, the CS6 subunits CssA and CssB, as heterodimers, elicit a potent IgG response against the individual CS6 subunits. In FIG. 19, Panel A illustrates the antigens administered. Panel B shows the anti-CS6 IgG response, for either CssA or CssB, elicited against the administered antigenic construct shown along the x-axis.

As illustrated in FIG. 19, the CS6 subunits fused to Class 5 subunits (i.e., groups 2-5) elicit a similar or even higher antibody response to the CS6 subunits in comparision to admixture of CfaEB and CssAB or CssBA (i.e., groups 6 and 7). The IgA response is shown in FIG. 20, for the same panel of antigens as in FIG. 19.

The above results illustrate that no interference from the non-CS6 subunit components occurs as a result of the fusion constructs, with modestly higher anti-CS6 responses observed for CssBA, compared with CssAB, especially for IgA. As such, the results, as well as those summarized in FIG. 15-18, indicate the operability of the constructs to elicit a strong immune response against the constitutent components of the multipartite fusion constructs.

Example 7

Method for the Induction of Immunity to ETEC Recombinant Polypeptide Construct

The adhesins are an important component for the induction of diarrheagenic *E. coli* bacterial immunity. An aspect of this invention is the construction of stable polypeptide constructs for use as immunogens against enterotoxigenic *Escherichia coli* mediated diarrhea.

Protection against pathology caused by ETEC can be mediated by inhibition of colonization of bacteria by blocking fimbriae-mediated adhesion, and therefore bacterial colonization by induction of a specific B-cell response to adhesin polypeptide regions. Another aspect of this invention, therefore, is the induction of immunity by administration of a conformationally-stable polypeptide construct. An additional aspect is the ability to induce immunity in mammals, such as in humans, against as many ETEC types as possible. For ease of administering of immunogens and production, it is highly advantageous to construct containing as many immunogens against as many ETEC types as possible.

Recombinant polypeptide constructs produced using the design of FIG. 1 and FIG. 2, as well as the examples listed in FIGS. 13 and 14, can be used in formulations for the induction of immunity to multiple ETEC types.

In one embodiment, constructs as immunogen, constructed based on FIG. 1 and/or FIG. 2 or the examples given in FIGS. 13 and 14, comprise the following steps:
  a. priming by administration of an immunogenic composition containing the polypeptide construct described in Examples 1 through 6, above. The immunogenic composition can be administered orally, nasally, subcutaneously, intradermally, transdermally, sublingually, transcutaneously intramuscularly, or rectally. The range of a unit dose of immunogen is 1 µg to 1 mg of the polypeptide construct. The immunogenic composition can be administered in any number of solutions with or without carrier protein or adjuvant or adsorbed onto particles such as microspheres;
  b. Subsequent to a priming dose, 2 to 4 boosting doses are also administered with unit dose range of 1 µg to 1 mg of polypeptide construct in a buffered aqueous solution or other suitable solution.

An alternative vaccine approach is the administration of a recombinant DNA construct capable of expressing the recombinant polypeptide. In this example, the recombinant DNA encoding the immunogen is inserted into a suitable expression system and expressed in host bacterial cells. The recombinant host cells can then be administered as a whole cell vaccine in order to confer immunity not only to the host cell but against the expressed ETEC recombinant adhesin polypeptides. Representative host cells include, but are not limited to *Escherichia coli*, members of the genus *Shigella*, members of the genus *Campylobacter*, members of the genus *Salmonella*, and members of the genus *Vibrio* including *Vibrio cholerae*.

A method for the induction of whole cell immunity contains the following steps:
  a. administration of a priming dose of comprising an adequate number of whole cell bacteria, containing DNA encoding and capable of expressing the polypeptide construct described in Examples 1 through 6, above, whereby the bacteria are selected from the group consisting of *Escherchia coli, Shigella* spp, *Salmonella* spp, *Camplylobacter* spp, *Vibrio* spp and *Vibrio cholera*.
  b. Subsequent to priming dose, administration of 1 to 4 boosting doses of whole cell bacteria, selected from the group consisting of *Escherchia coli, Shigella* spp, *Camplylobacter* spp, *Vibrio* spp and *Vibrio cholerae*, containing and capable of expressing DNA encoding the recombinant polypeptide described in Examples 1 through 6, above. Alternatively, the boosting doses can be protein comprising the recombinant polypeptide described in Examples 1 through 6, above, at unit dose range of 1 µg to 1 mg of immunogen in a buffered aqueous solution.

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. A recombinant polypeptide construct comprising a whole or immunogenic fragment of an *Escherichia coli* fimbrial minor or major subunit connected to one or more major fimbrial subunits or immunogenic fragments, thereof, of the same fimbrial type, via a polypeptide linker, and wherein each of the one or more major fimbrial subunits contain a donor β strand and are also connected to each other via a polypeptide linker, wherein the C-terminal *Escherichia coli* fimbrial major subunit is connected, via a linker, to a C-terminal donor β strand derived from a major *Escherichia coil* fimbrial subunit that is homologous or heterologous to the immediately N-terminal major subunit and wherein said composition can comprise a histidine tag at the C-terminus.

2. The recombinant polypeptide construct of claim 1, wherein fimbrial types are selected from fimbriae derived from *Escherichia coli* selected from the group consisting of class 5a, class 5b, class 5c, CS3 and CS6.

3. The recombinant polypeptide construct of claim 1, wherein donor β strand contains 12 to 16 amino acids.

4. The recombinant polypeptide construct of claim 1, wherein said N-terminus of said minor or major subunit contains an 18-22 amino acid signal peptide.

5. The recombinant polypeptide construct of claim 1, wherein the amino acid sequence of said polypeptide linker is SEQ ID No. 5 or a tri-glycine.

6. The recombinant polypeptide construct of claim 1, wherein one or more major subunits contain a deletion of the 14 to 18 N-terminal amino acids.

7. The recombinant polypeptide construct of claim 1, wherein said construct is connected to one or more constructs, according to claim 1, wherein each of the constructs contain fimbrial subunits derived from a different fimbrial type than any of the other constructs and wherein the recombinant polypeptide construct can contain a C-terminal histidine tag.

8. The recombinant polypeptide construct of claim 1, wherein the C-terminal homologous or heterologous donor β strand is connected, via a polypeptide linker, to a bacterial toxin to form a chimeric molecule and wherein said bacterial toxin is noncovalently connected to a bacterial toxin multimeric composition.

9. The recombinant polypeptide construct of claim 1, wherein said *Escherichia coli* fimbrial minor subunit is selected from the group consisting of CfaE, CsfD, CsuD, CooD, CsbD, CosD, CsdD, CotD and wherein said major subunit is selected from the group consisting of CfaB, CsfA, CsuA2, CooA, CsdA, CosA, CsbA, CotA, CstG, CstH, CssA, and CssB, or immunogenic fragments or derivatives, thereof.

10. The recombinant polypeptide construct of claim 7, wherein said constructs are connected via one or more glycine residues.

11. The recombinant polypeptide construct of claim 7, wherein said donor β strand contains 12 to 16 amino acids.

12. The recombinant polypeptide construct of claim 7, wherein said N-terminus of said minor or major subunit contains an 18-22 amino acid signal peptide.

13. The recombinant polypeptide construct of claim 7, wherein one or more major subunits contain a deletion of the N-terminal 14 to 18 amino acids.

14. The recombinant polypeptide construct of claim 7, wherein said minor or major *Escherichia coli* fimbrial subunits are derived from ETEC strains selected from the group consisting of Class 5, CS3 and CS6.

15. The recombinant polypeptide construct of claim 7, wherein said *Escherichia coli* fimbrial minor subunit is selected from the group consisting of CfaE, CsfD, CsuD, CooD, CsbD, CosD, CsdD, CotD and wherein said major subunit is selected from the group consisting of CfaB, CsfA, CsuA1, CsuA2, CooA, CsdA, CosA, CsbA, CotA, CstG, CstH, CssA, and CssB, or immunogenic fragments, or derivatives thereof.

16. The recombinant polypeptide construct of claim 7, wherein the amino acid sequence of said linker is SEQ ID No. 5 or a triglyicine.

17. The recombinant polypeptide construct of claim 8, wherein said bacterial toxin is cholera toxin and wherein said multimeric bacterial composition is LTB$_5$, wherein said construct has the amino acid sequence selected from the group consisting of SEQ ID No. 37, 41, and 43 and wherein said bacterial toxin multimeric composition has the amino acid sequence of SEQ ID No. 39.

18. The recombinant polypeptide of claim 9, wherein said amino acid sequence of said *Escherichia coli* fimbrial minor subunit is selected from the group consisting of SEQ ID Nos. 45, 46, 51, 52, 57, 58, 65, 71, 75, 79, 83, 88, 90, 93, 95, and 97, or derivatives thereof, and wherein said amino acid sequence of said *Escherichia coli* fimbrial major subunit is selected from the group consisting of SEQ ID Nos. 2, 4, 48, 49, 54, 55, 60, 61, 63, 67, 69, 73, 77, 81, 85, 87, 89, 91, 92, 94, 96, 98, 99, 101, 135, and 137, or derivatives thereof.

19. The recombinant polypeptide of claim 9, wherein said minor subunit is encoded by the nucleotide sequence selected from the group consisting of SEQ ID No. 44, 50, 56, 64, 70, 74, 78, 82, 115, 117, 119, 122, 124, 127, 129, and 133, or derivatives, thereof, and wherein said major subunit is encoded by the nucleotide sequence selected from the group consisting of SEQ ID No. 1, 3, 47, 53, 59, 62, 66, 68, 72, 76, 80, 84, 86, 116, 118, 120, 121, 123, 125, 126, 128, 130, 131, 132, 134, and 136, or derivatives thereof.

20. The recombinant polypeptide construct of claim 10, wherein said construct is encoded by the nucleotide sequence selected from the group consisting of SEQ ID No. 36, 40 and 42 and wherein said bacterial toxin multimeric composition has the amino acid sequence of SEQ ID No. 38.

21. The recombinant polypeptide of claim 15, wherein said amino acid sequence of said *Escherichia coli* fimbrial minor subunit is selected from the group consisting of SEQ ID Nos. 45, 46, 51, 52, 57, 58, 65, 71, 75, 79, 83, 88, 90, 93, 95, and 97, or derivatives thereof, and wherein said amino acid sequence of said *Escherichia coli* fimbrial major subunit is selected from the group consisting of SEQ ID Nos. 2, 4, 48, 49, 54, 55, 60, 61, 63, 67, 69, 73, 77, 81, 85, 87, 89, 91, 92, 94, 96, 98, 99, 101, 135, and 137, or derivatives thereof.

22. The recombinant polypeptide of claim 15, wherein said minor subunit is encoded by the nucleic acid sequence selected from the group consisting of SEQ ID No. 44, 50, 56, 64, 70, 74, 78, 82, 115, 117, 119, 122, 124, 127, 129, and 133, or derivatives thereof, and wherein said major subunit is encoded by the nucleic acid sequence selected from the group consisting of SEQ ID No. 1, 3, 47, 53, 59, 62, 66, 68, 72, 76, 80, 84, 86, 116, 118, 120, 121, 123, 125, 126, 128, 130, 131, 132, 134, and 136, or derivatives thereof.

* * * * *

SEQUENCE LISTING

```
<160> NUMBER OF SEQ ID NOS: 137

<210> SEQ ID NO 1
<211> LENGTH: 414
<212> TYPE: DNA
<213> ORGANISM: Escherichia coli

<400> SEQUENCE: 1
atgagaacag aaatagcgac taaaaacttc ccagtatcaa cgactatttc aaaaagtttt      60
tttgcgcctg aaccacaaat ccagccttct tttggtaaaa atgttggaaa ggaaggagat     120
ttattattta gtgtgagctt aattgttcct gaaaatgtat cccaggtaac ggtctaccct     180
gtttatgatg aagattatgg attaggacga ctcgtaaata ccgctgatga ttcccaatca     240
ataatctacc agattgttga tgataaaggg aaaaaaatgt taaagatca tggtacagag      300 gttacgccta atcaacaaat aacttttaaa gcgctgaatt atactagcgg agataaagaa     360
```

```
atacctcctg ggatatataa cgatcaggtt atggttggtt actatgtaaa ctaa          414
```

<210> SEQ ID NO 2
<211> LENGTH: 137
<212> TYPE: PRT
<213> ORGANISM: Escherichia coli

<400> SEQUENCE: 2

```
Met Arg Thr Glu Ile Ala Thr Lys Asn Phe Pro Val Ser Thr Thr Ile
1               5                   10                  15

Ser Lys Ser Phe Phe Ala Pro Glu Pro Gln Ile Gln Pro Ser Phe Gly
            20                  25                  30

Lys Asn Val Gly Lys Glu Gly Asp Leu Leu Phe Ser Val Ser Leu Ile
        35                  40                  45

Val Pro Glu Asn Val Ser Gln Val Thr Val Tyr Pro Val Tyr Asp Glu
    50                  55                  60

Asp Tyr Gly Leu Gly Arg Leu Val Asn Thr Ala Asp Asp Ser Gln Ser
65                  70                  75                  80

Ile Ile Tyr Gln Ile Val Asp Asp Lys Gly Lys Lys Met Leu Lys Asp
                85                  90                  95

His Gly Thr Glu Val Thr Pro Asn Gln Gln Ile Thr Phe Lys Ala Leu
            100                 105                 110

Asn Tyr Thr Ser Gly Asp Lys Glu Ile Pro Pro Gly Ile Tyr Asn Asp
        115                 120                 125

Gln Val Met Val Gly Tyr Tyr Val Asn
    130                 135
```

<210> SEQ ID NO 3
<211> LENGTH: 444
<212> TYPE: DNA
<213> ORGANISM: Escherichia coli

<400> SEQUENCE: 3

```
atgggaaact ggcaatataa atctctggat gtaaatgtaa atattgagca aaattttatt    60
ccagatattg attccgctgt tcgtataata cctgttaatt acgattcgga tccgaaactg   120
aattcacagt tatatacggt tgagatgacg atccctgcag gtgtaagcgc agttaaaatc   180
gtaccaacag atagtctgac atcttctgga cagcagatcg aaagctggt taatgtaaac    240
aatccagatc aaaatatgaa ttattatatc agaaaggatt ctggcgctgg taagtttatg   300
gcagggcaaa aaggatcctt ttctgtcaaa gagaatacgt catacacatt ctcagcaatt   360
tatactggtg gcgaataccc taatagcgga tattcgtctg gtacttatgc aggacatttg   420
actgtatcat tttacagcaa ttaa                                          444
```

<210> SEQ ID NO 4
<211> LENGTH: 147
<212> TYPE: PRT
<213> ORGANISM: Escherichia coli

<400> SEQUENCE: 4

```
Met Gly Asn Trp Gln Tyr Lys Ser Leu Asp Val Asn Val Asn Ile Glu
1               5                   10                  15

Gln Asn Phe Ile Pro Asp Ile Asp Ser Ala Val Arg Ile Ile Pro Val
            20                  25                  30

Asn Tyr Asp Ser Asp Pro Lys Leu Asn Ser Gln Leu Tyr Thr Val Glu
        35                  40                  45
```

```
Met Thr Ile Pro Ala Gly Val Ser Ala Val Lys Ile Val Pro Thr Asp
    50                  55                  60
Ser Leu Thr Ser Ser Gly Gln Gln Ile Gly Lys Leu Val Asn Val Asn
65                  70                  75                  80
Asn Pro Asp Gln Asn Met Asn Tyr Tyr Ile Arg Lys Asp Ser Gly Ala
                85                  90                  95
Gly Lys Phe Met Ala Gly Gln Lys Gly Ser Phe Ser Val Lys Glu Asn
            100                 105                 110
Thr Ser Tyr Thr Phe Ser Ala Ile Tyr Thr Gly Gly Glu Tyr Pro Asn
        115                 120                 125
Ser Gly Tyr Ser Ser Gly Thr Tyr Ala Gly His Leu Thr Val Ser Phe
    130                 135                 140
Tyr Ser Asn
145

<210> SEQ ID NO 5
<211> LENGTH: 4
<212> TYPE: PRT
<213> ORGANISM: Escherichia coli

<400> SEQUENCE: 5

Asp Asn Lys Gln
1

<210> SEQ ID NO 6
<211> LENGTH: 2502
<212> TYPE: DNA
<213> ORGANISM: Escherichia coli

<400> SEQUENCE: 6
atgaataaaa ttttatttat ttttacattg ttttttttctt cagggttttt tacatttgcc      60
gtatcggcag ataaaaatcc cggaagtgaa acatgactaa tactattgg tccccatgac      120
agggggggat cttcccccat atataatatc ttaaattcct atcttacagc atacaatgga     180
agccatcatc tgtatgatag gatgagtttt ttatgtttgt cttctcaaaa tacactgaat     240
ggagcatgcc caagcagtga tgcccctggc actgctacaa ttgatggcga acaaatata      300
acattacaat ttacggaaaa agaagtcta attaaagag aactgcaaat taaaggctat      360
aaacaatttt tgttcaaaaa tgctaattgc ccatctaaac tagcacttaa ctcatctcat     420
tttcaatgta atagagaaca agcttcaggt gctactttat cgttatacat accagctggt     480
gaattaaata aattaccttt tgggggggtc tggaatgccg ttctgaagct aaatgtaaaa     540
agacgatatg atacaaccta tgggacttac actataaaca tcacagttaa tttaactgat     600
aagggaaata ttcagatatg gttaccacag ttcaaaagta acgctcgtgt cgatcttaac     660
ttgcgtccaa ctggtggtgg tacatatatc ggaagaaatt ctgttgatat gtgctttat     720
gatggatata gtactaacag cagctcttta gagataagt ttcaggatga taattctaaa      780
tctgatggaa aattttatct aaagaaaata aatgatgact ccaaagaact tgtatacact     840
ttgtcacttc tcctggcagg taaaaattta acaccaacaa atggacaggc attaaatatt     900
aacactgctt ctctggaaac aaactggaat agaattacag ctgtcaccat gccagaaatc     960
agtgttccgg tgttgtgttg gcctggacgt ttgcaattgg atgcaaaagt gaaaaatccc    1020
gaggctggac aatatatggg gaatattaaa attactttca caccaagtag tcaaacactc    1080
gacaataaac aagtagagaa aaatattact gtaacagcta gtgttgatcc tgcaattgat    1140
cttttgcaag ctgatggcaa tgctctgcca tcagctgtaa agttagctta ttctcccgca    1200
```

-continued

```
tcaaaaactt tgaaagtta cagagtaatg actcaagttc atacaaacga tgcaactaaa     1260
aaagtaattg ttaaacttgc tgatacacca cagcttacag atgttctgaa ttcaactgtt     1320
caaatgccta tcagtgtgtc atggggagga caagtattat ctacaacagc caagaattt      1380 gaagctgctg ctttgggata ttctgcatcc ggtgtaaatg gcgtatcatc ttctcaagag     1440
ttagtaatta gcgctgcacc taaaactgcc ggtaccgccc caactgcagg aaactattca     1500
ggagtagtat ctcttgtaat gactttggga tccgacaata aacaagtaga gaaaatatt     1560 actgtaacag ctagtgtcga ccctgcaggg acattagcta ttgattttac gcctattgaa     1620
aatatttatg taggtgccaa ttatggtaaa gatattggaa cccttgtttt cacaacaaat     1680
gatttaacag atattacatt gatgtcatct cgcagcgttg ttgatggtcg ccagactggt     1740
ttttttacct tcatggactc atcagccact tacaaaatta gtacaaaact gggatcatcg     1800
aatgatgtaa acattcaaga aattactcaa ggagctaaaa ttactcctgt tagtggagag     1860
aaaactttgc ctaaaaaatt cactcttaag ctacatgcac acaggagtag cagtacagtt     1920
ccaggtacgt atactgttgg tcttaacgta accagtaacg ttattgataa caagcaggca     1980
gcggggccca ctctaaccaa agaactggca ttaaatgtgc tttctcctgc agctctggat     2040
gcaacttggg ctcctcagga taatttaaca ttatccaata ctggcgtttc taatactttg     2100
gtgggtgttt tgactctttc aaataccagt attgatacag ttagcattgc gagtacaaat     2160
gtttctgata catctaagaa tggtacagta acttttgcac atgagacaaa taactctgct     2220
agctttgcca ccaccatttc aacagataat gccaacatta cgttggataa aaatgctgga     2280
aatacgattg ttaaaactac aaatgggagt cagttgccaa ctaatttacc acttaagttt     2340
attaccactg aaggtaacga acatttagtt tcaggtaatt accgtgcaaa tataacaatt     2400
acttcgacaa ttaaagataa caagcaggcg gcaggtccaa ccctgactaa ggagttagcg     2460
ctgaacgttc tgagcctcga gcaccaccac caccaccact ga                        2502
```

<210> SEQ ID NO 7
<211> LENGTH: 833
<212> TYPE: PRT
<213> ORGANISM: Escherichia coli

<400> SEQUENCE: 7

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140
```

```
Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
            165                 170                 175

Leu Asn Val Lys Arg Arg Tyr Asp Thr Thr Tyr Gly Thr Tyr Thr Ile
        180                 185                 190

Asn Ile Thr Val Asn Leu Thr Asp Lys Gly Asn Ile Gln Ile Trp Leu
    195                 200                 205

Pro Gln Phe Lys Ser Asn Ala Arg Val Asp Leu Asn Leu Arg Pro Thr
210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Ile Arg Phe Gln Asp
            245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Ala Gly Thr Leu Ala Ile Asp Phe Thr Pro Ile Glu Asn Ile Tyr Val
    530                 535                 540

Gly Ala Asn Tyr Gly Lys Asp Ile Gly Thr Leu Val Phe Thr Thr Asn
545                 550                 555                 560
```

```
Asp Leu Thr Asp Ile Thr Leu Met Ser Ser Arg Ser Val Val Asp Gly
                565                 570                 575
Arg Gln Thr Gly Phe Phe Thr Phe Met Asp Ser Ser Ala Thr Tyr Lys
            580                 585                 590
Ile Ser Thr Lys Leu Gly Ser Ser Asn Asp Val Asn Ile Gln Glu Ile
        595                 600                 605
Thr Gln Gly Ala Lys Ile Thr Pro Val Ser Gly Glu Lys Thr Leu Pro
    610                 615                 620
Lys Lys Phe Thr Leu Lys Leu His Ala His Arg Ser Ser Ser Thr Val
625                 630                 635                 640
Pro Gly Thr Tyr Thr Val Gly Leu Asn Val Thr Ser Asn Val Ile Asp
                645                 650                 655
Asn Lys Gln Ala Ala Gly Pro Thr Leu Thr Lys Glu Leu Ala Leu Asn
            660                 665                 670
Val Leu Ser Pro Ala Ala Leu Asp Ala Thr Trp Ala Pro Gln Asp Asn
        675                 680                 685
Leu Thr Leu Ser Asn Thr Gly Val Ser Asn Thr Leu Val Gly Val Leu
    690                 695                 700
Thr Leu Ser Asn Thr Ser Ile Asp Thr Val Ser Ile Ala Ser Thr Asn
705                 710                 715                 720
Val Ser Asp Thr Ser Lys Asn Gly Thr Val Thr Phe Ala His Glu Thr
                725                 730                 735
Asn Asn Ser Ala Ser Phe Ala Thr Thr Ile Ser Thr Asp Asn Ala Asn
            740                 745                 750
Ile Thr Leu Asp Lys Asn Ala Gly Asn Thr Ile Val Lys Thr Thr Asn
        755                 760                 765
Gly Ser Gln Leu Pro Thr Asn Leu Pro Leu Lys Phe Ile Thr Thr Glu
    770                 775                 780
Gly Asn Glu His Leu Val Ser Gly Asn Tyr Arg Ala Asn Ile Thr Ile
785                 790                 795                 800
Thr Ser Thr Ile Lys Asp Asn Lys Gln Ala Ala Gly Pro Thr Leu Thr
                805                 810                 815
Lys Glu Leu Ala Leu Asn Val Leu Ser Leu Glu His His His His
            820                 825                 830
His

<210> SEQ ID NO 8
<211> LENGTH: 3414
<212> TYPE: DNA
<213> ORGANISM: Escherichia coli

<400> SEQUENCE: 8
atgaataaaa tttttatttat ttttacattg tttttttctt cagggttttt tacatttgcc      60
gtatcggcag ataaaaatcc cggaagtgaa acatgactaa atactattgg tccccatgac     120
agggggggat cttccccccat atataatatc ttaaattcct atcttacagc atacaatgga     180
agccatcatc tgtatgatag gatgagtttt ttatgtttgt cttctcaaaa tacactgaat     240
ggagcatgcc caagcagtga tgcccctggc actgctacaa ttgatggcga aacaaatata     300
acattacaat ttacggaaaa aagaagtcta attaaaagag aactgcaaat taaaggctat     360
aaacaatttt tgttcaaaaa tgctaattgc ccatctaaac tagcacttaa ctcatctcat     420
tttcaatgta atagagaaca agcttcaggt gctactttat cgttatacat accagctggt     480
gaattaaata aattaccttt tgggggggtc tggaatgccg ttctgaagct aaatgtaaaa     540
```

-continued

```
agacgatatg atacaaccta tgggacttac actataaaca tcacagttaa tttaactgat    600
aagggaaata ttcagatatg gttaccacag ttcaaaagta acgctcgtgt cgatcttaac    660
ttgcgtccaa ctggtggtgg tacatatatc ggaagaaatt ctgttgatat gtgcttttat    720
gatggatata gtactaacag cagctcttta gagataagat ttcaggatga taattctaaa    780
tctgatggaa aattttatct aaagaaaata aatgatgact ccaaagaact tgtatacact    840
ttgtcacttc tcctggcagg taaaaattta acaccaacaa atggacaggc attaaatatt    900
aacactgctt ctctggaaac aaactggaat agaattacag ctgtcaccat gccagaaatc    960
agtgttccgg tgttgtgttg gcctggacgt ttgcaattgg atgcaaaagt gaaaaatccc   1020
gaggctggac aatatatggg gaatattaaa attactttca caccaagtag tcaaacactc   1080
gacaataaac aagtagagaa aaatattact gtaacagcta gtgttgatcc tgcaattgat   1140
cttttgcaag ctgatggcaa tgctctgcca tcagctgtaa agttagctta ttctcccgca   1200
tcaaaaactt ttgaaagtta cagagtaatg actcaagttc atacaaacga tgcaactaaa   1260
aaagtaattg ttaaacttgc tgatacacca cagcttacag atgttctgaa ttcaactgtt   1320
caaatgccta tcagtgtgtc atggggagga caagtattat ctacaacagc caaagaattt   1380
gaagctgctg ctttgggata ttctgcatcc ggtgtaaatg gcgtatcatc ttctcaagag   1440
ttagtaatta gcgctgcacc taaaactgcc ggtaccgccc caactgcagg aaactattca   1500
ggagtagtat ctcttgtaat gactttggga tccgacaata aacaagtaga gaaaatatt    1560 actgtaacag ctagtgtcga ccctactatt gatattcttc aagcaaatgg ttctgcgcta   1620
ccgacagctg tagatttaac ttatctacct ggtgcaaaaa cttttgaaaa ttacagtgtt   1680
ctaacccaga tttacacaaa tgacccttca aaaggtttag atgttcgact ggttgataca   1740
ccgaaactta caaatatttt gcaaccgaca tctaccattc ctcttactgt ctcatgggca   1800
gggaagacat taagtacaag tgctcagaag attgcagttg gcgatctggg ttttggttcc   1860
accgaacggg caggtgtttc gaatagtaaa gaattagtaa ttggagcaac tacatccgga   1920
actgcaccaa gtgcaggtaa gtatcaaggc gtcgtttcca ttgtaatgac tcaatcgacc   1980
gacacagccg cgcctgttcc tgacaataaa caagtagaga aaatattac tgtgacagcc    2040 agtgttgatc ctactattga cattttgcaa gctgatggta gtagtttacc tactgctgta   2100
gaattaacct attcacctgc ggcaagtcgt tttgaaaatt ataaaatcgc aactaaagtt   2160
catacaaatg ttataaataa aaatgtacta gttaagcttg taaatgatcc aaaacttaca   2220
aatgttttgg attctacaaa acaactcccc attactgtat catatggagg aaagactcta   2280
tcaaccgcag atgtgacttt tgaacctgca gaattaaatt ttggaacgtc aggtgtaact   2340
ggtgtatctt cttcccaaga tttagtgatt ggtgcgacta cagcacaagc accaacggcg   2400
ggaaattata gtggggtcgt ttctatctta atgaccttag catcagacaa taaacaagtg   2460
gaaaaaaata tcactgtaac agctagtgtt gatcctacgg gcacattagc tattgatttt   2520
acgcctattg aaaatattta tgtaggtgcc aattatggta aagatattgg aacccttgtt   2580
ttcacaacaa atgatttaac agatattaca ttgatgtcat ctcgcagcgt tgttgatggt   2640
cgccagactg gttttttttac cttcatggac tcatcagcca cttacaaaat tagtacaaaa   2700
ctgggatcat cgaatgatgt aaacattcaa gaaattactc aaggagctaa aattactcct   2760
gttagtggag agaaaacttt gcctaaaaaa ttcactctta agctacatgc acacaggagt   2820
agcagtacag ttccaggtac gtatactgtt ggtcttaacg taaccagtaa cgttattgat   2880
aacaagcagg cagcggggcc cactctaacc aaagaactgg cattaaatgt gctttctcct   2940
```

```
gcagctctgg atgcaacttg ggctcctcag gataatttaa cattatccaa tactggcgtt   3000
tctaatactt tggtgggtgt tttgactctt tcaaatacca gtattgatac agttagcatt   3060
gcgagtacaa atgtttctga tacatctaag aatggtacag taacttttgc acatgagaca   3120
aataactctg ctagctttgc caccaccatt tcaacagata atgccaacat tacgttggat   3180
aaaaatgctg gaaatacgat tgttaaaact acaaatggga gtcagttgcc aactaattta   3240
ccacttaagt ttattaccac tgaaggtaac gaacatttag tttcaggtaa ttaccgtgca   3300
aatataacaa ttacttcgac aattaaagat aacaagcagg cggcaggtcc aaccctgact   3360
aaggagttag cgctgaacgt tctgagcctc gagcaccacc accaccacca ctga          3414
```

<210> SEQ ID NO 9
<211> LENGTH: 1137
<212> TYPE: PRT
<213> ORGANISM: Escherichia coli

<400> SEQUENCE: 9

```
Met Asn Lys Ile Leu Phe Ile Phe Thr Leu Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285
```

```
Asn Leu Thr Pro Thr Asn Gly Gln Ala Leu Asn Ile Asn Thr Ala Ser
    290             295                 300

Leu Glu Thr Asn Trp Asn Arg Ile Thr Ala Val Thr Met Pro Glu Ile
305             310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
            355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385             390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
            435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465             470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
            515                 520                 525

Thr Ile Asp Ile Leu Gln Ala Asn Gly Ser Ala Leu Pro Thr Ala Val
    530                 535                 540

Asp Leu Thr Tyr Leu Pro Gly Ala Lys Thr Phe Glu Asn Tyr Ser Val
545             550                 555                 560

Leu Thr Gln Ile Tyr Thr Asn Asp Pro Ser Lys Gly Leu Asp Val Arg
                565                 570                 575

Leu Val Asp Thr Pro Lys Leu Thr Asn Ile Leu Gln Pro Thr Ser Thr
            580                 585                 590

Ile Pro Leu Thr Val Ser Trp Ala Gly Lys Thr Leu Ser Thr Ser Ala
    595                 600                 605

Gln Lys Ile Ala Val Gly Asp Leu Gly Phe Gly Ser Thr Gly Thr Ala
    610                 615                 620

Gly Val Ser Asn Ser Lys Glu Leu Val Ile Gly Ala Thr Thr Ser Gly
625             630                 635                 640

Thr Ala Pro Ser Ala Gly Lys Tyr Gln Gly Val Val Ser Ile Val Met
                645                 650                 655

Thr Gln Ser Thr Asp Thr Ala Ala Pro Val Pro Asp Asn Lys Gln Val
            660                 665                 670

Glu Lys Asn Ile Thr Val Thr Ala Ser Val Asp Pro Thr Ile Asp Ile
            675                 680                 685

Leu Gln Ala Asp Gly Ser Ser Leu Pro Thr Ala Val Glu Leu Thr Tyr
    690                 695                 700

Ser Pro Ala Ala Ser Arg Phe Glu Asn Tyr Lys Ile Ala Thr Lys Val
```

-continued

```
            705                 710                 715                 720
        His Thr Asn Val Ile Asn Lys Asn Val Leu Val Lys Leu Val Asn Asp
                        725                 730                 735
        Pro Lys Leu Thr Asn Val Leu Asp Ser Thr Lys Gln Leu Pro Ile Thr
                        740                 745                 750
        Val Ser Tyr Gly Gly Lys Thr Leu Ser Thr Ala Asp Val Thr Phe Glu
                        755                 760                 765
        Pro Ala Glu Leu Asn Phe Gly Thr Ser Gly Val Thr Gly Val Ser Ser
                        770                 775                 780
        Ser Gln Asp Leu Val Ile Gly Ala Thr Thr Ala Gln Ala Pro Thr Ala
        785                 790                 795                 800
        Gly Asn Tyr Ser Gly Val Val Ser Ile Leu Met Thr Leu Ala Ser Asp
                        805                 810                 815
        Asn Lys Gln Val Glu Lys Asn Ile Thr Val Thr Ala Ser Val Asp Pro
                        820                 825                 830
        Thr Gly Thr Leu Ala Ile Asp Phe Thr Pro Ile Glu Asn Ile Tyr Val
                        835                 840                 845
        Gly Ala Asn Tyr Gly Lys Asp Ile Gly Thr Leu Val Phe Thr Thr Asn
                        850                 855                 860
        Asp Leu Thr Asp Ile Thr Leu Met Ser Ser Arg Ser Val Val Asp Gly
        865                 870                 875                 880
        Arg Gln Thr Gly Phe Phe Thr Phe Met Asp Ser Ser Ala Thr Tyr Lys
                        885                 890                 895
        Ile Ser Thr Lys Leu Gly Ser Ser Asn Asp Val Asn Ile Gln Glu Ile
                        900                 905                 910
        Thr Gln Gly Ala Lys Ile Thr Pro Val Ser Gly Glu Lys Thr Leu Pro
                        915                 920                 925
        Lys Lys Phe Thr Leu Lys Leu His Ala His Arg Ser Ser Ser Thr Val
                        930                 935                 940
        Pro Gly Thr Tyr Thr Val Gly Leu Asn Val Thr Ser Asn Val Ile Asp
        945                 950                 955                 960
        Asn Lys Gln Ala Ala Gly Pro Thr Leu Thr Lys Glu Leu Ala Leu Asn
                        965                 970                 975
        Val Leu Ser Pro Ala Ala Leu Asp Ala Thr Trp Ala Pro Gln Asp Asn
                        980                 985                 990
        Leu Thr Leu Ser Asn Thr Gly Val  Ser Asn Thr Leu  Gly Val Leu
                        995                 1000                1005
        Thr Leu  Ser Asn Thr Ser Ile  Asp Thr Val Ser Ile  Ala Ser Thr
                        1010                1015                1020
        Asn Val  Ser Asp Thr Ser Lys  Asn Gly Thr Val Thr  Phe Ala His
                        1025                1030                1035
        Glu Thr  Asn Asn Ser Ala Ser  Phe Ala Thr Thr Ile  Ser Thr Asp
                        1040                1045                1050
        Asn Ala  Asn Ile Thr Leu Asp  Lys Asn Ala Gly Asn  Thr Ile Val
                        1055                1060                1065
        Lys Thr   Thr Asn Gly Ser Gln  Leu Pro Thr Asn Leu  Pro Leu Lys
                        1070                1075                1080
        Phe Ile  Thr Thr Glu Gly Asn  Glu His Leu Val Ser  Gly Asn Tyr
                        1085                1090                1095
        Arg Ala  Asn Ile Thr Ile Thr  Ser Thr Ile Lys Asp  Asn Lys Gln
                        1100                1105                1110
        Ala Ala  Gly Pro Thr Leu Thr  Lys Glu Leu Ala Leu  Asn Val Leu
                        1115                1120                1125
```

Ser Leu Glu His His His His His His
    1130            1135

<210> SEQ ID NO 10
<211> LENGTH: 2952
<212> TYPE: DNA
<213> ORGANISM: Escherichia coli

<400> SEQUENCE: 10

| | | | | | |
|---|---|---|---|---|---|
| atgaaaaaga | tatttatttt | tttgtctatc | atattttctg | cggtggtcag | tgccgggcga | 60 |
| tacccggaaa | ctacagtagg | taatctgacg | aagagttttc | aagcccctcg | tcaggataga | 120 |
| agcgtacaat | caccaatata | taacatcttt | acgaatcatg | tggctggata | tagtttgagt | 180 |
| cataacttat | atgacaggat | tgttttttta | tgtacatcct | cgtcgaatcc | ggttaatggt | 240 |
| gcttgcccaa | ccattggaac | atctggagtt | caatacggta | ctacaaccat | aaccttgcag | 300 |
| tttacagaaa | aaagaagtct | gataaaaaga | aatattaatc | ttgcaggtaa | taagaaacca | 360 |
| atatgggaga | atcagagttg | cgacactagc | aatctaatgg | tgttgaattc | gaagtcttgg | 420 |
| tcctgtgggg | cttacggaaa | tgctaacgga | acacttctaa | atctgtatat | ccctgcagga | 480 |
| gaaatcaaca | aattgccttt | tggagggata | tgggaggcaa | ctctgatctt | acgcttatca | 540 |
| agatatggcg | aagtcagtag | cacccattac | ggcaattata | ccgtaaatat | tacggttgat | 600 |
| ttaactgata | aaggtaatat | tcaggtatgg | cttccagggt | ttcacagcaa | cccgcgtgta | 660 |
| gacctgaatc | tgcaccctat | cggtaattat | aaatatagtg | gtagtaattc | actcgacatg | 720 |
| tgtttctatg | atggatatag | tacaaacagt | gatagcatgg | taataaagtt | ccaggatgat | 780 |
| aatcctacct | attcatctga | atataatctt | tataagatag | ggggcactga | aaaattaccc | 840 |
| tatgctgttt | cactgcttat | gggagaaaaa | atattttatc | cagtgaatgg | tcaatcattt | 900 |
| actatcaatg | acagtagtgt | actcgaaaca | aactggaatc | gagtaaccgc | agttgctatg | 960 |
| ccggaagtta | atgttccagt | attatgctgg | ccagcaagat | tgctattaaa | tgctgatgta | 1020 |
| aatgctcccg | atgcaggaca | gtattcagga | cagatatata | acatttac | acccagtgtc | 1080 |
| gaaaatttag | gcggtggagt | cgaaaaaaat | attactgtga | gggcaagtgt | tgaccctaaa | 1140 |
| cttgatcttc | tgcaagcaga | tggaacttca | ctgccggact | ctatcgcatt | aacctattct | 1200 |
| tcggcttcaa | ataattttga | agtttactct | cttaatactg | ctattcatac | aaatgacaaa | 1260 |
| agcaagggag | ttgtagtgaa | gctgtcagct | tcaccagttc | tgtccaatat | tatgaagcca | 1320 |
| aactcgcaaa | ttccgatgaa | agtgactttg | ggggggaaga | cgctgaatac | aactgatact | 1380 |
| gagtttactg | ttgatactct | gaactttggt | acatctggtg | ttgaaaacgt | tcttccact | 1440 |
| caacagctta | cgattcatgc | agacacacaa | ggaactgcgc | ctgaggcagg | caattaccaa | 1500 |
| ggtattattt | ctcttatcat | gactcaaaaa | acaggggggcg | gtgtcgaaaa | aaatattact | 1560 |
| gtgagggcaa | gtcgaccc | taaacttgac | cttctgcaat | ctgatggctc | tgcgctgccg | 1620 |
| aactctgtcg | cattaaccta | ttctccggct | gtaaataatt | ttgaagctca | caccatcaac | 1680 |
| accgttgttc | atacaaatga | ctcagataaa | ggtgttgttg | tgaagctgtc | agcagatcca | 1740 |
| gtcctgtcca | atgttctgaa | tccaaccctg | caaattcctg | tttctgtgaa | tttcgcagga | 1800 |
| aaaccactga | gcacaacagg | cattaccatc | gactccaatg | atctgaactt | tgcttcgagt | 1860 |
| ggtgttaata | agtttcttc | tacgcagaaa | cttcaatcc | atgcagatgc | tactcgggta | 1920 |
| actggcggcg | cactaacagc | tggtcaatat | cagggactcg | tatcaattat | cctgactaag | 1980 |
| tcaacggggg | gcggtgtcga | gaagaccatt | agcgttacgg | cgagtgttga | cccgacgggc | 2040 |

-continued

```
acattagcta ttgattttac gcctattgaa aatatttatg taggtgccaa ttatggtaaa    2100
gatattggaa cccttgtttt cacaacaaat gatttaacag atattacatt gatgtcatct    2160
cgcagcgttg ttgatggtcg ccagactggt tttttacct tcatggactc atcagccact     2220
tacaaaatta gtacaaaact gggatcatcg aatgatgtaa acattcaaga aattactcaa    2280
ggagctaaaa ttactcctgt tagtggagag aaaactttgc ctaaaaaatt cactcttaag    2340
ctacatgcac acaggagtag cagtacagtt ccaggtacgt atactgttgg tcttaacgta    2400
accagtaacg ttattgataa caagcaggca gcggggccca ctctaaccaa agaactggca    2460
ttaaatgtgc tttctcctgc agctctggat gcaacttggg ctcctcagga taatttaaca    2520
ttatccaata ctggcgtttc taatactttg gtgggtgttt tgactctttc aaataccagt    2580
attgatacag ttagcattgc gagtacaaat gtttctgata catctaagaa tggtacagta    2640
acttttgcac atgagacaaa taactctgct agctttgcca ccaccatttc aacagataat    2700
gccaacatta cgttggataa aaatgctgga aatacgattg ttaaaactac aaatgggagt    2760
cagttgccaa ctaatttacc acttaagttt attaccactg aaggtaacga acatttagtt    2820
tcaggtaatt accgtgcaaa tataacaatt acttcgacaa ttaaagataa caagcaggcg    2880
gcaggtccaa ccctgactaa ggagttagcg ctgaacgttc tgagcctcga gcaccaccac    2940
caccaccact ga                                                        2952
```

<210> SEQ ID NO 11
<211> LENGTH: 983
<212> TYPE: PRT
<213> ORGANISM: Escherichia coli

<400> SEQUENCE: 11

```
Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Gln Asp Arg Ser Val Gln Ser Pro Ile Tyr Asn
        35                  40                  45

Ile Phe Thr Asn His Val Ala Gly Tyr Ser Leu Ser His Asn Leu Tyr
    50                  55                  60

Asp Arg Ile Val Phe Leu Cys Thr Ser Ser Asn Pro Val Asn Gly
65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Thr Ser Asn Leu Met Val Leu Asn Ser Lys Ser Trp Ser Cys Gly Ala
    130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205
```

```
Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Tyr Ser Ser Glu Tyr Asn Leu Tyr Lys
            260                 265                 270

Ile Gly Gly Thr Glu Lys Leu Pro Tyr Ala Val Ser Leu Leu Met Gly
        275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu Gly Gly Gly Val Glu
        355                 360                 365

Lys Asn Ile Thr Val Arg Ala Ser Val Asp Pro Lys Leu Asp Leu Leu
    370                 375                 380

Gln Ala Asp Gly Thr Ser Leu Pro Asp Ser Ile Ala Leu Thr Tyr Ser
385                 390                 395                 400

Ser Ala Ser Asn Asn Phe Glu Val Tyr Ser Leu Asn Thr Ala Ile His
                405                 410                 415

Thr Asn Asp Lys Ser Lys Gly Val Val Val Lys Leu Ser Ala Ser Pro
            420                 425                 430

Val Leu Ser Asn Ile Met Lys Pro Asn Ser Gln Ile Pro Met Lys Val
        435                 440                 445

Thr Leu Gly Gly Lys Thr Leu Asn Thr Thr Asp Thr Glu Phe Thr Val
    450                 455                 460

Asp Thr Leu Asn Phe Gly Thr Ser Gly Val Glu Asn Val Ser Ser Thr
465                 470                 475                 480

Gln Gln Leu Thr Ile His Ala Asp Thr Gln Gly Thr Ala Pro Glu Ala
                485                 490                 495

Gly Asn Tyr Gln Gly Ile Ile Ser Leu Ile Met Thr Gln Lys Thr Gly
            500                 505                 510

Gly Gly Val Glu Lys Asn Ile Thr Val Arg Ala Ser Val Asp Pro Lys
        515                 520                 525

Leu Asp Leu Leu Gln Ser Asp Gly Ser Ala Leu Pro Asn Ser Val Ala
    530                 535                 540

Leu Thr Tyr Ser Pro Ala Val Asn Asn Phe Glu Ala His Thr Ile Asn
545                 550                 555                 560

Thr Val Val His Thr Asn Asp Ser Asp Lys Gly Val Val Lys Leu
                565                 570                 575

Ser Ala Asp Pro Val Leu Ser Asn Val Leu Asn Pro Thr Leu Gln Ile
            580                 585                 590

Pro Val Ser Val Asn Phe Ala Gly Lys Pro Leu Ser Thr Thr Gly Ile
        595                 600                 605

Thr Ile Asp Ser Asn Asp Leu Asn Phe Ala Ser Ser Gly Val Asn Lys
    610                 615                 620
```

```
Val Ser Ser Thr Gln Lys Leu Ser Ile His Ala Asp Ala Thr Arg Val
625                 630                 635                 640

Thr Gly Gly Ala Leu Thr Ala Gly Gln Tyr Gln Gly Leu Val Ser Ile
            645                 650                 655

Ile Leu Thr Lys Ser Thr Gly Gly Val Glu Lys Thr Ile Ser Val
        660                 665                 670

Thr Ala Ser Val Asp Pro Thr Gly Thr Leu Ala Ile Asp Phe Thr Pro
        675                 680                 685

Ile Glu Asn Ile Tyr Val Gly Ala Asn Tyr Gly Lys Asp Ile Gly Thr
    690                 695                 700

Leu Val Phe Thr Thr Asn Asp Leu Thr Asp Ile Thr Leu Met Ser Ser
705                 710                 715                 720

Arg Ser Val Val Asp Gly Arg Gln Thr Gly Phe Thr Phe Met Asp
            725                 730                 735

Ser Ser Ala Thr Tyr Lys Ile Ser Thr Lys Leu Gly Ser Ser Asn Asp
            740                 745                 750

Val Asn Ile Gln Glu Ile Thr Gln Gly Ala Lys Ile Thr Pro Val Ser
        755                 760                 765

Gly Glu Lys Thr Leu Pro Lys Lys Phe Thr Leu Lys Leu His Ala His
770                 775                 780

Arg Ser Ser Ser Thr Val Pro Gly Thr Tyr Thr Val Gly Leu Asn Val
785                 790                 795                 800

Thr Ser Asn Val Ile Asp Asn Lys Gln Ala Ala Gly Pro Thr Leu Thr
            805                 810                 815

Lys Glu Leu Ala Leu Asn Val Leu Ser Pro Ala Ala Leu Asp Ala Thr
        820                 825                 830

Trp Ala Pro Gln Asp Asn Leu Thr Leu Ser Asn Thr Gly Val Ser Asn
        835                 840                 845

Thr Leu Val Gly Val Leu Thr Leu Ser Asn Thr Ser Ile Asp Thr Val
850                 855                 860

Ser Ile Ala Ser Thr Asn Val Ser Asp Thr Ser Lys Asn Gly Thr Val
865                 870                 875                 880

Thr Phe Ala His Glu Thr Asn Asn Ser Ala Ser Phe Ala Thr Thr Ile
            885                 890                 895

Ser Thr Asp Asn Ala Asn Ile Thr Leu Asp Lys Asn Ala Gly Asn Thr
            900                 905                 910

Ile Val Lys Thr Thr Asn Gly Ser Gln Leu Pro Thr Asn Leu Pro Leu
        915                 920                 925

Lys Phe Ile Thr Glu Gly Asn Glu His Leu Val Ser Gly Asn Tyr
        930                 935                 940

Arg Ala Asn Ile Thr Ile Thr Ser Thr Ile Lys Asp Asn Lys Gln Ala
945                 950                 955                 960

Ala Gly Pro Thr Leu Thr Lys Glu Leu Ala Leu Asn Val Leu Ser Leu
            965                 970                 975

Glu His His His His His
            980

<210> SEQ ID NO 12
<211> LENGTH: 2514
<212> TYPE: DNA
<213> ORGANISM: Escherichia coli

<400> SEQUENCE: 12
atgaaaaaag tgattttgt tttatccatg tttctatgtt ctcaggttta cgggcaatca    60
```

-continued

```
tggcatacga acgtagaggc tggttcaata aataaaacag agtcgatagg ccccatagac    120
cgaagtgctg ctgcatcgta tcctgctcat tatatatttc atgaacatgt tgctggttac    180
aataaagatc actctctttt tgacaggatg acgtttttat gtatgtcatc aacagatgca    240
tctaaaggtg catgtccgac aggagaaaac tccaaatcct ctcaagggga gactaatatt    300
aagctaatat ttactgaaaa gaaaagtctg gccagaaaaa cattaaactt aaaaggatat    360
aagagatttt tatatgaatc agatagatgc attcattatg tcgataaaat gaatctcaat    420
tctcatactg ttaaatgtgt aggttcattc acaagaggag tagatttcac tttatatatc    480
ccacaaggtg aaattgatgg gcttctaact ggaggtatat gggaggcaac actagagtta    540
cgagtcaaaa ggcattacga ctataatcat ggtacttaca aagttaatat cacagttgat    600
ttgacagaca aaggaaatat tcaggtctgg acaccaaagt tcatagcga tcctagaatt    660 gatctgaatt tacgtcctga aggtaatggt aaatattctg gtagtaacgt gcttgagatg    720
tgtctctatg atggctatag tacacatagt caaagtatag aaatgaggtt tcaggatgac    780
tcacaaacag gaataatga atataatctt ataaaaactg gagagccatt aaaaaaattg    840
ccatataaac tttctcttct tttaggagga cgagagtttt atccaaataa tggagaggct    900
tttactatta atgatacttc gtcattgttt ataaactgga atcgtattaa gtctgtatcc    960
ttaccacaga ttagtattcc agtactatgc tggccagcaa acttgacatt tatgtcagag    1020
ctaaataatc cagaagcggg tgagtattca ggaatactta cgtaacatt tactcctagt    1080 agttcaagcc tagacaataa acaagccgag aaaaatatca ctgtaactgc tagcgttgat    1140
ccaactatcg atctgatgca atctgatggc acagcgttac caagtgcagt taatattgca    1200
tatcttccag gagagaaaag atttgaatct gctcgtatca atacccaagt tcataccaat    1260
aataaaacta agggtattca gataaagctt actaatgata atgtggtaat gactaactta    1320
tctgatccaa gcaagactat tcctttagag gtttcattcg ctggcactaa gctgagcaca    1380
gctgcaacat ctattactgc cgatcaatta aattttggcg cagctggtgt agagacagtt    1440
tctgcaacta aggaactcgt tattaatgca ggaagcaccc agcaaactaa tattgtagct    1500
ggtaactatc aaggattggt gtcaattgtg cttactcaag aacctgacaa taaacaagcc    1560
gagaaaaata tcactgtaac tgctagcgtt gatccgacgg gcacattagc tattgatttt    1620
acgcctattg aaaatattta tgtaggtgcc aattatggta agatattgg aacccttgtt    1680 ttcacaacaa atgatttaac agatattaca ttgatgtcat ctcgcagcgt tgttgatggt    1740
cgccagactg gtttttttac cttcatggac tcatcagcca cttacaaaat tagtacaaaa    1800
ctgggatcat cgaatgatgt aaacattcaa gaaattactc aaggagctaa aattactcct    1860
gttagtggag agaaaacttt gcctaaaaaa ttcactctta agctacatgc acacaggagt    1920
agcagtacag ttccaggtac gtatactgtt ggtcttaacg taaccagtaa cgttattgat    1980
aacaagcagg cagcggggcc cactctaacc aaagaactgg cattaaatgt gctttctcct    2040
gcagctctgg atgcaacttg ggctcctcag gataatttaa cattatccaa tactggcgtt    2100
tctaatactt tggtgggtgt tttgactctt tcaaatacca gtattgatac agttagcatt    2160
gcgagtacaa atgtttctga tacatctaag aatggtacga taactttgc acatgagaca    2220 aataactctg ctagctttgc caccaccatt tcaacagata atgccaacat tacgttggat    2280
aaaaatgctg gaaatacgat tgttaaaact acaaatggga gtcagttgcc aactaattta    2340
ccacttaagt ttattaccac tgaaggtaac gaacatttag tttcaggtaa ttaccgtgca    2400
aatataacaa ttacttcgac aattaaagat aacaagcagg cggcaggtcc aaccctgact    2460
```
aaggagttag cgctgaacgt tctgagcctc gagcaccacc accaccacca ctga    2514

<210> SEQ ID NO 13
<211> LENGTH: 837
<212> TYPE: PRT
<213> ORGANISM: Escherichia coli

<400> SEQUENCE: 13

Met Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
                20                  25                  30

Thr Glu Ser Ile Gly Pro Ile Asp Arg Ser Ala Ala Ser Tyr Pro
            35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
            100                 105                 110

Lys Thr Leu Asn Leu Lys Gly Tyr Lys Arg Phe Leu Tyr Glu Ser Asp
        115                 120                 125

Arg Cys Ile His Tyr Val Asp Lys Met Asn Leu Asn Ser His Thr Val
    130                 135                 140

Lys Cys Val Gly Ser Phe Thr Arg Gly Val Asp Phe Thr Leu Tyr Ile
145                 150                 155                 160

Pro Gln Gly Glu Ile Asp Gly Leu Leu Thr Gly Gly Ile Trp Glu Ala
                165                 170                 175

Thr Leu Glu Leu Arg Val Lys Arg His Tyr Asp Tyr Asn His Gly Thr
            180                 185                 190

Tyr Lys Val Asn Ile Thr Val Asp Leu Thr Asp Lys Gly Asn Ile Gln
        195                 200                 205

Val Trp Thr Pro Lys Phe His Ser Asp Pro Arg Ile Asp Leu Asn Leu
    210                 215                 220

Arg Pro Glu Gly Asn Gly Lys Tyr Ser Gly Ser Asn Val Leu Glu Met
225                 230                 235                 240

Cys Leu Tyr Asp Gly Tyr Ser Thr His Ser Gln Ser Ile Glu Met Arg
                245                 250                 255

Phe Gln Asp Asp Ser Gln Thr Gly Asn Asn Glu Tyr Asn Leu Ile Lys
            260                 265                 270

Thr Gly Glu Pro Leu Lys Lys Leu Pro Tyr Lys Leu Ser Leu Leu Leu
        275                 280                 285

Gly Gly Arg Glu Phe Tyr Pro Asn Asn Gly Glu Ala Phe Thr Ile Asn
    290                 295                 300

Asp Thr Ser Ser Leu Phe Ile Asn Trp Asn Arg Ile Lys Ser Val Ser
305                 310                 315                 320

Leu Pro Gln Ile Ser Ile Pro Val Leu Cys Trp Pro Ala Asn Leu Thr
                325                 330                 335

Phe Met Ser Glu Leu Asn Asn Pro Glu Ala Gly Glu Tyr Ser Gly Ile
            340                 345                 350

Leu Asn Val Thr Phe Thr Pro Ser Ser Ser Ser Leu Asp Asn Lys Gln
        355                 360                 365

```
Ala Glu Lys Asn Ile Thr Val Thr Ala Ser Val Asp Pro Thr Ile Asp
    370                 375                 380

Leu Met Gln Ser Asp Gly Thr Ala Leu Pro Ser Ala Val Asn Ile Ala
385                 390                 395                 400

Tyr Leu Pro Gly Glu Lys Arg Phe Glu Ser Ala Arg Ile Asn Thr Gln
                405                 410                 415

Val His Thr Asn Asn Lys Thr Lys Gly Ile Gln Ile Lys Leu Thr Asn
            420                 425                 430

Asp Asn Val Val Met Thr Asn Leu Ser Asp Pro Ser Lys Thr Ile Pro
        435                 440                 445

Leu Glu Val Ser Phe Ala Gly Thr Lys Leu Ser Thr Ala Ala Thr Ser
450                 455                 460

Ile Thr Ala Asp Gln Leu Asn Phe Gly Ala Ala Gly Val Glu Thr Val
465                 470                 475                 480

Ser Ala Thr Lys Glu Leu Val Ile Asn Ala Gly Ser Thr Gln Gln Thr
                485                 490                 495

Asn Ile Val Ala Gly Asn Tyr Gln Gly Leu Val Ser Ile Val Leu Thr
            500                 505                 510

Gln Glu Pro Asp Asn Lys Gln Ala Glu Lys Asn Ile Thr Val Thr Ala
        515                 520                 525

Ser Val Asp Pro Thr Gly Thr Leu Ala Ile Asp Phe Thr Pro Ile Glu
530                 535                 540

Asn Ile Tyr Val Gly Ala Asn Tyr Gly Lys Asp Ile Gly Thr Leu Val
545                 550                 555                 560

Phe Thr Thr Asn Asp Leu Thr Asp Ile Thr Leu Met Ser Ser Arg Ser
                565                 570                 575

Val Val Asp Gly Arg Gln Thr Gly Phe Phe Thr Phe Met Asp Ser Ser
            580                 585                 590

Ala Thr Tyr Lys Ile Ser Thr Lys Leu Gly Ser Ser Asn Asp Val Asn
        595                 600                 605

Ile Gln Glu Ile Thr Gln Gly Ala Lys Ile Thr Pro Val Ser Gly Glu
610                 615                 620

Lys Thr Leu Pro Lys Lys Phe Thr Leu Lys Leu His Ala His Arg Ser
625                 630                 635                 640

Ser Ser Thr Val Pro Gly Thr Tyr Thr Val Gly Leu Asn Val Thr Ser
                645                 650                 655

Asn Val Ile Asp Asn Lys Gln Ala Ala Gly Pro Thr Leu Thr Lys Glu
            660                 665                 670

Leu Ala Leu Asn Val Leu Ser Pro Ala Ala Leu Asp Ala Thr Trp Ala
        675                 680                 685

Pro Gln Asp Asn Leu Thr Leu Ser Asn Thr Gly Val Ser Asn Thr Leu
690                 695                 700

Val Gly Val Leu Thr Leu Ser Asn Thr Ser Ile Asp Thr Val Ser Ile
705                 710                 715                 720

Ala Ser Thr Asn Val Ser Asp Thr Ser Lys Asn Gly Thr Val Thr Phe
                725                 730                 735

Ala His Glu Thr Asn Asn Ser Ala Ser Phe Ala Thr Thr Ile Ser Thr
            740                 745                 750

Asp Asn Ala Asn Ile Thr Leu Asp Lys Asn Ala Gly Asn Thr Ile Val
        755                 760                 765

Lys Thr Asn Gly Ser Gln Leu Pro Thr Asn Leu Pro Leu Lys Phe
770                 775                 780
```

Ile Thr Thr Glu Gly Asn Glu His Leu Val Ser Gly Asn Tyr Arg Ala
785                 790                 795                 800

Asn Ile Thr Ile Thr Ser Thr Ile Lys Asp Asn Lys Gln Ala Ala Gly
            805                 810                 815

Pro Thr Leu Thr Lys Glu Leu Ala Leu Asn Val Leu Ser Leu Glu His
            820                 825                 830

His His His His His
        835

<210> SEQ ID NO 14
<211> LENGTH: 1845
<212> TYPE: DNA
<213> ORGANISM: Escherichia coli

<400> SEQUENCE: 14

| | |
|---|---|
| atggcagtgg gcccaacgaa agatatgagt ttaggtgcaa atttaacttc agagcctaca | 60 |
| ttagctattg attttacgcc tattgaaaat atttatgtag gtgccaatta tggtaaagat | 120 |
| attggaaccc ttgttttcac aacaaatgat ttaacagata ttacattgat gtcatctcgc | 180 |
| agcgttgttg atggtcgcca gactggtttt tttaccttca tggactcatc agccacttac | 240 |
| aaaattagta caaaactggg atcatcgaat gatgtaaaca ttcaagaaat tactcaagga | 300 |
| gctaaaatta ctcctgttag tggagagaaa actttgccta aaaaattcac tcttaagcta | 360 |
| catgcacaca ggagtagcag tacagttcca ggtacgtata ctgttggtct aacgtaacc | 420 |
| agtaacgtta ttgataacaa gcaggcagcg gggcccactc taaccaaaga actggcatta | 480 |
| aatgtgcttt ctcctgcagc tctggatgca acttgggctc ctcaggataa tttaacatta | 540 |
| tccaatactg gcgtttctaa tactttggtg ggtgttttga ctctttcaaa taccagtatt | 600 |
| gatacagtta gcattgcgag tacaaatgtt tctgatacat ctaagaatgg tacagtaact | 660 |
| tttgcacatg agacaaataa ctctgctagc tttgccacca ccatttcaac agataatgcc | 720 |
| aacattacgt tggataaaaa tgctggaaat acgattgtta aaactacaaa tgggagtcag | 780 |
| ttgccaacta atttaccact taagtttatt accactgaag gtaacgaaca tttagtttca | 840 |
| ggtaattacc gtgcaaatat aacaattact tcgacaatta agataacaa gcaggcggca | 900 |
| ggtccaaccc tgactaagga gttagcgctg aacgttttaa gcggctcaaa agttttttt | 960 |
| gcacctgaac cacgaataca gccttctttt ggtgaaaatg ttggaaagga aggagcttta | 1020 |
| ttatttagtg tgaacttaac tgttcctgaa atgtatccc aggtaacggt ctaccctgtt | 1080 |
| tatgatgaag attatgggtt aggacgacta gtaaataccg ctgatgcttc ccaatcaata | 1140 |
| atctaccaga ttgttgatga aaagggaaa aaaatgttaa aagatcatgg tgcagaggtt | 1200 |
| acacctaatc aacaaataac ttttaaagcg ctgaattata ctagcgggga aaaaaaata | 1260 |
| tctcctggaa tatataacga tcaggttatg gttggttact acgtcaacga caataaacaa | 1320 |
| ggaaactggc aatataaatc tctggatgta aatgtaaata ttgagcaaaa ttttattcca | 1380 |
| gatattgatt ccgctgttcg tataataccct gttaattacg attcggaccc gaaactggat | 1440 |
| tcacagttat atacggttga tgatgacgatc cctgcaggtg taagcgcagt taaaatcgca | 1500 |
| ccaacagata gtctgacatc ttctggacag cagatcggaa agctggttaa tgtaaacaat | 1560 |
| ccagatcaaa atatgaatta ttatatcaga aaggattctg gcgctggtaa ctttatggca | 1620 |
| ggacaaaaag gatccttttcc tgtcaaagag aatacgtcat acacattctc agcaatttat | 1680 |
| actggtggcg aatacctaa tagcggatat tcgtctggta cttatgcagg aaatttgact | 1740 |
| gtatcatttt acagcaatga caataaacaa agaacagaaa tagcgactaa aaacttccca | 1800 | gtatcaacga ctatttcact cgagcaccac caccaccacc actga         1845

<210> SEQ ID NO 15
<211> LENGTH: 614
<212> TYPE: PRT
<213> ORGANISM: Escherichia coli

<400> SEQUENCE: 15

```
Met Ala Val Gly Pro Thr Lys Asp Met Ser Leu Gly Ala Asn Leu Thr
1               5                   10                  15

Ser Glu Pro Thr Leu Ala Ile Asp Phe Thr Pro Ile Glu Asn Ile Tyr
            20                  25                  30

Val Gly Ala Asn Tyr Gly Lys Asp Ile Gly Thr Leu Val Phe Thr Thr
        35                  40                  45

Asn Asp Leu Thr Asp Ile Thr Leu Met Ser Ser Arg Ser Val Val Asp
50                  55                  60

Gly Arg Gln Thr Gly Phe Phe Thr Phe Met Asp Ser Ser Ala Thr Tyr
65                  70                  75                  80

Lys Ile Ser Thr Lys Leu Gly Ser Ser Asn Asp Val Asn Ile Gln Glu
                85                  90                  95

Ile Thr Gln Gly Ala Lys Ile Thr Pro Val Ser Gly Glu Lys Thr Leu
            100                 105                 110

Pro Lys Lys Phe Thr Leu Lys Leu His Ala His Arg Ser Ser Ser Thr
        115                 120                 125

Val Pro Gly Thr Tyr Thr Val Gly Leu Asn Val Thr Ser Asn Val Ile
    130                 135                 140

Asp Asn Lys Gln Ala Ala Gly Pro Thr Leu Thr Lys Glu Leu Ala Leu
145                 150                 155                 160

Asn Val Leu Ser Pro Ala Ala Leu Asp Ala Thr Trp Ala Pro Gln Asp
                165                 170                 175

Asn Leu Thr Leu Ser Asn Thr Gly Val Ser Asn Thr Leu Val Gly Val
            180                 185                 190

Leu Thr Leu Ser Asn Thr Ser Ile Asp Thr Val Ser Ile Ala Ser Thr
        195                 200                 205

Asn Val Ser Asp Thr Ser Lys Asn Gly Thr Val Thr Phe Ala His Glu
    210                 215                 220

Thr Asn Asn Ser Ala Ser Phe Ala Thr Thr Ile Ser Thr Asp Asn Ala
225                 230                 235                 240

Asn Ile Thr Leu Asp Lys Asn Ala Gly Asn Thr Ile Val Lys Thr Thr
                245                 250                 255

Asn Gly Ser Gln Leu Pro Thr Asn Leu Pro Leu Lys Phe Ile Thr Thr
            260                 265                 270

Glu Gly Asn Glu His Leu Val Ser Gly Asn Tyr Arg Ala Asn Ile Thr
        275                 280                 285

Ile Thr Ser Thr Ile Lys Asp Asn Lys Gln Ala Ala Gly Pro Thr Leu
    290                 295                 300

Thr Lys Glu Leu Ala Leu Asn Val Leu Ser Gly Ser Lys Ser Phe Phe
305                 310                 315                 320

Ala Pro Glu Pro Arg Ile Gln Pro Ser Phe Gly Glu Asn Val Gly Lys
                325                 330                 335

Glu Gly Ala Leu Leu Phe Ser Val Asn Leu Thr Val Pro Glu Asn Val
            340                 345                 350

Ser Gln Val Thr Val Tyr Pro Val Tyr Asp Glu Asp Tyr Gly Leu Gly
        355                 360                 365
```

```
Arg Leu Val Asn Thr Ala Asp Ala Ser Gln Ser Ile Ile Tyr Gln Ile
    370                 375                 380

Val Asp Glu Lys Gly Lys Lys Met Leu Lys Asp His Gly Ala Glu Val
385                 390                 395                 400

Thr Pro Asn Gln Gln Ile Thr Phe Lys Ala Leu Asn Tyr Thr Ser Gly
                405                 410                 415

Glu Lys Lys Ile Ser Pro Gly Ile Tyr Asn Asp Gln Val Met Val Gly
                420                 425                 430

Tyr Tyr Val Asn Asp Asn Lys Gln Gly Asn Trp Gln Tyr Lys Ser Leu
            435                 440                 445

Asp Val Asn Val Asn Ile Glu Gln Asn Phe Ile Pro Asp Ile Asp Ser
450                 455                 460

Ala Val Arg Ile Ile Pro Val Asn Tyr Asp Ser Asp Pro Lys Leu Asp
465                 470                 475                 480

Ser Gln Leu Tyr Thr Val Glu Met Thr Ile Pro Ala Gly Val Ser Ala
                485                 490                 495

Val Lys Ile Ala Pro Thr Asp Ser Leu Thr Ser Ser Gly Gln Gln Ile
                500                 505                 510

Gly Lys Leu Val Asn Val Asn Asn Pro Asp Gln Asn Met Asn Tyr Tyr
            515                 520                 525

Ile Arg Lys Asp Ser Gly Ala Gly Asn Phe Met Ala Gly Gln Lys Gly
            530                 535                 540

Ser Phe Pro Val Lys Glu Asn Thr Ser Tyr Thr Phe Ser Ala Ile Tyr
545                 550                 555                 560

Thr Gly Gly Glu Tyr Pro Asn Ser Gly Tyr Ser Ser Gly Thr Tyr Ala
                565                 570                 575

Gly Asn Leu Thr Val Ser Phe Tyr Ser Asn Asp Asn Lys Gln Arg Thr
            580                 585                 590

Glu Ile Ala Thr Lys Asn Phe Pro Val Ser Thr Thr Ile Ser Leu Glu
            595                 600                 605

His His His His His His
    610
```

<210> SEQ ID NO 16
<211> LENGTH: 2487
<212> TYPE: DNA
<213> ORGANISM: Escherichia coli

<400> SEQUENCE: 16

```
atgaataaaa ttttatttat ttttacattg ttttttttctt cagggttttt tacatttgcc      60
gtatcggcag ataaaaatcc cggaagtgaa aacatgacta atactattgg tccccatgac     120
agggggggat cttcccccat atataatatc ttaaattcct atcttacagc atacaatgga     180
agccatcatc tgtatgatag gatgagtttt ttatgtttgt cttctcaaaa tacactgaat     240
ggagcatgcc caagcagtga tgcccctggc actgctacaa ttgatggcga acaaatata      300
acattacaat ttacggaaaa aagaagtcta attaaagag aactgcaaat taaaggctat      360
aaacaatttt tgttcaaaaa tgctaattgc ccatctaaac tagcacttaa ctcatctcat     420
tttcaatgta atagagaaca agcttcaggt gctactttat cgttatacat accagctggt     480
gaattaaata aattcccttt tggggggtc tggaatgccg ttctgaagct aaatgtaaaa      540
agacgatatg atacaaccta tgggacttac actataaaca tcacagttaa tttaactgat     600
aagggaaata ttcagatatg gttaccacag ttcaaaagta acgctcgtgt cgatcttaac     660
```

-continued

```
ttgcgtccaa ctggtggtgg tacatatatc ggaagaaatt ctgttgatat gtgcttttat      720
gatggatata gtactaacag cagctcttta gagataagat ttcaggatga taattctaaa      780
tctgatggaa aatttatct aaagaaaata aatgatgact ccaagaact tgtatacact       840 tgtcacttc tcctggcagg taaaaattta acaccaacaa atggacaggc attaaatatt       900
aacactgctt ctctggaaac aaactggaat agaattacag ctgtcaccat gccagaaatc      960
agtgttccgg tgttgtgttg gcctggacgt ttgcaattgg atgcaaaagt gaaaaatccc     1020
gaggctggac aatatatggg gaatattaaa attactttca caccaagtag tcaaacactc     1080
gacaataaac aagtagagaa aaatattact gtaacagcta gtgttgatcc tgcaattgat     1140
cttttgcaag ctgatggcaa tgctctgcca tcagctgtaa agttagctta ttctcccgca     1200
tcaaaaactt tgaaagtta cagagtaatg actcaagttc atacaaacga tgcaactaaa     1260
aaagtaattg ttaaacttgc tgatacacca cagcttacag atgttctgaa ttcaactgtt     1320
caaatgccta tcagtgtgtc atggggagga caagtattat ctacaacagc caaagaattt     1380
gaagctgctg ctttgggata ttctgcatcc ggtgtaaatg gcgtatcatc ttctcaagag     1440
ttagtaatta gcgctgcacc taaaactgcc ggtaccgccc caactgcagg aaactattca     1500
ggagtagtat ctcttgtaat gactttggga tccgacaata acaagtaga gaaaaatatt     1560 actgtaacag ctagtgtcga ccctgcaggg aattttattc cagatattga ttccgctgtt     1620 cgtataaatac ctgttaatta cgattcggac ccgaaactgg attcacagtt atatacggtt     1680
gagatgacga tccctgcagg tgtaagcgca gttaaaatcg caccaacaga tagtctgaca     1740
tcttctggac agcagatcgg aaagctggtt aatgtaaaca atccagatca aaatatgaat     1800
tattatatca gaaaggattc tggcgctggt aactttatgg caggacaaaa aggatccttt     1860
cctgtcaaag agaatcgtc atacacattc tcagcaattt atactggtgg cgaatacct      1920 aatagcggat attcgtctgg tacttatgca ggaaatttga ctgtatcatt ttacagcaat     1980
gacaataaac aaagaacaga aatagcgact aaaaacttcc cagtatcaac gactatttca     2040
aaaagttttt ttgcacctga accacgaata cagccttctt ttggtgaaaa tgttggaaag     2100
gaaggagctt tattatttag tgtgaactta actgttcctg aaaatgtatc ccaggtaacg     2160
gtctaccctg tttatgatga agattatggg ttaggacgac tagtaaatac cgctgatgct     2220
tcccaatcaa taatctacca gattgttgat gagaaaggga aaaaaatgtt aaaagatcat     2280
ggtgcagagg ttacacctaa tcaacaaata acttttaaag cgctgaatta tactagcggg     2340
gaaaaaaaaa tatctcctgg aatatataac gatcaggtta tggttggtta ctacgtaaac     2400
gacaataaac aacgtaccga gattgccacc aagaattttc cggtgagcac caccatcagc     2460
ctcgagcacc accaccacca ccactga                                         2487
```

<210> SEQ ID NO 17
<211> LENGTH: 828
<212> TYPE: PRT
<213> ORGANISM: Escherichia coli

<400> SEQUENCE: 17

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

```
Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
                115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Tyr Thr Tyr Ile
                180                 185                 190

Asn Ile Thr Val Asn Leu Thr Asp Lys Gly Asn Ile Gln Ile Trp Leu
                195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
                260                 265                 270

Asp Ser Lys Glu Leu Val Tyr Thr Leu Ser Leu Leu Leu Ala Gly Lys
    275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
                340                 345                 350

Phe Thr Pro Ser Ser Gln Thr Leu Asp Asn Lys Gln Val Glu Lys Asn
    355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
                420                 425                 430

Thr Asp Val Leu Asn Ser Thr Val Gln Met Pro Ile Ser Val Ser Trp
                435                 440                 445

Gly Gly Gln Val Leu Ser Thr Thr Ala Lys Glu Phe Glu Ala Ala Ala
450                 455                 460

Leu Gly Tyr Ser Ala Ser Gly Val Asn Gly Val Ser Ser Ser Gln Glu
```

```
            465                 470                 475                 480
Leu Val Ile Ser Ala Pro Lys Thr Ala Gly Thr Ala Pro Thr Ala
                    485                 490                 495
Gly Asn Tyr Ser Gly Val Val Ser Leu Val Met Thr Leu Gly Ser Asp
                500                 505                 510
Asn Lys Gln Val Glu Lys Asn Ile Thr Val Thr Ala Ser Val Asp Pro
            515                 520                 525
Ala Gly Asn Phe Ile Pro Asp Ile Asp Ser Ala Val Arg Ile Pro
    530                 535                 540
Val Asn Tyr Asp Ser Asp Pro Lys Leu Asp Ser Gln Leu Tyr Thr Val
545                 550                 555                 560
Glu Met Thr Ile Pro Ala Gly Val Ser Ala Val Lys Ile Ala Pro Thr
                    565                 570                 575
Asp Ser Leu Thr Ser Ser Gly Gln Gln Ile Gly Lys Leu Val Asn Val
                580                 585                 590
Asn Asn Pro Asp Gln Asn Met Asn Tyr Tyr Ile Arg Lys Asp Ser Gly
            595                 600                 605
Ala Gly Asn Phe Met Ala Gly Gln Lys Gly Ser Phe Pro Val Lys Glu
    610                 615                 620
Asn Thr Ser Tyr Thr Phe Ser Ala Ile Tyr Thr Gly Gly Glu Tyr Pro
625                 630                 635                 640
Asn Ser Gly Tyr Ser Ser Gly Thr Tyr Ala Gly Asn Leu Thr Val Ser
                    645                 650                 655
Phe Tyr Ser Asn Asp Asn Lys Gln Arg Thr Glu Ile Ala Thr Lys Asn
                660                 665                 670
Phe Pro Val Ser Thr Thr Ile Ser Lys Ser Phe Phe Ala Pro Glu Pro
            675                 680                 685
Arg Ile Gln Pro Ser Phe Gly Glu Asn Val Gly Lys Glu Gly Ala Leu
    690                 695                 700
Leu Phe Ser Val Asn Leu Thr Val Pro Glu Asn Val Ser Gln Val Thr
705                 710                 715                 720
Val Tyr Pro Val Tyr Asp Glu Asp Tyr Gly Leu Gly Arg Leu Val Asn
                    725                 730                 735
Thr Ala Asp Ala Ser Gln Ser Ile Ile Tyr Gln Ile Val Asp Glu Lys
                740                 745                 750
Gly Lys Lys Met Leu Lys Asp His Gly Ala Glu Val Thr Pro Asn Gln
            755                 760                 765
Gln Ile Thr Phe Lys Ala Leu Asn Tyr Thr Ser Gly Glu Lys Lys Ile
    770                 775                 780
Ser Pro Gly Ile Tyr Asn Asp Gln Val Met Val Gly Tyr Tyr Val Asn
785                 790                 795                 800
Asp Asn Lys Gln Arg Thr Glu Ile Ala Thr Lys Asn Phe Pro Val Ser
                    805                 810                 815
Thr Thr Ile Ser Leu Glu His His His His His His
                820                 825

<210> SEQ ID NO 18
<211> LENGTH: 2490
<212> TYPE: DNA
<213> ORGANISM: Escherichia coli

<400> SEQUENCE: 18
atgaataaaa ttttatttat ttttacattg ttttttttctt cagggttttt tacatttgcc      60
gtatcggcag ataaaaatcc cggaagtgaa aacatgacta atactattgg tcccccatgac    120
```

```
aggggggat   cttcccccat   atataatatc   ttaaattcct   atcttacagc   atacaatgga    180
agccatcatc   tgtatgatag   gatgagtttt   ttatgtttgt   cttctcaaaa   tacactgaat    240
ggagcatgcc   caagcagtga   tgccctggc    actgctacaa   ttgatggcga   aacaaatata    300
acattacaat   ttacgaaaaa   aagaagtcta   attaaaagag   aactgcaaat   taaaggctat    360
aaacaatttt   tgttcaaaaa   tgctaattgc   ccatctaaac   tagcacttaa   ctcatctcat    420
tttcaatgta   atagagaaca   agcttcaggt   gctactttat   cgttatacat   accagctggt    480
gaattaaata   aattaccttt   tgggggggtc   tggaatgccg   ttctgaagct   aaatgtaaaa    540
agacgatatg   atacaaccta   tgggacttac   actataaaca   tcacagttaa   tttaactgat    600
aagggaaata   ttcagatatg   gttaccacag   ttcaaaagta   acgctcgtgt   cgatcttaac    660
ttgcgtccaa   ctggtggtgg   tacatatatc   ggaagaaatt   ctgttgatat   gtgcttttat    720
gatggatata   gtactaacag   cagctctta    gagataagat   ttcaggatga   taattctaaa    780
tctgatggaa   aattttatct   aaagaaaata   aatgatgact   ccaaagaact   tgtatacact    840
ttgtcacttc   tcctggcagg   taaaaattta   acaccaacaa   atggacaggc   attaaatatt    900
aacactgctt   ctctggaaac   aaactggaat   agaattacag   ctgtcaccat   gccagaaatc    960
agtgttccgg   tgttgtgttg   gcctggacgt   ttgcaattgg   atgcaaaagt   gaaaaatccc   1020
gaggctggac   aatatatggg   gaatattaaa   attactttca   caccaagtag   tcaaacactc   1080
gacaataaac   aagtagagaa   aaatattact   gtaacagcta   gtgttgatcc   tgcaattgat   1140
cttttgcaag   ctgatggcaa   tgctctgcca   tcagctgtaa   agttagctta   ttctcccgca   1200
tcaaaaactt   ttgaaagtta   cagagtaatg   actcaagttc   atacaaacga   tgcaactaaa   1260
aaagtaattg   ttaaacttgc   tgatacacca   cagcttacag   atgttctgaa   ttcaactgtt   1320
caaatgccta   tcagtgtgtc   atggggagga   caagtattat   ctacaacagc   caaagaattt   1380
gaagctgctg   ctttgggata   ttctgcatcc   ggtgtaaatg   gcgtatcatc   ttctcaagag   1440
ttagtaatta   gcgctgcacc   taaaactgcc   ggtaccgccc   caactgcagg   aaactattca   1500
ggagtagtat   ctcttgtaat   gactttggga   tccgacaata   aacaagtaga   gaaaatatt    1560 actgtaacag   ctagtgtcga   ccctgcaggg   tcaaaaagtt   tttttgcacc   tgaaccacga   1620
atacagcctt   cttttggtga   aaatgttgga   aaggaaggag   ctttattatt   tagtgtgaac   1680
ttaactgttc   ctgaaaatgt   atcccaggta   acggtctacc   ctgtttatga   tgaagattat   1740
gggttaggac   gactagtaaa   taccgctgat   gcttcccaat   caataatcta   ccagattgtt   1800
gatgagaaag   ggaaaaaaat   gttaaaagat   catggtgcag   aggttacacc   taatcaacaa   1860 ataacttta    aagcgctgaa   ttatactagc   ggggaaaaaa   aaatatctcc   tggaatatat   1920
aacgatcagg   ttatggttgg   ttactacgtc   aacgacaata   aacaaggaaa   ctggcaatat   1980
aaatctctgg   atgtaaatgt   aaatattgag   caaaatttta   ttccagatat   tgattccgct   2040
gttcgtataa   tacctgttaa   ttacgattcg   gacccgaaac   tggattcaca   gttatatacg   2100
gttgagatga   cgatccctgc   aggtgtaagc   gcagttaaaa   tcgcaccaac   agatagtctg   2160
acatcttctg   gacagcagat   cggaaagctg   gttaatgtaa   acaatccaga   tcaaaatatg   2220
aattattata   tcagaaagga   ttctggcgct   ggtaacttta   tggcaggaca   aaaaggatcc   2280
tttcctgtca   aagagaatac   gtcatacaca   ttctcagcaa   tttatactgg   tggcgaatac   2340
cctaatagcg   gatattcgtc   tggtacttat   gcaggaaatt   tgactgtatc   attttacagc   2400
aatgacaata   aacaaggcaa   ttggcagtac   aagagcctcg   acgtgaacgt   gaacatcgaa   2460
```
cagctcgagc accaccacca ccaccactga 2490

<210> SEQ ID NO 19
<211> LENGTH: 829
<212> TYPE: PRT
<213> ORGANISM: Escherichia coli

<400> SEQUENCE: 19

| Met | Asn | Lys | Ile | Leu | Phe | Ile | Phe | Thr | Leu | Phe | Phe | Ser | Ser | Gly | Phe |
|---|---|---|---|---|---|---|---|---|---|---|---|---|---|---|---|
| 1 | | | | 5 | | | | | 10 | | | | | 15 | |

| Phe | Thr | Phe | Ala | Val | Ser | Ala | Asp | Lys | Asn | Pro | Gly | Ser | Glu | Asn | Met |
|---|---|---|---|---|---|---|---|---|---|---|---|---|---|---|---|
| | | | 20 | | | | | 25 | | | | | 30 | | |

| Thr | Asn | Thr | Ile | Gly | Pro | His | Asp | Arg | Gly | Gly | Ser | Ser | Pro | Ile | Tyr |
|---|---|---|---|---|---|---|---|---|---|---|---|---|---|---|---|
| | | 35 | | | | | 40 | | | | | 45 | | | |

| Asn | Ile | Leu | Asn | Ser | Tyr | Leu | Thr | Ala | Tyr | Asn | Gly | Ser | His | His | Leu |
|---|---|---|---|---|---|---|---|---|---|---|---|---|---|---|---|
| | 50 | | | | | 55 | | | | | 60 | | | | |

| Tyr | Asp | Arg | Met | Ser | Phe | Leu | Cys | Leu | Ser | Ser | Gln | Asn | Thr | Leu | Asn |
|---|---|---|---|---|---|---|---|---|---|---|---|---|---|---|---|
| 65 | | | | | 70 | | | | | 75 | | | | | 80 |

| Gly | Ala | Cys | Pro | Ser | Ser | Asp | Ala | Pro | Gly | Thr | Ala | Thr | Ile | Asp | Gly |
|---|---|---|---|---|---|---|---|---|---|---|---|---|---|---|---|
| | | | | 85 | | | | | 90 | | | | | 95 | |

| Glu | Thr | Asn | Ile | Thr | Leu | Gln | Phe | Thr | Glu | Lys | Arg | Ser | Leu | Ile | Lys |
|---|---|---|---|---|---|---|---|---|---|---|---|---|---|---|---|
| | | | | 100 | | | | | 105 | | | | | 110 | |

| Arg | Glu | Leu | Gln | Ile | Lys | Gly | Tyr | Lys | Gln | Phe | Leu | Phe | Lys | Asn | Ala |
|---|---|---|---|---|---|---|---|---|---|---|---|---|---|---|---|
| | | 115 | | | | | 120 | | | | | 125 | | | |

| Asn | Cys | Pro | Ser | Lys | Leu | Ala | Leu | Asn | Ser | Ser | His | Phe | Gln | Cys | Asn |
|---|---|---|---|---|---|---|---|---|---|---|---|---|---|---|---|
| | 130 | | | | | 135 | | | | | 140 | | | | |

| Arg | Glu | Gln | Ala | Ser | Gly | Ala | Thr | Leu | Ser | Leu | Tyr | Ile | Pro | Ala | Gly |
|---|---|---|---|---|---|---|---|---|---|---|---|---|---|---|---|
| 145 | | | | | 150 | | | | | 155 | | | | | 160 |

| Glu | Leu | Asn | Lys | Leu | Pro | Phe | Gly | Gly | Val | Trp | Asn | Ala | Val | Leu | Lys |
|---|---|---|---|---|---|---|---|---|---|---|---|---|---|---|---|
| | | | | 165 | | | | | 170 | | | | | 175 | |

| Leu | Asn | Val | Lys | Arg | Arg | Tyr | Asp | Thr | Thr | Tyr | Gly | Thr | Tyr | Thr | Ile |
|---|---|---|---|---|---|---|---|---|---|---|---|---|---|---|---|
| | | | 180 | | | | | 185 | | | | | 190 | | |

| Asn | Ile | Thr | Val | Asn | Leu | Thr | Asp | Lys | Gly | Asn | Ile | Gln | Ile | Trp | Leu |
|---|---|---|---|---|---|---|---|---|---|---|---|---|---|---|---|
| | 195 | | | | | 200 | | | | | 205 | | | | |

| Pro | Gln | Phe | Lys | Ser | Asn | Ala | Arg | Val | Asp | Leu | Asn | Leu | Arg | Pro | Thr |
|---|---|---|---|---|---|---|---|---|---|---|---|---|---|---|---|
| 210 | | | | | 215 | | | | | 220 | | | | | |

| Gly | Gly | Gly | Thr | Tyr | Ile | Gly | Arg | Asn | Ser | Val | Asp | Met | Cys | Phe | Tyr |
|---|---|---|---|---|---|---|---|---|---|---|---|---|---|---|---|
| 225 | | | | | 230 | | | | | 235 | | | | | 240 |

| Asp | Gly | Tyr | Ser | Thr | Asn | Ser | Ser | Ser | Leu | Glu | Ile | Arg | Phe | Gln | Asp |
|---|---|---|---|---|---|---|---|---|---|---|---|---|---|---|---|
| | | | | 245 | | | | | 250 | | | | | 255 | |

| Asp | Asn | Ser | Lys | Ser | Asp | Gly | Lys | Phe | Tyr | Leu | Lys | Lys | Ile | Asn | Asp |
|---|---|---|---|---|---|---|---|---|---|---|---|---|---|---|---|
| | | | 260 | | | | | 265 | | | | | 270 | | |

| Asp | Ser | Lys | Glu | Leu | Val | Tyr | Thr | Leu | Ser | Leu | Leu | Leu | Ala | Gly | Lys |
|---|---|---|---|---|---|---|---|---|---|---|---|---|---|---|---|
| | 275 | | | | | 280 | | | | | 285 | | | | |

| Asn | Leu | Thr | Pro | Thr | Asn | Gly | Gln | Ala | Leu | Asn | Ile | Asn | Thr | Ala | Ser |
|---|---|---|---|---|---|---|---|---|---|---|---|---|---|---|---|
| 290 | | | | | 295 | | | | | 300 | | | | | |

| Leu | Glu | Thr | Asn | Trp | Asn | Arg | Ile | Thr | Ala | Val | Thr | Met | Pro | Glu | Ile |
|---|---|---|---|---|---|---|---|---|---|---|---|---|---|---|---|
| 305 | | | | | 310 | | | | | 315 | | | | | 320 |

| Ser | Val | Pro | Val | Leu | Cys | Trp | Pro | Gly | Arg | Leu | Gln | Leu | Asp | Ala | Lys |
|---|---|---|---|---|---|---|---|---|---|---|---|---|---|---|---|
| | | | | 325 | | | | | 330 | | | | | 335 | |

| Val | Lys | Asn | Pro | Glu | Ala | Gly | Gln | Tyr | Met | Gly | Asn | Ile | Lys | Ile | Thr |
|---|---|---|---|---|---|---|---|---|---|---|---|---|---|---|---|
| | | | 340 | | | | | 345 | | | | | 350 | | |

| Phe | Thr | Pro | Ser | Ser | Gln | Thr | Leu | Asp | Asn | Lys | Gln | Val | Glu | Lys | Asn |
|---|---|---|---|---|---|---|---|---|---|---|---|---|---|---|---|
| | | 355 | | | | | 360 | | | | | 365 | | | |

```
Ile Thr Val Thr Ala Ser Val Asp Pro Ala Ile Asp Leu Leu Gln Ala
370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
                420                 425                 430

Thr Asp Val Leu Asn Ser Thr Val Gln Met Pro Ile Ser Val Ser Trp
                435                 440                 445

Gly Gly Gln Val Leu Ser Thr Ala Lys Glu Phe Glu Ala Ala
450                 455                 460

Leu Gly Tyr Ser Ala Ser Gly Val Asn Gly Val Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
                500                 505                 510

Asn Lys Gln Val Glu Lys Asn Ile Thr Val Thr Ala Ser Val Asp Pro
                515                 520                 525

Ala Gly Ser Lys Ser Phe Phe Ala Pro Glu Pro Arg Ile Gln Pro Ser
530                 535                 540

Phe Gly Glu Asn Val Gly Lys Glu Gly Ala Leu Leu Phe Ser Val Asn
545                 550                 555                 560

Leu Thr Val Pro Glu Asn Val Ser Gln Val Thr Val Tyr Pro Val Tyr
                565                 570                 575

Asp Glu Asp Tyr Gly Leu Gly Arg Leu Val Asn Thr Ala Asp Ala Ser
                580                 585                 590

Gln Ser Ile Ile Tyr Gln Ile Val Asp Glu Lys Gly Lys Lys Met Leu
                595                 600                 605

Lys Asp His Gly Ala Glu Val Thr Pro Asn Gln Ile Thr Phe Lys
610                 615                 620

Ala Leu Asn Tyr Thr Ser Gly Glu Lys Lys Ile Ser Pro Gly Ile Tyr
625                 630                 635                 640

Asn Asp Gln Val Met Val Gly Tyr Tyr Val Asn Asp Asn Lys Gln Gly
                645                 650                 655

Asn Trp Gln Tyr Lys Ser Leu Asp Val Asn Val Asn Ile Glu Gln Asn
                660                 665                 670

Phe Ile Pro Asp Ile Asp Ser Ala Val Arg Ile Pro Val Asn Tyr
                675                 680                 685

Asp Ser Asp Pro Lys Leu Asp Ser Gln Leu Tyr Thr Val Glu Met Thr
690                 695                 700

Ile Pro Ala Gly Val Ser Ala Val Lys Ile Ala Pro Thr Asp Ser Leu
705                 710                 715                 720

Thr Ser Ser Gly Gln Gln Ile Gly Lys Leu Val Asn Val Asn Asn Pro
                725                 730                 735

Asp Gln Asn Met Asn Tyr Tyr Ile Arg Lys Asp Ser Gly Ala Gly Asn
                740                 745                 750

Phe Met Ala Gly Gln Lys Gly Ser Phe Pro Val Lys Glu Asn Thr Ser
                755                 760                 765

Tyr Thr Phe Ser Ala Ile Tyr Thr Gly Gly Glu Tyr Pro Asn Ser Gly
                770                 775                 780

Tyr Ser Ser Gly Thr Tyr Ala Gly Asn Leu Thr Val Ser Phe Tyr Ser
```

| 785 | 790 | 795 | 800 |

Asn Asp Asn Lys Gln Gly Asn Trp Gln Tyr Lys Ser Leu Asp Val Asn
                 805                      810                   815

Val Asn Ile Glu Gln Leu Glu His His His His His His
                 820                      825

<210> SEQ ID NO 20
<211> LENGTH: 3405
<212> TYPE: DNA
<213> ORGANISM: Escherichia coli

<400> SEQUENCE: 20

```
atgaataaaa ttttatttat ttttacattg ttttttttctt cagggttttt tacatttgcc    60
gtatcggcag ataaaaatcc cggaagtgaa acatgactaa atactattgg tccccatgac   120
aggggggggat cttcccccat atataatatc ttaaattcct atcttacagc atacaatgga   180
agccatcatc tgtatgatag gatgagtttt ttatgtttgt cttctcaaaa tacactgaat   240
ggagcatgcc caagcagtga tgcccctggc actgctacaa ttgatggcga acaaatata    300
acattacaat ttacggaaaa agaagtctaa attaaagag aactgcaaat taaaggctat    360
aaacaatttt tgttcaaaaa tgctaattgc ccatctaaac tagcacttaa ctcatctcat    420
tttcaatgta atagagaaca agcttcaggt gctactttat cgttatacat accagctggt    480
gaattaaata aattaccttt tgggggggtc tggaatgccg ttctgaagct aaatgtaaaa    540
agacgatatg atacaaccta tgggacttac actataaaca tcacagttaa tttaactgat    600
aagggaaata ttcagatatg gttaccacag ttcaaaagta acgctcgtgt cgatcttaac    660
ttgcgtccaa ctggtggtgg tacatatatc ggaagaaatt ctgttgatat gtgcttttat    720
gatggatata gtactaacag cagctcttta gagataagtt tcaggatga taattctaaa    780
tctgatggaa aattttatct aaagaaaata aatgatgact ccaagaact tgtatacact    840
ttgtcacttc tcctggcagg taaaaattta acaccaacaa atggacaggc attaaatatt    900
aacactgctt ctctggaaac aaactggaat agaattacag ctgtcaccat gccagaaatc    960
agtgttccgg tgttgtgttg gcctggacgt ttgcaattgg atgcaaaagt gaaaaatccc   1020
gaggctggac aatatatggg gaatattaaa attactttca caccaagtag tcaaacactc   1080
gacaataaac aagtagagaa aaatattact gtaacagcta gtgttgatcc tgcaattgat   1140
cttttgcaag ctgatggcaa tgctctgcca tcagctgtaa agttagctta ttctcccgca   1200
tcaaaaactt tgaaagtta cagagtaatg actcaagttc atacaaacga tgcaactaaa   1260
aaagtaattg ttaaacttgc tgatacacca cagcttacag atgttctgaa ttcaactgtt   1320
caaatgccta tcagtgtgtc atggggagga caagtattat ctacaacagc caagaatttt   1380
gaagctgctg ctttgggata ttctgcatcc ggtgtaaatg gcgtatcatc ttctcaagag   1440
ttagtaatta gcgctgcacc taaaactgcc ggtaccgccc caactgcagg aaactattca   1500
ggagtagtat ctcttgtaat gactttggga tccgacaata acaagtaga gaaaaatatt   1560
actgtaacag ctagtgtcga ccctactatt gatattcttc aagcaaatgg ttctgcgcta   1620
ccgacagctg tagatttaac ttatctacct ggtgcaaaaa cttttgaaaa ttacagtgtt   1680
ctaacccaga tttacacaaa tgacccttca aaaggtttag atgttcgact ggttgataca   1740
ccgaaactta caaatatttt gcaaccgaca tctaccattc ctcttactgt ctcatgggca   1800
gggaagacat taagtacaag tgctcagaag attgcagttg gcgatctggg ttttggttcc   1860
accggaacgg caggtgtttc gaatagtaaa gaattagtaa ttggagcaac tacatccgga   1920
```

```
actgcaccaa gtgcaggtaa gtatcaaggc gtcgtttcca ttgtaatgac tcaatcgacc   1980
gacacagccg cgcctgttcc tgacaataaa caagtagaga aaatattac tgtgacagcc    2040 agtgttgatc ctactattga cattttgcaa gctgatggta gtagtttacc tactgctgta   2100
gaattaacct attcacctgc ggcaagtcgt tttgaaaatt ataaaatcgc aactaaagtt   2160
catacaaatg ttataaataa aaatgtacta gttaagcttg taaatgatcc aaaacttaca   2220
aatgttttgg attctacaaa acaactcccc attactgtat catatggagg aaagactcta   2280
tcaaccgcag atgtgacttt tgaacctgca gaattaaatt ttggaacgtc aggtgtaact   2340
ggtgtatctt cttcccaaga tttagtgatt ggtgcgacta cagcacaagc accaacggcg   2400
ggaaattata gtggggtcgt ttctatctta atgaccttag catcagacaa taaacaagtg   2460
gaaaaaaata tcactgtaac agctagtgtt gatcctacgg gcgagcaaaa ttttattcca   2520
gatattgatt ccgctgttcg tataatacct gttaattacg attcggatcc gaaactgaat   2580
tcacagttat atacggttga gatgacgatc cctgcaggtg taagcgcagt taaaatcgta   2640
ccaacagata gtctgacatc ttctggacag cagatcggaa agctggttaa tgtaaacaat   2700
ccagatcaaa atatgaatta ttatatcaga aaggattctg cgctggtaa gtttatggca    2760 gggcaaaaag gatccttttc tgtcaaagag aatacgtcat acacattctc agcaatttat   2820
actggtggcg ataccctaa tagcggatat tcgtctggta cttatgcagg acatttgact    2880
gtatcatttt acagcaatga caataaacaa agaacagaaa tagcgactaa aaacttccca   2940
gtatcaacga ctatttcaaa aagttttttt gcgcctgaac cacaaatcca gccttctttt   3000
ggtaaaaatg ttggaaagga aggagattta ttatttagtg tgagcttaat tgttcctgaa   3060
aatgtatccc aggtaacggt ctaccctgtt tatgatgaag attatggatt aggacgactc   3120
gtaaataccg ctgatgattc ccaatcaata atctaccaga ttgttgatga taagggaaa    3180 aaaatgttaa aagatcatgg tacagaggtt acgcctaatc aacaaataac ttttaaagcg   3240
ctgaattata ctagcggaga taagaaaata cctcctggga tatataacga tcaggttatg   3300
gttggttact acgtaaacga caataaacaa ggaaactggc aatataaatc tctggatgta   3360
aatgtaaata ttgagcaact cgagcaccac caccaccacc actga                  3405
```

<210> SEQ ID NO 21
<211> LENGTH: 1134
<212> TYPE: PRT
<213> ORGANISM: Escherichia coli

<400> SEQUENCE: 21

```
Met Asn Lys Ile Leu Phe Ile Phe Thr Leu Phe Phe Ser Ser Gly Phe
 1               5                  10                  15

Phe Thr Phe Ala Val Ser Ala Asp Lys Asn Pro Gly Ser Glu Asn Met
             20                  25                  30

Thr Asn Thr Ile Gly Pro His Asp Arg Gly Gly Ser Ser Pro Ile Tyr
         35                  40                  45

Asn Ile Leu Asn Ser Tyr Leu Thr Ala Tyr Asn Gly Ser His His Leu
     50                  55                  60

Tyr Asp Arg Met Ser Phe Leu Cys Leu Ser Ser Gln Asn Thr Leu Asn
 65                  70                  75                  80

Gly Ala Cys Pro Ser Ser Asp Ala Pro Gly Thr Ala Thr Ile Asp Gly
                 85                  90                  95

Glu Thr Asn Ile Thr Leu Gln Phe Thr Glu Lys Arg Ser Leu Ile Lys
            100                 105                 110
```

```
Arg Glu Leu Gln Ile Lys Gly Tyr Lys Gln Phe Leu Phe Lys Asn Ala
            115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
                180                 185                 190

Asn Ile Thr Val Asn Leu Thr Asp Lys Gly Asn Ile Gln Ile Trp Leu
            195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
    355                 360                 365

Ile Thr Val Thr Ala Ser Val Asp Pro Ala Ile Asp Leu Leu Gln Ala
        370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
    435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
                500                 505                 510

Asn Lys Gln Val Glu Lys Asn Ile Thr Val Thr Ala Ser Val Asp Pro
        515                 520                 525
```

```
Thr Ile Asp Ile Leu Gln Ala Asn Gly Ser Ala Leu Pro Thr Ala Val
        530                 535                 540

Asp Leu Thr Tyr Leu Pro Gly Ala Lys Thr Phe Glu Asn Tyr Ser Val
545                 550                 555                 560

Leu Thr Gln Ile Tyr Thr Asn Asp Pro Ser Lys Gly Leu Asp Val Arg
                565                 570                 575

Leu Val Asp Thr Pro Lys Leu Thr Asn Ile Leu Gln Pro Thr Ser Thr
            580                 585                 590

Ile Pro Leu Thr Val Ser Trp Ala Gly Lys Thr Leu Ser Thr Ser Ala
        595                 600                 605

Gln Lys Ile Ala Val Gly Asp Leu Gly Phe Gly Ser Thr Gly Thr Ala
610                 615                 620

Gly Val Ser Asn Ser Lys Glu Leu Val Ile Gly Ala Thr Thr Ser Gly
625                 630                 635                 640

Thr Ala Pro Ser Ala Gly Lys Tyr Gln Gly Val Val Ser Ile Val Met
                645                 650                 655

Thr Gln Ser Thr Asp Thr Ala Ala Pro Val Pro Asp Asn Lys Gln Val
            660                 665                 670

Glu Lys Asn Ile Thr Val Thr Ala Ser Val Asp Pro Thr Ile Asp Ile
        675                 680                 685

Leu Gln Ala Asp Gly Ser Ser Leu Pro Thr Ala Val Glu Leu Thr Tyr
690                 695                 700

Ser Pro Ala Ala Ser Arg Phe Glu Asn Tyr Lys Ile Ala Thr Lys Val
705                 710                 715                 720

His Thr Asn Val Ile Asn Lys Asn Val Leu Val Lys Leu Val Asn Asp
                725                 730                 735

Pro Lys Leu Thr Asn Val Leu Asp Ser Thr Lys Gln Leu Pro Ile Thr
            740                 745                 750

Val Ser Tyr Gly Gly Lys Thr Leu Ser Thr Ala Asp Val Thr Phe Glu
        755                 760                 765

Pro Ala Glu Leu Asn Phe Gly Thr Ser Gly Val Thr Gly Val Ser Ser
770                 775                 780

Ser Gln Asp Leu Val Ile Gly Ala Thr Thr Ala Gln Ala Pro Thr Ala
785                 790                 795                 800

Gly Asn Tyr Ser Gly Val Val Ser Ile Leu Met Thr Leu Ala Ser Asp
                805                 810                 815

Asn Lys Gln Val Glu Lys Asn Ile Thr Val Thr Ala Ser Val Asp Pro
            820                 825                 830

Thr Gly Glu Gln Asn Phe Ile Pro Asp Ile Asp Ser Ala Val Arg Ile
        835                 840                 845

Ile Pro Val Asn Tyr Asp Ser Asp Pro Lys Leu Asn Ser Gln Leu Tyr
850                 855                 860

Thr Val Glu Met Thr Ile Pro Ala Gly Val Ser Ala Val Lys Ile Val
865                 870                 875                 880

Pro Thr Asp Ser Leu Thr Ser Ser Gly Gln Gln Ile Gly Lys Leu Val
                885                 890                 895

Asn Val Asn Asn Pro Asp Gln Asn Met Asn Tyr Tyr Ile Arg Lys Asp
            900                 905                 910

Ser Gly Ala Gly Lys Phe Met Ala Gly Gln Lys Gly Ser Phe Ser Val
        915                 920                 925

Lys Glu Asn Thr Ser Tyr Thr Phe Ser Ala Ile Tyr Thr Gly Gly Glu
930                 935                 940

Tyr Pro Asn Ser Gly Tyr Ser Ser Gly Thr Tyr Ala Gly His Leu Thr
```

```
                945            950            955            960
Val Ser Phe Tyr Ser Asn Asp Asn Lys Gln Arg Thr Glu Ile Ala Thr
                    965            970            975
Lys Asn Phe Pro Val Ser Thr Thr Ile Ser Lys Ser Phe Phe Ala Pro
                    980            985            990
Glu Pro Gln Ile Gln Pro Ser Phe Gly Lys Asn Val Gly Lys Glu Gly
                    995            1000           1005
Asp Leu Leu Phe Ser Val Ser Leu Ile Val Pro Glu Asn Val Ser
                    1010           1015           1020
Gln Val Thr Val Tyr Pro Val Tyr Asp Glu Asp Tyr Gly Leu Gly
                    1025           1030           1035
Arg Leu Val Asn Thr Ala Asp Asp Ser Gln Ser Ile Ile Tyr Gln
                    1040           1045           1050
Ile Val Asp Asp Lys Gly Lys Lys Met Leu Lys Asp His Gly Thr
                    1055           1060           1065
Glu Val Thr Pro Asn Gln Gln Ile Thr Phe Lys Ala Leu Asn Tyr
                    1070           1075           1080
Thr Ser Gly Asp Lys Glu Ile Pro Pro Gly Ile Tyr Asn Asp Gln
                    1085           1090           1095
Val Met Val Gly Tyr Tyr Val Asn Asp Asn Lys Gln Gly Asn Trp
                    1100           1105           1110
Gln Tyr Lys Ser Leu Asp Val Asn Val Asn Ile Glu Gln Leu Glu
                    1115           1120           1125
His His His His His His
    1130

<210> SEQ ID NO 22
<211> LENGTH: 3342
<212> TYPE: DNA
<213> ORGANISM: Escherichia coli

<400> SEQUENCE: 22
atggcagata aaaatcccgg aagtgaaaac atgactaata ctattggtcc ccatgacagg    60
ggggatcttt cccccatata taatatctta aattcctatc ttacagcata caatggaagc   120
catcatctgt atgataggat gagttttttta tgtttgtctt ctcaaaatac actgaatgga   180
gcatgcccaa gcagtgatgc ccctggcact gctacaattg atggcgaaac aaatataaca   240
ttacaattta cggaaaaaag aagtctaatt aaaagagaac tgcaaattaa aggctataaa   300
caattttttgt tcaaaaatgc taattgccca tctaaactag cacttaactc atctcatttt   360
caatgtaata gagaacaagc ttcaggtgct actttatcgt tatacatacc agctggtgaa   420
ttaaataaat taccttttgg ggggtctgg aatgccgttc tgaagctaaa tgtaaaaaga   480
cgatatgata caacctatgg gacttacact ataaacatca cagttaattt aactgataag   540
ggaaatattc agatatggtt accacagttc aaaagtaacg ctcgtgtcga tcttaacttg   600
cgtccaactg gtggtggtac atatatcgga agaaattctg ttgatatgtg cttttatgat   660
ggatatagta ctaacagcag ctcttttagag ataagatttc aggatgataa ttctaaatct   720
gatggaaaat tttatctaaa gaaataaat gatgactcca agaacttgt atacactttg   780
tcacttctcc tggcaggtaa aaatttaaca ccaacaaatg gacaggcatt aaatattaac   840
actgcttctc tggaaacaaa ctggaataga attcagcgtg tcaccatgcc agaaatcagt   900
gttccggtgt tgtgttggcc tggacgtttg caattggatg caaaagtgaa aaatcccgag   960
gctggacaat atatggggaa tattaaaatt actttcacac caagtagtca aacactcgac  1020
```

```
aataaacaag tagagaaaaa tattactgta acagctagtg ttgatcctgc aattgatctt   1080
ttgcaagctg atggcaatgc tctgccatca gctgtaaagt tagcttattc tcccgcatca   1140
aaaacttttg aaagttacag agtaatgact caagttcata caaacgatgc aactaaaaaa   1200
gtaattgtta aacttgctga tacaccacag cttacagatg ttctgaattc aactgttcaa   1260
atgcctatca gtgtgtcatg gggaggacaa gtattatcta caacagccaa agaatttgaa   1320
gctgctgctt tgggatattc tgcatccggt gtaaatggcg tatcatcttc tcaagagtta   1380
gtaattagcg ctgcacctaa aactgccggt accgccccaa ctgcaggaaa ctattcagga   1440
gtagtatctc ttgtaatgac tttgggatcc gacaataaac aagtagagaa aaatattact   1500
gtaacagcta gtgtcgaccc tactattgat attcttcaag caaatggttc tgcgctaccg   1560
acagctgtag atttaactta tctacctggt gcaaaaactt ttgaaaatta cagtgttcta   1620
acccagattt acacaaatga cccttcaaaa ggtttagatg ttcgactggt tgatacaccg   1680
aaacttacaa atattttgca accgacatct accattcctc ttactgtctc atgggcaggg   1740
aagacattaa gtacaagtgc tcagaagatt gcagttggcg atctgggttt tggttccacc   1800
ggaacggcag gtgtttcgaa tagtaaagaa ttagtaattg gagcaactac atccggaact   1860
gcaccaagtg caggtaagta tcaaggcgtc gttcccattg taatgactca atcgaccgac   1920
acagccgcgc ctgttcctga caataaacaa gtagagaaaa atattactgt gacagccagt   1980
gttgatccta ctattgacat tttgcaagct gatggtagta gtttacctac tgctgtagaa   2040
ttaacctatt cacctgcggc aagtcgtttt gaaaattata aaatcgcaac taaagttcat   2100
acaaatgtta taaataaaaa tgtactagtt aagcttgtaa atgatccaaa acttacaaat   2160
gttttggatt ctacaaaaca actccccatt actgtatcat atggaggaaa gactctatca   2220
accgcagatg tgacttttga acctgcagaa ttaaattttg gaacgtcagg tgtaactggt   2280
gtatcttctt cccaagattt agtgattggt gcgactacag cacaagcacc aacggcggga   2340
aattatagtg gggtcgtttc tatcttaatg accttagcat cagacaataa acaagtggaa   2400
aaaaatatca ctgtaacagc tagtgttgat cctacgggcg agcaaaattt tattccagat   2460
attgattccg ctgttcgtat aatacctgtt aattacgatt cggatccgaa actgaattca   2520
cagttatata cggttgagat gacgatccct gcaggtgtaa gcgcagttaa atcgtacca   2580
acagatagtc tgacatcttc tggacagcag atcggaaagc tggttaatgt aaacaatcca   2640
gatcaaaata tgaattatta tatcagaaag gattctggcg ctggtaagtt tatggcaggg   2700
caaaaaggat cctttctgt caaagagaat acgtcataca cattctcagc aatttatact   2760
ggtggcgaat accctaatag cggatattcg tctggtactt atgcaggaca tttgactgta   2820
tcattttaca gcaatgacaa taaacaaaga acagaaatag cgactaaaaa cttcccagta   2880
tcaacgacta tttcaaaaag ttttttttgcg cctgaaccac aaatccagcc ttcttttggt   2940
aaaaatgttg gaaaggaagg agatttatta tttagtgtga gcttaattgt tcctgaaaat   3000
gtatcccagg taacggtcta ccctgtttat gatgaagatt atggattagg acgactcgta   3060
aataccgctg atgattccca atcaataatc taccagattg ttgatgataa agggaaaaaa   3120
atgttaaaag atcatggtac agaggttacg cctaatcaac aaataacttt taagcgctg   3180
aattatacta gcggagataa agaaataccct cctgggatat ataacgatca ggttatggtt   3240
ggttactacg taaacgacaa taacaagga aactggcaat ataaatctct ggatgtaaat   3300
gtaaatattg agcaactcga gcaccaccac caccaccact ga                      3342
```

<210> SEQ ID NO 23
<211> LENGTH: 1113
<212> TYPE: PRT
<213> ORGANISM: Escherichia coli

<400> SEQUENCE: 23

```
Met Ala Asp Lys Asn Pro Gly Ser Glu Asn Met Thr Asn Thr Ile Gly
  1               5                  10                  15

Pro His Asp Arg Gly Gly Ser Ser Pro Ile Tyr Asn Ile Leu Asn Ser
             20                  25                  30

Tyr Leu Thr Ala Tyr Asn Gly Ser His His Leu Tyr Asp Arg Met Ser
         35                  40                  45

Phe Leu Cys Leu Ser Ser Gln Asn Thr Leu Asn Gly Ala Cys Pro Ser
 50                  55                  60

Ser Asp Ala Pro Gly Thr Ala Thr Ile Asp Gly Glu Thr Asn Ile Thr
 65                  70                  75                  80

Leu Gln Phe Thr Glu Lys Arg Ser Leu Ile Lys Arg Glu Leu Gln Ile
                 85                  90                  95

Lys Gly Tyr Lys Gln Phe Leu Phe Lys Asn Ala Asn Cys Pro Ser Lys
            100                 105                 110

Leu Ala Leu Asn Ser Ser His Phe Gln Cys Asn Arg Glu Gln Ala Ser
        115                 120                 125

Gly Ala Thr Leu Ser Leu Tyr Ile Pro Ala Gly Glu Leu Asn Lys Leu
130                 135                 140

Pro Phe Gly Gly Val Trp Asn Ala Val Leu Lys Leu Asn Val Lys Arg
145                 150                 155                 160

Arg Tyr Asp Thr Thr Tyr Gly Thr Tyr Thr Ile Asn Ile Thr Val Asn
                165                 170                 175

Leu Thr Asp Lys Gly Asn Ile Gln Ile Trp Leu Pro Gln Phe Lys Ser
            180                 185                 190

Asn Ala Arg Val Asp Leu Asn Leu Arg Pro Thr Gly Gly Gly Thr Tyr
        195                 200                 205

Ile Gly Arg Asn Ser Val Asp Met Cys Phe Tyr Asp Gly Tyr Ser Thr
210                 215                 220

Asn Ser Ser Ser Leu Glu Ile Arg Phe Gln Asp Asn Ser Lys Ser
225                 230                 235                 240

Asp Gly Lys Phe Tyr Leu Lys Lys Ile Asn Asp Ser Lys Glu Leu
                245                 250                 255

Val Tyr Thr Leu Ser Leu Leu Leu Ala Gly Lys Asn Leu Thr Pro Thr
            260                 265                 270

Asn Gly Gln Ala Leu Asn Ile Asn Thr Ala Ser Leu Glu Thr Asn Trp
        275                 280                 285

Asn Arg Ile Thr Ala Val Thr Met Pro Glu Ile Ser Val Pro Val Leu
290                 295                 300

Cys Trp Pro Gly Arg Leu Gln Leu Asp Ala Lys Val Lys Asn Pro Glu
305                 310                 315                 320

Ala Gly Gln Tyr Met Gly Asn Ile Lys Ile Thr Phe Thr Pro Ser Ser
                325                 330                 335

Gln Thr Leu Asp Asn Lys Gln Val Glu Lys Asn Ile Val Thr Ala
            340                 345                 350

Ser Val Asp Pro Ala Ile Asp Leu Leu Gln Ala Asp Gly Asn Ala Leu
        355                 360                 365

Pro Ser Ala Val Lys Leu Ala Tyr Ser Pro Ala Ser Lys Thr Phe Glu
            370                 375                 380
```

```
Ser Tyr Arg Val Met Thr Gln Val His Thr Asn Asp Ala Thr Lys Lys
385                 390                 395                 400

Val Ile Val Lys Leu Ala Asp Thr Pro Gln Leu Thr Asp Val Leu Asn
                405                 410                 415

Ser Thr Val Gln Met Pro Ile Ser Val Ser Trp Gly Gly Gln Val Leu
            420                 425                 430

Ser Thr Thr Ala Lys Glu Phe Glu Ala Ala Leu Gly Tyr Ser Ala
        435                 440                 445

Ser Gly Val Asn Gly Val Ser Ser Gln Glu Leu Val Ile Ser Ala
    450                 455                 460

Ala Pro Lys Thr Ala Gly Thr Ala Pro Thr Ala Gly Asn Tyr Ser Gly
465                 470                 475                 480

Val Val Ser Leu Val Met Thr Leu Gly Ser Asp Asn Lys Gln Val Glu
                485                 490                 495

Lys Asn Ile Thr Val Thr Ala Ser Val Asp Pro Thr Ile Asp Ile Leu
            500                 505                 510

Gln Ala Asn Gly Ser Ala Leu Pro Thr Ala Val Asp Leu Thr Tyr Leu
        515                 520                 525

Pro Gly Ala Lys Thr Phe Glu Asn Tyr Ser Val Leu Thr Gln Ile Tyr
530                 535                 540

Thr Asn Asp Pro Ser Lys Gly Leu Asp Val Arg Leu Val Asp Thr Pro
545                 550                 555                 560

Lys Leu Thr Asn Ile Leu Gln Pro Thr Ser Ile Pro Leu Thr Val
                565                 570                 575

Ser Trp Ala Gly Lys Thr Leu Ser Thr Ser Ala Gln Lys Ile Ala Val
            580                 585                 590

Gly Asp Leu Gly Phe Gly Ser Thr Gly Thr Ala Gly Val Ser Asn Ser
            595                 600                 605

Lys Glu Leu Val Ile Gly Ala Thr Thr Ser Gly Thr Ala Pro Ser Ala
        610                 615                 620

Gly Lys Tyr Gln Gly Val Val Ser Ile Val Met Thr Gln Ser Thr Asp
625                 630                 635                 640

Thr Ala Ala Pro Val Pro Asp Asn Lys Gln Val Glu Lys Asn Ile Thr
                645                 650                 655

Val Thr Ala Ser Val Asp Pro Thr Ile Asp Ile Leu Gln Ala Asp Gly
            660                 665                 670

Ser Ser Leu Pro Thr Ala Val Glu Leu Thr Tyr Ser Pro Ala Ala Ser
        675                 680                 685

Arg Phe Glu Asn Tyr Lys Ile Ala Thr Lys Val His Thr Asn Val Ile
        690                 695                 700

Asn Lys Asn Val Leu Val Lys Leu Val Asn Asp Pro Lys Leu Thr Asn
705                 710                 715                 720

Val Leu Asp Ser Thr Lys Gln Leu Pro Ile Thr Val Ser Tyr Gly Gly
                725                 730                 735

Lys Thr Leu Ser Thr Ala Asp Val Thr Phe Glu Pro Ala Glu Leu Asn
            740                 745                 750

Phe Gly Thr Ser Gly Val Thr Gly Val Ser Ser Gln Asp Leu Val
        755                 760                 765

Ile Gly Ala Thr Thr Ala Gln Ala Pro Thr Ala Gly Asn Tyr Ser Gly
        770                 775                 780

Val Val Ser Ile Leu Met Thr Leu Ala Ser Asp Asn Lys Gln Val Glu
785                 790                 795                 800
```

Lys Asn Ile Thr Val Thr Ala Ser Val Asp Pro Thr Gly Glu Gln Asn
            805                 810                 815

Phe Ile Pro Asp Ile Asp Ser Ala Val Arg Ile Ile Pro Val Asn Tyr
            820                 825                 830

Asp Ser Asp Pro Lys Leu Asn Ser Gln Leu Tyr Thr Val Glu Met Thr
            835                 840                 845

Ile Pro Ala Gly Val Ser Ala Val Lys Ile Val Pro Thr Asp Ser Leu
            850                 855                 860

Thr Ser Ser Gly Gln Gln Ile Gly Lys Leu Val Asn Val Asn Asn Pro
865                 870                 875                 880

Asp Gln Asn Met Asn Tyr Tyr Ile Arg Lys Asp Ser Gly Ala Gly Lys
            885                 890                 895

Phe Met Ala Gly Gln Lys Gly Ser Phe Ser Val Lys Glu Asn Thr Ser
            900                 905                 910

Tyr Thr Phe Ser Ala Ile Tyr Thr Gly Gly Glu Tyr Pro Asn Ser Gly
            915                 920                 925

Tyr Ser Ser Gly Thr Tyr Ala Gly His Leu Thr Val Ser Phe Tyr Ser
            930                 935                 940

Asn Asp Asn Lys Gln Arg Thr Glu Ile Ala Thr Lys Asn Phe Pro Val
945                 950                 955                 960

Ser Thr Thr Ile Ser Lys Ser Phe Phe Ala Pro Glu Pro Gln Ile Gln
            965                 970                 975

Pro Ser Phe Gly Lys Asn Val Gly Lys Glu Gly Asp Leu Leu Phe Ser
            980                 985                 990

Val Ser Leu Ile Val Pro Glu Asn Val Ser Gln Val Thr Val Tyr Pro
            995                 1000                1005

Val Tyr Asp Glu Asp Tyr Gly Leu Gly Arg Leu Val Asn Thr Ala
            1010                1015                1020

Asp Asp Ser Gln Ser Ile Ile Tyr Gln Ile Val Asp Asp Lys Gly
            1025                1030                1035

Lys Lys Met Leu Lys Asp His Gly Thr Glu Val Thr Pro Asn Gln
            1040                1045                1050

Gln Ile Thr Phe Lys Ala Leu Asn Tyr Thr Ser Gly Asp Lys Glu
            1055                1060                1065

Ile Pro Pro Gly Ile Tyr Asn Asp Gln Val Met Val Gly Tyr Tyr
            1070                1075                1080

Val Asn Asp Asn Lys Gln Gly Asn Trp Gln Tyr Lys Ser Leu Asp
            1085                1090                1095

Val Asn Val Asn Ile Glu Gln Leu Glu His His His His His His
            1100                1105                1110

<210> SEQ ID NO 24
<211> LENGTH: 2943
<212> TYPE: DNA
<213> ORGANISM: Escherichia coli

<400> SEQUENCE: 24
atgaaaaaga tatttatttt tttgtctatc atattttctg cggtggtcag tgccgggcga      60
tacccggaaa ctacagtagg taatctgacg aagagttttc aagcccctcg tcaggataga     120
agcgtacaat caccaatata taacatcttt acgaatcatg tggctggata tagtttgagt     180
cataacttat atgacaggat tgttttttta tgtacatcct cgtcgaatcc ggttaatggt     240
gcttgcccaa ccattggaac atctggagtt caatacggta ctacaaccat aaccttgcag     300
tttacagaaa aaagaagtct gataaaaaga aatattaatc ttgcaggtaa taagaaacca     360

```
atatgggaga atcagagttg cgacactagc aatctaatgg tgttgaattc gaagtcttgg    420
tcctgtgggg cttacggaaa tgctaacgga acacttctaa atctgtatat ccctgcagga    480
gaaatcaaca aattgccttt tggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720
tgtttctatg atggatatag tacaaacagt gatagcatgg taataaagtt ccaggatgat    780
aatcctacct attcatctga atataatctt tataagatag ggggcactga aaaattaccc    840
tatgctgttt cactgcttat gggagaaaaa atattttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttag gcggtggagt cgaaaaaaat attactgtga gggcaagtgt tgaccctaaa   1140
cttgatcttc tgcaagcaga tggaacttca ctgccggact ctatcgcatt aacctattct   1200
tcggcttcaa ataattttga agtttactct cttaatactg ctattcatac aaatgacaaa   1260
agcaagggag ttgtagtgaa gctgtcagct tcaccagttc tgtccaatat tatgaagcca   1320
aactcgcaaa ttccgatgaa agtgactttg gggggaaga cgctgaatac aactgatact   1380
gagtttactg ttgatactct gaactttggt acatctggtg ttgaaaacgt ttcttccact   1440
caacagctta cgattcatgc agacacacaa ggaactgcgc ctgaggcagg caattaccaa   1500
ggtattattt ctcttatcat gactcaaaaa acagggggcg tgtcgaaaa aaatattact   1560 gtgagggcaa gtgtcgaccc taaacttgac cttctgcaat ctgatggctc tgcgctgccg   1620
aactctgtcg cattaaccta ttctccggct gtaaataatt ttgaagctca caccatcaac   1680
accgttgttc atacaaatga ctcagataaa ggtgttgttg tgaagctgtc agcagatcca   1740
gtcctgtcca atgttctgaa tccaacccctg caaattcctg tttctgtgaa tttcgcagga   1800
aaaccactga gcacaacagg cattaccatc gactccaatg atctgaactt tgcttcgagt   1860
ggtgttaata agtttcttc tacgcagaaa ctttcaatcc atgcagatgc tactcgggta   1920
actggcggcg cactaacagc tggtcaatat cagggactcg tatcaattat cctgactaag   1980
tcaacggggg gcggtgtcga gaagaccatt agcgttacgg cgagtgttga cccgacgggc   2040
gagcaaaatt ttattccaga tattgattcc gctgttcgta taatacctgt taattacgat   2100
tcggatccga aactgaattc acagttatat acggttgaga tgacgatccc tgcaggtgta   2160
agcgcagtta aaatcgtacc aacagatagt ctgacatctt ctggacagca gatcggaaag   2220
ctggttaatg taaacaatcc agatcaaaat atgaattatt atatcagaaa ggattctggc   2280
gctggtaagt ttatggcagg gcaaaaagga tcctttttctg tcaaagagaa tacgtcatac   2340
acattctcag caatttatac tggtggcgaa tacccctaata gcggatattc gtctggtact   2400
tatgcaggac atttgactgt atcatttttac agcaatgaca ataaacaaag aacagaaata   2460
gcgactaaaa acttcccagt atcaacgact atttcaaaaa gttttttttgc gcctgaacca   2520 caaatccagc cttcttttgg taaaaatgtt ggaaaggaag gagatttatt atttagtgtg   2580
agcttaattg ttcctgaaaa tgtatcccag gtaacggtct accctgttta tgatgaagat   2640
tatggattag gacgactcgt aaataccgct gatgattccc aatcaataat ctaccagatt   2700
```

```
gttgatgata aagggaaaaa aatgttaaaa gatcatggta cagaggttac gcctaatcaa    2760
caaataactt ttaaagcgct gaattatact agcggagata agaaatacc tcctgggata     2820 tataacgatc aggttatggt tggttactac gtaaacgaca ataaacaagg aaactggcaa    2880
tataaatctc tggatgtaaa tgtaaatatt gagcaactcg agcaccacca ccaccaccac    2940
tga                                                                  2943
```

```
<210> SEQ ID NO 25
<211> LENGTH: 980
<212> TYPE: PRT
<213> ORGANISM: Escherichia coli

<400> SEQUENCE: 25
```

| | | | | | | | | | | | | | | | |
|---|---|---|---|---|---|---|---|---|---|---|---|---|---|---|---|
| Met | Lys | Lys | Ile | Phe | Ile | Phe | Leu | Ser | Ile | Ile | Phe | Ser | Ala | Val | Val |
| 1 | | | | 5 | | | | | 10 | | | | | 15 | |
| Ser | Ala | Gly | Arg | Tyr | Pro | Glu | Thr | Thr | Val | Gly | Asn | Leu | Thr | Lys | Ser |
| | | | 20 | | | | | 25 | | | | | 30 | | |
| Phe | Gln | Ala | Pro | Arg | Gln | Asp | Arg | Ser | Val | Gln | Ser | Pro | Ile | Tyr | Asn |
| | | 35 | | | | | 40 | | | | | 45 | | | |
| Ile | Phe | Thr | Asn | His | Val | Ala | Gly | Tyr | Ser | Leu | Ser | His | Asn | Leu | Tyr |
| | 50 | | | | | 55 | | | | | 60 | | | | |
| Asp | Arg | Ile | Val | Phe | Leu | Cys | Thr | Ser | Ser | Asn | Pro | Val | Asn | Gly | |
| 65 | | | | | 70 | | | | | 75 | | | | | 80 |
| Ala | Cys | Pro | Thr | Ile | Gly | Thr | Ser | Gly | Val | Gln | Tyr | Gly | Thr | Thr | Thr |
| | | | | 85 | | | | | 90 | | | | | 95 | |
| Ile | Thr | Leu | Gln | Phe | Thr | Glu | Lys | Arg | Ser | Leu | Ile | Lys | Arg | Asn | Ile |
| | | | 100 | | | | | 105 | | | | | 110 | | |
| Asn | Leu | Ala | Gly | Asn | Lys | Lys | Pro | Ile | Trp | Glu | Asn | Gln | Ser | Cys | Asp |
| | | 115 | | | | | 120 | | | | | 125 | | | |
| Thr | Ser | Asn | Leu | Met | Val | Leu | Asn | Ser | Lys | Ser | Trp | Ser | Cys | Gly | Ala |
| | 130 | | | | | 135 | | | | | 140 | | | | |
| Tyr | Gly | Asn | Ala | Asn | Gly | Thr | Leu | Leu | Asn | Leu | Tyr | Ile | Pro | Ala | Gly |
| 145 | | | | | 150 | | | | | 155 | | | | | 160 |
| Glu | Ile | Asn | Lys | Leu | Pro | Phe | Gly | Gly | Ile | Trp | Glu | Ala | Thr | Leu | Ile |
| | | | | 165 | | | | | 170 | | | | | 175 | |
| Leu | Arg | Leu | Ser | Arg | Tyr | Gly | Glu | Val | Ser | Ser | Thr | His | Tyr | Gly | Asn |
| | | | 180 | | | | | 185 | | | | | 190 | | |
| Tyr | Thr | Val | Asn | Ile | Thr | Val | Asp | Leu | Thr | Asp | Lys | Gly | Asn | Ile | Gln |
| | | 195 | | | | | 200 | | | | | 205 | | | |
| Val | Trp | Leu | Pro | Gly | Phe | His | Ser | Asn | Pro | Arg | Val | Asp | Leu | Asn | Leu |
| | 210 | | | | | 215 | | | | | 220 | | | | |
| His | Pro | Ile | Gly | Asn | Tyr | Lys | Tyr | Ser | Gly | Ser | Asn | Ser | Leu | Asp | Met |
| 225 | | | | | 230 | | | | | 235 | | | | | 240 |
| Cys | Phe | Tyr | Asp | Gly | Tyr | Ser | Thr | Asn | Ser | Asp | Ser | Met | Val | Ile | Lys |
| | | | | 245 | | | | | 250 | | | | | 255 | |
| Phe | Gln | Asp | Asp | Asn | Pro | Thr | Tyr | Ser | Ser | Glu | Tyr | Asn | Leu | Tyr | Lys |
| | | | 260 | | | | | 265 | | | | | 270 | | |
| Ile | Gly | Gly | Thr | Glu | Lys | Leu | Pro | Tyr | Ala | Val | Ser | Leu | Leu | Met | Gly |
| | | 275 | | | | | 280 | | | | | 285 | | | |
| Glu | Lys | Ile | Phe | Tyr | Pro | Val | Asn | Gly | Gln | Ser | Phe | Thr | Ile | Asn | Asp |
| | 290 | | | | | 295 | | | | | 300 | | | | |
| Ser | Ser | Val | Leu | Glu | Thr | Asn | Trp | Asn | Arg | Val | Thr | Ala | Val | Ala | Met |
| 305 | | | | | 310 | | | | | 315 | | | | | 320 |
| Pro | Glu | Val | Asn | Val | Pro | Val | Leu | Cys | Trp | Pro | Ala | Arg | Leu | Leu | Leu |

```
                    325                 330                 335
Asn Ala Asp Val Asn Ala Pro Asp Ala Gly Gln Tyr Ser Gly Gln Ile
                340                 345                 350
Tyr Ile Thr Phe Thr Pro Ser Val Glu Asn Leu Gly Gly Val Glu
                355                 360                 365
Lys Asn Ile Thr Val Arg Ala Ser Val Asp Pro Lys Leu Asp Leu Leu
                370                 375                 380
Gln Ala Asp Gly Thr Ser Leu Pro Asp Ser Ile Ala Leu Thr Tyr Ser
385                 390                 395                 400
Ser Ala Ser Asn Asn Phe Glu Val Tyr Ser Leu Asn Thr Ala Ile His
                405                 410                 415
Thr Asn Asp Lys Ser Lys Gly Val Val Val Lys Leu Ser Ala Ser Pro
                420                 425                 430
Val Leu Ser Asn Ile Met Lys Pro Asn Ser Gln Ile Pro Met Lys Val
                435                 440                 445
Thr Leu Gly Gly Lys Thr Leu Asn Thr Thr Asp Thr Glu Phe Thr Val
                450                 455                 460
Asp Thr Leu Asn Phe Gly Thr Ser Gly Val Glu Asn Val Ser Ser Thr
465                 470                 475                 480
Gln Gln Leu Thr Ile His Ala Asp Thr Gln Gly Thr Ala Pro Glu Ala
                485                 490                 495
Gly Asn Tyr Gln Gly Ile Ile Ser Leu Ile Met Thr Gln Lys Thr Gly
                500                 505                 510
Gly Gly Val Glu Lys Asn Ile Thr Val Arg Ala Ser Val Asp Pro Lys
                515                 520                 525
Leu Asp Leu Leu Gln Ser Asp Gly Ser Ala Leu Pro Asn Ser Val Ala
                530                 535                 540
Leu Thr Tyr Ser Pro Ala Val Asn Asn Phe Glu Ala His Thr Ile Asn
545                 550                 555                 560
Thr Val Val His Thr Asn Asp Ser Asp Lys Gly Val Val Lys Leu
                565                 570                 575
Ser Ala Asp Pro Val Leu Ser Asn Val Leu Asn Pro Thr Leu Gln Ile
                580                 585                 590
Pro Val Ser Val Asn Phe Ala Gly Lys Pro Leu Ser Thr Thr Gly Ile
                595                 600                 605
Thr Ile Asp Ser Asn Asp Leu Asn Phe Ala Ser Ser Gly Val Asn Lys
                610                 615                 620
Val Ser Ser Thr Gln Lys Leu Ser Ile His Ala Asp Ala Thr Arg Val
625                 630                 635                 640
Thr Gly Gly Ala Leu Thr Ala Gly Gln Tyr Gln Gly Leu Val Ser Ile
                645                 650                 655
Ile Leu Thr Lys Ser Thr Gly Gly Val Glu Lys Thr Ile Ser Val
                660                 665                 670
Thr Ala Ser Val Asp Pro Thr Gly Glu Gln Asn Phe Ile Pro Asp Ile
                675                 680                 685
Asp Ser Ala Val Arg Ile Ile Pro Val Asn Tyr Asp Ser Asp Pro Lys
                690                 695                 700
Leu Asn Ser Gln Leu Tyr Thr Val Glu Met Thr Ile Pro Ala Gly Val
705                 710                 715                 720
Ser Ala Val Lys Ile Val Pro Thr Asp Ser Leu Thr Ser Ser Gly Gln
                725                 730                 735
Gln Ile Gly Lys Leu Val Asn Val Asn Asn Pro Asp Gln Asn Met Asn
                740                 745                 750
```

Tyr Tyr Ile Arg Lys Asp Ser Gly Ala Gly Lys Phe Met Ala Gly Gln
            755                 760                 765
Lys Gly Ser Phe Ser Val Lys Glu Asn Thr Ser Tyr Thr Phe Ser Ala
        770                 775                 780
Ile Tyr Thr Gly Gly Glu Tyr Pro Asn Ser Gly Tyr Ser Ser Gly Thr
785                 790                 795                 800
Tyr Ala Gly His Leu Thr Val Ser Phe Tyr Ser Asn Asp Asn Lys Gln
                805                 810                 815
Arg Thr Glu Ile Ala Thr Lys Asn Phe Pro Val Ser Thr Thr Ile Ser
            820                 825                 830
Lys Ser Phe Phe Ala Pro Glu Pro Gln Ile Gln Pro Ser Phe Gly Lys
        835                 840                 845
Asn Val Gly Lys Glu Gly Asp Leu Leu Phe Ser Val Ser Leu Ile Val
850                 855                 860
Pro Glu Asn Val Ser Gln Val Thr Val Tyr Pro Val Tyr Asp Glu Asp
865                 870                 875                 880
Tyr Gly Leu Gly Arg Leu Val Asn Thr Ala Asp Ser Gln Ser Ile
                885                 890                 895
Ile Tyr Gln Ile Val Asp Asp Lys Gly Lys Met Leu Lys Asp His
        900                 905                 910
Gly Thr Glu Val Thr Pro Asn Gln Gln Ile Thr Phe Lys Ala Leu Asn
            915                 920                 925
Tyr Thr Ser Gly Asp Lys Glu Ile Pro Pro Gly Ile Tyr Asn Asp Gln
        930                 935                 940
Val Met Val Gly Tyr Tyr Val Asn Asp Asn Lys Gln Gly Asn Trp Gln
945                 950                 955                 960
Tyr Lys Ser Leu Asp Val Asn Val Asn Ile Glu Gln Leu Glu His His
                965                 970                 975
His His His His
        980

<210> SEQ ID NO 26
<211> LENGTH: 2795
<212> TYPE: DNA
<213> ORGANISM: Escherichia coli

<400> SEQUENCE: 26
ttacgaatca tgtggctgga tatagtttga gtcataactt atatgacagg attgtttttt      60
tatgtacatc ctcgtcgaat ccggttaatg gtgcttgccc aaccattgga acatctggag     120
ttcaatacgg tactacaacc ataaccttgc agtttacaga aaaagaagt ctgataaaaa     180
gaaatattaa tcttgcaggt aataagaaac caatatggga gaatcagagt tgcgacacta     240
gcaatctaat ggtgttgaat tcgaagtctt ggtcctgtgg ggcttacgga aatgctaacg     300
gaacacttct aaatctgtat atccctgcag gagaaatcaa caattgcct tttggaggga     360
tatgggaggc aactctgatc ttacgcttat caagatatgg cgaagtcagt agcacccatt     420
acggcaatta taccgtaaat attacggttg atttaactga taaaggtaat attcaggtat     480
ggcttccagg gttcacagc aacccgcgtg tagacctgaa tctgcaccct atcgtaatt     540
ataaatatag tggtagtaat tcactcgaca tgtgtttcta tgatggatat agtacaaaca     600
gtgatagcat ggtaataaag ttccaggatg ataatcctac ctattcatct gaatataatc     660
tttataagat aggggggcact gaaaaattac cctatgctgt ttcactgctt atgggagaaa     720
aaatatttta tccagtgaat ggtcaatcat ttactatcaa tgacagtagt gtactcgaaa     780

| | | | | |
|---|---|---|---|---|
| caaactggaa | tcgagtaacc | gcagttgcta | tgccggaagt | taatgttcca | gtattatgct | 840 |
| ggccagcaag | attgctatta | aatgctgatg | taaatgctcc | cgatgcagga | cagtattcag | 900 |
| gacagatata | tataacattt | acacccagtg | tcgaaaattt | aggcggtgga | gtcgaaaaaa | 960 |
| atattactgt | gagggcaagt | gttgacccta | aacttgatct | tctgcaagca | gatggaactt | 1020 |
| cactgccgga | ctctatcgca | ttaacctatt | cttcggcttc | aaataatttt | gaagtttact | 1080 |
| ctcttaatac | tgctattcat | acaaatgaca | aaagcaaggg | agttgtagtg | aagctgtcag | 1140 |
| cttcaccagt | tctgtccaat | attatgaagc | caaactcgca | aattccgatg | aaagtgactt | 1200 |
| tgggggggaa | gacgctgaat | acaactgata | ctgagtttac | tgttgatact | ctgaactttg | 1260 |
| gtacatctgg | tgttgaaaac | gtttcttcca | ctcaacagct | tacgattcat | gcagacacac | 1320 |
| aaggaactgc | gcctgaggca | ggcaattacc | aaggtattat | ttctcttatc | atgactcaaa | 1380 |
| aaacaggggg | cggtgtcgaa | aaaaatatta | ctgtgagggc | aagtgtcgac | cctaaacttg | 1440 |
| accttctgca | atctgatggc | tctgcgctgc | cgaactctgt | cgcattaacc | tattctccgg | 1500 |
| ctgtaaataa | ttttgaagct | cacaccatca | acaccgttgt | tcatacaaat | gactcagata | 1560 |
| aaggtgttgt | tgtgaagctg | tcagcagatc | cagtcctgtc | caatgttctg | aatccaaccc | 1620 |
| tgcaaattcc | tgtttctgtg | aatttcgcag | gaaaaccact | gagcacaaca | ggcattacca | 1680 |
| tcgactccaa | tgatctgaac | tttgcttcga | gtggtgttaa | taaagtttct | tctacgcaga | 1740 |
| aactttcaat | ccatgcagat | gctactcggg | taactggcgg | cgcactaaca | gctggtcaat | 1800 |
| atcagggact | cgtatcaatt | atcctgacta | agtcaacggg | gggcggtgtc | gagaagacca | 1860 |
| ttagcgttac | ggcgagtgtt | gacccgacgg | gcgagcaaaa | ttttattcca | gatattgatt | 1920 |
| ccgctgttcg | tataatacct | gttaattacg | attcggatcc | gaaactgaat | tcacagttat | 1980 |
| atacggttga | gatgacgatc | cctgcaggtg | taagcgcagt | taaaatcgta | ccaacagata | 2040 |
| gtctgacatc | ttctggacag | cagatcggaa | agctggttaa | tgtaaacaat | ccagatcaaa | 2100 |
| atatgaatta | ttatatcaga | aaggattctg | gcgctggtaa | gtttatggca | gggcaaaaag | 2160 |
| gatcctttc | tgtcaaagag | aatacgtcat | acacattctc | agcaatttat | actggtggcg | 2220 |
| aatacccctaa | tagcggatat | tcgtctggta | cttatgcagg | acatttgact | gtatcatttt | 2280 |
| acagcaatga | caataaacaa | agaacagaaa | tagcgactaa | aaacttccca | gtatcaacga | 2340 |
| ctatttcaaa | aagttttttt | gcgcctgaac | cacaaatcca | gccttctttt | ggtaaaaatg | 2400 |
| ttggaaagga | aggagattta | ttatttagtg | tgagcttaat | tgttcctgaa | aatgtatccc | 2460 |
| aggtaacggt | ctaccctgtt | tatgatgaag | attatggatt | aggacgactc | gtaaataccg | 2520 |
| ctgatgattc | ccaatcaata | atctaccaga | ttgttgatga | taaagggaaa | aaaatgttaa | 2580 |
| aagatcatgg | tacagaggtt | acgcctaatc | aacaaataac | ttttaaagcg | ctgaattata | 2640 |
| ctagcggaga | taaagaaata | cctcctggga | tatataacga | tcaggttatg | gttggttact | 2700 |
| acgtaaacga | caataaacaa | ggaaactggc | aatataaatc | tctggatgta | aatgtaaata | 2760 |
| ttgagcaact | cgagcaccac | caccaccacc | actga | | | 2795 |

<210> SEQ ID NO 27
<211> LENGTH: 963
<212> TYPE: PRT
<213> ORGANISM: Escherichia coli

<400> SEQUENCE: 27

Met Gly Arg Tyr Pro Glu Thr Thr Val Gly Asn Leu Thr Lys Ser Phe
1               5                   10                  15

```
Gln Ala Pro Arg Gln Asp Arg Ser Val Gln Ser Pro Ile Tyr Asn Ile
            20                  25                  30

Phe Thr Asn His Val Ala Gly Tyr Ser Leu Ser His Asn Leu Tyr Asp
        35                  40                  45

Arg Ile Val Phe Leu Cys Thr Ser Ser Ser Asn Pro Val Asn Gly Ala
    50                  55                  60

Cys Pro Thr Ile Gly Thr Ser Gly Val Gln Tyr Gly Thr Thr Thr Ile
65                  70                  75                  80

Thr Leu Gln Phe Thr Glu Lys Arg Ser Leu Ile Lys Arg Asn Ile Asn
                85                  90                  95

Leu Ala Gly Asn Lys Lys Pro Ile Trp Glu Asn Gln Ser Cys Asp Thr
            100                 105                 110

Ser Asn Leu Met Val Leu Asn Ser Lys Ser Trp Ser Cys Gly Ala Tyr
        115                 120                 125

Gly Asn Ala Asn Gly Thr Leu Leu Asn Leu Tyr Ile Pro Ala Gly Glu
130                 135                 140

Ile Asn Lys Leu Pro Phe Gly Gly Ile Trp Glu Ala Thr Leu Ile Leu
145                 150                 155                 160

Arg Leu Ser Arg Tyr Gly Glu Val Ser Ser Thr His Tyr Gly Asn Tyr
                165                 170                 175

Thr Val Asn Ile Thr Val Asp Leu Thr Asp Lys Gly Asn Ile Gln Val
            180                 185                 190

Trp Leu Pro Gly Phe His Ser Asn Pro Arg Val Asp Leu Asn Leu His
        195                 200                 205

Pro Ile Gly Asn Tyr Lys Tyr Ser Gly Ser Asn Ser Leu Asp Met Cys
    210                 215                 220

Phe Tyr Asp Gly Tyr Ser Thr Asn Ser Asp Ser Met Val Ile Lys Phe
225                 230                 235                 240

Gln Asp Asp Asn Pro Thr Tyr Ser Ser Glu Tyr Asn Leu Tyr Lys Ile
                245                 250                 255

Gly Gly Thr Glu Lys Leu Pro Tyr Ala Val Ser Leu Leu Met Gly Glu
            260                 265                 270

Lys Ile Phe Tyr Pro Val Asn Gly Gln Ser Phe Thr Ile Asn Asp Ser
        275                 280                 285

Ser Val Leu Glu Thr Asn Trp Asn Arg Val Thr Ala Val Ala Met Pro
290                 295                 300

Glu Val Asn Val Pro Val Leu Cys Trp Pro Ala Arg Leu Leu Leu Asn
305                 310                 315                 320

Ala Asp Val Asn Ala Pro Asp Ala Gly Gln Tyr Ser Gly Gln Ile Tyr
                325                 330                 335

Ile Thr Phe Thr Pro Ser Val Glu Asn Leu Gly Gly Gly Val Glu Lys
            340                 345                 350

Asn Ile Thr Val Arg Ala Ser Val Asp Pro Lys Leu Asp Leu Leu Gln
        355                 360                 365

Ala Asp Gly Thr Ser Leu Pro Asp Ser Ile Ala Leu Thr Tyr Ser Ser
370                 375                 380

Ala Ser Asn Asn Phe Glu Val Tyr Ser Leu Asn Thr Ala Ile His Thr
385                 390                 395                 400

Asn Asp Lys Ser Lys Gly Val Val Lys Leu Ser Ala Ser Pro Val
                405                 410                 415

Leu Ser Asn Ile Met Lys Pro Asn Ser Gln Ile Pro Met Lys Val Thr
            420                 425                 430
```

```
Leu Gly Gly Lys Thr Leu Asn Thr Thr Asp Thr Glu Phe Thr Val Asp
            435                 440                 445

Thr Leu Asn Phe Gly Thr Ser Gly Val Glu Asn Val Ser Ser Thr Gln
450                 455                 460

Gln Leu Thr Ile His Ala Asp Thr Gln Gly Thr Ala Pro Glu Ala Gly
465                 470                 475                 480

Asn Tyr Gln Gly Ile Ile Ser Leu Ile Met Thr Gln Lys Thr Gly Gly
            485                 490                 495

Gly Val Glu Lys Asn Ile Thr Val Arg Ala Ser Val Asp Pro Lys Leu
            500                 505                 510

Asp Leu Leu Gln Ser Asp Gly Ser Ala Leu Pro Asn Ser Val Ala Leu
            515                 520                 525

Thr Tyr Ser Pro Ala Val Asn Asn Phe Glu Ala His Thr Ile Asn Thr
            530                 535                 540

Val Val His Thr Asn Asp Ser Asp Lys Gly Val Val Lys Leu Ser
545                 550                 555                 560

Ala Asp Pro Val Leu Ser Asn Val Leu Asn Pro Thr Leu Gln Ile Pro
            565                 570                 575

Val Ser Val Asn Phe Ala Gly Lys Pro Leu Ser Thr Thr Gly Ile Thr
            580                 585                 590

Ile Asp Ser Asn Asp Leu Asn Phe Ala Ser Ser Gly Val Asn Lys Val
            595                 600                 605

Ser Ser Thr Gln Lys Leu Ser Ile His Ala Asp Ala Thr Arg Val Thr
            610                 615                 620

Gly Gly Ala Leu Thr Ala Gly Gln Tyr Gln Gly Leu Val Ser Ile Ile
625                 630                 635                 640

Leu Thr Lys Ser Thr Gly Gly Val Glu Lys Thr Ile Ser Val Thr
            645                 650                 655

Ala Ser Val Asp Pro Thr Gly Glu Gln Asn Phe Ile Pro Asp Ile Asp
            660                 665                 670

Ser Ala Val Arg Ile Ile Pro Val Asn Tyr Asp Ser Asp Pro Lys Leu
            675                 680                 685

Asn Ser Gln Leu Tyr Thr Val Glu Met Thr Ile Pro Ala Gly Val Ser
            690                 695                 700

Ala Val Lys Ile Val Pro Thr Asp Ser Leu Thr Ser Ser Gly Gln Gln
705                 710                 715                 720

Ile Gly Lys Leu Val Asn Val Asn Asn Pro Asp Gln Asn Met Asn Tyr
            725                 730                 735

Tyr Ile Arg Lys Asp Ser Gly Ala Gly Lys Phe Met Ala Gly Gln Lys
            740                 745                 750

Gly Ser Phe Ser Val Lys Glu Asn Thr Ser Tyr Thr Phe Ser Ala Ile
            755                 760                 765

Tyr Thr Gly Gly Glu Tyr Pro Asn Ser Gly Tyr Ser Ser Gly Thr Tyr
            770                 775                 780

Ala Gly His Leu Thr Val Ser Phe Tyr Ser Asn Asp Asn Lys Gln Arg
785                 790                 795                 800

Thr Glu Ile Ala Thr Lys Asn Phe Pro Val Ser Thr Thr Ile Ser Lys
            805                 810                 815

Ser Phe Phe Ala Pro Glu Pro Gln Ile Gln Pro Ser Phe Gly Lys Asn
            820                 825                 830

Val Gly Lys Glu Gly Asp Leu Leu Phe Ser Val Ser Leu Ile Val Pro
            835                 840                 845

Glu Asn Val Ser Gln Val Thr Val Tyr Pro Val Tyr Asp Glu Asp Tyr
```

```
                      850                 855                 860
Gly Leu Gly Arg Leu Val Asn Thr Ala Asp Asp Ser Gln Ser Ile Ile
865                 870                 875                 880

Tyr Gln Ile Val Asp Asp Lys Gly Lys Lys Met Leu Lys Asp His Gly
                885                 890                 895

Thr Glu Val Thr Pro Asn Gln Gln Ile Thr Phe Lys Ala Leu Asn Tyr
                    900                 905                 910

Thr Ser Gly Asp Lys Glu Ile Pro Pro Gly Ile Tyr Asn Asp Gln Val
            915                 920                 925

Met Val Gly Tyr Tyr Val Asn Asp Asn Lys Gln Gly Asn Trp Gln Tyr
        930                 935                 940

Lys Ser Leu Asp Val Asn Val Asn Ile Glu Gln Leu Glu His His His
945                 950                 955                 960

His His His

<210> SEQ ID NO 28
<211> LENGTH: 2505
<212> TYPE: DNA
<213> ORGANISM: Escherichia coli

<400> SEQUENCE: 28
atgaaaaaag tgatttttgt tttatccatg tttctatgtt ctcaggttta cgggcaatca     60
tggcatacga acgtagaggc tggttcaata aataaaacag agtcgatagg ccccatagac    120
cgaagtgctg ctgcatcgta tcctgctcat tatatatttc atgaacatgt tgctggttac    180
aataaagatc actctctttt tgacaggatg acgtttttat gtatgtcatc aacagatgca    240
tctaaaggtg catgtccgac aggagaaaac tccaaatcct ctcaagggga gactaatatt    300
aagctaatat ttactgaaaa gaaagtctg gccagaaaaa cattaaactt aaaaggatat    360
aagagatttt tatatgaatc agatagatgc attcattatg tcgataaaat gaatctcaat    420
tctcatactg ttaaatgtgt aggttcattc acaagaggag tagatttcac tttatatatc    480
ccacaaggtg aaattgatgg gcttctaact ggaggtatat gggaggcaac actagagtta    540
cgagtcaaaa ggcattacga ctataatcat ggtacttaca agttaatat cacagttgat    600 ttgacagaca aaggaaatat tcaggtctgg acaccaaagt ttcatagcga tcctagaatt    660
gatctgaatt tacgtcctga aggtaatggt aaatattctg gtagtaacgt gcttgagatg    720
tgtctctatg atggctatag tacacatagt caaagtatag aaatgaggtt tcaggatgac    780
tcacaaacag gaaataatga atataatcct taaaaactg gagagccatt aaaaaaattg    840
ccatataaac tttctcttct tttaggagga cgagagtttt atccaaataa tggagaggct    900
tttactatta atgatacttc gtcattgttt ataaactgga atcgtattaa gtctgtatcc    960
ttaccacaga ttagtattcc agtactatgc tggccagcaa acttgacatt tatgtcagag   1020
ctaaataatc cagaagcggg tgagtattca ggaatactta cgtaacatt tactcctagt   1080 agttcaagcc tagacaataa acaagccgag aaaaatatca ctgtaactgc tagcgttgat   1140
ccaactatcg atctgatgca atctgatggc acagcgttac caagtgcagt taatattgca   1200
tatcttccag gagagaaaag atttgaatct gctcgtatca atcccaagt tcataccaat   1260 aataaaacta agggtattca gataaagctt actaatgata atgtggtaat gactaactta   1320
tctgatccaa gcaagactat tccttagag gttttcattcg ctggcactaa gctgagcaca   1380 gctgcaaacat ctattactgc cgatcaatta aattttggcg cagctggtgt agagacagtt   1440
tctgcaacta aggaactcgt tattaatgca ggaagcaccc agcaaactaa tattgtagct   1500
```

-continued

```
ggtaactatc aaggattggt gtcaattgtg cttactcaag aacctgacaa taaacaagcc    1560
gagaaaaata tcactgtaac tgctagcgtt gatccgacgg gcgagcaaaa ttttattcca    1620
gatattgatt ccgctgttcg tataatacct gttaattacg attcggatcc gaaactgaat    1680
tcacagttat atacggttga gatgacgatc cctgcaggtg taagcgcagt taaaatcgta    1740
ccaacagata gtctgacatc ttctggacag cagatcggaa agctggttaa tgtaaacaat    1800
ccagatcaaa atatgaatta ttatatcaga aaggattctg gcgctggtaa gtttatggca    1860
gggcaaaaag gatccttttc tgtcaaagag aatacgtcat acacattctc agcaatttat    1920
actggtggcg aataccctaa tagcggatat tcgtctggta cttatgcagg acatttgact    1980
gtatcatttt acagcaatga caataaacaa agaacagaaa tagcgactaa aaacttccca    2040
gtatcaacga ctatttcaaa aagttttttt gcgcctgaac cacaaatcca gccttctttt    2100
ggtaaaaatg ttggaaagga aggagattta ttatttagtg tgagcttaat tgttcctgaa    2160
aatgtatccc aggtaacggt ctaccctgtt tatgatgaag attatggatt aggacgactc    2220
gtaaataccg ctgatgattc ccaatcaata atctaccaga ttgttgatga taaagggaaa    2280
aaaatgttaa aagatcatgg tacagaggtt acgcctaatc aacaaataac ttttaaagcg    2340
ctgaattata ctagcggaga taaagaaata cctcctggga tatataacga tcaggttatg    2400
gttggttact acgtaaacga caataaacaa ggaaactggc aatataaatc tctggatgta    2460
aatgtaaata ttgagcaact cgagcaccac caccaccacc actga                    2505
```

<210> SEQ ID NO 29
<211> LENGTH: 834
<212> TYPE: PRT
<213> ORGANISM: Escherichia coli

<400> SEQUENCE: 29

| | | | | | | | | | | | | | | | |
|---|---|---|---|---|---|---|---|---|---|---|---|---|---|---|---|
| Met | Lys | Lys | Val | Ile | Phe | Val | Leu | Ser | Met | Phe | Leu | Cys | Ser | Gln | Val |
| 1 | | | | 5 | | | | | 10 | | | | | 15 | |
| Tyr | Gly | Gln | Ser | Trp | His | Thr | Asn | Val | Glu | Ala | Gly | Ser | Ile | Asn | Lys |
| | | | 20 | | | | | 25 | | | | | 30 | | |
| Thr | Glu | Ser | Ile | Gly | Pro | Ile | Asp | Arg | Ser | Ala | Ala | Ser | Tyr | Pro | |
| | | 35 | | | | | 40 | | | | | 45 | | | |
| Ala | His | Tyr | Ile | Phe | His | Glu | His | Val | Ala | Gly | Tyr | Asn | Lys | Asp | His |
| | 50 | | | | | 55 | | | | | 60 | | | | |
| Ser | Leu | Phe | Asp | Arg | Met | Thr | Phe | Leu | Cys | Met | Ser | Ser | Thr | Asp | Ala |
| 65 | | | | | 70 | | | | | 75 | | | | | 80 |
| Ser | Lys | Gly | Ala | Cys | Pro | Thr | Gly | Glu | Asn | Ser | Lys | Ser | Ser | Gln | Gly |
| | | | | 85 | | | | | 90 | | | | | 95 | |
| Glu | Thr | Asn | Ile | Lys | Leu | Ile | Phe | Thr | Glu | Lys | Lys | Ser | Leu | Ala | Arg |
| | | | 100 | | | | | 105 | | | | | 110 | | |
| Lys | Thr | Leu | Asn | Leu | Lys | Gly | Tyr | Lys | Arg | Phe | Leu | Tyr | Glu | Ser | Asp |
| | | | 115 | | | | | 120 | | | | | 125 | | |
| Arg | Cys | Ile | His | Tyr | Val | Asp | Lys | Met | Asn | Leu | Asn | Ser | His | Thr | Val |
| | 130 | | | | | 135 | | | | | 140 | | | | |
| Lys | Cys | Val | Gly | Ser | Phe | Thr | Arg | Gly | Val | Asp | Phe | Thr | Leu | Tyr | Ile |
| 145 | | | | | 150 | | | | | 155 | | | | | 160 |
| Pro | Gln | Gly | Glu | Ile | Asp | Gly | Leu | Leu | Thr | Gly | Gly | Ile | Trp | Glu | Ala |
| | | | | 165 | | | | | 170 | | | | | 175 | |
| Thr | Leu | Glu | Leu | Arg | Val | Lys | Arg | His | Tyr | Asp | Tyr | Asn | His | Gly | Thr |
| | | | 180 | | | | | 185 | | | | | 190 | | |

```
Tyr Lys Val Asn Ile Thr Val Asp Leu Thr Asp Lys Gly Asn Ile Gln
            195                 200                 205

Val Trp Thr Pro Lys Phe His Ser Asp Pro Arg Ile Asp Leu Asn Leu
    210                 215                 220

Arg Pro Glu Gly Asn Gly Lys Tyr Ser Gly Ser Asn Val Leu Glu Met
225                 230                 235                 240

Cys Leu Tyr Asp Gly Tyr Ser Thr His Ser Gln Ser Ile Glu Met Arg
                245                 250                 255

Phe Gln Asp Asp Ser Gln Thr Gly Asn Asn Glu Tyr Asn Leu Ile Lys
            260                 265                 270

Thr Gly Glu Pro Leu Lys Lys Leu Pro Tyr Lys Leu Ser Leu Leu Leu
        275                 280                 285

Gly Gly Arg Glu Phe Tyr Pro Asn Asn Gly Glu Ala Phe Thr Ile Asn
    290                 295                 300

Asp Thr Ser Ser Leu Phe Ile Asn Trp Asn Arg Ile Lys Ser Val Ser
305                 310                 315                 320

Leu Pro Gln Ile Ser Ile Pro Val Leu Cys Trp Pro Ala Asn Leu Thr
                325                 330                 335

Phe Met Ser Glu Leu Asn Asn Pro Glu Ala Gly Glu Tyr Ser Gly Ile
            340                 345                 350

Leu Asn Val Thr Phe Thr Pro Ser Ser Ser Leu Asp Asn Lys Gln
        355                 360                 365

Ala Glu Lys Asn Ile Thr Val Thr Ala Ser Val Asp Pro Thr Ile Asp
    370                 375                 380

Leu Met Gln Ser Asp Gly Thr Ala Leu Pro Ser Ala Val Asn Ile Ala
385                 390                 395                 400

Tyr Leu Pro Gly Glu Lys Arg Phe Glu Ser Ala Arg Ile Asn Thr Gln
                405                 410                 415

Val His Thr Asn Asn Lys Thr Lys Gly Ile Gln Ile Lys Leu Thr Asn
            420                 425                 430

Asp Asn Val Val Met Thr Asn Leu Ser Asp Pro Ser Lys Thr Ile Pro
        435                 440                 445

Leu Glu Val Ser Phe Ala Gly Thr Lys Leu Ser Thr Ala Ala Thr Ser
    450                 455                 460

Ile Thr Ala Asp Gln Leu Asn Phe Gly Ala Ala Gly Val Glu Thr Val
465                 470                 475                 480

Ser Ala Thr Lys Glu Leu Val Ile Asn Ala Gly Ser Thr Gln Gln Thr
                485                 490                 495

Asn Ile Val Ala Gly Asn Tyr Gln Gly Leu Val Ser Ile Val Leu Thr
            500                 505                 510

Gln Glu Pro Asp Asn Lys Gln Ala Glu Lys Asn Ile Thr Val Thr Ala
        515                 520                 525

Ser Val Asp Pro Thr Gly Glu Gln Asn Phe Ile Pro Asp Ile Asp Ser
    530                 535                 540

Ala Val Arg Ile Ile Pro Val Asn Tyr Asp Ser Asp Pro Lys Leu Asn
545                 550                 555                 560

Ser Gln Leu Tyr Thr Val Glu Met Thr Ile Pro Ala Gly Val Ser Ala
                565                 570                 575

Val Lys Ile Val Pro Thr Asp Ser Leu Thr Ser Ser Gly Gln Gln Ile
            580                 585                 590

Gly Lys Leu Val Asn Val Asn Asn Pro Asp Gln Asn Met Asn Tyr Tyr
        595                 600                 605

Ile Arg Lys Asp Ser Gly Ala Gly Lys Phe Met Ala Gly Gln Lys Gly
```

```
                610               615                620
Ser Phe Ser Val Lys Glu Asn Thr Ser Tyr Thr Phe Ser Ala Ile Tyr
625                 630                635                640

Thr Gly Gly Glu Tyr Pro Asn Ser Gly Tyr Ser Ser Gly Thr Tyr Ala
                645                650                655

Gly His Leu Thr Val Ser Phe Tyr Ser Asn Asp Asn Lys Gln Arg Thr
                660                665                670

Glu Ile Ala Thr Lys Asn Phe Pro Val Ser Thr Ile Ser Lys Ser
                675                680                685

Phe Phe Ala Pro Glu Pro Gln Ile Gln Pro Ser Phe Gly Lys Asn Val
                690                695                700

Gly Lys Glu Gly Asp Leu Leu Phe Ser Val Ser Leu Ile Val Pro Glu
705                710                715                720

Asn Val Ser Gln Val Thr Val Tyr Pro Val Tyr Asp Glu Asp Tyr Gly
                725                730                735

Leu Gly Arg Leu Val Asn Thr Ala Asp Asp Ser Gln Ser Ile Ile Tyr
                740                745                750

Gln Ile Val Asp Asp Lys Gly Lys Lys Met Leu Lys Asp His Gly Thr
                755                760                765

Glu Val Thr Pro Asn Gln Gln Ile Thr Phe Lys Ala Leu Asn Tyr Thr
                770                775                780

Ser Gly Asp Lys Glu Ile Pro Pro Gly Ile Tyr Asn Asp Gln Val Met
785                790                795                800

Val Gly Tyr Tyr Val Asn Asp Asn Lys Gln Gly Asn Trp Gln Tyr Lys
                805                810                815

Ser Leu Asp Val Asn Val Asn Ile Glu Gln Leu Glu His His His
                820                825                830

His His
```

<210> SEQ ID NO 30
<211> LENGTH: 2454
<212> TYPE: DNA
<213> ORGANISM: Escherichia coli

<400> SEQUENCE: 30

```
atgcaatcat ggcatacgaa cgtagaggct ggttcaataa ataaaacaga gtcgataggc     60
cccatagacc gaagtgctgc tgcatcgtat cctgctcatt atatatttca tgaacatgtt    120
gctggttaca ataaagatca ctctcttttt gacaggatga cgttttatg tatgtcatca    180
acagatgcat ctaaaggtgc atgtccgaca ggagaaaact ccaaatcctc tcaaggggag    240
actaatatta agctaatatt tactgaaaag aaaagtctgg ccagaaaaac attaaactta    300
aaaggatata agagatttt atatgaatca gatagatgca ttcattatgt cgataaaatg    360
aatctcaatt ctcatactgt taaatgtgta ggttcattca agaggagt agatttcact    420
ttatatatcc cacaaggtga aattgatggg cttctaactg gaggtatatg ggaggcaaca    480
ctagagttac gagtcaaaag gcattacgac tataatcatg gtacttacaa agttaatatc    540
acagttgatt tgacagacaa aggaaatatt caggtctgga caccaaagtt tcatagcgat    600
cctagaattg atctgaattt acgtcctgaa ggtaatggta atattctgg tagtaacgtg    660
cttgagatgt gtctctatga tggctatagt acacatagtc aaagtataga atgaggttt    720
caggatgact cacaaacagg aaataatgaa tataatctta aaaaactgg agagccatta    780
aaaaaattgc catataaact ttctcttctt ttaggaggac gagagttta tccaaataat    840
```

```
ggagaggctt ttactattaa tgatacttcg tcattgttta taaactggaa tcgtattaag    900
tctgtatcct taccacagat tagtattcca gtactatgct ggccagcaaa cttgacattt    960
atgtcagagc taaataatcc agaagcgggt gagtattcag gaatacttaa cgtaacattt   1020
actcctagta gttcaagcct agacaataaa caagccgaga aaatatcac tgtaactgct    1080
agcgttgatc caactatcga tctgatgcaa tctgatggca cagcgttacc aagtgcagtt   1140
aatattgcat atcttccagg agagaaaaga tttgaatctg ctcgtatcaa tacccaagtt   1200
cataccaata ataaaactaa gggtattcag ataaagctta ctaatgataa tgtggtaatg   1260
actaacttat ctgatccaag caagactatt cctttagagg tttcattcgc tggcactaag   1320
ctgagcacag ctgcaacatc tattactgcc gatcaattaa attttggcgc agctggtgta   1380
gagacagttt ctgcaactaa ggaactcgtt attaatgcag gaagcaccca gcaaactaat   1440
attgtagctg gtaactatca aggattggtg tcaattgtgc ttactcaaga acctgacaat   1500
aaacaagccg agaaaaatat cactgtaact gctagcgttg atccgacggg cgagcaaaat   1560
tttattccag atattgattc cgctgttcgt ataatacctg ttaattacga ttcggatccg   1620
aaactgaatt cacagttata tacggttgag atgacgatcc ctgcaggtgt aagcgcagtt   1680
aaaatcgtac aacagatag tctgacatct tctggacagc agatcggaaa gctggttaat   1740
gtaaacaatc cagatcaaaa tatgaattat tatatcagaa aggattctgg cgctggtaag   1800
tttatggcag ggcaaaaagg atccttttct gtcaaagaga atacgtcata cattctca     1860
gcaatttata ctggtggcga ataccctaat agcggatatt cgtctggtac ttatgcagga   1920
catttgactg tatcattta cagcaatgac aataaacaaa gaacagaaat agcgactaaa    1980
aacttcccag tatcaacgac tatttcaaaa gttttttttg cgcctgaacc acaaatccag   2040
ccttcttttg gtaaaaatgt tggaaaggaa ggagatttat tatttagtgt gagcttaatt   2100
gttcctgaaa atgtatccca ggtaacggtc taccctgttt atgatgaaga ttatggatta   2160
ggacgactcg taaataccgc tgatgattcc caatcaataa tctaccagat tgttgatgat   2220
aaagggaaaa aaatgttaaa agatcatggt acagaggtta cgcctaatca acaaataact   2280
tttaaagcgc tgaattatac tagcggagat aaagaaatac ctcctgggat atataacgat   2340
caggttatgg ttggttacta cgtaaacgac aataaacaag gaaactggca atataaatct   2400
ctggatgtaa atgtaaatat tgagcaactc gagcaccacc accaccacca ctga          2454
```

<210> SEQ ID NO 31
<211> LENGTH: 817
<212> TYPE: PRT
<213> ORGANISM: Escherichia coli

<400> SEQUENCE: 31

Met Gln Ser Trp His Thr Asn Val Glu Ala Gly Ser Ile Asn Lys Thr
1               5                   10                  15

Glu Ser Ile Gly Pro Ile Asp Arg Ser Ala Ala Ser Tyr Pro Ala
            20                  25                  30

His Tyr Ile Phe His Glu His Val Ala Gly Tyr Asn Lys Asp His Ser
        35                  40                  45

Leu Phe Asp Arg Met Thr Phe Leu Cys Met Ser Thr Asp Ala Ser
    50                  55                  60

Lys Gly Ala Cys Pro Thr Gly Glu Asn Ser Lys Ser Ser Gln Gly Glu
65                  70                  75                  80

Thr Asn Ile Lys Leu Ile Phe Thr Glu Lys Lys Ser Leu Ala Arg Lys
                85                  90                  95

```
Thr Leu Asn Leu Lys Gly Tyr Lys Arg Phe Leu Tyr Glu Ser Asp Arg
            100                 105                 110

Cys Ile His Tyr Val Asp Lys Met Asn Leu Asn Ser His Thr Val Lys
            115                 120                 125

Cys Val Gly Ser Phe Thr Arg Gly Val Asp Phe Thr Leu Tyr Ile Pro
            130                 135                 140

Gln Gly Glu Ile Asp Gly Leu Leu Thr Gly Gly Ile Trp Glu Ala Thr
145                 150                 155                 160

Leu Glu Leu Arg Val Lys Arg His Tyr Asp Tyr Asn His Gly Thr Tyr
                165                 170                 175

Lys Val Asn Ile Thr Val Asp Leu Thr Asp Lys Gly Asn Ile Gln Val
            180                 185                 190

Trp Thr Pro Lys Phe His Ser Asp Pro Arg Ile Asp Leu Asn Leu Arg
            195                 200                 205

Pro Glu Gly Asn Gly Lys Tyr Ser Gly Ser Asn Val Leu Glu Met Cys
            210                 215                 220

Leu Tyr Asp Gly Tyr Ser Thr His Ser Gln Ser Ile Glu Met Arg Phe
225                 230                 235                 240

Gln Asp Asp Ser Gln Thr Gly Asn Asn Glu Tyr Asn Leu Ile Lys Thr
                245                 250                 255

Gly Glu Pro Leu Lys Lys Leu Pro Tyr Lys Leu Ser Leu Leu Leu Gly
            260                 265                 270

Gly Arg Glu Phe Tyr Pro Asn Asn Gly Glu Ala Phe Thr Ile Asn Asp
            275                 280                 285

Thr Ser Ser Leu Phe Ile Asn Trp Asn Arg Ile Lys Ser Val Ser Leu
            290                 295                 300

Pro Gln Ile Ser Ile Pro Val Leu Cys Trp Pro Ala Asn Leu Thr Phe
305                 310                 315                 320

Met Ser Glu Leu Asn Asn Pro Glu Ala Gly Glu Tyr Ser Gly Ile Leu
                325                 330                 335

Asn Val Thr Phe Thr Pro Ser Ser Ser Leu Asp Asn Lys Gln Ala
            340                 345                 350

Glu Lys Asn Ile Thr Val Thr Ala Ser Val Asp Pro Thr Ile Asp Leu
            355                 360                 365

Met Gln Ser Asp Gly Thr Ala Leu Pro Ser Ala Val Asn Ile Ala Tyr
370                 375                 380

Leu Pro Gly Glu Lys Arg Phe Glu Ser Ala Arg Ile Asn Thr Gln Val
385                 390                 395                 400

His Thr Asn Asn Lys Thr Lys Gly Ile Gln Ile Lys Leu Thr Asn Asp
                405                 410                 415

Asn Val Val Met Thr Asn Leu Ser Asp Pro Ser Lys Thr Ile Pro Leu
            420                 425                 430

Glu Val Ser Phe Ala Gly Thr Lys Leu Ser Thr Ala Ala Thr Ser Ile
            435                 440                 445

Thr Ala Asp Gln Leu Asn Phe Gly Ala Ala Gly Val Glu Thr Val Ser
            450                 455                 460

Ala Thr Lys Glu Leu Val Ile Asn Ala Gly Ser Thr Gln Gln Thr Asn
465                 470                 475                 480

Ile Val Ala Gly Asn Tyr Gln Gly Leu Val Ser Ile Val Leu Thr Gln
                485                 490                 495

Glu Pro Asp Asn Lys Gln Ala Glu Lys Asn Ile Thr Val Thr Ala Ser
            500                 505                 510
```

Val Asp Pro Thr Gly Glu Gln Asn Phe Ile Pro Asp Ile Asp Ser Ala
            515                 520                 525

Val Arg Ile Ile Pro Val Asn Tyr Asp Ser Asp Pro Lys Leu Asn Ser
530                 535                 540

Gln Leu Tyr Thr Val Glu Met Thr Ile Pro Ala Gly Val Ser Ala Val
545                 550                 555                 560

Lys Ile Val Pro Thr Asp Ser Leu Thr Ser Ser Gly Gln Gln Ile Gly
                565                 570                 575

Lys Leu Val Asn Val Asn Pro Asp Gln Asn Met Asn Tyr Tyr Ile
            580                 585                 590

Arg Lys Asp Ser Gly Ala Gly Lys Phe Met Ala Gly Gln Lys Gly Ser
            595                 600                 605

Phe Ser Val Lys Glu Asn Thr Ser Tyr Thr Phe Ser Ala Ile Tyr Thr
            610                 615                 620

Gly Gly Glu Tyr Pro Asn Ser Gly Tyr Ser Ser Gly Thr Tyr Ala Gly
625                 630                 635                 640

His Leu Thr Val Ser Phe Tyr Ser Asn Asp Asn Lys Gln Arg Thr Glu
                645                 650                 655

Ile Ala Thr Lys Asn Phe Pro Val Ser Thr Thr Ile Ser Lys Ser Phe
            660                 665                 670

Phe Ala Pro Glu Pro Gln Ile Gln Pro Ser Phe Gly Lys Asn Val Gly
            675                 680                 685

Lys Glu Gly Asp Leu Leu Phe Ser Val Ser Leu Ile Val Pro Glu Asn
            690                 695                 700

Val Ser Gln Val Thr Val Tyr Pro Val Tyr Asp Glu Asp Tyr Gly Leu
705                 710                 715                 720

Gly Arg Leu Val Asn Thr Ala Asp Asp Ser Gln Ser Ile Ile Tyr Gln
                725                 730                 735

Ile Val Asp Asp Lys Gly Lys Lys Met Leu Lys Asp His Gly Thr Glu
            740                 745                 750

Val Thr Pro Asn Gln Gln Ile Thr Phe Lys Ala Leu Asn Tyr Thr Ser
            755                 760                 765

Gly Asp Lys Glu Ile Pro Pro Gly Ile Tyr Asn Asp Gln Val Met Val
770                 775                 780

Gly Tyr Tyr Val Asn Asp Asn Lys Gln Gly Asn Trp Gln Tyr Lys Ser
785                 790                 795                 800

Leu Asp Val Asn Val Asn Ile Glu Gln Leu Glu His His His His
                805                 810                 815

His

<210> SEQ ID NO 32
<211> LENGTH: 1848
<212> TYPE: DNA
<213> ORGANISM: Escherichia coli

<400> SEQUENCE: 32
atggcagtgg gcccaacgaa agatatgagt ttaggtgcaa atttaacttc agagcctaca      60
ttagctattg attttacgcc tattgaaaat atttatgtag gtgccaatta tggtaaagat     120 attgaaccc ttgttttcac aacaaatgat ttaacagata ttacattgat gtcatctcgc      180
agcgttgttg atggtcgcca gactgggttt tttaccttca tggactcatc agccacttac     240
aaaattagta caaaactggg atcatcgaat gatgtaaaca ttcaagaaat tactcaagga     300
gctaaaatta ctcctgttag tggagagaaa actttgccta aaaaattcac tcttaagcta     360

-continued

```
catgcacaca ggagtagcag tacagttcca ggtacgtata ctgttggtct taacgtaacc    420
agtaacgtta ttgataacaa gcaggcagcg gggcccactc taaccaaaga actggcatta    480
aatgtgcttt ctcctgcagc tctggatgca acttgggctc ctcaggataa tttaacatta    540
tccaatactg gcgtttctaa tactttggtg ggtgttttga ctctttcaaa taccagtatt    600
gatacagtta gcattgcgag tacaaatgtt tctgatacat ctaagaatgg tacagtaact    660
tttgcacatg agacaaataa ctctgctagc tttgccacca ccatttcaac agataatgcc    720
aacattacgt tggataaaaa tgctggaaat acgattgtta aaactacaaa tgggagtcag    780
ttgccaacta atttaccact taagtttatt accactgaag gtaacgaaca tttagtttca    840
ggtaattacc gtgcaaatat aacaattact tcgacaatta agataacaa gcaggcggca    900
ggtccaaccc tgactaagga gttagcgctg aacgttttaa gcggcgagca aaatttatt    960
ccagatattg attccgctgt tcgtataata cctgttaatt acgattcgga tccgaaactg   1020
aattcacagt tatatacggt tgagatgacg atccctgcag gtgtaagcgc agttaaaatc   1080
gtaccaacag atagtctgac atcttctgga cagcagatcg gaaagctggt taatgtaaac   1140
aatccagatc aaaatatgaa ttattatatc agaaaggatt ctggcgctgg taagtttatg   1200
gcagggcaaa aaggatcctt ttctgtcaaa gagaatacgt catacacatt ctcagcaatt   1260
tatactggtg gcgaataccc taatagcgga tattcgtctg gtacttatgc aggacatttg   1320
actgtatcat tttacagcaa tgacaataaa caaagaacag aaatagcgac taaaaacttc   1380
ccagtatcaa cgactatttc aaaaagtttt tttgcgcctg aaccacaaat ccagccttct   1440
tttggtaaaa atgttggaaa ggaaggagat ttattattta gtgtgagctt aattgttcct   1500
gaaaatgtat cccaggtaac ggtctaccct gtttatgatg aagattatgg attaggacga   1560
ctcgtaaata ccgctgatga ttcccaatca ataatctacc agattgttga tgataaaggg   1620
aaaaaaatgt taaagatca tggtacagag gttacgccta atcaacaaat aacttttaaa   1680
gcgctgaatt atactagcgg agataaagaa atacctcctg gatatataaa cgatcaggtt   1740
atggttggtt actacgtaaa cgacaataaa caaggaaact ggcaatataa atctctggat   1800
gtaaatgtaa atattgagca actcgagcac caccaccacc accactga                1848
```

<210> SEQ ID NO 33
<211> LENGTH: 615
<212> TYPE: PRT
<213> ORGANISM: Escherichia coli

<400> SEQUENCE: 33

```
Met Ala Val Gly Pro Thr Lys Asp Met Ser Leu Gly Ala Asn Leu Thr
1               5                   10                  15

Ser Glu Pro Thr Leu Ala Ile Asp Phe Thr Pro Ile Glu Asn Ile Tyr
            20                  25                  30

Val Gly Ala Asn Tyr Gly Lys Asp Ile Gly Thr Leu Val Phe Thr Thr
        35                  40                  45

Asn Asp Leu Thr Asp Ile Thr Leu Met Ser Ser Arg Ser Val Val Asp
    50                  55                  60

Gly Arg Gln Thr Gly Phe Phe Thr Phe Met Asp Ser Ser Ala Thr Tyr
65                  70                  75                  80

Lys Ile Ser Thr Lys Leu Gly Ser Ser Asn Asp Val Asn Ile Gln Glu
                85                  90                  95

Ile Thr Gln Gly Ala Lys Ile Thr Pro Val Ser Gly Glu Lys Thr Leu
            100                 105                 110
```

-continued

```
Pro Lys Lys Phe Thr Leu Lys Leu His Ala His Arg Ser Ser Ser Thr
        115                 120                 125
Val Pro Gly Thr Tyr Thr Val Gly Leu Asn Val Thr Ser Asn Val Ile
130                 135                 140
Asp Asn Lys Gln Ala Ala Gly Pro Thr Leu Thr Lys Glu Leu Ala Leu
145                 150                 155                 160
Asn Val Leu Ser Pro Ala Ala Leu Asp Ala Thr Trp Ala Pro Gln Asp
                165                 170                 175
Asn Leu Thr Leu Ser Asn Thr Gly Val Ser Asn Thr Leu Val Gly Val
            180                 185                 190
Leu Thr Leu Ser Asn Thr Ser Ile Asp Thr Val Ser Ile Ala Ser Thr
        195                 200                 205
Asn Val Ser Asp Thr Ser Lys Asn Gly Thr Val Thr Phe Ala His Glu
210                 215                 220
Thr Asn Asn Ser Ala Ser Phe Ala Thr Thr Ile Ser Thr Asp Asn Ala
225                 230                 235                 240
Asn Ile Thr Leu Asp Lys Asn Ala Gly Asn Thr Ile Val Lys Thr Thr
                245                 250                 255
Asn Gly Ser Gln Leu Pro Thr Asn Leu Pro Leu Lys Phe Ile Thr Thr
            260                 265                 270
Glu Gly Asn Glu His Leu Val Ser Gly Asn Tyr Arg Ala Asn Ile Thr
        275                 280                 285
Ile Thr Ser Thr Ile Lys Asp Asn Lys Gln Ala Ala Gly Pro Thr Leu
        290                 295                 300
Thr Lys Glu Leu Ala Leu Asn Val Leu Ser Gly Glu Gln Asn Phe Ile
305                 310                 315                 320
Pro Asp Ile Asp Ser Ala Val Arg Ile Ile Pro Val Asn Tyr Asp Ser
                325                 330                 335
Asp Pro Lys Leu Asn Ser Gln Leu Tyr Thr Val Glu Met Thr Ile Pro
            340                 345                 350
Ala Gly Val Ser Ala Val Lys Ile Val Pro Thr Asp Ser Leu Thr Ser
        355                 360                 365
Ser Gly Gln Gln Ile Gly Lys Leu Val Asn Val Asn Asn Pro Asp Gln
    370                 375                 380
Asn Met Asn Tyr Tyr Ile Arg Lys Asp Ser Gly Ala Gly Lys Phe Met
385                 390                 395                 400
Ala Gly Gln Lys Gly Ser Phe Ser Val Lys Glu Asn Thr Ser Tyr Thr
                405                 410                 415
Phe Ser Ala Ile Tyr Thr Gly Gly Glu Tyr Pro Asn Ser Gly Tyr Ser
            420                 425                 430
Ser Gly Thr Tyr Ala Gly His Leu Thr Val Ser Phe Tyr Ser Asn Asp
        435                 440                 445
Asn Lys Gln Arg Thr Glu Ile Ala Thr Lys Asn Phe Pro Val Ser Thr
    450                 455                 460
Thr Ile Ser Lys Ser Phe Phe Ala Pro Glu Pro Gln Ile Gln Pro Ser
465                 470                 475                 480
Phe Gly Lys Asn Val Gly Lys Glu Gly Asp Leu Leu Phe Ser Val Ser
                485                 490                 495
Leu Ile Val Pro Glu Asn Val Ser Gln Val Thr Val Tyr Pro Val Tyr
            500                 505                 510
Asp Glu Asp Tyr Gly Leu Gly Arg Leu Val Asn Thr Ala Asp Asp Ser
        515                 520                 525
Gln Ser Ile Ile Tyr Gln Ile Val Asp Asp Lys Gly Lys Lys Met Leu
```

```
                530             535             540
Lys Asp His Gly Thr Glu Val Thr Pro Asn Gln Gln Ile Thr Phe Lys
545             550             555             560

Ala Leu Asn Tyr Thr Ser Gly Asp Lys Glu Ile Pro Pro Gly Ile Tyr
                565             570             575

Asn Asp Gln Val Met Val Gly Tyr Tyr Val Asn Asp Asn Lys Gln Gly
                580             585             590

Asn Trp Gln Tyr Lys Ser Leu Asp Val Asn Val Asn Ile Glu Gln Leu
        595             600             605

Glu His His His His His His
    610             615

<210> SEQ ID NO 34
<211> LENGTH: 1794
<212> TYPE: DNA
<213> ORGANISM: Escherichia coli

<400> SEQUENCE: 34
atggagcaaa attttattcc agatattgat tccgctgttc gtataatacc tgttaattac      60
gattcggatc cgaaactgaa ttcacagtta tatacggttg agatgacgat ccctgcaggt     120
gtaagcgcag ttaaaatcgt accaacagat agtctgacat cttctggaca gcagatcgga     180
aagctggtta atgtaaacaa tccagatcaa aatatgaatt attatatcag aaaggattct     240
ggcgctggta agtttatggc agggcaaaaa ggatcctttt ctgtcaaaga gaatacgtca     300
tacacattct cagcaatttta tactggtggc gaatacccta atagcggata ttcgtctggt     360
acttatgcag acatttgac tgtatcattt tacagcaatg acaataaaca agaacagaa       420 atagcgacta aaaacttccc agtatcaacg actatttcaa aagttttttt tgcgcctgaa     480
ccacaaatcc agccttcttt tggtaaaaat gttggaaagg aaggagattt attatttagt     540
gtgagcttaa ttgttcctga aaatgtatcc caggtaacgg tctaccctgt ttatgatgaa     600
gattatggat taggacgact cgtaaatacc gctgatgatt cccaatcaat aatctaccag     660
attgttgatg ataaagggaa aaaaatgtta aaagatcatg gtacagaggt tacgcctaat     720
caacaaataa cttttaaagc gctgaattat actagcggag ataaagaaat acctcctggg     780
atatataacg atcaggttat ggttggttac tacgtaaacg acaataaaca aggaaactgg     840
caatataaat ctctggacgt gaatgtaaat attgagcaag gcacattagc tattgatttt     900
acgcctattg aaaatatatta tgtaggtgcc aattatggta agatattgg aaccccttgtt    960 ttcacaacaa atgatttaac agatattaca ttgatgtcat ctcgcagcgt tgttgatggt    1020
cgccagactg gttttttttac cttcatggac tcatcagcca cttacaaaat tagtacaaaa    1080
ctgggatcat cgaatgatgt aaacattcaa gaaattactc aaggagctaa aattactcct    1140
gttagtggag agaaaacttt gcctaaaaaa ttcactctta agctacatgc acacaggagt    1200
agcagtacag ttccaggtac gtatactgtt ggtcttaacg taaccagtaa cgttattgat    1260
aacaagcagg cagcggggcc cactctaacc aaagaactgg cattaaatgt gctttctcct    1320
gcagctctgg atgcaacttg ggctcctcag gataatttaa cattatccaa tactggcgtt    1380
tctaatactt tggtgggtgt tttgactctt tcaaatacca gtattgatac agttagcatt    1440
gcgagtacaa atgtttctga tacatctaag aatggtacag taacttttgc acatgagaca    1500
aataactctg ctagctttgc caccaccatt tcaacagata tgccaacat tacgttggat     1560 aaaaatgctg gaaatacgat tgttaaaact acaaatggga gtcagttgcc aactaattta    1620
```

```
ccacttaagt ttattaccac tgaaggtaac gaacatttag tttcaggtaa ttaccgtgca      1680
aatataacaa ttacttcgac aattaaagat aacaagcagg cggcaggtcc aaccctgact      1740
aaggagttag cgctgaacgt tctgagcctc gagcaccacc accaccacca ctga            1794

<210> SEQ ID NO 35
<211> LENGTH: 597
<212> TYPE: PRT
<213> ORGANISM: Escherichia coli

<400> SEQUENCE: 35
```

Met Glu Gln Asn Phe Ile Pro Asp Ile Asp Ser Ala Val Arg Ile Ile
1               5                   10                  15

Pro Val Asn Tyr Asp Ser Asp Pro Lys Leu Asn Ser Gln Leu Tyr Thr
            20                  25                  30

Val Glu Met Thr Ile Pro Ala Gly Val Ser Ala Val Lys Ile Val Pro
        35                  40                  45

Thr Asp Ser Leu Thr Ser Ser Gly Gln Gln Ile Gly Lys Leu Val Asn
    50                  55                  60

Val Asn Asn Pro Asp Gln Asn Met Asn Tyr Tyr Ile Arg Lys Asp Ser
65                  70                  75                  80

Gly Ala Gly Lys Phe Met Ala Gly Gln Lys Gly Ser Phe Ser Val Lys
                85                  90                  95

Glu Asn Thr Ser Tyr Thr Phe Ser Ala Ile Tyr Thr Gly Gly Glu Tyr
            100                 105                 110

Pro Asn Ser Gly Tyr Ser Ser Gly Thr Tyr Ala Gly His Leu Thr Val
        115                 120                 125

Ser Phe Tyr Ser Asn Asp Asn Lys Gln Arg Thr Glu Ile Ala Thr Lys
    130                 135                 140

Asn Phe Pro Val Ser Thr Thr Ile Ser Lys Ser Phe Phe Ala Pro Glu
145                 150                 155                 160

Pro Gln Ile Gln Pro Ser Phe Gly Lys Asn Val Gly Lys Glu Gly Asp
                165                 170                 175

Leu Leu Phe Ser Val Ser Leu Ile Val Pro Glu Asn Val Ser Gln Val
            180                 185                 190

Thr Val Tyr Pro Val Tyr Asp Glu Asp Tyr Gly Leu Gly Arg Leu Val
        195                 200                 205

Asn Thr Ala Asp Asp Ser Gln Ser Ile Ile Tyr Gln Ile Val Asp Asp
    210                 215                 220

Lys Gly Lys Lys Met Leu Lys Asp His Gly Thr Glu Val Thr Pro Asn
225                 230                 235                 240

Gln Gln Ile Thr Phe Lys Ala Leu Asn Tyr Thr Ser Gly Asp Lys Glu
                245                 250                 255

Ile Pro Pro Gly Ile Tyr Asn Asp Gln Val Met Val Gly Tyr Tyr Val
            260                 265                 270

Asn Asp Asn Lys Gln Gly Asn Trp Gln Tyr Lys Ser Leu Asp Val Asn
        275                 280                 285

Val Asn Ile Glu Gln Gly Thr Leu Ala Ile Asp Phe Thr Pro Ile Glu
    290                 295                 300

Asn Ile Tyr Val Gly Ala Asn Tyr Gly Lys Asp Ile Gly Thr Leu Val
305                 310                 315                 320

Phe Thr Thr Asn Asp Leu Thr Asp Ile Thr Leu Met Ser Ser Arg Ser
                325                 330                 335

Val Val Asp Gly Arg Gln Thr Gly Phe Phe Thr Phe Met Asp Ser Ser
            340                 345                 350

```
Ala Thr Tyr Lys Ile Ser Thr Lys Leu Gly Ser Ser Asn Asp Val Asn
            355                 360                 365

Ile Gln Glu Ile Thr Gln Gly Ala Lys Ile Thr Pro Val Ser Gly Glu
    370                 375                 380

Lys Thr Leu Pro Lys Lys Phe Thr Leu Lys Leu His Ala His Arg Ser
385                 390                 395                 400

Ser Ser Thr Val Pro Gly Thr Tyr Thr Val Gly Leu Asn Val Thr Ser
                405                 410                 415

Asn Val Ile Asp Asn Lys Gln Ala Ala Gly Pro Thr Leu Thr Lys Glu
            420                 425                 430

Leu Ala Leu Asn Val Leu Ser Pro Ala Ala Leu Asp Ala Thr Trp Ala
        435                 440                 445

Pro Gln Asp Asn Leu Thr Leu Ser Asn Thr Gly Val Ser Asn Thr Leu
    450                 455                 460

Val Gly Val Leu Thr Leu Ser Asn Thr Ser Ile Asp Thr Val Ser Ile
465                 470                 475                 480

Ala Ser Thr Asn Val Ser Asp Thr Ser Lys Asn Gly Thr Val Thr Phe
                485                 490                 495

Ala His Glu Thr Asn Asn Ser Ala Ser Phe Ala Thr Thr Ile Ser Thr
            500                 505                 510

Asp Asn Ala Asn Ile Thr Leu Asp Lys Asn Ala Gly Asn Thr Ile Val
        515                 520                 525

Lys Thr Thr Asn Gly Ser Gln Leu Pro Thr Asn Leu Pro Leu Lys Phe
530                 535                 540

Ile Thr Thr Glu Gly Asn Glu His Leu Val Ser Gly Asn Tyr Arg Ala
545                 550                 555                 560

Asn Ile Thr Ile Thr Ser Thr Ile Lys Asp Asn Lys Gln Ala Ala Gly
                565                 570                 575

Pro Thr Leu Thr Lys Glu Leu Ala Leu Asn Val Leu Ser Leu Glu His
            580                 585                 590

His His His His His
        595

<210> SEQ ID NO 36
<211> LENGTH: 1104
<212> TYPE: DNA
<213> ORGANISM: Escherichia coli

<400> SEQUENCE: 36
atgaaatacc tgctgccgac cgctgctgct ggtctgctgc tcctcgctgc ccagccggcg      60
atggccatgg cagtgggccc aacgaaagat atgagtttag gtgcaaattt aacttcagag     120
cctacattag ctattgattt tacgcctatt gaaaatattt atgtaggtgc aattatggt      180 aaagatattg aacccttgt tttcacaaca atgatttaa cagatattac attgatgtca      240
tctcgcagcg ttgttgatgg tcgccagact ggtttttta ccttcatgga ctcatcagcc      300
acttacaaaa ttagtacaaa actgggatca tcgaatgatg taaacattca gaaaattact     360
caaggagcta aaattactcc tgttagtgga gagaaaactt tgcctaaaaa attcactctt     420
aagctacatg cacacaggag tagcagtaca gttccaggta cgtatactgt tggtcttaac     480
gtaaccagta acgttattga taacaagcag gcagcggggc ccactctaac caagaactg     540 gcattaaatg tgctttctcc tgcagctctg gatgcaactt gggctcctca ggataattta     600
acattatcca atactggcgt ttctaatact ttggtgggtg ttttgactct ttcaaatacc     660
```

```
agtattgata cagttagcat tgcgagtaca aatgtttctg atacatctaa gaatggtaca    720
gtaacttttg cacatgagac aaataactct gctagctttg ccaccaccat ttcaacagat    780
aatgccaaca ttacgttgga taaaaatgct ggaaatacga ttgttaaaac tacaaatggg    840
agtcagttgc caactaattt accacttaag tttattacca ctgaaggtaa cgaacattta    900
gtttcaggta attaccgtgc aaatataaca attacttcga caattaaaga taacaagcag    960
gcggcaggtc caaccctgac taaggagtta gcgctgaacg ttctatcgat acttgacgaa   1020
taccaatcta aagttaaaag acaaatattt tcaggctatc aatctgatat tgatacacat   1080
aatagaatta aggatgaatt atga                                           1104
```

<210> SEQ ID NO 37
<211> LENGTH: 367
<212> TYPE: PRT
<213> ORGANISM: Escherichia coli

<400> SEQUENCE: 37

```
Met Lys Tyr Leu Leu Pro Thr Ala Ala Ala Gly Leu Leu Leu Leu Ala
1               5                   10                  15

Ala Gln Pro Ala Met Ala Met Ala Val Gly Pro Thr Lys Asp Met Ser
            20                  25                  30

Leu Gly Ala Asn Leu Thr Ser Glu Pro Thr Leu Ala Ile Asp Phe Thr
        35                  40                  45

Pro Ile Glu Asn Ile Tyr Val Gly Ala Asn Tyr Gly Lys Asp Ile Gly
    50                  55                  60

Thr Leu Val Phe Thr Thr Asn Asp Leu Thr Asp Ile Thr Leu Met Ser
65                  70                  75                  80

Ser Arg Ser Val Val Asp Gly Arg Gln Thr Gly Phe Phe Thr Phe Met
                85                  90                  95

Asp Ser Ser Ala Thr Tyr Lys Ile Ser Thr Lys Leu Gly Ser Ser Asn
            100                 105                 110

Asp Val Asn Ile Gln Glu Ile Thr Gln Gly Ala Lys Ile Thr Pro Val
        115                 120                 125

Ser Gly Glu Lys Thr Leu Pro Lys Lys Phe Thr Leu Lys Leu His Ala
130                 135                 140

His Arg Ser Ser Ser Thr Val Pro Gly Thr Tyr Thr Val Gly Leu Asn
145                 150                 155                 160

Val Thr Ser Asn Val Ile Asp Asn Lys Gln Ala Ala Gly Pro Thr Leu
                165                 170                 175

Thr Lys Glu Leu Ala Leu Asn Val Leu Ser Pro Ala Ala Leu Asp Ala
            180                 185                 190

Thr Trp Ala Pro Gln Asp Asn Leu Thr Leu Ser Asn Thr Gly Val Ser
        195                 200                 205

Asn Thr Leu Val Gly Val Leu Thr Leu Ser Asn Thr Ser Ile Asp Thr
    210                 215                 220

Val Ser Ile Ala Ser Thr Asn Val Ser Asp Thr Ser Lys Asn Gly Thr
225                 230                 235                 240

Val Thr Phe Ala His Glu Thr Asn Asn Ser Ala Ser Phe Ala Thr Thr
                245                 250                 255

Ile Ser Thr Asp Asn Ala Asn Ile Thr Leu Asp Lys Asn Ala Gly Asn
            260                 265                 270

Thr Ile Val Lys Thr Asn Gly Ser Gln Leu Pro Thr Asn Leu Pro
        275                 280                 285

Leu Lys Phe Ile Thr Thr Glu Gly Asn Glu His Leu Val Ser Gly Asn
```

```
                290              295              300
Tyr Arg Ala Asn Ile Thr Ile Thr Ser Thr Ile Lys Asp Asn Lys Gln
305                      310                  315                  320

Ala Ala Gly Pro Thr Leu Thr Lys Glu Leu Ala Leu Asn Val Leu Ser
            325                  330                  335

Ile Leu Asp Glu Tyr Gln Ser Lys Val Lys Arg Gln Ile Phe Ser Gly
                340                  345                  350

Tyr Gln Ser Asp Ile Asp Thr His Asn Arg Ile Lys Asp Glu Leu
            355                  360                  365

<210> SEQ ID NO 38
<211> LENGTH: 381
<212> TYPE: DNA
<213> ORGANISM: Escherichia coli

<400> SEQUENCE: 38
atgagcttta agaaaattat caaggcattt gttatcatgg ctgctttggt atctgttcag    60
gcgcatgccg ctccccagtc tattacagaa ctatgttcgg aatatcacaa cacacaaata   120
tatacgataa atgacaagat actatcatat acggaatcca tggcaggcaa aagagaaatg   180
gttatcatta catttaagag cggcgcaaca tttcaggtcg aagtcccggg cagtcaacat   240
atagactccc aaaaaaaagc cattgaaagg atgaaggaca cattaagaat cgcatatctg   300
accgagacca aaattgataa attatgtgta tggaataata aaccccgca ttcaattgcg    360 gcaatcagta tggaaaacta a                                             381

<210> SEQ ID NO 39
<211> LENGTH: 126
<212> TYPE: PRT
<213> ORGANISM: Escherichia coli

<400> SEQUENCE: 39

Met Ser Phe Lys Lys Ile Ile Lys Ala Phe Val Ile Met Ala Ala Leu
1               5                   10                  15

Val Ser Val Gln Ala His Ala Ala Pro Gln Ser Ile Thr Glu Leu Cys
            20                  25                  30

Ser Glu Tyr His Asn Thr Gln Ile Tyr Thr Ile Asn Asp Lys Ile Leu
        35                  40                  45

Ser Tyr Thr Glu Ser Met Ala Gly Lys Arg Glu Met Val Ile Ile Thr
    50                  55                  60

Phe Lys Ser Gly Ala Thr Phe Gln Val Glu Val Pro Gly Ser Gln His
65                  70                  75                  80

Ile Asp Ser Gln Lys Lys Ala Ile Glu Arg Met Lys Asp Thr Leu Arg
                85                  90                  95

Ile Ala Tyr Leu Thr Glu Thr Lys Ile Asp Lys Leu Cys Val Trp Asn
            100                 105                 110

Asn Lys Thr Pro His Ser Ile Ala Ala Ile Ser Met Glu Asn
        115                 120                 125

<210> SEQ ID NO 40
<211> LENGTH: 1038
<212> TYPE: DNA
<213> ORGANISM: Escherichia coli

<400> SEQUENCE: 40
atgaaatacc tgctgccgac cgctgctgct ggtctgctgc tcctcgctgc ccagccggcg    60
atggccatgt caaaaagttt ttttgcacct gaaccacgaa tacagccttc ttttggtgaa   120
```

```
aatgttggaa aggaaggagc tttattattt agtgtgaact taactgttcc tgaaaatgta    180
tcccaggtaa cggtctaccc tgtttatgat gaagattatg ggttaggacg actagtaaat    240
accgctgatg cttcccaatc aataatctac cagattgttg atgagaaagg gaaaaaaatg    300
ttaaaagatc atggtgcaga ggttacacct aatcaacaaa taacttttaa agcgctgaat    360
tatactagcg gggaaaaaaa aatatctcct ggaatatata acgatcaggt tatggttggt    420
tactacgtca acgacaataa acaaggaaac tggcaatata aatctctgga tgtaaatgta    480
aatattgagc aaaatttat tccagatatt gattccgctg ttcgtataat acctgttaat    540
tacgattcgg acccgaaact ggattcacag ttatatacgg ttgagatgac gatccctgca    600
ggtgtaagcg cagttaaaat cgcaccaaca gatagtctga catcttctgg acagcagatc    660
ggaaagctgg ttaatgtaaa caatccagat caaaatatga attattatat cagaaaggat    720
tctggcgctg gtaactttat ggcaggacaa aaaggatcct ttcctgtcaa agagaatacg    780
tcatacacat tctcagcaat ttatactggt ggcgaatacc ctaatagcgg atattcgtct    840
ggtacttatg caggaaattt gactgtatca ttttacagca atgacaataa acaaagaaca    900
gaaatagcga ctaaaaactt cccagtatca acgactatat cgatacttga cgaataccaa    960
tctaaagtta aagacaaat attttcaggc tatcaatctg atattgatac acataataga   1020
attaaggatg aattatga                                                  1038

<210> SEQ ID NO 41
<211> LENGTH: 347
<212> TYPE: PRT
<213> ORGANISM: Escherichia coli

<400> SEQUENCE: 41

Met Lys Tyr Leu Leu Pro Thr Ala Ala Ala Gly Leu Leu Leu Leu Ala
1               5                   10                  15

Ala Gln Pro Ala Met Ala Met Glu Gln Asn Phe Ile Pro Asp Ile Asp
                20                  25                  30

Ser Ala Val Arg Ile Ile Pro Val Asn Tyr Asp Ser Asp Pro Lys Leu
            35                  40                  45

Asn Ser Gln Leu Tyr Thr Val Glu Met Thr Ile Pro Ala Gly Val Ser
        50                  55                  60

Ala Val Lys Ile Val Pro Thr Asp Ser Leu Thr Ser Ser Gly Gln Gln
65                  70                  75                  80

Ile Gly Lys Leu Val Asn Val Asn Asn Pro Asp Gln Asn Met Asn Tyr
                85                  90                  95

Tyr Ile Arg Lys Asp Ser Gly Ala Gly Lys Phe Met Ala Gly Gln Lys
            100                 105                 110

Gly Ser Phe Ser Val Lys Glu Asn Thr Ser Tyr Thr Phe Ser Ala Ile
        115                 120                 125

Tyr Thr Gly Gly Glu Tyr Pro Asn Ser Gly Tyr Ser Ser Gly Thr Tyr
    130                 135                 140

Ala Gly His Leu Thr Val Ser Phe Tyr Ser Asn Asp Asn Lys Gln Arg
145                 150                 155                 160

Thr Glu Ile Ala Thr Lys Asn Phe Pro Val Ser Thr Thr Ile Ser Lys
                165                 170                 175

Ser Phe Phe Ala Pro Glu Pro Gln Ile Gln Pro Ser Phe Gly Lys Asn
            180                 185                 190

Val Gly Lys Glu Gly Asp Leu Leu Phe Ser Val Ser Leu Ile Val Pro
        195                 200                 205
```

```
Glu Asn Val Ser Gln Val Thr Val Tyr Pro Val Tyr Asp Glu Asp Tyr
    210                 215                 220

Gly Leu Gly Arg Leu Val Asn Thr Ala Asp Asp Ser Gln Ser Ile Ile
225                 230                 235                 240

Tyr Gln Ile Val Asp Asp Lys Gly Lys Lys Met Leu Lys Asp His Gly
                245                 250                 255

Thr Glu Val Thr Pro Asn Gln Gln Ile Thr Phe Lys Ala Leu Asn Tyr
            260                 265                 270

Thr Ser Gly Asp Lys Glu Ile Pro Pro Gly Ile Tyr Asn Asp Gln Val
        275                 280                 285

Met Val Gly Tyr Tyr Val Asn Asp Asn Lys Gln Gly Asn Trp Gln Tyr
    290                 295                 300

Lys Ser Leu Asp Val Asn Val Asn Ile Glu Gln Ser Ile Leu Asp Glu
305                 310                 315                 320

Tyr Gln Ser Lys Val Lys Arg Gln Ile Phe Ser Gly Tyr Gln Ser Asp
                325                 330                 335

Ile Asp Thr His Asn Arg Ile Lys Asp Glu Leu
                340                 345

<210> SEQ ID NO 42
<211> LENGTH: 1038
<212> TYPE: DNA
<213> ORGANISM: Escherichia coli

<400> SEQUENCE: 42
atgaaatacc tgctgccgac cgctgctgct ggtctgctgc tcctcgctgc ccagccggcg      60
atggccatgt caaaaagttt ttttgcacct gaaccacgaa tacagccttc ttttggtgaa     120
aatgttggaa aggaaggagc tttattattt agtgtgaact taactgttcc tgaaaatgta     180
tcccaggtaa cggtctaccc tgtttatgat gaagattatg ggttaggacg actagtaaat     240
accgctgatg cttcccaatc aataatctac cagattgttg atgagaaagg gaaaaaaatg     300
ttaaaagatc atggtgcaga ggttacacct aatcaacaaa taacttttaa agcgctgaat     360
tatactagcg gggaaaaaaa aatatctcct ggaatatata cgatcaggt tatggttggt      420 tactacgtca acgacaataa acaaggaaac tggcaatata atctctgga tgtaaatgta      480 aatattgagc aaaattttat tccagatatt gattccgctg ttcgtataat acctgttaat     540
tacgattcgg acccgaaact ggattcacag ttatatacgg ttgagatgac gatccctgca     600
ggtgtaagcg cagttaaaat cgcaccaaca gatagtctga catcttctgg acagcagatc     660
ggaaagctgg ttaatgtaaa caatccagat caaaatatga attattatat cagaaaggat     720
tctggcgctg gtaactttat ggcaggacaa aaaggatcct ttcctgtcaa agagaatacg     780
tcatacacat tctcagcaat ttatactggt ggcgaatacc taatagcgg atattcgtct      840 ggtacttatg caggaaattt gactgtatca ttttacagca tgacaataa acaaagaaca     900 gaaatagcga ctaaaaactt cccagtatca acgactatat cgatacttga cgaataccaa     960
tctaaagtta aaagacaaat attttcaggc tatcaatctg atattgatac acataataga    1020
attaaggatg aattatga                                                  1038

<210> SEQ ID NO 43
<211> LENGTH: 345
<212> TYPE: PRT
<213> ORGANISM: Escherichia coli

<400> SEQUENCE: 43
```

```
Met Lys Tyr Leu Leu Pro Thr Ala Ala Ala Gly Leu Leu Leu Ala
1               5                   10                  15

Ala Gln Pro Ala Met Ala Met Ser Lys Ser Phe Phe Ala Pro Glu Pro
            20                  25                  30

Arg Ile Gln Pro Ser Phe Gly Glu Asn Val Gly Lys Glu Gly Ala Leu
        35                  40                  45

Leu Phe Ser Val Asn Leu Thr Val Pro Glu Asn Val Ser Gln Val Thr
50                  55                  60

Val Tyr Pro Val Tyr Asp Glu Asp Tyr Gly Leu Gly Arg Leu Val Asn
65                  70                  75                  80

Thr Ala Asp Ala Ser Gln Ser Ile Ile Tyr Gln Ile Val Asp Glu Lys
                85                  90                  95

Gly Lys Lys Met Leu Lys Asp His Gly Ala Glu Val Thr Pro Asn Gln
            100                 105                 110

Gln Ile Thr Phe Lys Ala Leu Asn Tyr Thr Ser Gly Glu Lys Lys Ile
        115                 120                 125

Ser Pro Gly Ile Tyr Asn Asp Gln Val Met Val Gly Tyr Tyr Val Asn
130                 135                 140

Asp Asn Lys Gln Gly Asn Trp Gln Tyr Lys Ser Leu Asp Val Asn Val
145                 150                 155                 160

Asn Ile Glu Gln Asn Phe Ile Pro Asp Ile Asp Ser Ala Val Arg Ile
                165                 170                 175

Ile Pro Val Asn Tyr Asp Ser Asp Pro Lys Leu Asp Ser Gln Leu Tyr
            180                 185                 190

Thr Val Glu Met Thr Ile Pro Ala Gly Val Ser Ala Val Lys Ile Ala
        195                 200                 205

Pro Thr Asp Ser Leu Thr Ser Ser Gly Gln Gln Ile Gly Lys Leu Val
210                 215                 220

Asn Val Asn Asn Pro Asp Gln Asn Met Asn Tyr Tyr Ile Arg Lys Asp
225                 230                 235                 240

Ser Gly Ala Gly Asn Phe Met Ala Gly Gln Lys Gly Ser Phe Pro Val
                245                 250                 255

Lys Glu Asn Thr Ser Tyr Thr Phe Ser Ala Ile Tyr Thr Gly Gly Glu
            260                 265                 270

Tyr Pro Asn Ser Gly Tyr Ser Ser Gly Thr Tyr Ala Gly Asn Leu Thr
        275                 280                 285

Val Ser Phe Tyr Ser Asn Asp Asn Lys Gln Arg Thr Glu Ile Ala Thr
290                 295                 300

Lys Asn Phe Pro Val Ser Thr Thr Ile Ser Ile Leu Asp Glu Tyr Gln
305                 310                 315                 320

Ser Lys Val Lys Arg Gln Ile Phe Ser Gly Tyr Gln Ser Asp Ile Asp
                325                 330                 335

Thr His Asn Arg Ile Lys Asp Glu Leu
            340                 345

<210> SEQ ID NO 44
<211> LENGTH: 1092
<212> TYPE: DNA
<213> ORGANISM: Escherichia coli

<400> SEQUENCE: 44
atgaaaaaga tatttatttt tttgtctatc atattttctg cggtggtcag tgccgggcga      60
tacccggaaa ctacagtagg taatctgacg aagagttttc aagcccctcg tcaggataga     120
```

-continued

```
agcgtacaat caccaatata taacatcttt acgaatcatg tggctggata tagtttgagt    180
cataacttat atgacaggat tgttttttta tgtacatcct cgtcgaatcc ggttaatggt    240
gcttgcccaa ccattggaac atctggagtt caatacggta ctacaaccat aaccttgcag    300
tttacagaaa aaagaagtct gataaaaaga aatattaatc ttgcaggtaa taagaaacca    360
atatgggaga atcagagttg cgacactagc aatctaatgg tgttgaattc gaagtcttgg    420
tcctgtgggg cttacggaaa tgctaacgga acacttctaa atctgtatat ccctgcagga    480
gaaatcaaca aattgccttt tggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720
tgtttctatg atggatatag tacaaacagt gatagcatgg taataaagtt ccaggatgat    780
aatcctacct attcatctga atataatctt tataagatag ggggcactga aaaattacca    840
tatgctgttt cactgcttat gggagaaaaa atatttttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttat ga                                                      1092
```

<210> SEQ ID NO 45
<211> LENGTH: 363
<212> TYPE: PRT
<213> ORGANISM: Escherichia coli

<400> SEQUENCE: 45

```
Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Gln Asp Arg Ser Val Gln Ser Pro Ile Tyr Asn
        35                  40                  45

Ile Phe Thr Asn His Val Ala Gly Tyr Ser Leu Ser His Asn Leu Tyr
    50                  55                  60

Asp Arg Ile Val Phe Leu Cys Thr Ser Ser Asn Pro Val Asn Gly
65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Thr Ser Asn Leu Met Val Leu Asn Ser Lys Ser Trp Ser Cys Gly Ala
    130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
```

```
            195                 200                 205
Val Trp Leu Pro Gly Phe His Ser Asn Pro Arg Val Asp Leu Asn Leu
210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Tyr Ser Ser Glu Tyr Asn Leu Tyr Lys
                260                 265                 270

Ile Gly Gly Thr Glu Lys Leu Pro Tyr Ala Val Ser Leu Leu Met Gly
                275                 280                 285

Glu Lys Ile Phe Tyr Pro Val Asn Gly Gln Ser Phe Thr Ile Asn Asp
290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
                340                 345                 350

Tyr Ile Thr Phe Thr Pro Ser Val Glu Asn Leu
                355                 360

<210> SEQ ID NO 46
<211> LENGTH: 345
<212> TYPE: PRT
<213> ORGANISM: Escherichia coli

<400> SEQUENCE: 46

Gly Arg Tyr Pro Glu Thr Thr Val Gly Asn Leu Thr Lys Ser Phe Gln
1               5                   10                  15

Ala Pro Arg Gln Asp Arg Ser Val Gln Ser Pro Ile Tyr Asn Ile Phe
                20                  25                  30

Thr Asn His Val Ala Gly Tyr Ser Leu Ser His Asn Leu Tyr Asp Arg
            35                  40                  45

Ile Val Phe Leu Cys Thr Ser Ser Asn Pro Val Asn Gly Ala Cys
        50                  55                  60

Pro Thr Ile Gly Thr Ser Gly Val Gln Tyr Gly Thr Thr Thr Ile Thr
65                  70                  75                  80

Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Thr Ser
                100                 105                 110

Asn Leu Met Val Leu Asn Ser Lys Ser Trp Ser Cys Gly Ala Tyr Gly
            115                 120                 125

Asn Ala Asn Gly Thr Leu Leu Asn Leu Tyr Ile Pro Ala Gly Glu Ile
130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
                180                 185                 190

Leu Pro Gly Phe His Ser Asn Pro Arg Val Asp Leu Asn Leu His Pro
            195                 200                 205
```

Ile Gly Asn Tyr Lys Tyr Ser Gly Ser Asn Ser Leu Asp Met Cys Phe
210                 215                 220

Tyr Asp Gly Tyr Ser Thr Asn Ser Asp Ser Met Val Ile Lys Phe Gln
225                 230                 235                 240

Asp Asp Asn Pro Thr Tyr Ser Ser Glu Tyr Asn Leu Tyr Lys Ile Gly
                245                 250                 255

Gly Thr Glu Lys Leu Pro Tyr Ala Val Ser Leu Leu Met Gly Glu Lys
            260                 265                 270

Ile Phe Tyr Pro Val Asn Gly Gln Ser Phe Thr Ile Asn Asp Ser Ser
            275                 280                 285

Val Leu Glu Thr Asn Trp Asn Arg Val Thr Ala Val Ala Met Pro Glu
290                 295                 300

Val Asn Val Pro Val Leu Cys Trp Pro Ala Arg Leu Leu Leu Asn Ala
305                 310                 315                 320

Asp Val Asn Ala Pro Asp Ala Gly Gln Tyr Ser Gly Gln Ile Tyr Ile
                325                 330                 335

Thr Phe Thr Pro Ser Val Glu Asn Leu
            340                 345

<210> SEQ ID NO 47
<211> LENGTH: 507
<212> TYPE: DNA
<213> ORGANISM: Escherichia coli

<400> SEQUENCE: 47
atgaaactga agaaaacaat tggcgcaatg ctatggcga ctctgtttgc caccatggct      60
gcctctgcag tcgaaaaaaa tattactgtg agggcaagtg ttgaccctaa acttgatctt     120
ctgcaagcag atggaacttc actgccggac tctatcgcat taacctattc ttcggcttca     180
aataattttg aagtttactc tcttaatact gctattcata caaatgacaa agcaaggga      240 gttgtagtga agctgtcagc ttcaccagtt ctgtccaata ttatgaagcc aaactcgcaa     300
attccgatga aagtgacttt ggggggaag acgctgaata caactgatac tgagtttact      360
gttgatactc tgaactttgg tacatctggt gttgaaaacg tttcttccac tcaacagctt     420
acgattcatg cagacacaca aggaactgcg cctgaggcag gcaattacca aggtattatt     480
tctcttatca tgactcaaaa aacttaa                                         507

<210> SEQ ID NO 48
<211> LENGTH: 168
<212> TYPE: PRT
<213> ORGANISM: Escherichia coli

<400> SEQUENCE: 48

Met Lys Leu Lys Lys Thr Ile Gly Ala Met Ala Met Ala Thr Leu Phe
1               5                   10                  15

Ala Thr Met Ala Ala Ser Ala Val Glu Lys Asn Ile Thr Val Arg Ala
            20                  25                  30

Ser Val Asp Pro Lys Leu Asp Leu Gln Ala Asp Gly Thr Ser Leu
        35                  40                  45

Pro Asp Ser Ile Ala Leu Thr Tyr Ser Ser Ala Ser Asn Asn Phe Glu
50                  55                  60

Val Tyr Ser Leu Asn Thr Ala Ile His Thr Asn Asp Lys Ser Lys Gly
65                  70                  75                  80

Val Val Val Lys Leu Ser Ala Ser Pro Val Leu Ser Asn Ile Met Lys
                85                  90                  95

```
Pro Asn Ser Gln Ile Pro Met Lys Val Thr Leu Gly Gly Lys Thr Leu
                100                 105                 110

Asn Thr Thr Asp Thr Glu Phe Thr Val Asp Thr Leu Asn Phe Gly Thr
            115                 120                 125

Ser Gly Val Glu Asn Val Ser Ser Thr Gln Gln Leu Thr Ile His Ala
    130                 135                 140

Asp Thr Gln Gly Thr Ala Pro Glu Ala Gly Asn Tyr Gln Gly Ile Ile
145                 150                 155                 160

Ser Leu Ile Met Thr Gln Lys Thr
                165

<210> SEQ ID NO 49
<211> LENGTH: 145
<212> TYPE: PRT
<213> ORGANISM: Escherichia coli

<400> SEQUENCE: 49

Val Glu Lys Asn Ile Thr Val Arg Ala Ser Val Asp Pro Lys Leu Asp
1               5                   10                  15

Leu Leu Gln Ala Asp Gly Thr Ser Leu Pro Asp Ser Ile Ala Leu Thr
            20                  25                  30

Tyr Ser Ser Ala Ser Asn Asn Phe Glu Val Tyr Ser Leu Asn Thr Ala
        35                  40                  45

Ile His Thr Asn Asp Lys Ser Lys Gly Val Val Lys Leu Ser Ala
    50                  55                  60

Ser Pro Val Leu Ser Asn Ile Met Lys Pro Asn Ser Gln Ile Pro Met
65                  70                  75                  80

Lys Val Thr Leu Gly Gly Lys Thr Leu Asn Thr Thr Asp Thr Glu Phe
                85                  90                  95

Thr Val Asp Thr Leu Asn Phe Gly Thr Ser Gly Val Glu Asn Val Ser
                100                 105                 110

Ser Thr Gln Gln Leu Thr Ile His Ala Asp Thr Gln Gly Thr Ala Pro
            115                 120                 125

Glu Ala Gly Asn Tyr Gln Gly Ile Ile Ser Leu Ile Met Thr Gln Lys
    130                 135                 140

Thr
145

<210> SEQ ID NO 50
<211> LENGTH: 1095
<212> TYPE: DNA
<213> ORGANISM: Escherichia coli

<400> SEQUENCE: 50
ttgaaaaaag tgattttgt tttatccatg tttctatgtt ctcaggttta cgggcaatca    60
tggcatacga acgtagaggc tggttcaata aataaaacag agtcgatagg ccccatagac   120
cgaagtgctg ctgcatcgta tcctgctcat tatatatttc atgaacatgt tgctggttac   180
aataaagatc actctctttt tgacaggatg acgtttttat gtatgtcatc aacagatgca   240
tctaaaggtg catgtccgac aggagaaaac tccaaatcct ctcaagggga gactaatatt   300
aagctaatat ttactgaaaa gaaagtctg gccagaaaaa cattaaactt aaaaggatat   360
aagagatttt tatatgaatc agatagatgc attcattatg tcgataaaat gaatctcaat   420
tctcatactg ttaaatgtgt aggttcattc acaagaggag tagatttcac tttatatatc   480
ccacaaggtg aaattgatgg gcttctaact ggaggtatat gggaggcaac actagagtta   540
```

```
cgagtcaaaa ggcattacga ctataatcat ggtacttaca aagttaatat cacagttgat      600
ttgacagaca aaggaaatat tcaggtctgg acaccaaagt ttcatagcga tcctagaatt      660
gatctgaatt tacgtcctga aggtaatggt aaatattctg gtagtaacgt gcttgagatg      720
tgtctctatg atggctatag tacacatagt caaagtatag aaatgaggtt tcaggatgac      780
tcacaaacag gaaataatga atataatctt ataaaaactg gagagccatt aaaaaaattg      840
ccatataaac tttctcttct tttaggagga cgagagtttt atccaaataa tggagaggct      900
tttactatta atgatacttc gtcattgttt ataaactgga atcgtattaa gtctgtatcc      960
ttaccacaga ttagtattcc agtactatgc tggccagcaa acttgacatt tatgtcagag     1020
ctaaataatc cagaagcggg tgagtattca ggaatactta acgtaacatt tactcctagt     1080
agttcaagtc tgtaa                                                      1095

<210> SEQ ID NO 51
<211> LENGTH: 364
<212> TYPE: PRT
<213> ORGANISM: Escherichia coli

<400> SEQUENCE: 51

Leu Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
            20                  25                  30

Thr Glu Ser Ile Gly Pro Ile Asp Arg Ser Ala Ala Ser Tyr Pro
        35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
            100                 105                 110

Lys Thr Leu Asn Leu Lys Gly Tyr Lys Arg Phe Leu Tyr Glu Ser Asp
        115                 120                 125

Arg Cys Ile His Tyr Val Asp Lys Met Asn Leu Asn Ser His Thr Val
    130                 135                 140

Lys Cys Val Gly Ser Phe Thr Arg Gly Val Asp Phe Thr Leu Tyr Ile
145                 150                 155                 160

Pro Gln Gly Glu Ile Asp Gly Leu Leu Thr Gly Gly Ile Trp Glu Ala
                165                 170                 175

Thr Leu Glu Leu Arg Val Lys Arg His Tyr Asp Tyr Asn His Gly Thr
            180                 185                 190

Tyr Lys Val Asn Ile Thr Val Asp Leu Thr Lys Gly Asn Ile Gln
        195                 200                 205

Val Trp Thr Pro Lys Phe His Ser Asp Pro Arg Ile Asp Leu Asn Leu
    210                 215                 220

Arg Pro Glu Gly Asn Gly Lys Tyr Ser Gly Ser Asn Val Leu Glu Met
225                 230                 235                 240

Cys Leu Tyr Asp Gly Tyr Ser Thr His Ser Gln Ser Ile Glu Met Arg
                245                 250                 255

Phe Gln Asp Asp Ser Gln Thr Gly Asn Asn Glu Tyr Asn Leu Ile Lys
            260                 265                 270
```

```
Thr Gly Glu Pro Leu Lys Lys Leu Pro Tyr Lys Leu Ser Leu Leu Leu
            275                 280                 285

Gly Gly Arg Glu Phe Tyr Pro Asn Asn Gly Glu Ala Phe Thr Ile Asn
290                 295                 300

Asp Thr Ser Ser Leu Phe Ile Asn Trp Asn Arg Ile Lys Ser Val Ser
305                 310                 315                 320

Leu Pro Gln Ile Ser Ile Pro Val Leu Cys Trp Pro Ala Asn Leu Thr
                325                 330                 335

Phe Met Ser Glu Leu Asn Asn Pro Glu Ala Gly Glu Tyr Ser Gly Ile
            340                 345                 350

Leu Asn Val Thr Phe Thr Pro Ser Ser Ser Leu
            355                 360

<210> SEQ ID NO 52
<211> LENGTH: 346
<212> TYPE: PRT
<213> ORGANISM: Escherichia coli

<400> SEQUENCE: 52

Gln Ser Trp His Thr Asn Val Glu Ala Gly Ser Ile Asn Lys Thr Glu
1               5                   10                  15

Ser Ile Gly Pro Ile Asp Arg Ser Ala Ala Ser Tyr Pro Ala His
            20                  25                  30

Tyr Ile Phe His Glu His Val Ala Gly Tyr Asn Lys Asp His Ser Leu
            35                  40                  45

Phe Asp Arg Met Thr Phe Leu Cys Met Ser Ser Thr Asp Ala Ser Lys
        50                  55                  60

Gly Ala Cys Pro Thr Gly Glu Asn Ser Lys Ser Ser Gln Gly Glu Thr
65                  70                  75                  80

Asn Ile Lys Leu Ile Phe Thr Glu Lys Lys Ser Leu Ala Arg Lys Thr
                85                  90                  95

Leu Asn Leu Lys Gly Tyr Lys Arg Phe Leu Tyr Glu Ser Asp Arg Cys
            100                 105                 110

Ile His Tyr Val Asp Lys Met Asn Leu Asn Ser His Thr Val Lys Cys
        115                 120                 125

Val Gly Ser Phe Thr Arg Gly Val Asp Phe Thr Leu Tyr Ile Pro Gln
    130                 135                 140

Gly Glu Ile Asp Gly Leu Leu Thr Gly Gly Ile Trp Glu Ala Thr Leu
145                 150                 155                 160

Glu Leu Arg Val Lys Arg His Tyr Asp Tyr Asn His Gly Thr Tyr Lys
                165                 170                 175

Val Asn Ile Thr Val Asp Leu Thr Asp Lys Gly Asn Ile Gln Val Trp
            180                 185                 190

Thr Pro Lys Phe His Ser Asp Pro Arg Ile Asp Leu Asn Leu Arg Pro
        195                 200                 205

Glu Gly Asn Gly Lys Tyr Ser Gly Ser Asn Val Leu Glu Met Cys Leu
    210                 215                 220

Tyr Asp Gly Tyr Ser Thr His Ser Gln Ser Ile Glu Met Arg Phe Gln
225                 230                 235                 240

Asp Asp Ser Gln Thr Gly Asn Asn Glu Tyr Asn Leu Ile Lys Thr Gly
                245                 250                 255

Glu Pro Leu Lys Lys Leu Pro Tyr Lys Leu Ser Leu Leu Leu Gly Gly
            260                 265                 270

Arg Glu Phe Tyr Pro Asn Asn Gly Glu Ala Phe Thr Ile Asn Asp Thr
        275                 280                 285
```

```
Ser Ser Leu Phe Ile Asn Trp Asn Arg Ile Lys Ser Val Ser Leu Pro
    290                 295                 300

Gln Ile Ser Ile Pro Val Leu Cys Trp Pro Ala Asn Leu Thr Phe Met
305                 310                 315                 320

Ser Glu Leu Asn Asn Pro Glu Ala Gly Glu Tyr Ser Gly Ile Leu Asn
            325                 330                 335

Val Thr Phe Thr Pro Ser Ser Ser Ser Leu
            340                 345

<210> SEQ ID NO 53
<211> LENGTH: 513
<212> TYPE: DNA
<213> ORGANISM: Escherichia coli

<400> SEQUENCE: 53
atgaaactca ataagattat tggagcatta gttctttcat ctacatttgt tagcatgggg      60
gcttctgctg ccgagaaaaa tatcactgta actgctagcg ttgatccaac tatcgatctg     120
atgcaatctg atggcacagc gttaccaagt gcagttaata ttgcatatct tccaggagag     180
aaaagatttg aatctgctcg tatcaatacc caagttcata ccaataataa aactaagggt     240
attcagataa agcttactaa tgataatgtg gtaatgacta acttatctga tccaagcaag     300
actattcctt tagaggtttc attcgctggc actaagctga gcacagctgc aacatctatt     360
actgccgatc aattaaattt tggcgcagct ggtgtagaga cagtttctgc aactaaggaa     420
ctcgttatta atgcaggaag cacccagcaa actaatattg tagctggtaa ctatcaagga     480
ttggtgtcaa ttgtgcttac tcaagaacct taa                                  513

<210> SEQ ID NO 54
<211> LENGTH: 170
<212> TYPE: PRT
<213> ORGANISM: Escherichia coli

<400> SEQUENCE: 54

Met Lys Leu Asn Lys Ile Ile Gly Ala Leu Val Leu Ser Ser Thr Phe
1               5                   10                  15

Val Ser Met Gly Ala Ser Ala Ala Glu Lys Asn Ile Thr Val Thr Ala
            20                  25                  30

Ser Val Asp Pro Thr Ile Asp Leu Met Gln Ser Asp Gly Thr Ala Leu
        35                  40                  45

Pro Ser Ala Val Asn Ile Ala Tyr Leu Pro Gly Glu Lys Arg Phe Glu
    50                  55                  60

Ser Ala Arg Ile Asn Thr Gln Val His Thr Asn Asn Lys Thr Lys Gly
65                  70                  75                  80

Ile Gln Ile Lys Leu Thr Asn Asp Asn Val Val Met Thr Asn Leu Ser
                85                  90                  95

Asp Pro Ser Lys Thr Ile Pro Leu Glu Val Ser Phe Ala Gly Thr Lys
            100                 105                 110

Leu Ser Thr Ala Ala Thr Ser Ile Thr Ala Asp Gln Leu Asn Phe Gly
        115                 120                 125

Ala Ala Gly Val Glu Thr Val Ser Ala Thr Lys Glu Leu Val Ile Asn
    130                 135                 140

Ala Gly Ser Thr Gln Gln Thr Asn Ile Val Ala Gly Asn Tyr Gln Gly
145                 150                 155                 160

Leu Val Ser Ile Val Leu Thr Gln Glu Pro
                165                 170
```

<210> SEQ ID NO 55
<211> LENGTH: 147
<212> TYPE: PRT
<213> ORGANISM: Escherichia coli

<400> SEQUENCE: 55

```
Ala Glu Lys Asn Ile Thr Val Thr Ala Ser Val Asp Pro Thr Ile Asp
1               5                   10                  15
Leu Met Gln Ser Asp Gly Thr Ala Leu Pro Ser Ala Val Asn Ile Ala
            20                  25                  30
Tyr Leu Pro Gly Glu Lys Arg Phe Glu Ser Ala Arg Ile Asn Thr Gln
        35                  40                  45
Val His Thr Asn Asn Lys Thr Lys Gly Ile Gln Ile Lys Leu Thr Asn
    50                  55                  60
Asp Asn Val Val Met Thr Asn Leu Ser Asp Pro Ser Lys Thr Ile Pro
65                  70                  75                  80
Leu Glu Val Ser Phe Ala Gly Thr Lys Leu Ser Thr Ala Ala Thr Ser
                85                  90                  95
Ile Thr Ala Asp Gln Leu Asn Phe Gly Ala Ala Gly Val Glu Thr Val
            100                 105                 110
Ser Ala Thr Lys Glu Leu Val Ile Asn Ala Gly Ser Thr Gln Gln Thr
        115                 120                 125
Asn Ile Val Ala Gly Asn Tyr Gln Gly Leu Val Ser Ile Val Leu Thr
    130                 135                 140
Gln Glu Pro
145
```

<210> SEQ ID NO 56
<211> LENGTH: 1083
<212> TYPE: DNA
<213> ORGANISM: Escherichia coli

<400> SEQUENCE: 56

```
atgaataaaa tttatttat ttttacattg ttttttctt cagggttttt tacatttgcc      60
gtatcggcag ataaaaatcc cggaagtgaa aacatgacta atactattgg tccccatgac   120
agggggggat cttcccccat atataatatc ttaaattcct atcttacagc atacaatgga   180
agccatcatc tgtatgatag gatgagtttt ttatgtttgt cttctcaaaa tacactgaat   240
ggagcatgcc caagcagtga tgcccctggc actgctacaa ttgatggcga acaaatata    300
acattacaat ttacggaaaa aagaagtcta attaaaagag aactgcaaat taaaggctat   360
aaacaatttt tgttcaaaaa tgctaattgc ccatctaaac tagcacttaa ctcatctcat   420
tttcaatgta atagagaaca agcttcaggt gctactttat cgttatacat accagctggt   480
gaattaaata aattaccttt tgggggggtc tggaatgccg ttctgaagct aaatgtaaaa   540
agacgatatg atacaaccta tgggacttac actataaaca tcacagttaa tttaactgat   600
aagggaaata ttcagatatg gttaccacag ttcaaaagta cgctcgtgt cgatcttaac    660
ttgcgtccaa ctggtggtgg tacatatatc ggaagaaatt ctgttgatat gtgcttttat   720
gatggatata gtactaacag cagctctttg gagataagt tcaggatga taattctaaa    780
tctgatggaa attttatct aaagaaaata aatgatgact ccaagaact tgtatacact    840
ttgtcacttc tcctggcagg taaaaattta acaccaacaa atggacaggc attaaatatt   900
aacactgctt ctctggaaac aaactggaat agaattacag ctgtcaccat gccagaaatc   960
```

```
agtgttccgg tgttgtgttg gcctggacgt ttgcaattgg atgcaaaagt gaaaaatccc    1020
gaggctggac aatatatggg gaatattaaa attactttca caccaagtag tcaaacactc    1080
tag                                                                  1083
```

<210> SEQ ID NO 57
<211> LENGTH: 360
<212> TYPE: PRT
<213> ORGANISM: Escherichia coli

<400> SEQUENCE: 57

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350
```

```
Phe Thr Pro Ser Ser Gln Thr Leu
        355                 360

<210> SEQ ID NO 58
<211> LENGTH: 338
<212> TYPE: PRT
<213> ORGANISM: Escherichia coli

<400> SEQUENCE: 58

Ala Asp Lys Asn Pro Gly Ser Glu Asn Met Thr Asn Thr Ile Gly Pro
1               5                   10                  15

His Asp Arg Gly Gly Ser Ser Pro Ile Tyr Asn Ile Leu Asn Ser Tyr
            20                  25                  30

Leu Thr Ala Tyr Asn Gly Ser His His Leu Tyr Asp Arg Met Ser Phe
        35                  40                  45

Leu Cys Leu Ser Ser Gln Asn Thr Leu Asn Gly Ala Cys Pro Ser Ser
    50                  55                  60

Asp Ala Pro Gly Thr Ala Thr Ile Asp Gly Glu Thr Asn Ile Thr Leu
65                  70                  75                  80

Gln Phe Thr Glu Lys Arg Ser Leu Ile Lys Arg Glu Leu Gln Ile Lys
                85                  90                  95

Gly Tyr Lys Gln Phe Leu Phe Lys Asn Ala Asn Cys Pro Ser Lys Leu
            100                 105                 110

Ala Leu Asn Ser Ser His Phe Gln Cys Asn Arg Glu Gln Ala Ser Gly
        115                 120                 125

Ala Thr Leu Ser Leu Tyr Ile Pro Ala Gly Glu Leu Asn Lys Leu Pro
130                 135                 140

Phe Gly Gly Val Trp Asn Ala Val Leu Lys Leu Asn Val Lys Arg Arg
145                 150                 155                 160

Tyr Asp Thr Thr Tyr Gly Thr Tyr Thr Ile Asn Ile Thr Val Asn Leu
                165                 170                 175

Thr Asp Lys Gly Asn Ile Gln Ile Trp Leu Pro Gln Phe Lys Ser Asn
            180                 185                 190

Ala Arg Val Asp Leu Asn Leu Arg Pro Thr Gly Gly Thr Tyr Ile
        195                 200                 205

Gly Arg Asn Ser Val Asp Met Cys Phe Tyr Asp Gly Tyr Ser Thr Asn
210                 215                 220

Ser Ser Ser Leu Glu Ile Arg Phe Gln Asp Asn Ser Lys Ser Asp
225                 230                 235                 240

Gly Lys Phe Tyr Leu Lys Lys Ile Asn Asp Asp Ser Lys Glu Leu Val
                245                 250                 255

Tyr Thr Leu Ser Leu Leu Leu Ala Gly Lys Asn Leu Thr Pro Thr Asn
            260                 265                 270

Gly Gln Ala Leu Asn Ile Asn Thr Ala Ser Leu Glu Thr Asn Trp Asn
        275                 280                 285

Arg Ile Thr Ala Val Thr Met Pro Glu Ile Ser Val Pro Val Leu Cys
290                 295                 300

Trp Pro Gly Arg Leu Gln Leu Asp Ala Lys Val Lys Asn Pro Glu Ala
305                 310                 315                 320

Gly Gln Tyr Met Gly Asn Ile Lys Ile Thr Phe Thr Pro Ser Ser Gln
                325                 330                 335

Thr Leu

<210> SEQ ID NO 59
```

<211> LENGTH: 513
<212> TYPE: DNA
<213> ORGANISM: Escherichia coli

<400> SEQUENCE: 59

```
atgaaattta aaaaaactat tggtgcaatg gctctgacca caatgtttgt agcagtgagt      60
gcttcagcag tagagaaaaa tattactgta acagctagtg ttgatcctgc aattgatctt     120
ttgcaagctg atggcaatgc tctgccatca gctgtaaagt tagcttattc tcccgcatca     180
aaaactttg aaagttacag agtaatgact caagttcata caaacgatgc aactaaaaaa      240
gtaattgtta aacttgctga tacaccacag cttacagatg ttctgaattc aactgttcaa     300
atgcctatca gtgtgtcatg gggaggacaa gtattatcta caacagccaa agaatttgaa     360
gctgctgctt gggatattc tgcatccggt gtaaatggcg tatcatcttc tcaagagtta      420
gtaattagcg ctgcacctaa aactgccggt accgccccaa ctgcaggaaa ctattcagga     480
gtagtatctc ttgtaatgac tttgggatcc tga                                  513
```

<210> SEQ ID NO 60
<211> LENGTH: 170
<212> TYPE: PRT
<213> ORGANISM: Escherichia coli

<400> SEQUENCE: 60

Met Lys Phe Lys Lys Thr Ile Gly Ala Met Ala Leu Thr Thr Met Phe
1               5                   10                  15

Val Ala Val Ser Ala Ser Ala Val Glu Lys Asn Ile Thr Val Thr Ala
            20                  25                  30

Ser Val Asp Pro Ala Ile Asp Leu Leu Gln Ala Asp Gly Asn Ala Leu
        35                  40                  45

Pro Ser Ala Val Lys Leu Ala Tyr Ser Pro Ala Ser Lys Thr Phe Glu
    50                  55                  60

Ser Tyr Arg Val Met Thr Gln Val His Thr Asn Asp Ala Thr Lys Lys
65                  70                  75                  80

Val Ile Val Lys Leu Ala Asp Thr Pro Gln Leu Thr Asp Val Leu Asn
                85                  90                  95

Ser Thr Val Gln Met Pro Ile Ser Val Ser Trp Gly Gly Gln Val Leu
            100                 105                 110

Ser Thr Thr Ala Lys Glu Phe Glu Ala Ala Ala Leu Gly Tyr Ser Ala
        115                 120                 125

Ser Gly Val Asn Gly Val Ser Ser Ser Gln Glu Leu Val Ile Ser Ala
    130                 135                 140

Ala Pro Lys Thr Ala Gly Thr Ala Pro Thr Ala Gly Asn Tyr Ser Gly
145                 150                 155                 160

Val Val Ser Leu Val Met Thr Leu Gly Ser
                165                 170

<210> SEQ ID NO 61
<211> LENGTH: 147
<212> TYPE: PRT
<213> ORGANISM: Escherichia coli

<400> SEQUENCE: 61

Val Glu Lys Asn Ile Thr Val Thr Ala Ser Val Asp Pro Ala Ile Asp
1               5                   10                  15

Leu Leu Gln Ala Asp Gly Asn Ala Leu Pro Ser Ala Val Lys Leu Ala
            20                  25                  30

```
Tyr Ser Pro Ala Ser Lys Thr Phe Glu Ser Tyr Arg Val Met Thr Gln
         35                  40                  45
Val His Thr Asn Asp Ala Thr Lys Lys Val Ile Val Lys Leu Ala Asp
 50                  55                  60
Thr Pro Gln Leu Thr Asp Val Leu Asn Ser Thr Val Gln Met Pro Ile
 65                  70                  75                  80
Ser Val Ser Trp Gly Gly Gln Val Leu Ser Thr Thr Ala Lys Glu Phe
                 85                  90                  95
Glu Ala Ala Ala Leu Gly Tyr Ser Ser Gly Val Asn Gly Val Ser
             100                 105                 110
Ser Ser Gln Glu Leu Val Ile Ser Ala Ala Pro Lys Thr Ala Gly Thr
         115                 120                 125
Ala Pro Thr Ala Gly Asn Tyr Ser Gly Val Val Ser Leu Val Met Thr
     130                 135                 140
Leu Gly Ser
145
```

<210> SEQ ID NO 62
<211> LENGTH: 504
<212> TYPE: DNA
<213> ORGANISM: Escherichia coli

<400> SEQUENCE: 62

```
atgaaattaa aaaaaactat tggtgcaatg gcactgacca caatgtttgt agctatgagt      60
gcttctgcag tagagaaaaa tatcactgta acagctagtg ttgatcctac aattgatatt     120
ttgcaagctg atggtagtag tttacctact gctgtagaat taacctattc acctgcggca     180
agtcgttttg aaaattataa aatcgcaact aaagttcata caaatgttat aaataaaaat     240
gtactagtta agcttgtaaa tgatccaaaa cttacaaatg ttttggattc tacaaaacaa     300
ctccccatta ctgtatcata tggaggaaag actctatcaa ccgcagatgt gacttttgaa     360
cctgcagaat taaattttgg aacgtcaggt gtaactggtg tatcttcttc ccaagattta     420
gtgattggtg cgactacagc acaagcacca acggcgggaa attatagtgg ggtcgtttct     480
atcttaatga ccttagcatc ataa                                           504
```

<210> SEQ ID NO 63
<211> LENGTH: 167
<212> TYPE: PRT
<213> ORGANISM: Escherichia coli

<400> SEQUENCE: 63

```
Met Lys Leu Lys Lys Thr Ile Gly Ala Met Ala Leu Thr Thr Met Phe
  1               5                  10                  15
Val Ala Met Ser Ala Ser Ala Val Glu Lys Asn Ile Thr Val Thr Ala
             20                  25                  30
Ser Val Asp Pro Thr Ile Asp Ile Leu Gln Ala Asp Gly Ser Ser Leu
         35                  40                  45
Pro Thr Ala Val Glu Leu Thr Tyr Ser Pro Ala Ala Ser Arg Phe Glu
 50                  55                  60
Asn Tyr Lys Ile Ala Thr Lys Val His Thr Asn Val Ile Asn Lys Asn
 65                  70                  75                  80
Val Leu Val Lys Leu Val Asn Asp Pro Lys Leu Thr Asn Val Leu Asp
                 85                  90                  95
Ser Thr Lys Gln Leu Pro Ile Thr Val Ser Tyr Gly Gly Lys Thr Leu
             100                 105                 110
```

```
Ser Thr Ala Asp Val Thr Phe Glu Pro Ala Glu Leu Asn Phe Gly Thr
        115                 120                 125

Ser Gly Val Thr Gly Val Ser Ser Gln Asp Leu Val Ile Gly Ala
    130                 135                 140

Thr Thr Ala Gln Ala Pro Thr Ala Gly Asn Tyr Ser Gly Val Val Ser
145                 150                 155                 160

Ile Leu Met Thr Leu Ala Ser
                165

<210> SEQ ID NO 64
<211> LENGTH: 1086
<212> TYPE: DNA
<213> ORGANISM: Escherichia coli

<400> SEQUENCE: 64
atgaataaga ttttatttat ttttacattg ttttttctctt cagtactttt tacatttgct    60
gtatcggcag ataaaattcc cggagatgaa agcataacta atattttggg cccgcgtgac   120
aggaacgaat cttcccccaa acataatata ttaaataacc atattacagc atacagtgaa   180
agtcatactc tgtatgatag gatgactttt ttatgtttgt cttctcacaa tacacttaat   240
ggagcatgtc aaccagtgaa gaatcctagc agttcatcgg tcagcggtga aacaaatata   300
acattacaat ttacggaaaa aagaagttta ataaaagag agctacaaat taaaggctat   360
aaacaattat tgttcaaaag tgttaactgc ccatccggcc taacacttaa ctcagctcat   420
tttaactgta ataaaaacgc ggcttcaggt gcaagtttat atttatatat tcctgctggc   480
gaactaaaaa atttgccttt tggtggtatc tgggatgcta ctctgaagtt aagagtaaaa   540
agacgatata gtgagaccta tggaacttac actataaata tcactattaa attaactgat   600
aagggaaata ttcagatatg gttacctcag ttcaaaagtg acgctcgcgt cgatcttaac   660
ttgcgtccaa ctggtggggg cacatatatt ggaagaaatt ctgttgatat gtgcttttat   720
gatggatata gtactaacag cagctctttg gagataagt ttcaggataa caatcctaaa   780
tctgatggga aattttatct aaggaaaata aatgatgaca ccaagaaaat tgcatatact   840
ttgtcacttc tcttggcggg taaaagttta actccaacaa atggaacgtc attaaatatt   900
gctgacgcag cttctctgga aacaaactgg aatagaatta cagctgtcac catgccagaa   960
atcagtgttc cggtgttgtg ttggcctgga cgtttgcaat ggatgcaaa agtggaaaat   1020 cccgaggctg acaatatat gggtaatatt aatgttactt tcacaccaag tagtcaaaca  1080
ctctag                                                              1086

<210> SEQ ID NO 65
<211> LENGTH: 361
<212> TYPE: PRT
<213> ORGANISM: Escherichia coli

<400> SEQUENCE: 65

Met Asn Lys Ile Leu Phe Ile Phe Thr Leu Phe Phe Ser Ser Val Leu
1               5                   10                  15

Phe Thr Phe Ala Val Ser Ala Asp Lys Ile Pro Gly Asp Glu Ser Ile
            20                  25                  30

Thr Asn Ile Phe Gly Pro Arg Asp Arg Asn Glu Ser Pro Lys His
        35                  40                  45

Asn Ile Leu Asn Asn His Ile Thr Ala Tyr Ser Glu Ser His Thr Leu
    50                  55                  60

Tyr Asp Arg Met Thr Phe Leu Cys Leu Ser Ser His Asn Thr Leu Asn
```

```
            65                  70                  75                  80
Gly Ala Cys Pro Thr Ser Glu Asn Pro Ser Ser Ser Val Ser Gly
                85                  90                  95

Glu Thr Asn Ile Thr Leu Gln Phe Thr Glu Lys Arg Ser Leu Ile Lys
                100                 105                 110

Arg Glu Leu Gln Ile Lys Gly Tyr Lys Gln Leu Leu Phe Lys Ser Val
                115                 120                 125

Asn Cys Pro Ser Gly Leu Thr Leu Asn Ser Ala His Phe Asn Cys Asn
130                 135                 140

Lys Asn Ala Ala Ser Gly Ala Ser Leu Tyr Leu Tyr Ile Pro Ala Gly
145                 150                 155                 160

Glu Leu Lys Asn Leu Pro Phe Gly Gly Ile Trp Asp Ala Thr Leu Lys
                165                 170                 175

Leu Arg Val Lys Arg Tyr Ser Glu Thr Tyr Gly Tyr Thr Ile
                180                 185                 190

Asn Ile Thr Ile Lys Leu Thr Asp Lys Gly Asn Ile Gln Ile Trp Leu
                195                 200                 205

Pro Gln Phe Lys Ser Asp Ala Arg Val Asp Leu Asn Leu Arg Pro Thr
210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asn Asn Pro Lys Ser Asp Gly Lys Phe Tyr Leu Arg Lys Ile Asn Asp
                260                 265                 270

Asp Thr Lys Glu Ile Ala Tyr Thr Leu Ser Leu Leu Ala Gly Lys
                275                 280                 285

Ser Leu Thr Pro Thr Asn Gly Thr Ser Leu Asn Ile Ala Asp Ala Ala
                290                 295                 300

Ser Leu Glu Thr Asn Trp Asn Arg Ile Thr Ala Val Thr Met Pro Glu
305                 310                 315                 320

Ile Ser Val Pro Val Leu Cys Trp Pro Gly Arg Leu Gln Leu Asp Ala
                325                 330                 335

Lys Val Glu Asn Pro Glu Ala Gly Gln Tyr Met Gly Asn Ile Asn Val
                340                 345                 350

Thr Phe Thr Pro Ser Ser Gln Thr Leu
                355                 360

<210> SEQ ID NO 66
<211> LENGTH: 510
<212> TYPE: DNA
<213> ORGANISM: Escherichia coli

<400> SEQUENCE: 66
atgaaattaa aaaaaactat tggcgcaatg gctctgagca caatatttgt agcggtgagt      60
gcttcagcag tagagaaaaa tattactgtg acagccagtg ttgatcctac tattgatatt     120
cttcaagcaa atggttctgc gctaccgaca gctgtagatt taacttatct acctggtgca     180 aaaactttg aaaattacag tgttctaacc cagatttaca caaatgaccc ttcaaaaggt     240
ttagatgttc gactggttga tacaccgaaa cttacaaata ttttgcaacc gacatctacc     300
attcctctta ctgtctcatg ggcagggagg acattaagta caagtgctca gaagatcgca     360
gttggcgatc tgggttttgg ttccaccgga acggcaggtg tttcgaatag taaagaatta     420
gtaattggag caactacatc cggaactgca ccaagtgcag gtaagtatca aggcgtcgtt     480
```
tccattgtaa tgactcaatc gacaaactaa						510

<210> SEQ ID NO 67
<211> LENGTH: 169
<212> TYPE: PRT
<213> ORGANISM: Escherichia coli

<400> SEQUENCE: 67

Met Lys Leu Lys Lys Thr Ile Gly Ala Met Ala Leu Ser Thr Ile Phe
1               5                   10                  15

Val Ala Val Ser Ala Ser Ala Val Glu Lys Asn Ile Thr Val Thr Ala
            20                  25                  30

Ser Val Asp Pro Thr Ile Asp Ile Leu Gln Ala Asn Gly Ser Ala Leu
        35                  40                  45

Pro Thr Ala Val Asp Leu Thr Tyr Leu Pro Gly Ala Lys Thr Phe Glu
    50                  55                  60

Asn Tyr Ser Val Leu Thr Gln Ile Tyr Thr Asn Asp Pro Ser Lys Gly
65                  70                  75                  80

Leu Asp Val Arg Leu Val Asp Thr Pro Lys Leu Thr Asn Ile Leu Gln
                85                  90                  95

Pro Thr Ser Thr Ile Pro Leu Thr Val Ser Trp Ala Gly Arg Thr Leu
            100                 105                 110

Ser Thr Ser Ala Gln Lys Ile Ala Val Gly Asp Leu Gly Phe Gly Ser
        115                 120                 125

Thr Gly Thr Ala Gly Val Ser Asn Ser Lys Glu Leu Val Ile Gly Ala
    130                 135                 140

Thr Thr Ser Gly Thr Ala Pro Ser Ala Gly Lys Tyr Gln Gly Val Val
145                 150                 155                 160

Ser Ile Val Met Thr Gln Ser Thr Asn
                165

<210> SEQ ID NO 68
<211> LENGTH: 528
<212> TYPE: DNA
<213> ORGANISM: Escherichia coli

<400> SEQUENCE: 68
atgaaattaa aaaaaactat tggcgcaatg gctctgagca caatgtttgt agcggtgagt		60 gcttcagcag tagagaaaaa tattactgtg acagccagtg ttgatcctac tattgatatt		120 cttcaagcaa atggttctgc gctaccgaca gctgtagatt taacttatct acctggtgca		180 aaaacttttg aaaattacag tgttctaacc cagatttaca caaatgaccc ttcaaaaggt		240 ttagatgttc gactggttga tacaccgaaa cttacaaata ttttgcaacc gacatctacc		300 attcctctta ctgtctcatg ggcagggaag acattaagta caagtgctca gaagattgca		360 gttggcgatc tgggttttgg ttccaccgga acggcaggtg tttcgaatag taaagaatta		420 gtaattggag caactacatc cggaactgca ccaagtgcag gtaagtatca aggcgtcgtt		480 tccattgtaa tgactcaatc gacagacaca gccgcgcctg ttccttaa		528

<210> SEQ ID NO 69
<211> LENGTH: 175
<212> TYPE: PRT
<213> ORGANISM: Escherichia coli

<400> SEQUENCE: 69

Met Lys Leu Lys Lys Thr Ile Gly Ala Met Ala Leu Ser Thr Met Phe

```
  1               5                  10                 15
Val Ala Val Ser Ala Ser Ala Val Glu Lys Asn Ile Thr Val Thr Ala
            20                  25                  30
Ser Val Asp Pro Thr Ile Asp Ile Leu Gln Ala Asn Gly Ser Ala Leu
            35                  40                  45
Pro Thr Ala Val Asp Leu Thr Tyr Leu Pro Gly Ala Lys Thr Phe Glu
 50                  55                  60
Asn Tyr Ser Val Leu Thr Gln Ile Tyr Thr Asn Asp Pro Ser Lys Gly
 65                  70                  75                  80
Leu Asp Val Arg Leu Val Asp Thr Pro Lys Leu Thr Asn Ile Leu Gln
                85                  90                  95
Pro Thr Ser Thr Ile Pro Leu Thr Val Ser Trp Ala Gly Lys Thr Leu
                100                 105                 110
Ser Thr Ser Ala Gln Lys Ile Ala Val Gly Asp Leu Gly Phe Gly Ser
                115                 120                 125
Thr Gly Thr Ala Gly Val Ser Asn Ser Lys Glu Leu Val Ile Gly Ala
            130                 135                 140
Thr Thr Ser Gly Thr Ala Pro Ser Ala Gly Lys Tyr Gln Gly Val Val
145                 150                 155                 160
Ser Ile Val Met Thr Gln Ser Thr Asp Thr Ala Ala Pro Val Pro
                165                 170                 175

<210> SEQ ID NO 70
<211> LENGTH: 1086
<212> TYPE: DNA
<213> ORGANISM: Escherichia coli

<400> SEQUENCE: 70
atgaataaga ttttatttat ttttacattg tttttctctt cagtactttt tacatttgct      60
gtatcggcag ataaaattcc cggagatgag aatataacta atattttttgg cccgcgtgac    120
aggaacgaat cttcccccaa acataatata ttaaatgact atattacagc atacagtgaa    180
agtcatactc tgtatgatag gatgattttt ttatgtttgt cttctcaaaa tacacttaat    240
ggagcatgtc caaccagtga gaatcctagc agttcatcgg tcagtggcga aacaaatata    300
acattacaat ttacggaaaa aagaagttta attaaagag agctacaaat taaaggctat    360
aaacgattat tgttcaaagg tgctaactgc ccatcctacc taacacttaa ctcagctcat    420
tatacctgca atagaaactc ggcttcaggt gcaagtttat atttatatat tcctgctggc    480
gaactaaaaa atttacccttt tggtggtatc tgggatgcta ctctgaagtt aagagtaaaa    540
agacgatatg atcagaccta tggaacttac actataaata tcactgttaa attaactgat    600
aagggaaata ttcagatatg gttacctcag ttcaaaagtg acgctcgcgt cgatcttaac    660
ttgcgtccaa ctggtggggg cacatatatt ggaagaaatt ctgttgatat gtgcttttat    720
gatggatata gtactaacag cagctctttg gagctaagat ttcaggataa caatcctaaa    780
tctgatggga attttatct aaggaaaata aatgatgaca ccaaagaaat tgcatatact    840
ttgtcacttc tcttggcggg taaaagttta actccaacaa atggaacgtc attaaatatt    900
gctgacgcag cttctctgga aataaactgg aatagaatta cagctgtcac catgccagaa    960
atcagtgttc cggtgttgtg ttggcctgga cgtttgcaat ggatgcaaa agtggaaaat   1020
cccgaggccg acaatatat gggtaatatt aatattactt tcacaccaag tagtcaaaca   1080
ctctag                                                            1086
```

```
<210> SEQ ID NO 71
<211> LENGTH: 361
<212> TYPE: PRT
<213> ORGANISM: Escherichia coli

<400> SEQUENCE: 71

Met Asn Lys Ile Leu Phe Ile Phe Thr Leu Phe Phe Ser Ser Val Leu
1               5                   10                  15

Phe Thr Phe Ala Val Ser Ala Asp Lys Ile Pro Gly Asp Glu Asn Ile
            20                  25                  30

Thr Asn Ile Phe Gly Pro Arg Asp Arg Asn Glu Ser Ser Pro Lys His
        35                  40                  45

Asn Ile Leu Asn Asp Tyr Ile Thr Ala Tyr Ser Glu Ser His Thr Leu
    50                  55                  60

Tyr Asp Arg Met Ile Phe Leu Cys Leu Ser Ser Gln Asn Thr Leu Asn
65                  70                  75                  80

Gly Ala Cys Pro Thr Ser Glu Asn Pro Ser Ser Ser Val Ser Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Arg Leu Leu Phe Lys Gly Ala
        115                 120                 125

Asn Cys Pro Ser Tyr Leu Thr Leu Asn Ser Ala His Tyr Thr Cys Asn
130                 135                 140

Arg Asn Ser Ala Ser Gly Ala Ser Leu Tyr Leu Tyr Ile Pro Ala Gly
145                 150                 155                 160

Glu Leu Lys Asn Leu Pro Phe Gly Gly Ile Trp Asp Ala Thr Leu Lys
                165                 170                 175

Leu Arg Val Lys Arg Arg Tyr Asp Gln Thr Tyr Gly Thr Tyr Thr Ile
            180                 185                 190

Asn Ile Thr Val Lys Leu Thr Asp Lys Gly Asn Ile Gln Ile Trp Leu
        195                 200                 205

Pro Gln Phe Lys Ser Asp Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Leu Arg Phe Gln Asp
                245                 250                 255

Asn Asn Pro Lys Ser Asp Gly Lys Phe Tyr Leu Arg Lys Ile Asn Asp
            260                 265                 270

Asp Thr Lys Glu Ile Ala Tyr Thr Leu Ser Leu Leu Ala Gly Lys
        275                 280                 285

Ser Leu Thr Pro Thr Asn Gly Thr Ser Leu Asn Ile Ala Asp Ala Ala
    290                 295                 300

Ser Leu Glu Ile Asn Trp Asn Arg Ile Thr Ala Val Thr Met Pro Glu
305                 310                 315                 320

Ile Ser Val Pro Val Leu Cys Trp Pro Gly Arg Leu Gln Leu Asp Ala
                325                 330                 335

Lys Val Glu Asn Pro Glu Ala Gly Gln Tyr Met Gly Asn Ile Asn Ile
            340                 345                 350

Thr Phe Thr Pro Ser Ser Gln Thr Leu
        355                 360

<210> SEQ ID NO 72
<211> LENGTH: 516
```

<212> TYPE: DNA
<213> ORGANISM: Escherichia coli

<400> SEQUENCE: 72

```
atgaaactaa agaaaacaat tggcgcaatg gctctggcga cattatttgc aactatggga      60
gcatctgcgg tcgagaagac cattagcgtt acggcgagtg ttgacccgac tgttgacctt     120
ctgcaatctg atggctctgc gctgccgaac tctgtcgcat taacctattc tccggctgta     180
aataattttg aagctcacac catcaacacc gttgttcata caaatgactc agataaaggt     240
gttgttgtga agctgtcagc agatccagtc ctgtccaatg ttctgaatcc aaccctgcaa     300
attcctgttt ctgtgaattt cgcaggaaaa ccactgagca acaggcat taccatcgac       360
tccaatgatc tgaactttgc ttcgagtggt gttaataaag tttcttctac gcagaaactt     420
tcaatccatg cagatgctac tcgggtaact ggcggcgcac taacagctgg tcaatatcag     480
ggactcgtat caattatcct gactaagtca acgtaa                               516
```

<210> SEQ ID NO 73
<211> LENGTH: 171
<212> TYPE: PRT
<213> ORGANISM: Escherichia coli

<400> SEQUENCE: 73

```
Met Lys Leu Lys Lys Thr Ile Gly Ala Met Ala Leu Ala Thr Leu Phe
1               5                   10                  15
Ala Thr Met Gly Ala Ser Ala Val Glu Lys Thr Ile Ser Val Thr Ala
            20                  25                  30
Ser Val Asp Pro Thr Val Asp Leu Leu Gln Ser Asp Gly Ser Ala Leu
        35                  40                  45
Pro Asn Ser Val Ala Leu Thr Tyr Ser Pro Ala Val Asn Asn Phe Glu
    50                  55                  60
Ala His Thr Ile Asn Thr Val Val His Thr Asn Asp Ser Asp Lys Gly
65                  70                  75                  80
Val Val Val Lys Leu Ser Ala Asp Pro Val Leu Ser Asn Val Leu Asn
                85                  90                  95
Pro Thr Leu Gln Ile Pro Val Ser Val Asn Phe Ala Gly Lys Pro Leu
            100                 105                 110
Ser Thr Thr Gly Ile Thr Ile Asp Ser Asn Asp Leu Asn Phe Ala Ser
        115                 120                 125
Ser Gly Val Asn Lys Val Ser Ser Thr Gln Lys Leu Ser Ile His Ala
    130                 135                 140
Asp Ala Thr Arg Val Thr Gly Gly Ala Leu Thr Ala Gly Gln Tyr Gln
145                 150                 155                 160
Gly Leu Val Ser Ile Ile Leu Thr Lys Ser Thr
                165                 170
```

<210> SEQ ID NO 74
<211> LENGTH: 1092
<212> TYPE: DNA
<213> ORGANISM: Escherichia coli

<400> SEQUENCE: 74

```
atgaaaaaga tatttatttt tttgtctatc atattttctg cggtggtcag tgccgggcga      60
tacccggaaa ctacagtagg taatctgacg aagagttttc aagcccctcg tctggataga    120
agcgtacaat caccaatata taacatcttt acgaatcatg tggctggata tagttttgagt   180
catagcttat atgacaggat tgttttttta tgtacatcct cgtcgaatcc ggttaatggt    240
```

```
gcttgcccaa ccattggaac atctggagtt caatacggta ctacaaccat aaccttgcag    300
tttacagaaa aaagaagtct gataaaaaga aatattaatc ttgcaggtaa taagaaacca    360
atatgggaga atcagagttg cgactttagc aatctaatgg tgttgaattc gaagtcttgg    420
agctgtgggg cttacggaaa tgctaacgga acacttctaa atctgtatat ccctgcagga    480
gaaatcaaca aattgccttt tggagggata tgggaggcaa ctctgatctt acgcttatca    540
agatatggcg aagtcagtag cacccattac ggcaattata ccgtaaatat tacgcgttgat   600 ttaactgata aaggtaatat tcaggtatgg cttccagggt ttcacagcaa cccgcgtgta    660
gacctgaatc tgcgccctat cggtaattat aaatatagtg gtagtaattc actcgacatg    720
tgtttctatg atggatatag tacaaacagt gatagcatgg taataaagtt ccaggatgat    780
aatcctacca attcatctga atataatctt tataagatag ggggcactga aaaattacca    840
tatgctgttt cactgcttat gggagaaaaa atattttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttat ga                                                      1092
```

<210> SEQ ID NO 75
<211> LENGTH: 363
<212> TYPE: PRT
<213> ORGANISM: Escherichia coli

<400> SEQUENCE: 75

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
                20                  25                  30

Phe Gln Ala Pro Arg Leu Asp Arg Ser Val Gln Ser Pro Ile Tyr Asn
            35                  40                  45

Ile Phe Thr Asn His Val Ala Gly Tyr Ser Leu Ser His Ser Leu Tyr
        50                  55                  60

Asp Arg Ile Val Phe Leu Cys Thr Ser Ser Asn Pro Val Asn Gly
65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Phe Ser Asn Leu Met Val Leu Asn Ser Lys Ser Trp Ser Cys Gly Ala
    130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu

```
            210                 215                 220
Arg Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Asn Ser Ser Glu Tyr Asn Leu Tyr Lys
            260                 265                 270

Ile Gly Gly Thr Glu Lys Leu Pro Tyr Ala Val Ser Leu Leu Met Gly
        275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu
        355                 360

<210> SEQ ID NO 76
<211> LENGTH: 501
<212> TYPE: DNA
<213> ORGANISM: Escherichia coli

<400> SEQUENCE: 76
atgaaactga agaaaacaat tggcgcaatg gctatggcga ctctgtttgc caccatggct      60
gcctctgcag tcgaaaaaaa tattactgtg agggcaagtg ttgaccctaa acttgatctt     120
ctgcaagcag atggaacttc actgccggac tctatcgcat taacctattc ttcggcttca     180
aataattttg aagtttactc tcttaatact gctattcata caaatgacaa aaccaaggca     240
gttgtagtga agctgtcagc tccagcagtt ctgtccaata ttatgaagcc aagctcgcaa     300
attccgatga agtgactttt ggggggggaag acgctgagta cagctgatgc tgagtttgct     360
gctgatactc tgaactttgg tgcatctggt gttgaaaacg tttcttccgt tcaacagctt     420
acgattcatg cagaagctgc tccgcctgag gcaggtaatt accaaggtgt tatttctctt     480
atcatgactc aaaaaactta a                                                501

<210> SEQ ID NO 77
<211> LENGTH: 166
<212> TYPE: PRT
<213> ORGANISM: Escherichia coli

<400> SEQUENCE: 77

Met Lys Leu Lys Lys Thr Ile Gly Ala Met Ala Met Ala Thr Leu Phe
1               5                   10                  15

Ala Thr Met Ala Ala Ser Ala Val Glu Lys Asn Ile Thr Val Arg Ala
                20                  25                  30

Ser Val Asp Pro Lys Leu Asp Leu Leu Gln Ala Asp Gly Thr Ser Leu
            35                  40                  45

Pro Asp Ser Ile Ala Leu Thr Tyr Ser Ser Ala Ser Asn Asn Phe Glu
        50                  55                  60

Val Tyr Ser Leu Asn Thr Ala Ile His Thr Asn Asp Lys Thr Lys Ala
65                  70                  75                  80

Val Val Val Lys Leu Ser Ala Pro Ala Val Leu Ser Asn Ile Met Lys
```

```
                       85                  90                  95
Pro Ser Ser Gln Ile Pro Met Lys Val Thr Leu Gly Gly Lys Thr Leu
            100                 105                 110

Ser Thr Ala Asp Ala Glu Phe Ala Ala Asp Thr Leu Asn Phe Gly Ala
        115                 120                 125

Ser Gly Val Glu Asn Val Ser Ser Val Gln Gln Leu Thr Ile His Ala
    130                 135                 140

Glu Ala Ala Pro Pro Glu Ala Gly Asn Tyr Gln Gly Val Ile Ser Leu
145                 150                 155                 160

Ile Met Thr Gln Lys Thr
                165

<210> SEQ ID NO 78
<211> LENGTH: 1092
<212> TYPE: DNA
<213> ORGANISM: Escherichia coli

<400> SEQUENCE: 78
atgaaaaaga tatttatttt tttgtctatc atattttctg cggtggtcag tgccgggcga     60
tacccggaaa ctacagtagg taatctgacg aagagttttc aagcccctcg tctggataga    120
agcgtacaat caccaatata taacatcttt acgaatcatg tggctggata gtttgagt     180 catagattat atgacaggat tgttttttgta tgtacatcct cgtcgaatcc ggttaatggt    240
gcttgcccaa ccattggaac atctagagtt gaatacggta ctacaaccat aaccttgcag    300
tttacagaaa aagaagtct gataaaaaga aatattaatc ttgcaggtaa taagaaacca    360
atatgggaga atcagagttg cgacactagc aatctaatgg tgttgaattc gaagtcttgg    420
tcctgtgggg ctctaggaaa tgctaacgga acacttctaa atctgtatat ccctgcagga    480
gaaatcaaca aattgccttt tggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720 tgttttctatg atggatatag tacaaacagt gatagcatgg taataaagtt ccaggatgat    780
aatcctacca attcatctga atataatctt tataagatag ggggcactga aaaattacca    840
tatgctgttt cactgcttat gggaggaaaa atatttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata acatttac acccagtgtc   1080 gaaaatttat ga                                                       1092

<210> SEQ ID NO 79
<211> LENGTH: 363
<212> TYPE: PRT
<213> ORGANISM: Escherichia coli

<400> SEQUENCE: 79

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Leu Asp Arg Ser Val Gln Ser Pro Ile Tyr Asn
        35                  40                  45
```

Ile Phe Thr Asn His Val Ala Gly Tyr Ser Leu Ser His Arg Leu Tyr
50                  55                  60

Asp Arg Ile Val Phe Val Cys Thr Ser Ser Asn Pro Val Asn Gly
65                  70                  75                  80

Ala Cys Pro Thr Ile Gly Thr Ser Arg Val Glu Tyr Gly Thr Thr Thr
                85                  90                  95

Ile Thr Leu Gln Phe Thr Glu Lys Arg Ser Leu Ile Lys Arg Asn Ile
                100                 105                 110

Asn Leu Ala Gly Asn Lys Lys Pro Ile Trp Glu Asn Gln Ser Cys Asp
                115                 120                 125

Thr Ser Asn Leu Met Val Leu Asn Ser Lys Ser Trp Ser Cys Gly Ala
130                 135                 140

Leu Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
                180                 185                 190

Tyr Thr Val Asn Ile Thr Val Asp Leu Thr Asp Lys Gly Asn Ile Gln
                195                 200                 205

Val Trp Leu Pro Gly Phe His Ser Asn Pro Arg Val Asp Leu Asn Leu
210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Asn Ser Ser Glu Tyr Asn Leu Tyr Lys
                260                 265                 270

Ile Gly Gly Thr Glu Lys Leu Pro Tyr Ala Val Ser Leu Leu Met Gly
                275                 280                 285

Gly Lys Ile Phe Tyr Pro Val Asn Gly Gln Ser Phe Thr Ile Asn Asp
                290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
                340                 345                 350

Tyr Ile Thr Phe Thr Pro Ser Val Glu Asn Leu
                355                 360

<210> SEQ ID NO 80
<211> LENGTH: 513
<212> TYPE: DNA
<213> ORGANISM: Escherichia coli

<400> SEQUENCE: 80
atgaaactaa agaaaacaat tggcgcaatg gctctggcga cattatttgc aaccatggga      60
gcatctgcgg tcgagaagac cattagcgtt acgcgagtg ttgacccgac tgttgacctt     120
ctgcaatctg atggctctgc gctgccgaac tctgtcgcat taacctattc tccggctgta     180
gggggttttg aagctcacac catcaacacc gttgttcata caaatgaccc agctaaaggt     240
gttattgtga agctgtcagc agaaccagtc ctgtccaatg tactgaatcc aaccctgcaa     300

```
attcctgttt ctgtgaattt cgcaggaaaa aaactgacca caacaggcac taccatcgaa    360
tccaataaac tgaactttgc ttcgagtggt gttgataaag tttcttctac gcagaaactt    420
tcaatccatg cagatactac tcaggtaact ggcggactaa cagctggtca atatcagggg    480
ctcgtatcaa ttatcctgac tcagtcaacg taa                                 513
```

<210> SEQ ID NO 81
<211> LENGTH: 170
<212> TYPE: PRT
<213> ORGANISM: Escherichia coli

<400> SEQUENCE: 81

```
Met Lys Leu Lys Lys Thr Ile Gly Ala Met Ala Leu Ala Thr Leu Phe
1               5                   10                  15

Ala Thr Met Gly Ala Ser Ala Val Glu Lys Thr Ile Ser Val Thr Ala
            20                  25                  30

Ser Val Asp Pro Thr Val Asp Leu Leu Gln Ser Asp Gly Ser Ala Leu
        35                  40                  45

Pro Asn Ser Val Ala Leu Thr Tyr Ser Pro Ala Val Gly Gly Phe Glu
    50                  55                  60

Ala His Thr Ile Asn Thr Val Val His Thr Asn Asp Pro Ala Lys Gly
65                  70                  75                  80

Val Ile Val Lys Leu Ser Ala Glu Pro Val Leu Ser Asn Val Leu Asn
                85                  90                  95

Pro Thr Leu Gln Ile Pro Val Ser Val Asn Phe Ala Gly Lys Lys Leu
            100                 105                 110

Thr Thr Thr Gly Thr Thr Ile Glu Ser Asn Lys Leu Asn Phe Ala Ser
        115                 120                 125

Ser Gly Val Asp Lys Val Ser Ser Thr Gln Lys Leu Ser Ile His Ala
    130                 135                 140

Asp Thr Thr Gln Val Thr Gly Gly Leu Thr Ala Gly Gln Tyr Gln Gly
145                 150                 155                 160

Leu Val Ser Ile Ile Leu Thr Gln Ser Thr
                165                 170
```

<210> SEQ ID NO 82
<211> LENGTH: 1092
<212> TYPE: DNA
<213> ORGANISM: Escherichia coli

<400> SEQUENCE: 82

```
atgaaaaaga tatttatttt tttgtctatc atattttctg cggtggtcag tgccgggcga     60
tacccggaaa ctacagtagg taatctgacg aagagttttc aagcccctcg tctggataga    120
agcgtacaat caccaatata taacatcttt acgaatcatg tggctggata tagtttgagt    180
catagattat atgacaggat tgttttttgta tgtacatcct cgtcgaatcc ggttaatggt    240
gcttgcccaa ccattggaac atctggagtt gaatacggta ctacaaccat aaccttgcag    300
tttacagaaa aagaagtctc gataaaaaga atattaatcc ttgcaggtaa taagaaacca    360
atatgggaga tcagagttg cgactttagc aatctaatgg tgttgaattc gaagtcttgg    420
tcctgtgggg ctcaaggaaa tgctaacgga acacttctaa atctgtatat ccctgcagga    480
gaaatcaaca aattgccttt tggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
```

-continued

```
gacctgaatc tgcaccctat cggtaattat aaatatagtg gtagtaattc actcgacatg    720
tgtttctatg atggatatag tacaaacagt gatagcatgg taataaagtt ccaggatgat    780
aatcctacca attcatctga atataatctt tataagagag ggggcactga aaaattacca    840
tatgctgttt cactgcttat gggaggaaaa atattttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttat ga                                                       1092
```

<210> SEQ ID NO 83
<211> LENGTH: 363
<212> TYPE: PRT
<213> ORGANISM: Escherichia coli

<400> SEQUENCE: 83

```
Met Lys Lys Ile Phe Ile Phe Leu Ser Ile Ile Phe Ser Ala Val Val
  1               5                  10                  15

Ser Ala Gly Arg Tyr Pro Glu Thr Thr Val Gly Asn Leu Thr Lys Ser
             20                  25                  30

Phe Gln Ala Pro Arg Leu Asp Arg Ser Val Gln Ser Pro Ile Tyr Asn
         35                  40                  45

Ile Phe Thr Asn His Val Ala Gly Tyr Ser Leu Ser His Arg Leu Tyr
     50                  55                  60

Asp Arg Ile Val Phe Val Cys Thr Ser Ser Asn Pro Val Asn Gly
 65                  70                  75                  80

Ala Cys Pro Thr Ile Gly Thr Ser Gly Val Glu Tyr Gly Thr Thr Thr
                 85                  90                  95

Ile Thr Leu Gln Phe Thr Glu Lys Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Phe Ser Asn Leu Met Val Leu Asn Ser Lys Ser Trp Ser Cys Gly Ala
    130                 135                 140

Gln Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Ser Met Val Ile Lys
                245                 250                 255

Phe Gln Asp Asp Asn Pro Thr Asn Ser Ser Glu Tyr Asn Leu Tyr Lys
            260                 265                 270

Arg Gly Gly Thr Glu Lys Leu Pro Tyr Ala Val Ser Leu Leu Met Gly
        275                 280                 285

Gly Lys Ile Phe Tyr Pro Val Asn Gly Gln Ser Phe Thr Ile Asn Asp
```

```
                      290                 295                 300
Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu
            355                 360

<210> SEQ ID NO 84
<211> LENGTH: 507
<212> TYPE: DNA
<213> ORGANISM: Escherichia coli

<400> SEQUENCE: 84
atgttaaaaa taaatactt attaataggt ctttcactgt cagctatgag ttcatactca     60
ctagctgcag cggggcccac tctaaccaaa gaactggcat aaatgtgct ttctcctgca   120 gctctggatg caacttgggc tcctcaggat aatttaacat tatccaatac tggcgtttct   180
aatactttgg tgggtgtttt gactctttca ataccagta ttgatacagt tagcattgcg   240
agtacaaatg tttctgatac atctaagaat ggtacagtaa cttttgcaca tgagacaaat   300
aactctgcta gctttgccac caccatttca acagataatg ccaacattac gttggataaa   360
aatgctggaa atacgattgt taaaactaca atgggagtc agttgccaac taatttacca   420
cttaagttta ttaccactga aggtaacgaa catttagttt caggtaatta ccgtgcaaat   480
ataacaatta cttcgacaat taaataa                                       507

<210> SEQ ID NO 85
<211> LENGTH: 168
<212> TYPE: PRT
<213> ORGANISM: Escherichia coli

<400> SEQUENCE: 85

Met Leu Lys Ile Lys Tyr Leu Leu Ile Gly Leu Ser Leu Ser Ala Met
1               5                   10                  15

Ser Ser Tyr Ser Leu Ala Ala Ala Gly Pro Thr Leu Thr Lys Glu Leu
                20                  25                  30

Ala Leu Asn Val Leu Ser Pro Ala Ala Leu Asp Ala Thr Trp Ala Pro
            35                  40                  45

Gln Asp Asn Leu Thr Leu Ser Asn Thr Gly Val Ser Asn Thr Leu Val
        50                  55                  60

Gly Val Leu Thr Leu Ser Asn Thr Ser Ile Asp Thr Val Ser Ile Ala
65                  70                  75                  80

Ser Thr Asn Val Ser Asp Thr Ser Lys Asn Gly Thr Val Thr Phe Ala
                85                  90                  95

His Glu Thr Asn Asn Ser Ala Ser Phe Ala Thr Thr Ile Ser Thr Asp
            100                 105                 110

Asn Ala Asn Ile Thr Leu Asp Lys Asn Ala Gly Asn Thr Ile Val Lys
        115                 120                 125

Thr Thr Asn Gly Ser Gln Leu Pro Thr Asn Leu Pro Leu Lys Phe Ile
    130                 135                 140

Thr Thr Glu Gly Asn Glu His Leu Val Ser Gly Asn Tyr Arg Ala Asn
145                 150                 155                 160

Ile Thr Ile Thr Ser Thr Ile Lys
                165
```

-continued

165

<210> SEQ ID NO 86
<211> LENGTH: 480
<212> TYPE: DNA
<213> ORGANISM: Escherichia coli

<400> SEQUENCE: 86

```
atgattttag cattgacttt gatgtcggtg tggggaggtg cgtttgccgc agtgggccca      60
acgaaagata tgagtttagg tgcaaattta acttcagagc ctacattagc tattgatttt     120
acgcctattg aaaatattta tgtaggtgcc aattatggta aagatattgg aacccttgtt     180
ttcacaacaa atgatttaac agatattaca ttgatgtcat ctcgcagcgt tgttgatggt     240
cgccagactg ttttttttac cttcatggac tcatcagcca cttacaaaat tagtacaaaa     300
ctgggatcat cgaatgatgt aaacattcaa gaaattactc aaggagctaa aattactcct     360
gttagtggag agaaaacttt gcctaaaaaa ttcactctta agctacatgc acacaggagt     420
agcagtacag ttccaggtac gtatactgtt ggtcttaacg taaccagtaa tgttatttaa     480
```

<210> SEQ ID NO 87
<211> LENGTH: 159
<212> TYPE: PRT
<213> ORGANISM: Escherichia coli

<400> SEQUENCE: 87

```
Met Ile Leu Ala Leu Thr Leu Met Ser Val Trp Gly Gly Ala Phe Ala
1               5                   10                  15

Ala Val Gly Pro Thr Lys Asp Met Ser Leu Gly Ala Asn Leu Thr Ser
            20                  25                  30

Glu Pro Thr Leu Ala Ile Asp Phe Thr Pro Ile Glu Asn Ile Tyr Val
        35                  40                  45

Gly Ala Asn Tyr Gly Lys Asp Ile Gly Thr Leu Val Phe Thr Thr Asn
    50                  55                  60

Asp Leu Thr Asp Ile Thr Leu Met Ser Ser Arg Ser Val Val Asp Gly
65                  70                  75                  80

Arg Gln Thr Gly Phe Phe Thr Phe Met Asp Ser Ser Ala Thr Tyr Lys
                85                  90                  95

Ile Ser Thr Lys Leu Gly Ser Ser Asn Asp Val Asn Ile Gln Glu Ile
            100                 105                 110

Thr Gln Gly Ala Lys Ile Thr Pro Val Ser Gly Glu Lys Thr Leu Pro
        115                 120                 125

Lys Lys Phe Thr Leu Lys Leu His Ala His Arg Ser Ser Thr Val
    130                 135                 140

Pro Gly Thr Tyr Thr Val Gly Leu Asn Val Thr Ser Asn Val Ile
145                 150                 155
```

<210> SEQ ID NO 88
<211> LENGTH: 339
<212> TYPE: PRT
<213> ORGANISM: Escherichia coli

<400> SEQUENCE: 88

```
Ala Asp Lys Ile Pro Gly Asp Glu Ser Ile Thr Asn Ile Phe Gly Pro
1               5                   10                  15

Arg Asp Arg Asn Glu Ser Ser Pro Lys His Asn Ile Leu Asn Asn His
            20                  25                  30

Ile Thr Ala Tyr Ser Glu Ser His Thr Leu Tyr Asp Arg Met Thr Phe
```

```
            35                  40                  45
Leu Cys Leu Ser Ser His Asn Thr Leu Asn Gly Ala Cys Pro Thr Ser
 50                  55                  60

Glu Asn Pro Ser Ser Ser Val Ser Gly Glu Thr Asn Ile Thr Leu
 65                  70                  75                  80

Gln Phe Thr Glu Lys Arg Ser Leu Ile Lys Arg Glu Leu Gln Ile Lys
                 85                  90                  95

Gly Tyr Lys Gln Leu Leu Phe Lys Ser Val Asn Cys Pro Ser Gly Leu
            100                 105                 110

Thr Leu Asn Ser Ala His Phe Asn Cys Asn Lys Asn Ala Ala Ser Gly
        115                 120                 125

Ala Ser Leu Tyr Leu Tyr Ile Pro Ala Gly Glu Leu Lys Asn Leu Pro
    130                 135                 140

Phe Gly Gly Ile Trp Asp Ala Thr Leu Lys Leu Arg Val Lys Arg Arg
145                 150                 155                 160

Tyr Ser Glu Thr Tyr Gly Thr Tyr Thr Ile Asn Ile Thr Ile Lys Leu
                165                 170                 175

Thr Asp Lys Gly Asn Ile Gln Ile Trp Leu Pro Gln Phe Lys Ser Asp
            180                 185                 190

Ala Arg Val Asp Leu Asn Leu Arg Pro Thr Gly Gly Thr Tyr Ile
        195                 200                 205

Gly Arg Asn Ser Val Asp Met Cys Phe Tyr Asp Gly Tyr Ser Thr Asn
210                 215                 220

Ser Ser Ser Leu Glu Ile Arg Phe Gln Asp Asn Asn Pro Lys Ser Asp
225                 230                 235                 240

Gly Lys Phe Tyr Leu Arg Lys Ile Asn Asp Asp Thr Lys Glu Ile Ala
                245                 250                 255

Tyr Thr Leu Ser Leu Leu Leu Ala Gly Lys Ser Leu Thr Pro Thr Asn
            260                 265                 270

Gly Thr Ser Leu Asn Ile Ala Asp Ala Ala Ser Leu Glu Thr Asn Trp
        275                 280                 285

Asn Arg Ile Thr Ala Val Thr Met Pro Glu Ile Ser Val Pro Val Leu
    290                 295                 300

Cys Trp Pro Gly Arg Leu Gln Leu Asp Ala Lys Val Glu Asn Pro Glu
305                 310                 315                 320

Ala Gly Gln Tyr Met Gly Asn Ile Asn Val Thr Phe Thr Pro Ser Ser
                325                 330                 335

Gln Thr Leu

<210> SEQ ID NO 89
<211> LENGTH: 144
<212> TYPE: PRT
<213> ORGANISM: Escherichia coli

<400> SEQUENCE: 89

Val Glu Lys Asn Ile Thr Val Thr Ala Ser Val Asp Pro Thr Ile Asp
  1               5                  10                  15

Ile Leu Gln Ala Asp Gly Ser Ser Leu Pro Thr Ala Val Glu Leu Thr
             20                  25                  30

Tyr Ser Pro Ala Ala Ser Arg Phe Glu Asn Tyr Lys Ile Ala Thr Lys
         35                  40                  45

Val His Thr Asn Val Ile Asn Lys Asn Val Leu Val Lys Leu Val Asn
     50                  55                  60

Asp Pro Lys Leu Thr Asn Val Leu Asp Ser Thr Lys Gln Leu Pro Ile
```

```
            65                  70                  75                  80
Thr Val Ser Tyr Gly Gly Lys Thr Leu Ser Thr Ala Asp Val Thr Phe
                    85                  90                  95
Glu Pro Ala Glu Leu Asn Phe Gly Thr Ser Gly Val Thr Gly Val Ser
                100                 105                 110
Ser Ser Gln Asp Leu Val Ile Gly Ala Thr Thr Ala Gln Ala Pro Thr
                115                 120                 125
Ala Gly Asn Tyr Ser Gly Val Val Ser Ile Leu Met Thr Leu Ala Ser
            130                 135                 140

<210> SEQ ID NO 90
<211> LENGTH: 339
<212> TYPE: PRT
<213> ORGANISM: Escherichia coli

<400> SEQUENCE: 90

Ala Asp Lys Ile Pro Gly Asp Glu Asn Ile Thr Asn Ile Phe Gly Pro
1               5                   10                  15
Arg Asp Arg Asn Glu Ser Ser Pro Lys His Asn Ile Leu Asn Asp Tyr
                20                  25                  30
Ile Thr Ala Tyr Ser Glu Ser His Thr Leu Tyr Asp Arg Met Ile Phe
            35                  40                  45
Leu Cys Leu Ser Ser Gln Asn Thr Leu Asn Gly Ala Cys Pro Thr Ser
        50                  55                  60
Glu Asn Pro Ser Ser Ser Val Ser Gly Glu Thr Asn Ile Thr Leu
65                  70                  75                  80
Gln Phe Thr Glu Lys Arg Ser Leu Ile Lys Arg Glu Leu Gln Ile Lys
                85                  90                  95
Gly Tyr Lys Arg Leu Leu Phe Lys Gly Ala Asn Cys Pro Ser Tyr Leu
                100                 105                 110
Thr Leu Asn Ser Ala His Tyr Thr Cys Asn Arg Asn Ser Ala Ser Gly
            115                 120                 125
Ala Ser Leu Tyr Leu Tyr Ile Pro Ala Gly Glu Leu Lys Asn Leu Pro
        130                 135                 140
Phe Gly Gly Ile Trp Asp Ala Thr Leu Lys Leu Arg Val Lys Arg Arg
145                 150                 155                 160
Tyr Asp Gln Thr Tyr Gly Thr Tyr Thr Ile Asn Ile Thr Val Lys Leu
                165                 170                 175
Thr Asp Lys Gly Asn Ile Gln Ile Trp Leu Pro Gln Phe Lys Ser Asp
                180                 185                 190
Ala Arg Val Asp Leu Asn Leu Arg Pro Thr Gly Gly Thr Tyr Ile
            195                 200                 205
Gly Arg Asn Ser Val Asp Met Cys Phe Tyr Asp Gly Tyr Ser Thr Asn
        210                 215                 220
Ser Ser Ser Leu Glu Leu Arg Phe Gln Asp Asn Asn Pro Lys Ser Asp
225                 230                 235                 240
Gly Lys Phe Tyr Leu Arg Lys Ile Asn Asp Asp Thr Lys Glu Ile Ala
                245                 250                 255
Tyr Thr Leu Ser Leu Leu Leu Ala Gly Lys Ser Leu Thr Pro Thr Asn
                260                 265                 270
Gly Thr Ser Leu Asn Ile Ala Asp Ala Ala Ser Leu Glu Ile Asn Trp
            275                 280                 285
Asn Arg Ile Thr Ala Val Thr Met Pro Glu Ile Ser Val Pro Val Leu
        290                 295                 300
```

```
Cys Trp Pro Gly Arg Leu Gln Leu Asp Ala Lys Val Glu Asn Pro Glu
305                 310                 315                 320

Ala Gly Gln Tyr Met Gly Asn Ile Asn Ile Thr Phe Thr Pro Ser Ser
                325                 330                 335

Gln Thr Leu

<210> SEQ ID NO 91
<211> LENGTH: 152
<212> TYPE: PRT
<213> ORGANISM: Escherichia coli

<400> SEQUENCE: 91

Val Glu Lys Asn Ile Thr Val Thr Ala Ser Val Asp Pro Thr Ile Asp
1               5                   10                  15

Ile Leu Gln Ala Asn Gly Ser Ala Leu Pro Thr Ala Val Asp Leu Thr
            20                  25                  30

Tyr Leu Pro Gly Ala Lys Thr Phe Glu Asn Tyr Ser Val Leu Thr Gln
        35                  40                  45

Ile Tyr Thr Asn Asp Pro Ser Lys Gly Leu Asp Val Arg Leu Val Asp
    50                  55                  60

Thr Pro Lys Leu Thr Asn Ile Leu Gln Pro Thr Ser Thr Ile Pro Leu
65                  70                  75                  80

Thr Val Ser Trp Ala Gly Lys Thr Leu Ser Thr Ser Ala Gln Lys Ile
                85                  90                  95

Ala Val Gly Asp Leu Gly Phe Gly Ser Thr Gly Thr Ala Gly Val Ser
            100                 105                 110

Asn Ser Lys Glu Leu Val Ile Gly Ala Thr Thr Ser Gly Thr Ala Pro
        115                 120                 125

Ser Ala Gly Lys Tyr Gln Gly Val Val Ser Ile Val Met Thr Gln Ser
    130                 135                 140

Thr Asp Thr Ala Ala Pro Val Pro
145                 150

<210> SEQ ID NO 92
<211> LENGTH: 146
<212> TYPE: PRT
<213> ORGANISM: Escherichia coli

<400> SEQUENCE: 92

Val Glu Lys Asn Ile Thr Val Thr Ala Ser Val Asp Pro Thr Ile Asp
1               5                   10                  15

Ile Leu Gln Ala Asn Gly Ser Ala Leu Pro Thr Ala Val Asp Leu Thr
            20                  25                  30

Tyr Leu Pro Gly Ala Lys Thr Phe Glu Asn Tyr Ser Val Leu Thr Gln
        35                  40                  45

Ile Tyr Thr Asn Asp Pro Ser Lys Gly Leu Asp Val Arg Leu Val Asp
    50                  55                  60

Thr Pro Lys Leu Thr Asn Ile Leu Gln Pro Thr Ser Thr Ile Pro Leu
65                  70                  75                  80

Thr Val Ser Trp Ala Gly Arg Thr Leu Ser Thr Ser Ala Gln Lys Ile
                85                  90                  95

Ala Val Gly Asp Leu Gly Phe Gly Ser Thr Gly Thr Ala Gly Val Ser
            100                 105                 110

Asn Ser Lys Glu Leu Val Ile Gly Ala Thr Thr Ser Gly Thr Ala Pro
        115                 120                 125

Ser Ala Gly Lys Tyr Gln Gly Val Val Ser Ile Val Met Thr Gln Ser
```

Thr Asn
145

<210> SEQ ID NO 93
<211> LENGTH: 345
<212> TYPE: PRT
<213> ORGANISM: Escherichia coli

<400> SEQUENCE: 93

Gly Arg Tyr Pro Glu Thr Thr Val Gly Asn Leu Thr Lys Ser Phe Gln
1               5                   10                  15

Ala Pro Arg Leu Asp Arg Ser Val Gln Ser Pro Ile Tyr Asn Ile Phe
            20                  25                  30

Thr Asn His Val Ala Gly Tyr Ser Leu Ser His Ser Leu Tyr Asp Arg
        35                  40                  45

Ile Val Phe Leu Cys Thr Ser Ser Asn Pro Val Asn Gly Ala Cys
    50                  55                  60

Pro Thr Ile Gly Thr Ser Gly Val Gln Tyr Gly Thr Thr Ile Thr
65                  70                  75                  80

Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Phe Ser
            100                 105                 110

Asn Leu Met Val Leu Asn Ser Lys Ser Trp Ser Cys Gly Ala Tyr Gly
        115                 120                 125

Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
            180                 185                 190

Leu Pro Gly Phe His Ser Asn Pro Arg Val Asp Leu Asn Leu Arg Pro
        195                 200                 205

Ile Gly Asn Tyr Lys Tyr Ser Gly Ser Asn Ser Leu Asp Met Cys Phe
    210                 215                 220

Tyr Asp Gly Tyr Ser Thr Asn Ser Asp Ser Met Val Ile Lys Phe Gln
225                 230                 235                 240

Asp Asp Asn Pro Thr Asn Ser Ser Glu Tyr Asn Leu Tyr Lys Ile Gly
                245                 250                 255

Gly Thr Glu Lys Leu Pro Tyr Ala Val Ser Leu Leu Met Gly Glu Lys
            260                 265                 270

Ile Phe Tyr Pro Val Asn Gly Gln Ser Phe Thr Ile Asn Asp Ser Ser
        275                 280                 285

Val Leu Glu Thr Asn Trp Asn Arg Val Thr Ala Val Ala Met Pro Glu
    290                 295                 300

Val Asn Val Pro Val Leu Cys Trp Pro Ala Arg Leu Leu Asn Ala
305                 310                 315                 320

Asp Val Asn Ala Pro Asp Ala Gly Gln Tyr Ser Gly Gln Ile Tyr Ile
                325                 330                 335

Thr Phe Thr Pro Ser Val Glu Asn Leu
            340                 345

<210> SEQ ID NO 94
<211> LENGTH: 148
<212> TYPE: PRT
<213> ORGANISM: Escherichia coli

<400> SEQUENCE: 94

```
Val Glu Lys Thr Ile Ser Val Thr Ala Ser Val Asp Pro Thr Val Asp
1               5                   10                  15

Leu Leu Gln Ser Asp Gly Ser Ala Leu Pro Asn Ser Val Ala Leu Thr
            20                  25                  30

Tyr Ser Pro Ala Val Asn Asn Phe Glu Ala His Thr Ile Asn Thr Val
        35                  40                  45

Val His Thr Asn Asp Ser Asp Lys Gly Val Val Lys Leu Ser Ala
    50                  55                  60

Asp Pro Val Leu Ser Asn Val Leu Asn Pro Thr Leu Gln Ile Pro Val
65                  70                  75                  80

Ser Val Asn Phe Ala Gly Lys Pro Leu Ser Thr Thr Gly Ile Thr Ile
                85                  90                  95

Asp Ser Asn Asp Leu Asn Phe Ala Ser Ser Gly Val Asn Lys Val Ser
            100                 105                 110

Ser Thr Gln Lys Leu Ser Ile His Ala Asp Ala Thr Arg Val Thr Gly
        115                 120                 125

Gly Ala Leu Thr Ala Gly Gln Tyr Gln Gly Leu Val Ser Ile Ile Leu
    130                 135                 140

Thr Lys Ser Thr
145
```

<210> SEQ ID NO 95
<211> LENGTH: 345
<212> TYPE: PRT
<213> ORGANISM: Escherichia coli

<400> SEQUENCE: 95

```
Gly Arg Tyr Pro Glu Thr Thr Val Gly Asn Leu Thr Lys Ser Phe Gln
1               5                   10                  15

Ala Pro Arg Leu Asp Arg Ser Val Gln Ser Pro Ile Tyr Asn Ile Phe
            20                  25                  30

Thr Asn His Val Ala Gly Tyr Ser Leu Ser His Arg Leu Tyr Asp Arg
        35                  40                  45

Ile Val Phe Val Cys Thr Ser Ser Asn Pro Val Asn Gly Ala Cys
    50                  55                  60

Pro Thr Ile Gly Thr Ser Arg Val Glu Tyr Gly Thr Thr Thr Ile Thr
65                  70                  75                  80

Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Thr Ser
            100                 105                 110

Asn Leu Met Val Leu Asn Ser Lys Ser Trp Ser Cys Gly Ala Leu Gly
        115                 120                 125

Asn Ala Asn Gly Thr Leu Leu Asn Leu Tyr Ile Pro Ala Gly Glu Ile
    130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175
```

```
Val Asn Ile Thr Val Asp Leu Thr Asp Lys Gly Asn Ile Gln Val Trp
            180                 185                 190

Leu Pro Gly Phe His Ser Asn Pro Arg Val Asp Leu Asn Leu His Pro
        195                 200                 205

Ile Gly Asn Tyr Lys Tyr Ser Gly Ser Asn Ser Leu Asp Met Cys Phe
    210                 215                 220

Tyr Asp Gly Tyr Ser Thr Asn Ser Asp Ser Met Val Ile Lys Phe Gln
225                 230                 235                 240

Asp Asp Asn Pro Thr Asn Ser Ser Glu Tyr Asn Leu Tyr Lys Ile Gly
                245                 250                 255

Gly Thr Glu Lys Leu Pro Tyr Ala Val Ser Leu Leu Met Gly Gly Lys
            260                 265                 270

Ile Phe Tyr Pro Val Asn Gly Gln Ser Phe Thr Ile Asn Asp Ser Ser
        275                 280                 285

Val Leu Glu Thr Asn Trp Asn Arg Val Thr Ala Val Ala Met Pro Glu
    290                 295                 300

Val Asn Val Pro Val Leu Cys Trp Pro Ala Arg Leu Leu Leu Asn Ala
305                 310                 315                 320

Asp Val Asn Ala Pro Asp Ala Gly Gln Tyr Ser Gly Gln Ile Tyr Ile
                325                 330                 335

Thr Phe Thr Pro Ser Val Glu Asn Leu
            340                 345

<210> SEQ ID NO 96
<211> LENGTH: 143
<212> TYPE: PRT
<213> ORGANISM: Escherichia coli

<400> SEQUENCE: 96

Val Glu Lys Asn Ile Thr Val Arg Ala Ser Val Asp Pro Lys Leu Asp
1               5                   10                  15

Leu Leu Gln Ala Asp Gly Thr Ser Leu Pro Asp Ser Ile Ala Leu Thr
            20                  25                  30

Tyr Ser Ser Ala Ser Asn Asn Phe Glu Val Tyr Ser Leu Asn Thr Ala
        35                  40                  45

Ile His Thr Asn Asp Lys Thr Lys Ala Val Val Lys Leu Ser Ala
    50                  55                  60

Pro Ala Val Leu Ser Asn Ile Met Lys Pro Ser Ser Gln Ile Pro Met
65                  70                  75                  80

Lys Val Thr Leu Gly Gly Lys Thr Leu Ser Thr Ala Asp Ala Glu Phe
                85                  90                  95

Ala Ala Asp Thr Leu Asn Phe Gly Ala Ser Gly Val Glu Asn Val Ser
            100                 105                 110

Ser Val Gln Gln Leu Thr Ile His Ala Glu Ala Ala Pro Pro Glu Ala
        115                 120                 125

Gly Asn Tyr Gln Gly Val Ile Ser Leu Ile Met Thr Gln Lys Thr
    130                 135                 140

<210> SEQ ID NO 97
<211> LENGTH: 345
<212> TYPE: PRT
<213> ORGANISM: Escherichia coli

<400> SEQUENCE: 97

Gly Arg Tyr Pro Glu Thr Thr Val Gly Asn Leu Thr Lys Ser Phe Gln
1               5                   10                  15
```

Ala Pro Arg Leu Asp Arg Ser Val Gln Ser Pro Ile Tyr Asn Ile Phe
            20                  25                  30

Thr Asn His Val Ala Gly Tyr Ser Leu Ser His Arg Leu Tyr Asp Arg
        35                  40                  45

Ile Val Phe Val Cys Thr Ser Ser Asn Pro Val Asn Gly Ala Cys
    50                  55                  60

Pro Thr Ile Gly Thr Ser Gly Val Glu Tyr Gly Thr Thr Ile Thr
65                  70                  75                  80

Leu Gln Phe Thr Glu Lys Arg Ser Leu Ile Lys Arg Asn Ile Asn Leu
                85                  90                  95

Ala Gly Asn Lys Lys Pro Ile Trp Glu Asn Gln Ser Cys Asp Phe Ser
            100                 105                 110

Asn Leu Met Val Leu Asn Ser Lys Ser Trp Ser Cys Gly Ala Gln Gly
            115                 120                 125

Asn Ala Asn Gly Thr Leu Leu Asn Leu Tyr Ile Pro Ala Gly Glu Ile
            130                 135                 140

Asn Lys Leu Pro Phe Gly Gly Ile Trp Glu Ala Thr Leu Ile Leu Arg
145                 150                 155                 160

Leu Ser Arg Tyr Gly Glu Val Ser Ser Thr His Tyr Gly Asn Tyr Thr
                165                 170                 175

Val Asn Ile Thr Val Asp Leu Thr Asp Lys Gly Asn Ile Gln Val Trp
            180                 185                 190

Leu Pro Gly Phe His Ser Asn Pro Arg Val Asp Leu Asn Leu His Pro
            195                 200                 205

Ile Gly Asn Tyr Lys Tyr Ser Gly Ser Asn Ser Leu Asp Met Cys Phe
            210                 215                 220

Tyr Asp Gly Tyr Ser Thr Asn Ser Asp Ser Met Val Ile Lys Phe Gln
225                 230                 235                 240

Asp Asp Asn Pro Thr Asn Ser Ser Glu Tyr Asn Leu Tyr Lys Arg Gly
                245                 250                 255

Gly Thr Glu Lys Leu Pro Tyr Ala Val Ser Leu Leu Met Gly Gly Lys
            260                 265                 270

Ile Phe Tyr Pro Val Asn Gly Gln Ser Phe Thr Ile Asn Asp Ser Ser
            275                 280                 285

Val Leu Glu Thr Asn Trp Asn Arg Val Thr Ala Val Ala Met Pro Glu
            290                 295                 300

Val Asn Val Pro Val Leu Cys Trp Pro Ala Arg Leu Leu Leu Asn Ala
305                 310                 315                 320

Asp Val Asn Ala Pro Asp Ala Gly Gln Tyr Ser Gly Gln Ile Tyr Ile
                325                 330                 335

Thr Phe Thr Pro Ser Val Glu Asn Leu
            340                 345

<210> SEQ ID NO 98
<211> LENGTH: 147
<212> TYPE: PRT
<213> ORGANISM: Escherichia coli

<400> SEQUENCE: 98

Val Glu Lys Thr Ile Ser Val Thr Ala Ser Val Asp Pro Thr Val Asp
1               5                   10                  15

Leu Leu Gln Ser Asp Gly Ser Ala Leu Pro Asn Ser Val Ala Leu Thr
            20                  25                  30

Tyr Ser Pro Ala Val Gly Gly Phe Glu Ala His Thr Ile Asn Thr Val
            35                  40                  45

```
Val His Thr Asn Asp Pro Ala Lys Gly Val Ile Val Lys Leu Ser Ala
 50                  55                  60

Glu Pro Val Leu Ser Asn Val Leu Asn Pro Thr Leu Gln Ile Pro Val
 65                  70                  75                  80

Ser Val Asn Phe Ala Gly Lys Lys Leu Thr Thr Thr Gly Thr Thr Ile
                 85                  90                  95

Glu Ser Asn Lys Leu Asn Phe Ala Ser Ser Gly Val Asp Lys Val Ser
                100                 105                 110

Ser Thr Gln Lys Leu Ser Ile His Ala Asp Thr Thr Gln Val Thr Gly
            115                 120                 125

Gly Leu Thr Ala Gly Gln Tyr Gln Gly Leu Val Ser Ile Ile Leu Thr
        130                 135                 140

Gln Ser Thr
145

<210> SEQ ID NO 99
<211> LENGTH: 146
<212> TYPE: PRT
<213> ORGANISM: Escherichia coli

<400> SEQUENCE: 99

Ala Ala Gly Pro Thr Leu Thr Lys Glu Leu Ala Leu Asn Val Leu Ser
 1                5                  10                  15

Pro Ala Ala Leu Asp Ala Thr Trp Ala Pro Gln Asp Asn Leu Thr Leu
                 20                  25                  30

Ser Asn Thr Gly Val Ser Asn Thr Leu Val Gly Val Leu Thr Leu Ser
             35                  40                  45

Asn Thr Ser Ile Asp Thr Val Ser Ile Ala Ser Thr Asn Val Ser Asp
 50                  55                  60

Thr Ser Lys Asn Gly Thr Val Thr Phe Ala His Glu Thr Asn Asn Ser
 65                  70                  75                  80

Ala Ser Phe Ala Thr Thr Ile Ser Thr Asp Asn Ala Asn Ile Thr Leu
                 85                  90                  95

Asp Lys Asn Ala Gly Asn Thr Ile Val Lys Thr Thr Asn Gly Ser Gln
                100                 105                 110

Leu Pro Thr Asn Leu Pro Leu Lys Phe Ile Thr Thr Glu Gly Asn Glu
            115                 120                 125

His Leu Val Ser Gly Asn Tyr Arg Ala Asn Ile Thr Ile Thr Ser Thr
        130                 135                 140

Ile Lys
145

<210> SEQ ID NO 100
<211> LENGTH: 143
<212> TYPE: PRT
<213> ORGANISM: Escherichia coli

<400> SEQUENCE: 100

Ala Val Gly Pro Thr Lys Asp Met Ser Leu Gly Ala Asn Leu Thr Ser
 1                5                  10                  15

Glu Pro Thr Leu Ala Ile Asp Phe Thr Pro Ile Glu Asn Ile Tyr Val
                 20                  25                  30

Gly Ala Asn Tyr Gly Lys Asp Ile Gly Thr Leu Val Phe Thr Thr Asn
             35                  40                  45

Asp Leu Thr Asp Ile Thr Leu Met Ser Ser Arg Ser Val Val Asp Gly
 50                  55                  60
```

```
Arg Gln Thr Gly Phe Phe Thr Phe Met Asp Ser Ser Ala Thr Tyr Lys
 65                  70                  75                  80

Ile Ser Thr Lys Leu Gly Ser Ser Asn Asp Val Asn Ile Gln Glu Ile
             85                  90                  95

Thr Gln Gly Ala Lys Ile Thr Pro Val Ser Gly Glu Lys Thr Leu Pro
            100                 105                 110

Lys Lys Phe Thr Leu Lys Leu His Ala His Arg Ser Ser Ser Thr Val
            115                 120                 125

Pro Gly Thr Tyr Thr Val Gly Leu Asn Val Thr Ser Asn Val Ile
            130                 135                 140
```

<210> SEQ ID NO 101
<211> LENGTH: 1836
<212> TYPE: DNA
<213> ORGANISM: Escherichia coli

<400> SEQUENCE: 101

| | | | | | |
|---|---|---|---|---|---|
| atgagaacag | aaatagcgac | taaaaacttc | ccagtatcaa | cgactatttc | aaaaagtttt | 60 |
| tttgcacctg | aaccacgaat | acagccttct | tttggtgaaa | atgttggaaa | ggaaggagct | 120 |
| ttattattta | gtgtgaactt | aactgttcct | gaaaatgtat | cccaggtaac | ggtctaccct | 180 |
| gtttatgatg | aagattatgg | gttaggacga | ctagtaaata | ccgctgatgc | ttcccaatca | 240 |
| ataatctacc | agattgttga | tgagaaaggg | aaaaaaatgt | aaaagatca | tggtgcagag | 300 |
| gttacaccta | tcaacaaat | aacttttaaa | gcgctgaatt | atactagcgg | ggaaaaaaaa | 360 |
| atatctcctg | gaatatataa | cgatcaggtt | atggttggtt | actacgtcaa | cgacaataaa | 420 |
| caaggaaact | ggcaatataa | atctctggat | gtaaatgtaa | atattgagca | aaattttatt | 480 |
| ccagatattg | attccgctgt | tcgtataata | cctgttaatt | acgattcgga | cccgaaactg | 540 |
| gattcacagt | tatatacggt | tgagatgacg | atccctgcag | gtgtaagcgc | agttaaaatc | 600 |
| gcaccaacag | atagtctgac | atcttctgga | cagcagatcg | aaagctggt | taatgtaaac | 660 |
| aatccagatc | aaaatatgaa | ttattatatc | agaaaggatt | ctggcgctgg | taactttatg | 720 |
| gcaggacaaa | aaggatcctt | tcctgtcaaa | gagaatacgt | catacacatt | ctcagcaatt | 780 |
| tatactggtg | gcgaataccc | taatagcgga | tattcgtctg | gtacttatgc | aggaaatttg | 840 |
| actgtatcat | tttacagcaa | tgacaataaa | caaagaacag | aaatagcgac | taaaaacttc | 900 |
| ccagtatcca | cgactatttc | aggcacatta | gctattgatt | ttacgcctat | tgaaaatatt | 960 |
| tatgtaggtg | ccaattatgg | taaagatatt | ggaacccttg | ttttcacaac | aaatgattta | 1020 |
| acagatatta | cattgatgtc | atctcgcagc | gttgttgatg | gtcgccagac | tggtttttttt | 1080 |
| accttcatgg | actcatcagc | cacttacaaa | attagtacaa | actgggatc | atcgaatgat | 1140 |
| gtaaacattc | aagaaattac | tcaaggagct | aaaattactc | ctgttagtgg | agagaaaact | 1200 |
| ttgcctaaaa | aattcactct | taagctacat | gcacacagga | gtagcagtac | agttccaggt | 1260 |
| acgtatactg | ttggtcttaa | cgtaaccagt | aacgttattg | ataacaagca | ggcagcgggg | 1320 |
| cccactctaa | ccaaagaact | ggcattaaat | gtgctttctc | ctgcagctct | ggatgcaact | 1380 |
| tgggctcctc | aggataattt | aacattatcc | aatactggcg | tttctaatac | tttggtgggt | 1440 |
| gttttgactc | tttcaaatac | cagtattgat | acagttagca | ttgcgagtac | aaatgtttct | 1500 |
| gatacatcta | agaatggtac | agtaactttt | gcacatgaga | caaataactc | tgctagcttt | 1560 |
| gccaccacca | tttcaacaga | taatgccaac | attacgttgg | ataaaaatgc | tggaaatacg | 1620 |
| attgttaaaa | ctacaaatgg | gagtcagttg | ccaactaatt | taccacttaa | gtttattacc | 1680 |

-continued

```
actgaaggta acgaacattt agtttcaggt aattaccgtg caaatataac aattacttcg    1740
acaattaaag ataacaagca ggcggcaggt ccaaccctga ctaaggagtt agcgctgaac    1800
gttctgagcc tcgagcacca ccaccaccac cactga                              1836
```

<210> SEQ ID NO 102
<211> LENGTH: 611
<212> TYPE: PRT
<213> ORGANISM: Escherichia coli

<400> SEQUENCE: 102

```
Met Arg Thr Glu Ile Ala Thr Lys Asn Phe Pro Val Ser Thr Thr Ile
1               5                   10                  15

Ser Lys Ser Phe Phe Ala Pro Glu Pro Arg Ile Gln Pro Ser Phe Gly
            20                  25                  30

Glu Asn Val Gly Lys Glu Gly Ala Leu Leu Phe Ser Val Asn Leu Thr
        35                  40                  45

Val Pro Glu Asn Val Ser Gln Val Thr Val Tyr Pro Val Tyr Asp Glu
    50                  55                  60

Asp Tyr Gly Leu Gly Arg Leu Val Asn Thr Ala Asp Ala Ser Gln Ser
65                  70                  75                  80

Ile Ile Tyr Gln Ile Val Asp Glu Lys Gly Lys Met Leu Lys Asp
                85                  90                  95

His Gly Ala Glu Val Thr Pro Asn Gln Gln Ile Thr Phe Lys Ala Leu
            100                 105                 110

Asn Tyr Thr Ser Gly Glu Lys Lys Ile Ser Pro Gly Ile Tyr Asn Asp
        115                 120                 125

Gln Val Met Val Gly Tyr Tyr Val Asn Asp Asn Lys Gln Gly Asn Trp
    130                 135                 140

Gln Tyr Lys Ser Leu Asp Val Asn Val Asn Ile Glu Gln Asn Phe Ile
145                 150                 155                 160

Pro Asp Ile Asp Ser Ala Val Arg Ile Ile Pro Val Asn Tyr Asp Ser
                165                 170                 175

Asp Pro Lys Leu Asp Ser Gln Leu Tyr Thr Val Glu Met Thr Ile Pro
            180                 185                 190

Ala Gly Val Ser Ala Val Lys Ile Ala Pro Thr Asp Ser Leu Thr Ser
        195                 200                 205

Ser Gly Gln Gln Ile Gly Lys Leu Val Asn Val Asn Asn Pro Asp Gln
    210                 215                 220

Asn Met Asn Tyr Tyr Ile Arg Lys Asp Ser Gly Ala Gly Asn Phe Met
225                 230                 235                 240

Ala Gly Gln Lys Gly Ser Phe Pro Val Lys Glu Asn Thr Ser Tyr Thr
                245                 250                 255

Phe Ser Ala Ile Tyr Thr Gly Glu Tyr Pro Asn Ser Gly Tyr Ser
            260                 265                 270

Ser Gly Thr Tyr Ala Gly Asn Leu Thr Val Ser Phe Tyr Ser Asn Asp
        275                 280                 285

Asn Lys Gln Arg Thr Glu Ile Ala Thr Lys Asn Phe Pro Val Ser Thr
    290                 295                 300

Thr Ile Ser Gly Thr Leu Ala Ile Asp Phe Thr Pro Ile Glu Asn Ile
305                 310                 315                 320

Tyr Val Gly Ala Asn Tyr Gly Lys Asp Ile Gly Thr Leu Val Phe Thr
                325                 330                 335

Thr Asn Asp Leu Thr Asp Ile Thr Leu Met Ser Ser Arg Ser Val Val
```

```
                   340                 345                 350

Asp Gly Arg Gln Thr Gly Phe Phe Thr Phe Met Asp Ser Ser Ala Thr
            355                 360                 365

Tyr Lys Ile Ser Thr Lys Leu Gly Ser Ser Asn Asp Val Asn Ile Gln
        370                 375                 380

Glu Ile Thr Gln Gly Ala Lys Ile Thr Pro Val Ser Gly Glu Lys Thr
385                 390                 395                 400

Leu Pro Lys Lys Phe Thr Leu Lys Leu His Ala His Arg Ser Ser Ser
                405                 410                 415

Thr Val Pro Gly Thr Tyr Thr Val Gly Leu Asn Val Thr Ser Asn Val
            420                 425                 430

Ile Asp Asn Lys Gln Ala Ala Gly Pro Thr Leu Thr Lys Glu Leu Ala
        435                 440                 445

Leu Asn Val Leu Ser Pro Ala Ala Leu Asp Ala Thr Trp Ala Pro Gln
    450                 455                 460

Asp Asn Leu Thr Leu Ser Asn Thr Gly Val Ser Asn Thr Leu Val Gly
465                 470                 475                 480

Val Leu Thr Leu Ser Asn Thr Ser Ile Asp Thr Val Ser Ile Ala Ser
                485                 490                 495

Thr Asn Val Ser Asp Thr Ser Lys Asn Gly Thr Val Thr Phe Ala His
            500                 505                 510

Glu Thr Asn Asn Ser Ala Ser Phe Ala Thr Thr Ile Ser Thr Asp Asn
        515                 520                 525

Ala Asn Ile Thr Leu Asp Lys Asn Ala Gly Asn Thr Ile Val Lys Thr
    530                 535                 540

Thr Asn Gly Ser Gln Leu Pro Thr Asn Leu Pro Leu Lys Phe Ile Thr
545                 550                 555                 560

Thr Glu Gly Asn Glu His Leu Val Ser Gly Asn Tyr Arg Ala Asn Ile
                565                 570                 575

Thr Ile Thr Ser Thr Ile Lys Asp Asn Lys Gln Ala Ala Gly Pro Thr
            580                 585                 590

Leu Thr Lys Glu Leu Ala Leu Asn Val Leu Ser Leu Glu His His His
        595                 600                 605

His His His
    610

<210> SEQ ID NO 103
<211> LENGTH: 841
<212> TYPE: PRT
<213> ORGANISM: Escherichia coli

<400> SEQUENCE: 103

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95
```

Glu Thr Asn Ile Thr Leu Gln Phe Thr Glu Lys Arg Ser Leu Ile Lys
                100                 105                 110

Arg Glu Leu Gln Ile Lys Gly Tyr Lys Gln Phe Leu Phe Lys Asn Ala
            115                 120                 125

Asn Cys Pro Ser Lys Leu Ala Leu Asn Ser Ser His Phe Gln Cys Asn
        130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro

```
                515                 520                 525
Thr Ile Asp Ile Leu Gln Ala Asn Gly Ser Ala Leu Pro Thr Ala Val
        530                 535                 540
Asp Leu Thr Tyr Leu Pro Gly Ala Lys Thr Phe Glu Asn Tyr Ser Val
545                 550                 555                 560
Leu Thr Gln Ile Tyr Thr Asn Asp Pro Ser Lys Gly Leu Asp Val Arg
                565                 570                 575
Leu Val Asp Thr Pro Lys Leu Thr Asn Ile Leu Gln Pro Thr Ser Thr
            580                 585                 590
Ile Pro Leu Thr Val Ser Trp Ala Gly Lys Thr Leu Ser Thr Ser Ala
                595                 600                 605
Gln Lys Ile Ala Val Gly Asp Leu Gly Phe Gly Ser Thr Gly Thr Ala
        610                 615                 620
Gly Val Ser Asn Ser Lys Glu Leu Val Ile Gly Ala Thr Thr Ser Gly
625                 630                 635                 640
Thr Ala Pro Ser Ala Gly Lys Tyr Gln Gly Val Val Ser Ile Val Met
                645                 650                 655
Thr Gln Ser Thr Asp Thr Ala Ala Pro Val Pro Asp Asn Lys Gln Val
            660                 665                 670
Glu Lys Asn Ile Thr Val Thr Ala Ser Val Asp Pro Thr Ile Asp Ile
        675                 680                 685
Leu Gln Ala Asp Gly Ser Ser Leu Pro Thr Ala Val Glu Leu Thr Tyr
            690                 695                 700
Ser Pro Ala Ala Ser Arg Phe Glu Asn Tyr Lys Ile Ala Thr Lys Val
705                 710                 715                 720
His Thr Asn Val Ile Asn Lys Asn Val Leu Val Lys Leu Val Asn Asp
                725                 730                 735
Pro Lys Leu Thr Asn Val Leu Asp Ser Thr Lys Gln Leu Pro Ile Thr
            740                 745                 750
Val Ser Tyr Gly Gly Lys Thr Leu Ser Thr Ala Asp Val Thr Phe Glu
            755                 760                 765
Pro Ala Glu Leu Asn Phe Gly Thr Ser Gly Val Thr Gly Val Ser Ser
        770                 775                 780
Ser Gln Asp Leu Val Ile Gly Ala Thr Thr Ala Gln Ala Pro Thr Ala
785                 790                 795                 800
Gly Asn Tyr Ser Gly Val Val Ser Ile Leu Met Thr Leu Ala Ser Asp
                805                 810                 815
Asn Lys Gln Val Glu Lys Asn Ile Thr Val Thr Ala Ser Val Asp Pro
            820                 825                 830
Thr Leu Glu His His His His His His
        835                 840

<210> SEQ ID NO 104
<211> LENGTH: 2526
<212> TYPE: DNA
<213> ORGANISM: Escherichia coli

<400> SEQUENCE: 104
atgaataaaa tttatttat ttttacattg ttttttcctt cagggttttt tacatttgcc    60
gtatcggcag ataaaaatcc cggaagtgaa acatgactaa tactattgg tccccatgac   120 agggggggat cttcccccat atataatatc ttaaattcct atcttacagc atacaatgga   180
agccatcatc tgtatgatag gatgagtttt ttatgtttgt cttctcaaaa tacactgaat   240
ggagcatgcc caagcagtga tgcccctggc actgctacaa ttgatggcga aacaaatata   300
```

```
acattacaat ttacggaaaa aagaagtcta attaaaagag aactgcaaat taaaggctat    360
aaacaatttt tgttcaaaaa tgctaattgc ccatctaaac tagcacttaa ctcatctcat    420
tttcaatgta atagagaaca agcttcaggt gctactttat cgttatacat accagctggt    480
gaattaaata aattacctttt tggggggggtc tggaatgccg ttctgaagct aaatgtaaaa    540
agacgatatg atacaaccta tgggacttac actataaaca tcacagttaa tttaactgat    600
aagggaaata ttcagatatg gttaccacag ttcaaaagta acgctcgtgt cgatcttaac    660
ttgcgtccaa ctggtggtgg tacatatatc ggaagaaatt ctgttgatat gtgctttttat    720 gatggatata gtactaacag cagctcttta gagataagat ttcaggatga taattctaaa    780
tctgatggaa aattttatct aaagaaaata aatgatgact ccaaagaact tgtatacact    840
ttgtcacttc tcctggcagg taaaaattta acaccaacaa atggacaggc attaaatatt    900
aacactgctt ctctggaaac aaactggaat agaattacag ctgtcaccat gccagaaatc    960
agtgttccgg tgttgtgttg gcctggacgt ttgcaattgg atgcaaaagt gaaaaatccc   1020
gaggctggac aatatatggg gaatattaaa attactttca caccaagtag tcaaacactc   1080
gacaataaac aagtagagaa aaatattact gtaacagcta gtgttgatcc tgcaattgat   1140
cttttgcaag ctgatggcaa tgctctgcca tcagctgtaa agttagctta ttctcccgca   1200
tcaaaaactt tgaaagtta cagagtaatg actcaagttc atacaaacga tgcaactaaa   1260
aaagtaattg ttaaacttgc tgatacacca cagcttacag atgttctgaa ttcaactgtt   1320
caaatgccta tcagtgtgtc atggggagga caagtattat ctacaacagc caaagaattt   1380
gaagctgctg ctttgggata ttctgcatcc ggtgtaaatg gcgtatcatc ttctcaagag   1440
ttagtaatta gcgctgcacc taaaactgcc ggtaccgccc caactgcagg aaactattca   1500
ggagtagtat ctcttgtaat gactttggga tccgacaata aacaagtaga gaaaaatatt   1560
actgtaacag ctagtgtcga ccctactatt gatattcttc aagcaaatgg ttctgcgcta   1620
ccgacagctg tagatttaac ttatctacct ggtgcaaaaa cttttgaaaa ttacagtgtt   1680
ctaacccaga tttacacaaa tgacccttca aaaggtttag atgttcgact ggttgataca   1740
ccgaaactta caaatatttt gcaaccgaca tctaccattc ctcttactgt ctcatgggca   1800
gggaagacat taagtacaag tgctcagaag attgcagttg gcgatctggg ttttggttcc   1860
accggaacgg caggtgtttc gaatagtaaa gaattagtaa ttggagcaac tacatccgga   1920
actgcaccaa gtgcaggtaa gtatcaaggc gtcgtttcca ttgtaatgac tcaatcgacc   1980
gacacagccg cgcctgttcc tgacaataaa caagtagaga aaatattac tgtgacagcc   2040 agtgttgatc ctactattga cattttgcaa gctgatggta gtagtttacc tactgctgta   2100
gaattaacct attcacctgc ggcaagtcgt tttgaaaatt ataaaatcgc aactaaagtt   2160
catacaaatg ttataaataa aaatgtacta gttaagcttg taaatgatcc aaaacttaca   2220
aatgttttgg attctacaaa acaactcccc attactgtat catatggagg aaagactcta   2280
tcaaccgcag atgtgacttt tgaacctgca gaattaaatt ttggaacgtc aggtgtaact   2340
ggtgtatctt cttcccaaga tttagtgatt ggtgcgacta cagcacaagc accaacggcg   2400
ggaaattata gtggggtcgt ttctatctta atgaccttag catcagacaa taaacaagtg   2460
gaaaaaaata tcactgtaac agctagtgtt gatcctacgc tcgagcacca ccaccaccac   2520
cactga                                                              2526
```

<210> SEQ ID NO 105

```
<211> LENGTH: 687
<212> TYPE: PRT
<213> ORGANISM: Escherichia coli

<400> SEQUENCE: 105

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Gln Asp Arg Ser Val Gln Ser Pro Ile Tyr Asn
        35                  40                  45

Ile Phe Thr Asn His Val Ala Gly Tyr Ser Leu Ser His Asn Leu Tyr
    50                  55                  60

Asp Arg Ile Val Phe Leu Cys Thr Ser Ser Asn Pro Val Asn Gly
65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Thr Ser Asn Leu Met Val Leu Asn Ser Lys Ser Trp Ser Cys Gly Ala
130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Tyr Ser Ser Glu Tyr Asn Leu Tyr Lys
            260                 265                 270

Ile Gly Gly Thr Glu Lys Leu Pro Tyr Ala Val Ser Leu Leu Met Gly
        275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu Gly Gly Val Glu
        355                 360                 365

Lys Asn Ile Thr Val Arg Ala Ser Val Asp Pro Lys Leu Asp Leu Leu
    370                 375                 380

Gln Ala Asp Gly Thr Ser Leu Pro Asp Ser Ile Ala Leu Thr Tyr Ser
```

```
                385                 390                 395                 400
        Ser Ala Ser Asn Asn Phe Glu Val Tyr Ser Leu Asn Thr Ala Ile His
                        405                 410                 415

Thr Asn Asp Lys Ser Lys Gly Val Val Lys Leu Ser Ala Ser Pro
                        420                 425                 430

Val Leu Ser Asn Ile Met Lys Pro Asn Ser Gln Ile Pro Met Lys Val
                        435                 440                 445

Thr Leu Gly Gly Lys Thr Leu Asn Thr Thr Asp Thr Glu Phe Thr Val
                450                 455                 460

Asp Thr Leu Asn Phe Gly Thr Ser Gly Val Glu Asn Val Ser Ser Thr
        465                 470                 475                 480

Gln Gln Leu Thr Ile His Ala Asp Thr Gln Gly Thr Ala Pro Glu Ala
                        485                 490                 495

Gly Asn Tyr Gln Gly Ile Ile Ser Leu Ile Met Thr Gln Lys Thr Gly
                        500                 505                 510

Gly Gly Val Glu Lys Asn Ile Thr Val Arg Ala Ser Val Asp Pro Lys
                        515                 520                 525

Leu Asp Leu Leu Gln Ser Asp Gly Ser Ala Leu Pro Asn Ser Val Ala
                530                 535                 540

Leu Thr Tyr Ser Pro Ala Val Asn Asn Phe Glu Ala His Thr Ile Asn
        545                 550                 555                 560

Thr Val His Thr Asn Asp Ser Asp Lys Gly Val Val Lys Leu
                        565                 570                 575

Ser Ala Asp Pro Val Leu Ser Asn Val Leu Asn Pro Thr Leu Gln Ile
                        580                 585                 590

Pro Val Ser Val Asn Phe Ala Gly Lys Pro Leu Ser Thr Thr Gly Ile
                        595                 600                 605

Thr Ile Asp Ser Asn Asp Leu Asn Phe Ala Ser Ser Gly Val Asn Lys
                        610                 615                 620

Val Ser Ser Thr Gln Lys Leu Ser Ile His Ala Asp Ala Thr Arg Val
        625                 630                 635                 640

Thr Gly Gly Ala Leu Thr Ala Gly Gln Tyr Gln Gly Leu Val Ser Ile
                        645                 650                 655

Ile Leu Thr Lys Ser Thr Gly Gly Val Glu Lys Thr Ile Ser Val
                        660                 665                 670

Thr Ala Ser Val Asp Pro Thr Leu Glu His His His His His His
                675                 680                 685

<210> SEQ ID NO 106
<211> LENGTH: 2164
<212> TYPE: DNA
<213> ORGANISM: Escherichia coli

<400> SEQUENCE: 106
atgaaaaaga tatttatttt tttgtctatc atattttctg cggtggtcag tgccgggcga      60
tacccggaaa ctacagtagg taatctgacg aagagttttc aagcccctcg tcaggataga     120
agcgtacaat caccaatata taacatcttt acgaatcatg tggctggata gtttgagt      180 cataacttat atgacaggat tgttttttta tgtacatcct cgtcgaatcc ggttaatggt     240
gcttgcccaa ccattggaac atctggagtt caatacggta ctacaaccat aaccttgcag     300
tttacagaaa aagaagtct gataaaaaga atattaatc ttgcaggtaa taagaaacca      360
atatgggaga atcagagttg cgacactagc aatctaatgg tgttgaattc gaagtcttgg     420
tcctgtgggg cttacggaaa tgctaacgga acacttctaa atctgtatat ccctgcagga     480
```

```
gaaatcaaca aattgccttt tggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720
tgtttctatg atggatatag tacaaacagt gatagcatgg taataaagtt ccaggatgat    780
aatcctacct attcatctga atataatctt tataagatag ggggcactga aaaattaccc    840
tatgctgttt cactgcttat gggagaaaaa atattttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttag gcggtggagt cgaaaaaaat attactgtga gggcaagtgt tgaccctaaa   1140
cttgatcttc tgcaagcaga tggaacttca ctgccggact ctatcgcatt aacctattct   1200
tcggcttcaa ataattttga agtttactct cttaatactg ctattcatac aaatgacaaa   1260
agcaagggag ttgtagtgaa gctgtcagct tcaccagttc tgtccaatat tatgaagcca   1320
aactcgcaaa ttccgatgaa agtgactttg ggggggaaga cgctgaatac aactgatact   1380
gagtttactg ttgatactct gaactttggt acatctggtg ttgaaaacgt tcttccact    1440 caacagctta cgattcatgc agacacacaa ggaactgcgc ctgaggcagg caattaccaa   1500
ggtattattt ctcttatcat gactcaaaaa acaggggcg gtgtcgaaaa aaatattact    1560
gtgagggcaa gtgtcgaccc taaacttgac cttctgcaat ctgatggctc tgcgctgccg   1620
aactctgtcg cattaaccta ttctccggct gtaaataatt ttgaagctca caccatcaac   1680
accgttgttc atacaaatga ctcagataaa ggtgttgttg tgaagctgtc agcagatcca   1740
gtcctgtcca atgttctgaa tccaaccctg caaattcctg tttctgtgaa tttcgcagga   1800
aaaccactga gcacaacagg cattaccatc gactccaatg atctgaactt tgcttcgagt   1860
ggtgttaata agtttcttc tacgcagaaa ctttcaatcc atgcagatgc tactcgggta   1920
actggcggcg cactaacagc tggtcaatat cagggactcg tatcaattat cctgactaag   1980
tcaacggggg gcggtgtcga aagaccatt agcgttacgg cgagtgttga cccgacgggc   2040
acattagcta ttgattttac gcctattgaa aatatttatg taggtgccaa ttatggtaaa   2100
gatattggaa cccttgtttt cacaacaaat gatttaactc gagcaccacc accaccacca   2160
ctga                                                                2164
```

<210> SEQ ID NO 107
<211> LENGTH: 703
<212> TYPE: PRT
<213> ORGANISM: Escherichia coli

<400> SEQUENCE: 107

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Gln Asp Arg Ser Val Gln Ser Pro Ile Tyr Asn
        35                  40                  45

Ile Phe Thr Asn His Val Ala Gly Tyr Ser Leu Ser His Asn Leu Tyr
    50                  55                  60

```
Asp Arg Ile Val Phe Leu Cys Thr Ser Ser Asn Pro Val Asn Gly
 65                  70                  75                  80

Ala Cys Pro Thr Ile Gly Thr Ser Gly Val Gln Tyr Gly Thr Thr Thr
                 85                  90                  95

Ile Thr Leu Gln Phe Thr Glu Lys Arg Ser Leu Ile Lys Arg Asn Ile
                100                 105                 110

Asn Leu Ala Gly Asn Lys Lys Pro Ile Trp Glu Asn Gln Ser Cys Asp
                115                 120                 125

Thr Ser Asn Leu Met Val Leu Asn Ser Lys Ser Trp Ser Cys Gly Ala
        130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
                180                 185                 190

Tyr Thr Val Asn Ile Thr Val Asp Leu Thr Asp Lys Gly Asn Ile Gln
            195                 200                 205

Val Trp Leu Pro Gly Phe His Ser Asn Pro Arg Val Asp Leu Asn Leu
        210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Tyr Ser Ser Glu Tyr Asn Leu Tyr Lys
                260                 265                 270

Ile Gly Gly Thr Glu Lys Leu Pro Tyr Ala Val Ser Leu Leu Met Gly
            275                 280                 285

Glu Lys Ile Phe Tyr Pro Val Asn Gly Gln Ser Phe Thr Ile Asn Asp
        290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
                340                 345                 350

Tyr Ile Thr Phe Thr Pro Ser Val Glu Asn Leu Gly Gly Gly Val Glu
            355                 360                 365

Lys Asn Ile Thr Val Arg Ala Ser Val Asp Pro Lys Leu Asp Leu Leu
        370                 375                 380

Gln Ala Asp Gly Thr Ser Leu Pro Asp Ser Ile Ala Leu Thr Tyr Ser
385                 390                 395                 400

Ser Ala Ser Asn Asn Phe Glu Val Tyr Ser Leu Asn Thr Ala Ile His
                405                 410                 415

Thr Asn Asp Lys Ser Lys Gly Val Val Lys Leu Ser Ala Ser Pro
                420                 425                 430

Val Leu Ser Asn Ile Met Lys Pro Asn Ser Gln Ile Pro Met Lys Val
        435                 440                 445

Thr Leu Gly Gly Lys Thr Leu Asn Thr Thr Asp Thr Glu Phe Thr Val
            450                 455                 460

Asp Thr Leu Asn Phe Gly Thr Ser Gly Val Glu Asn Val Ser Ser Thr
465                 470                 475                 480

Gln Gln Leu Thr Ile His Ala Asp Thr Gln Gly Thr Ala Pro Glu Ala
```

```
                   485                 490                 495
Gly Asn Tyr Gln Gly Ile Ile Ser Leu Ile Met Thr Gln Lys Thr Gly
                500                 505                 510

Gly Gly Val Glu Lys Asn Ile Thr Val Arg Ala Ser Val Asp Pro Lys
            515                 520                 525

Leu Asp Val Glu Lys Thr Ile Ser Val Thr Ala Ser Val Asp Pro Thr
        530                 535                 540

Val Asp Leu Leu Gln Ser Asp Gly Ser Ala Leu Pro Asn Ser Val Ala
545                 550                 555                 560

Leu Thr Tyr Ser Pro Ala Val Asn Asn Phe Glu Ala His Thr Ile Asn
                565                 570                 575

Thr Val Val His Thr Asn Asp Ser Asp Lys Gly Val Val Lys Leu
            580                 585                 590

Ser Ala Asp Pro Val Leu Ser Asn Val Leu Asn Pro Thr Leu Gln Ile
        595                 600                 605

Pro Val Ser Val Asn Phe Ala Gly Lys Pro Leu Ser Thr Thr Gly Ile
610                 615                 620

Thr Ile Asp Ser Asn Asp Leu Asn Phe Ala Ser Ser Gly Val Asn Lys
625                 630                 635                 640

Val Ser Ser Thr Gln Lys Leu Ser Ile His Ala Asp Ala Thr Arg Val
                645                 650                 655

Thr Gly Gly Ala Leu Thr Ala Gly Gln Tyr Gln Gly Leu Val Ser Ile
            660                 665                 670

Ile Leu Thr Lys Ser Thr Gly Gly Val Glu Lys Thr Ile Ser Val
        675                 680                 685

Thr Ala Ser Val Asp Pro Thr Leu Glu His His His His His
    690                 695                 700

<210> SEQ ID NO 108
<211> LENGTH: 2278
<212> TYPE: DNA
<213> ORGANISM: Escherichia coli

<400> SEQUENCE: 108
atgaaaaaga tatttatttt tttgtctatc atattttctg cggtggtcag tgccgggcga      60
tacccggaaa ctacagtagg taatctgacg aagagttttc aagcccctcg tcaggataga     120
agcgtacaat caccaatata taacatcttt acgaatcatg tggctggata tagtttgagt     180
cataacttat atgacaggat tgttttttta tgtacatcct cgtcgaatcc ggttaatggt     240
gcttgcccaa ccattggaac atctggagtt caatacggta ctacaaccat aaccttgcag     300
tttacagaaa aagaagtct gataaaaaga aatattaatc ttgcaggtaa taagaaacca     360
atatgggaga atcagagttg cgacactagc aatctaatgg tgttgaattc gaagtcttgg     420
tcctgtgggg cttacggaaa tgctaacgga acacttctaa atctgtatat ccctgcagga     480
gaaatcaaca aattgccttt tggagggata tgggaggcaa ctctgatctt acgcttatca     540
agatatggcg aagtcagtag cacccattac ggcaattata ccgtaaatat tacggttgat     600
ttaactgata aagtaatat tcaggtatgg cttccagggt ttcacagcaa cccgcgtgta     660
gacctgaatc tgcaccctat cggtaattat aaatatagtg gtagtaattc actcgacatg     720
tgtttctatg atggatatag tacaaacagt gatagcatgg taataaagtt ccaggatgat     780
aatcctacct attcatctga atataatctt tataagatag ggggcactga aaaattaccc     840
tatgctgttt cactgcttat gggagaaaaa atattttatc cagtgaatgg tcaatcattt     900
```

-continued

```
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttag gcggtggagt cgaaaaaaat attactgtga gggcaagtgt tgaccctaaa   1140
cttgatcttc tgcaagcaga tggaacttca ctgccggact ctatcgcatt aacctattct   1200
tcggcttcaa ataattttga agtttactct cttaatactg ctattcatac aaatgacaaa   1260
agcaagggag ttgtagtgaa gctgtcagct tcaccagttc tgtccaatat tatgaagcca   1320
aactcgcaaa ttccgatgaa agtgactttg gggggggaaga cgctgaatac aactgatact   1380
gagtttactg ttgatactct gaactttggt acatctggtg ttgaaaacgt ttcttccact   1440
caacagctta cgattcatgc agacacacaa ggaactgcgc ctgaggcagg caattaccaa   1500
ggtattattt ctcttatcat gactcaaaaa acagggggcg gtgtcgaaaa aaatattact   1560
gtgagggcaa gtgtcgaccc taaacttaaa ctaaagaaaa caattggcgc aatggctctg   1620
gcgacattat ttgcaactat gggagcatct gcggtcgaga agaccattag cgttacggcg   1680
agtgttgacc cgactgttga ccttctgcaa tctgatggct ctgcgctgcc gaactctgtc   1740
gcattaacct attctccggc tgtaaataat tttgaagctc acaccatcaa caccgttgtt   1800
catacaaatg actcagataa aggtgttgtt gtgaagctgt cagcagatcc agtcctgtcc   1860
aatgttctga atccaaccct gcaaattcct gtttctgtga atttcgcagg aaaaccactg   1920
agcacaacag gcattaccat cgactccaat gatctgaact ttgcttcgag tggtgttaat   1980
aaagtttctt ctacgcagaa actttcaatc catgcagatg ctactcgggt aactggcggc   2040
gcactaacag ctggtcaata tcagggactc gtatcaatta tcctgactaa gtcaacgtaa   2100
gggggcggtg tcgagaagac cattagcgtt acggcgagtt tgacccgac gggcacatta   2160
gctattgatt ttacgcctat tgaaaatatt tatgtaggtg ccaattatgg taaagatatt   2220
ggaacccttg ttttcacaac aaatgattta actcgagcac caccaccacc accactga    2278
```

<210> SEQ ID NO 109
<211> LENGTH: 539
<212> TYPE: PRT
<213> ORGANISM: Escherichia coli

<400> SEQUENCE: 109

```
Met Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
            20                  25                  30

Thr Glu Ser Ile Gly Pro Ile Asp Arg Ser Ala Ala Ser Tyr Pro
        35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
            100                 105                 110

Lys Thr Leu Asn Leu Lys Gly Tyr Lys Arg Phe Leu Tyr Glu Ser Asp
        115                 120                 125

Arg Cys Ile His Tyr Val Asp Lys Met Asn Leu Asn Ser His Thr Val
```

```
            130                 135                 140
Lys Cys Val Gly Ser Phe Thr Arg Gly Val Asp Phe Thr Leu Tyr Ile
145                 150                 155                 160

Pro Gln Gly Glu Ile Asp Gly Leu Leu Thr Gly Ile Trp Glu Ala
                165                 170                 175

Thr Leu Glu Leu Arg Val Lys Arg His Tyr Asp Tyr Asn His Gly Thr
                180                 185                 190

Tyr Lys Val Asn Ile Thr Val Asp Leu Thr Asp Lys Gly Asn Ile Gln
                195                 200                 205

Val Trp Thr Pro Lys Phe His Ser Asp Pro Arg Ile Asp Leu Asn Leu
            210                 215                 220

Arg Pro Glu Gly Asn Gly Lys Tyr Ser Gly Ser Asn Val Leu Glu Met
225                 230                 235                 240

Cys Leu Tyr Asp Gly Tyr Ser Thr His Ser Gln Ser Ile Glu Met Arg
                245                 250                 255

Phe Gln Asp Asp Ser Gln Thr Gly Asn Asn Glu Tyr Asn Leu Ile Lys
                260                 265                 270

Thr Gly Glu Pro Leu Lys Lys Leu Pro Tyr Lys Leu Ser Leu Leu Leu
                275                 280                 285

Gly Gly Arg Glu Phe Tyr Pro Asn Asn Gly Glu Ala Phe Thr Ile Asn
                290                 295                 300

Asp Thr Ser Ser Leu Phe Ile Asn Trp Asn Arg Ile Lys Ser Val Ser
305                 310                 315                 320

Leu Pro Gln Ile Ser Ile Pro Val Leu Cys Trp Pro Ala Asn Leu Thr
                325                 330                 335

Phe Met Ser Glu Leu Asn Asn Pro Glu Ala Gly Glu Tyr Ser Gly Ile
                340                 345                 350

Leu Asn Val Thr Phe Thr Pro Ser Ser Ser Leu Asp Asn Lys Gln
                355                 360                 365

Ala Glu Lys Asn Ile Thr Val Thr Ala Ser Val Asp Pro Thr Ile Asp
                370                 375                 380

Leu Met Gln Ser Asp Gly Thr Ala Leu Pro Ser Ala Val Asn Ile Ala
385                 390                 395                 400

Tyr Leu Pro Gly Glu Lys Arg Phe Glu Ser Ala Arg Ile Asn Thr Gln
                405                 410                 415

Val His Thr Asn Asn Lys Thr Lys Gly Ile Gln Ile Lys Leu Thr Asn
                420                 425                 430

Asp Asn Val Val Met Thr Asn Leu Ser Asp Pro Ser Lys Thr Ile Pro
                435                 440                 445

Leu Glu Val Ser Phe Ala Gly Thr Lys Leu Ser Thr Ala Ala Thr Ser
            450                 455                 460

Ile Thr Ala Asp Gln Leu Asn Phe Gly Ala Gly Val Glu Thr Val
465                 470                 475                 480

Ser Ala Thr Lys Glu Leu Val Ile Asn Ala Gly Ser Thr Gln Gln Thr
                485                 490                 495

Asn Ile Val Ala Gly Asn Tyr Gln Gly Leu Val Ser Ile Val Leu Thr
                500                 505                 510

Gln Glu Pro Asp Asn Lys Gln Ala Glu Lys Asn Ile Thr Val Thr Ala
            515                 520                 525

Ser Val Asp Pro Thr His His His His His
            530                 535

<210> SEQ ID NO 110
```

```
<211> LENGTH: 1620
<212> TYPE: DNA
<213> ORGANISM: Escherichia coli

<400> SEQUENCE: 110
atgaaaaaag tgattttgt tttatccatg tttctatgtt ctcaggttta cgggcaatca        60
tggcatacga acgtagaggc tggttcaata aataaaacag agtcgatagg ccccatagac      120
cgaagtgctg ctgcatcgta tcctgctcat tatatatttc atgaacatgt tgctggttac      180
aataaagatc actctctttt tgacaggatg acgtttttat gtatgtcatc aacagatgca      240
tctaaaggtg catgtccgac aggagaaaac tccaaatcct ctcaagggga gactaatatt      300
aagctaatat ttactgaaaa gaaagtctg gccagaaaaa cattaaactt aaaaggatat       360
aagagatttt tatatgaatc agatagatgc attcattatg tcgataaaat gaatctcaat      420
tctcatactg ttaaatgtgt aggttcattc acaagaggag tagatttcac tttatatatc      480
ccacaaggtg aaattgatgg gcttctaact ggaggtatat gggaggcaac actagagtta      540
cgagtcaaaa ggcattacga ctataatcat ggtacttaca agttaatat cacagttgat       600 ttgacagaca aaggaaatat tcaggtctgg acaccaaagt tcatagcga tcctagaatt       660 gatctgaatt tacgtcctga aggtaatggt aaatattctg gtagtaacgt gcttgagatg      720
tgtctctatg atggctatag tacacatagt caaagtatag aaatgaggtt tcaggatgac      780
tcacaaacag gaataatga atataatctt ataaaaactg agagccatt aaaaaaattg        840 ccatataaac tttctcttct tttaggagga cgagagtttt atccaaataa tggagaggct      900
tttactatta tgatacttc gtcattgttt ataaactgga atcgtattaa gtctgtatcc      960
ttaccacaga ttagtattcc agtactatgc tggccagcaa acttgacatt tatgtcagag     1020
ctaaataatc cagaagcggg tgagtattca ggaatactta cgtaacatt tactcctagt     1080 agttcaagcc tagacaataa acaagccgag aaaaatatca ctgtaactgc tagcgttgat     1140
ccaactatcg atctgatgca atctgatggc acagcgttac caagtgcagt taatattgca     1200
tatcttccag agagaaaag attttgaatct gctcgtatca ataccaagt tcataccaat      1260 aataaaacta agggtattca gataaagctt actaatgata atgtggtaat gactaactta     1320
tctgatccaa gcaagactat tccttttagag gttttcattcg ctggcactaa gctgagcaca     1380
gctgcaacat ctattactgc cgatcaatta aatttttggcg cagctggtgt agagacagtt     1440
tctgcaacta aggaactcgt tattaatgca ggaagcaccc agcaaactaa tattgtagct     1500
ggtaactatc aaggattggt gtcaattgtg cttactcaag aacctgacaa taaacaagcc     1560
gagaaaaata tcactgtaac tgctagcgtt gatccgacgc accaccacca ccaccactga     1620

<210> SEQ ID NO 111
<211> LENGTH: 2490
<212> TYPE: DNA
<213> ORGANISM: Escherichia coli

<400> SEQUENCE: 111
atgaataaaa ttttatttat ttttacattg ttttttttctt cagggttttt tacatttgcc        60
gtatcggcag ataaaaatcc cggaagtgaa aacatgacta atactattgg tccccatgac      120 aggggggggat cttcccccat atataatatc ttaaattcct atcttacagc atacaatgga     180
agccatcatc tgtatgatag gatgagtttt ttatgttgtg cttctcaaaa tacactgaat      240
ggagcatgcc caagcagtga tgcccctggc actgctacaa ttgatggcga acaaatata       300 acattacaat ttacggaaaa aagaagtcta attaaaagag aactgcaaat taaaggctat     360
```

```
aaacaatttt tgttcaaaaa tgctaattgc ccatctaaac tagcacttaa ctcatctcat    420
tttcaatgta atagagaaca agcttcaggt gctactttat cgttatacat accagctggt    480
gaattaaata aattacctttt tggggggtc tggaatgccg ttctgaagct aaatgtaaaa    540
agacgatatg atacaaccta tgggacttac actataaaca tcacagttaa tttaactgat    600
aagggaaata ttcagatatg gttaccacag ttcaaaagta acgctcgtgt cgatcttaac    660
ttgcgtccaa ctggtggtgg tacatatatc ggaagaaatt ctgttgatat gtgcttttat    720
gatggatata gtactaacag cagctcttta gagataagat ttcaggatga taattctaaa    780
tctgatggaa aattttatct aaagaaaata aatgatgact ccaaagaact tgtatacact    840
ttgtcacttc tcctggcagg taaaaattta acaccaacaa atggacaggc attaaatatt    900
aacactgctt ctctggaaac aaactggaat agaattacag ctgtcaccat gccagaaatc    960
agtgttccgg tgttgtgttg gcctggacgt ttgcaattgg atgcaaaagt gaaaaatccc   1020
gaggctggac aatatatggg gaatattaaa attactttca caccaagtag tcaaacactc   1080
gacaataaac aagtagagaa aaatattact gtaacagcta gtgttgatcc tgcaattgat   1140
cttttgcaag ctgatggcaa tgctctgcca tcagctgtaa agttagctta ttctcccgca   1200
tcaaaaactt ttgaaagtta cagagtaatg actcaagttc atacaaacga tgcaactaaa   1260
aaagtaattg ttaaacttgc tgatacacca cagcttacag atgttctgaa ttcaactgtt   1320
caaatgccta tcagtgtgtc atggggagga caagtattat ctacaacagc caagaatttt   1380
gaagctgctg ctttgggata ttctgcatcc ggtgtaaatg gcgtatcatc ttctcaagag   1440
ttagtaatta gcgctgcacc taaaactgcc ggtaccgccc caactgcagg aaactattca   1500
ggagtagtat ctcttgtaat gactttggga tccgacaata aacaagtaga gaaaatatt    1560 actgtaacag ctagtgtcga ccctgcaggg tcaaaaagtt ttttttgcacc tgaaccacga   1620 atacagcctt cttttggtga aaatgttgga aaggaaggag ctttattatt tagtgtgaac   1680
ttaactgttc ctgaaaatgt atcccaggta acggtctacc ctgtttatga tgaagattat   1740
gggttaggac gactagtaaa taccgctgat gcttcccaat caataatcta ccagattgtt   1800
gatgagaaag ggaaaaaaat gttaaaagat catggtgcag aggttacacc taatcaacaa   1860 ataacttttta aagcgctgaa ttatactagc ggggaaaaaa aaatatctcc tggaatatat   1920
aacgatcagg ttatggttgg ttactacgtc aacgacaata aacaaggaaa ctggcaatat   1980
aaatctctgg atgtaaatgt aaatattgag caaaattttta ttccagatat tgattccgct   2040
gttcgtataa tacctgttaa ttacgattcg gacccgaaac tggattcaca gttatatacg   2100
gttgagatga cgatccctgc aggtgtaagc gcagttaaaa tcgcaccaac agatagtctg   2160
acatcttctg gacagcagat cggaaagctg gttaatgtaa acaatccaga tcaaaatatg   2220
aattattata tcagaaagga ttctggcgct ggtaacttta tggcaggaca aaaaggatcc   2280
tttcctgtca aagagaatac gtcatacaca ttctcagcaa tttatactgg tggcgaatac   2340
cctaatagcg atattcgtc tggtacttat gcaggaaatt tgactgtatc attttacagc   2400
aatgacaata acaacgtac cgagattgcc accaagaatt ttccggtgag caccaccatc   2460
agcctcgagc accaccacca ccaccactga                                     2490

<210> SEQ ID NO 112
<211> LENGTH: 829
<212> TYPE: PRT
<213> ORGANISM: Escherichia coli
```

```
<400> SEQUENCE: 112

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
        355                 360                 365

Ile Thr Val Thr Ala Ser Val Asp Pro Ala Ile Asp Leu Leu Gln Ala
    370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415
```

```
Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
            435                 440                 445

Gly Gly Gln Val Leu Ser Thr Ala Lys Glu Phe Glu Ala Ala
        450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
            485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
            515                 520                 525

Ala Gly Ser Lys Ser Phe Phe Ala Pro Glu Pro Arg Ile Gln Pro Ser
            530                 535                 540

Phe Gly Glu Asn Val Gly Lys Glu Gly Ala Leu Leu Phe Ser Val Asn
545                 550                 555                 560

Leu Thr Val Pro Glu Asn Val Ser Gln Val Thr Val Tyr Pro Val Tyr
                565                 570                 575

Asp Glu Asp Tyr Gly Leu Gly Arg Leu Val Asn Thr Ala Asp Ala Ser
            580                 585                 590

Gln Ser Ile Ile Tyr Gln Ile Val Asp Glu Lys Gly Lys Lys Met Leu
            595                 600                 605

Lys Asp His Gly Ala Glu Val Thr Pro Asn Gln Gln Ile Thr Phe Lys
610                 615                 620

Ala Leu Asn Tyr Thr Ser Gly Glu Lys Lys Ile Ser Pro Gly Ile Tyr
625                 630                 635                 640

Asn Asp Gln Val Met Val Gly Tyr Tyr Val Asn Asp Asn Lys Gln Gly
                645                 650                 655

Asn Trp Gln Tyr Lys Ser Leu Asp Val Asn Val Asn Ile Glu Gln Asn
            660                 665                 670

Phe Ile Pro Asp Ile Asp Ser Ala Val Arg Ile Ile Pro Val Asn Tyr
            675                 680                 685

Asp Ser Asp Pro Lys Leu Asp Ser Gln Leu Tyr Thr Val Glu Met Thr
690                 695                 700

Ile Pro Ala Gly Val Ser Ala Val Lys Ile Ala Pro Thr Asp Ser Leu
705                 710                 715                 720

Thr Ser Ser Gly Gln Gln Ile Gly Lys Leu Val Asn Val Asn Asn Pro
                725                 730                 735

Asp Gln Asn Met Asn Tyr Tyr Ile Arg Lys Asp Ser Gly Ala Gly Asn
            740                 745                 750

Phe Met Ala Gly Gln Lys Gly Ser Phe Pro Val Lys Glu Asn Thr Ser
            755                 760                 765

Tyr Thr Phe Ser Ala Ile Tyr Thr Gly Gly Glu Tyr Pro Asn Ser Gly
            770                 775                 780

Tyr Ser Ser Gly Thr Tyr Ala Gly Asn Leu Thr Val Ser Phe Tyr Ser
785                 790                 795                 800

Asn Asp Asn Lys Gln Arg Thr Glu Ile Ala Thr Lys Asn Phe Pro Val
            805                 810                 815

Ser Thr Thr Ile Ser Leu Glu His His His His His
                820                 825
```

<210> SEQ ID NO 113
<211> LENGTH: 2487
<212> TYPE: DNA
<213> ORGANISM: Escherichia coli

<400> SEQUENCE: 113

| | | | | | | |
|---|---|---|---|---|---|---|
| atgaataaaa | tttatttat | ttttacattg | tttttttctt | cagggttttt | tacatttgcc | 60 |
| gtatcggcag | ataaaaatcc | cggaagtgaa | aacatgacta | atactattgg | tccccatgac | 120 |
| agggggggat | cttcccccat | atataatatc | ttaaattcct | atcttacagc | atacaatgga | 180 |
| agccatcatc | tgtatgatag | gatgagtttt | ttatgtttgt | cttctcaaaa | tacactgaat | 240 |
| ggagcatgcc | caagcagtga | tgcccctggc | actgctacaa | ttgatggcga | aacaaatata | 300 |
| acattacaat | ttacggaaaa | aagaagtcta | attaaaagag | aactgcaaat | taaaggctat | 360 |
| aaacaatttt | tgttcaaaaa | tgctaattgc | ccatctaaac | tagcacttaa | ctcatctcat | 420 |
| tttcaatgta | atagagaaca | agcttcaggt | gctactttat | cgttatacat | accagctggt | 480 |
| gaattaaata | aattaccttt | tgggggggtc | tggaatgccg | ttctgaagct | aaatgtaaaa | 540 |
| agacgatatg | atacaaccta | tgggacttac | actataaaca | tcacagttaa | tttaactgat | 600 |
| aagggaaata | ttcagatatg | gttaccacag | ttcaaaagta | acgctcgtgt | cgatcttaac | 660 |
| ttgcgtccaa | ctggtggtgg | tacatatatc | ggaagaaatt | ctgttgatat | gtgcttttat | 720 |
| gatggatata | gtactaacag | cagctcttta | gagataagtt | ttcaggatga | taattctaaa | 780 |
| tctgatggaa | aattttatct | aaagaaaata | aatgatgact | ccaagaact | tgtatacact | 840 |
| tgtcacttc | tcctggcagg | taaaaattta | acaccaacaa | atggacaggc | attaaatatt | 900 |
| aacactgctt | ctctggaaac | aaactggaat | agaattacag | ctgtcaccat | gccagaaatc | 960 |
| agtgttccgg | tgttgtgttg | gcctggacgt | ttgcaattgg | atgcaaaagt | gaaaaatccc | 1020 |
| gaggctggac | aatatatggg | gaatattaaa | attactttca | caccaagtag | tcaaacactc | 1080 |
| gacaataaac | aagtagagaa | aaatattact | gtaacagcta | gtgttgatcc | tgcaattgat | 1140 |
| cttttgcaag | ctgatggcaa | tgctctgcca | tcagctgtaa | agttagctta | ttctcccgca | 1200 |
| tcaaaaactt | tgaaagtta | cagagtaatg | actcaagttc | atacaaacga | tgcaactaaa | 1260 |
| aaagtaattg | ttaaacttgc | tgatacacca | cagcttacag | atgttctgaa | ttcaactgtt | 1320 |
| caaatgccta | tcagtgtgtc | atggggagga | caagtattat | ctacaacagc | caagaatttt | 1380 |
| gaagctgctg | ctttgggata | ttctgcatcc | ggtgtaaatg | gcgtatcatc | ttctcaagag | 1440 |
| ttagtaatta | gcgctgcacc | taaaactgcc | ggtaccgccc | caactgcagg | aaactattca | 1500 |
| ggagtagtat | ctcttgtaat | gactttggga | tccgacaata | aacaagtaga | gaaaaatatt | 1560 |
| actgtaacag | ctagtgtcga | ccctgcaggg | aattttattc | cagatattga | ttccgctgtt | 1620 |
| cgtataatac | ctgttaatta | cgattcggac | ccgaaactgg | attcacagtt | atatacggtt | 1680 |
| gagatgacga | tccctgcagg | tgtaagcgca | gttaaaatcg | caccaacaga | tagtctgaca | 1740 |
| tcttctggac | agcagatcgg | aaagctggtt | aatgtaaaca | atccagatca | aaatatgaat | 1800 |
| tattatatca | gaaaggattc | tggcgctggt | aactttatgg | caggacaaaa | aggatccttt | 1860 |
| cctgtcaaag | agaatacgtc | atacacattc | tcagcaattt | atactggtgg | cgaataccct | 1920 |
| aatagcggat | attcgtctgg | tacttatgca | ggaaatttga | ctgtatcatt | ttacagcaat | 1980 |
| gacaataaac | aaagaacaga | aatagcgact | aaaaacttcc | cagtatcaac | gactatttca | 2040 |
| aaaagttttt | ttgcacctga | accacgaata | cagccttctt | ttggtgaaaa | tgttggaaag | 2100 |
| gaaggagctt | tattatttag | tgtgaactta | actgttcctg | aaaatgtatc | ccaggtaacg | 2160 |

```
gtctaccctg tttatgatga agattatggg ttaggacgac tagtaaatac cgctgatgct    2220
tcccaatcaa taatctacca gattgttgat gagaaaggga aaaaaatgtt aaagatcat     2280 ggtgcagagg ttacacctaa tcaacaaata actttaaag cgctgaatta tactagcggg    2340
gaaaaaaaaa tatctcctgg aatatataac gatcaggtta tggttggtta ctacgtaaac   2400
gacaataaac aaaccgagat tgccaccaag aattttccgg tgagcaccac catcagcctc   2460
ctcgagcacc accaccacca ccactga                                        2487
```

<210> SEQ ID NO 114
<211> LENGTH: 828
<212> TYPE: PRT
<213> ORGANISM: Escherichia coli

<400> SEQUENCE: 114

```
Met Asn Lys Ile Leu Phe Ile Phe Thr Leu Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
    210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Ala Gly Lys
        275                 280                 285

Asn Leu Thr Pro Thr Asn Gly Gln Ala Leu Asn Ile Asn Thr Ala Ser
    290                 295                 300

Leu Glu Thr Asn Trp Asn Arg Ile Thr Ala Val Thr Met Pro Glu Ile
```

```
        305                 310                 315                 320
Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu Asp Asn Lys Gln Val Glu Lys Asn
            355                 360                 365

Ile Thr Val Thr Ala Ser Val Asp Pro Ala Ile Asp Leu Leu Gln Ala
        370                 375                 380

Asp Gly Asn Ala Leu Pro Ser Ala Val Lys Leu Ala Tyr Ser Pro Ala
385                 390                 395                 400

Ser Lys Thr Phe Glu Ser Tyr Arg Val Met Thr Gln Val His Thr Asn
                405                 410                 415

Asp Ala Thr Lys Lys Val Ile Val Lys Leu Ala Asp Thr Pro Gln Leu
            420                 425                 430

Thr Asp Val Leu Asn Ser Thr Val Gln Met Pro Ile Ser Val Ser Trp
        435                 440                 445

Gly Gly Gln Val Leu Ser Thr Thr Ala Lys Glu Phe Glu Ala Ala Ala
    450                 455                 460

Leu Gly Tyr Ser Ala Ser Gly Val Asn Gly Val Ser Ser Ser Gln Glu
465                 470                 475                 480

Leu Val Ile Ser Ala Ala Pro Lys Thr Ala Gly Thr Ala Pro Thr Ala
                485                 490                 495

Gly Asn Tyr Ser Gly Val Val Ser Leu Val Met Thr Leu Gly Ser Asp
            500                 505                 510

Asn Lys Gln Val Glu Lys Asn Ile Thr Val Thr Ala Ser Val Asp Pro
        515                 520                 525

Ala Gly Asn Phe Ile Pro Asp Ile Asp Ser Ala Val Arg Ile Ile Pro
    530                 535                 540

Val Asn Tyr Asp Ser Asp Pro Lys Leu Asp Ser Gln Leu Tyr Thr Val
545                 550                 555                 560

Glu Met Thr Ile Pro Ala Gly Val Ser Ala Val Lys Ile Ala Pro Thr
                565                 570                 575

Asp Ser Leu Thr Ser Ser Gly Gln Gln Ile Gly Lys Leu Val Asn Val
            580                 585                 590

Asn Asn Pro Asp Gln Asn Met Asn Tyr Ile Arg Lys Asp Ser Gly
        595                 600                 605

Ala Gly Asn Phe Met Ala Gly Gln Lys Gly Ser Phe Pro Val Lys Glu
    610                 615                 620

Asn Thr Ser Tyr Thr Phe Ser Ala Ile Tyr Thr Gly Glu Tyr Pro
625                 630                 635                 640

Asn Ser Gly Tyr Ser Gly Thr Tyr Ala Gly Asn Leu Thr Val Ser
                645                 650                 655

Phe Tyr Ser Asn Asp Asn Lys Gln Arg Thr Glu Ile Ala Thr Lys Asn
            660                 665                 670

Phe Pro Val Ser Thr Thr Ile Ser Lys Ser Phe Phe Ala Pro Glu Pro
        675                 680                 685

Arg Ile Gln Pro Ser Phe Gly Glu Asn Val Gly Lys Glu Gly Ala Leu
    690                 695                 700

Leu Phe Ser Val Asn Leu Thr Val Pro Glu Asn Val Ser Gln Val Thr
705                 710                 715                 720

Val Tyr Pro Val Tyr Asp Glu Asp Tyr Gly Leu Gly Arg Leu Val Asn
                725                 730                 735
```

Thr Ala Asp Ala Ser Gln Ser Ile Ile Tyr Gln Ile Val Asp Glu Lys
             740                 745                 750

Gly Lys Lys Met Leu Lys Asp His Gly Ala Glu Val Thr Pro Asn Gln
    755                 760                 765

Gln Ile Thr Phe Lys Ala Leu Asn Tyr Thr Ser Gly Glu Lys Lys Ile
770                 775                 780

Ser Pro Gly Ile Tyr Asn Asp Gln Val Met Val Gly Tyr Tyr Val Asn
785                 790                 795                 800

Asp Asn Lys Gln Gly Asn Trp Gln Tyr Lys Ser Leu Asp Val Asn Val
                805                 810                 815

Asn Ile Glu Gln Leu Glu His His His His His His
            820                 825

<210> SEQ ID NO 115
<211> LENGTH: 1014
<212> TYPE: DNA
<213> ORGANISM: Escherichia coli

<400> SEQUENCE: 115
gcagataaaa atcccggaag tgaaaacatg actaatacta ttggtcccca tgacagggg       60 ggatcttccc ccatatataa tatcttaaat tcctatctta cagcatacaa tggaagccat     120
catctgtatg ataggatgag tttttttatgt ttgtcttctc aaaatacact gaatggagca    180
tgcccaagca gtgatgcccc tggcactgct acaattgatg gcgaaacaaa tataacatta    240
caatttacgg aaaaagaag tctaattaaa agagaactgc aaattaaagg ctataaacaa      300
tttttgttca aaaatgctaa ttgcccatct aaactagcac ttaactcatc tcattttcaa    360
tgtaatagag aacaagcttc aggtgctact ttatcgttat ataccagc tggtgaatta      420 aataaattac cttttggggg ggtctggaat gccgttctga agctaaatgt aaaaagacga    480
tatgatacaa cctatgggac ttacactata aacatcacag ttaatttaac tgataaggga    540
aatattcaga tatggttacc acagttcaaa agtaacgctc gtgtcgatct taacttgcgt    600
ccaactggtg gtggtacata tatcggaaga aattctgttg atatgtgctt ttatgatgga    660
tatagtacta acagcagctc tttagagata agatttcagg atgataattc taaatctgat    720
ggaaaatttt atctaaagaa aataaatgat gactccaaag aacttgtata cactttgtca    780
cttctcctgg caggtaaaaa tttaacacca acaaatggac aggcattaaa tattaacact    840
gcttctctgg aaacaaactg gaatagaatt acagctgtca ccatgccaga aatcagtgtt    900
ccggtgttgt gttggcctgg acgtttgcaa ttggatgcaa aagtgaaaaa tcccgaggct    960
ggacaatata tgggaatat taaaattact tcacaccaa gtagtcaaac actc          1014

<210> SEQ ID NO 116
<211> LENGTH: 441
<212> TYPE: DNA
<213> ORGANISM: Escherichia coli

<400> SEQUENCE: 116
gtagagaaaa atattactgt aacagctagt gttgatcctg caattgatct tttgcaagct       60
gatggcaatg ctctgccatc agctgtaaag ttagcttatt ctcccgcatc aaaaactttt     120
gaaagttaca gagtaatgac tcaagttcat acaaacgatg caactaaaaa agtaattgtt    180
aaacttgctg atacaccaca gcttacagat gttctgaatt caactgttca aatgcctatc    240
agtgtgtcat ggggaggaca agtattatct acaacagcca aagaatttga agctgctgct    300

```
ttgggatatt ctgcatccgg tgtaaatggc gtatcatctt ctcaagagtt agtaattagc      360
gctgcaccta aaactgccgg taccgcccca actgcaggaa actattcagg agtagtatct      420
cttgtaatga ctttgggatc c                                                441

<210> SEQ ID NO 117
<211> LENGTH: 1020
<212> TYPE: DNA
<213> ORGANISM: Escherichia coli

<400> SEQUENCE: 117
gcagataaaa ttcccggaga tgaaagcata actaatatt ttggcccgcg tgacaggaac        60
gaatcttccc ccaaacataa tatattaaat aaccatatta cagcatacag tgaaagtcat      120
actctgtatg ataggatgac ttttttatgt ttgtcttctc acaatacact taatggagca      180
tgtccaacca gtgagaatcc tagcagttca tcggtcagcg gtgaaacaaa tataacatta      240
caatttacgg aaaaagaag tttaataaaa agagagctac aaattaaagg ctataaacaa      300
ttattgttca aaagtgttaa ctgcccatcc ggcctaacac ttaactcagc tcattttaac      360
tgtaataaaa acgcggcttc aggtgcaagt ttatatttat atattcctgc tggcgaacta      420
aaaaatttgc cttttggtgg tatctgggat gctactctga agttaagagt aaaaagacga      480
tatagtgaga cctatggaac ttacactata aatatcacta ttaaattaac tgataaggga      540
aatattcaga tatggttacc tcagttcaaa agtgacgctc gcgtcgatct taacttgcgt      600
ccaactggtg ggggcacata tattggaaga aattctgttg atatgtgctt ttatgatgga      660
tatagtacta acagcagctc tttggagata agattcagg ataacaatcc taatctgat       720 gggaaatttt atctaaggaa aataaatgat gacaccaaag aaattgcata ctttgtca        780 cttctcttgg cgggtaaaag tttaactcca acaaatggaa cgtcattaaa tattgctgac      840
gcagcttctc tggaaacaaa ctggaataga attacagctg tcaccatgcc agaaatcagt      900
gttccggtgt tgtgttggcc tggacgtttg caattggatg caaaagtgga aaatcccgag      960
gctggacaat atatgggtaa tattaatgtt actttcacac caagtagtca aacactctag     1020

<210> SEQ ID NO 118
<211> LENGTH: 435
<212> TYPE: DNA
<213> ORGANISM: Escherichia coli

<400> SEQUENCE: 118
gtagagaaaa atatcactgt aacagctagt gttgatccta caattgatat tttgcaagct       60
gatggtagta gtttacctac tgctgtagaa ttaacctatt cacctgcggc aagtcgtttt      120
gaaaattata aaatcgcaac taagttcat acaaatgtta taaataaaaa tgtactagtt       180
aagcttgtaa atgatccaaa acttacaaat gttttggatt ctacaaaaca actccccatt      240
actgtatcat atggaggaaa gactctatca accgcagatg tgacttttga acctgcagaa      300
ttaaattttg gaacgtcagg tgtaactggt gtatcttctt cccaagattt agtgattggt      360
gcgactacag cacaagcacc aacggcggga aattatagtg gggtcgtttc tatcttaatg      420
accttagcat cataa                                                       435

<210> SEQ ID NO 119
<211> LENGTH: 1020
<212> TYPE: DNA
<213> ORGANISM: Escherichia coli

<400> SEQUENCE: 119
```

```
gcagataaaa ttcccggaga tgagaatata actaatatttt ttggcccgcg tgacaggaac      60
gaatcttccc ccaaacataa tatattaaat gactatatta cagcatacag tgaaagtcat     120
actctgtatg ataggatgat ttttttatgt ttgtcttctc aaaatacact taatggagca     180
tgtccaacca gtgagaatcc tagcagttca tcggtcagtg gcgaaacaaa tataacatta     240
caatttacgg aaaaaagaag tttaattaaa agagagctac aaattaaagg ctataaacga     300
ttattgttca aaggtgctaa ctgcccatcc tacctaacac ttaactcagc tcattatacc     360
tgcaatagaa actcggcttc aggtgcaagt ttatatttat atattcctgc tggcgaacta     420
aaaaatttac cttttggtgg tatctgggat gctactctga agttaagagt aaaaagacga     480
tatgatcaga cctatggaac ttacactata aatatcactg ttaaattaac tgataaggga     540
aatattcaga tatggttacc tcagttcaaa agtgacgctc gcgtcgatct taacttgcgt     600
ccaactggtg ggggcacata tattggaaga aattctgttg atatgtgctt ttatgatgga     660
tatagtacta cagcagctc tttggagcta agatttcagg ataacaatcc taaatctgat     720
gggaaatttt atctaaggaa aataaatgat gacaccaaag aaaattgcata actttgtca     780 cttctcttgg cgggtaaaag tttaactcca acaaatggaa cgtcattaaa tattgctgac     840
gcagcttctc tggaaataaa ctggaataga attacagctg tcaccatgcc agaaatcagt     900
gttccggtgt tgtgttggcc tggacgtttg caattggatg caaaagtgga aaatcccgag     960
gccggacaat atatgggtaa tattaatatt actttcacac caagtagtca aacactctag    1020

<210> SEQ ID NO 120
<211> LENGTH: 459
<212> TYPE: DNA
<213> ORGANISM: Escherichia coli

<400> SEQUENCE: 120
gtagagaaaa atattactgt gacagccagt gttgatccta ctattgatat tcttcaagca      60
aatggttctg cgctaccgac agctgtagat ttaacttatc tacctggtgc aaaaactttt     120
gaaaattaca gtgttctaac ccagatttac acaaatgacc cttcaaaagg tttagatgtt     180
cgactggttg atacaccgaa acttacaaat attttgcaac cgacatctac cattcctctt     240
actgtctcat gggcagggaa gacattaagt acaagtgctc agaagattgc agttggcgat     300 ctgggtttg gttccaccgg aacggcaggt gtttcgaata gtaaagaatt agtaattgga     360
gcaactacat ccggaactgc accaagtgca ggtaagtatc aaggcgtcgt tccattgta     420 atgactcaat cgacagacac agccgcgcct gttccttaa                            459

<210> SEQ ID NO 121
<211> LENGTH: 441
<212> TYPE: DNA
<213> ORGANISM: Escherichia coli

<400> SEQUENCE: 121
gtagagaaaa atattactgt gacagccagt gttgatccta ctattgatat tcttcaagca      60
aatggttctg cgctaccgac agctgtagat ttaacttatc tacctggtgc aaaaactttt     120
gaaaattaca gtgttctaac ccagatttac acaaatgacc cttcaaaagg tttagatgtt     180
cgactggttg atacaccgaa acttacaaat attttgcaac cgacatctac cattcctctt     240
actgtctcat gggcagggag gacattaagt acaagtgctc agaagatcgc agttggcgat     300 ctgggtttg gttccaccgg aacggcaggt gtttcgaata gtaaagaatt agtaattgga     360
```

```
gcaactacat ccggaactgc accaagtgca ggtaagtatc aaggcgtcgt ttccattgta      420
atgactcaat cgacaaacta a                                                441
```

<210> SEQ ID NO 122
<211> LENGTH: 1038
<212> TYPE: DNA
<213> ORGANISM: Escherichia coli

<400> SEQUENCE: 122

```
gggcgatacc cggaaactac agtaggtaat ctgacgaaga gttttcaagc ccctcgtctg       60
gatagaagcg tacaatcacc aatatataac atctttacga atcatgtggc tggatatagt      120
ttgagtcata gcttatatga caggattgtt tttttatgta catcctcgtc gaatccggtt      180
aatggtgctt gcccaaccat tggaacatct ggagttcaat acggtactac aaccataacc      240
ttgcagttta cagaaaaaag aagtctgata aaagaaata ttaatcttgc aggtaataag       300
aaaccaatat gggagaatca gagttgcgac tttagcaatc taatggtgtt gaattcgaag      360
tcttggagct gtggggctta cggaaatgct aacggaacac ttctaaatct gtatatccct      420
gcaggagaaa tcaacaaatt gccttttgga gggatatggg aggcaactct gatcttacgc      480
ttatcaagat atggcgaagt cagtagcacc cattacggca attataccgt aaatattacg      540
gttgatttaa ctgataaagg taatattcag gtatggcttc cagggtttca cagcaacccg      600
cgtgtagacc tgaatctgcg ccctatcggt aattataaat atagtggtag taattcactc      660
gacatgtgtt tctatgatgg atatagtaca acagtgata gcatggtaat aaagttccag       720
gatgataatc ctaccaattc atctgaatat aatctttata agatagggg cactgaaaaa       780 ttaccatatg ctgtttcact gcttatggga gaaaaatat tttatccagt gaatggtcaa       840
tcatttacta tcaatgacag tagtgtactc gaaacaaact ggaatcgagt aaccgcagtt      900
gctatgccgg aagttaatgt tccagtatta tgctggccag caagattgct attaaatgct      960
gatgtaaatg ctcccgatgc aggacagtat tcaggacaga tatatataac atttacaccc     1020
agtgtcgaaa atttatga                                                   1038
```

<210> SEQ ID NO 123
<211> LENGTH: 447
<212> TYPE: DNA
<213> ORGANISM: Escherichia coli

<400> SEQUENCE: 123

```
gtcgagaaga ccattagcgt tacggcgagt gttgacccga ctgttgacct tctgcaatct       60
gatggctctg cgctgccgaa ctctgtcgca ttaacctatt ctccggctgt aaataatttt      120
gaagctcaca ccatcaacac cgttgttcat acaaatgact cagataaagg tgttgttgtg      180
aagctgtcag cagatccagt cctgtccaat gttctgaatc caaccctgca aattcctgtt      240
tctgtgaatt tcgcaggaaa accactgagc acaacaggca ttaccatcga ctccaatgat      300
ctgaactttg cttcgagtgg tgttaataaa gtttcttcta cgcagaaact ttcaatccat      360
gcagatgcta ctcgggtaac tggcggcgca ctaacagctg gtcaatatca gggactcgta      420
tcaattatcc tgactaagtc aacgtaa                                          447
```

<210> SEQ ID NO 124
<211> LENGTH: 1038
<212> TYPE: DNA
<213> ORGANISM: Escherichia coli

<400> SEQUENCE: 124

```
gggcgatacc cggaaactac agtaggtaat ctgacgaaga gttttcaagc ccctcgtctg      60
gatagaagcg tacaatcacc aatatataac atctttacga atcatgtggc tggatatagt     120
ttgagtcata gattatatga caggattgtt tttgtatgta catcctcgtc gaatccggtt     180
aatggtgctt gcccaaccat tggaacatct agagttgaat acggtactac aaccataacc     240
ttgcagttta cagaaaaaag aagtctgata aaagaaata ttaatcttgc aggtaataag      300
aaaccaatat gggagaatca gagttgcgac actagcaatc taatggtgtt gaattcgaag     360
tcttggtcct gtggggctct aggaaatgct aacgaacac ttctaaatct gtatatccct      420
gcaggagaaa tcaacaaatt gccttttgga gggatatggg aggcaactct gatcttacgc     480
ttatcaagat atggcgaagt cagtagcacc cattacggca attataccgt aaatattacg     540
gttgatttaa ctgataaagg taatattcag gtatggcttc cagggtttca cagcaacccg     600
cgtgtagacc tgaatctgca ccctatcggt aattataaat atagtggtag taattcactc     660
gacatgtgtt tctatgatgg atatagtaca aacagtgata gcatggtaat aaagttccag     720
gatgataatc ctaccaattc atctgaatat aatctttata agataggggg cactgaaaaa     780
ttaccatatg ctgtttcact gcttatggga ggaaaaatat tttatccagt gaatggtcaa     840
tcatttacta tcaatgacag tagtgtactc gaaacaaact ggaatcgagt aaccgcagtt     900
gctatgccgg aagttaatgt tccagtatta tgctggccag caagattgct attaaatgct     960
gatgtaaatg ctcccgatgc aggacagtat tcaggacaga tatatataac atttacaccc    1020
agtgtcgaaa atttatga                                                  1038

<210> SEQ ID NO 125
<211> LENGTH: 432
<212> TYPE: DNA
<213> ORGANISM: Escherichia coli

<400> SEQUENCE: 125
gtcgaaaaaa atattactgt gagggcaagt gttgacccta aacttgatct tctgcaagca      60
gatggaactt cactgccgga ctctatcgca ttaacctatt cttcggcttc aaataatttt     120
gaagtttact ctcttaatac tgctattcat acaaatgaca aaaccaaggc agttgtagtg     180
aagctgtcag ctccagcagt tctgtccaat attatgaagc caagctcgca aattccgatg     240
aaagtgactt tggggggga acgctgagt acagctgatg ctgagtttgc tgctgatact      300
ctgaactttg gtgcatctgg tgttgaaaac gtttcttccg ttcaacagct tacgattcat     360
gcagaagctg ctccgcctga ggcaggtaat taccaaggtg ttatttctct tatcatgact     420
caaaaaactt aa                                                         432

<210> SEQ ID NO 126
<211> LENGTH: 444
<212> TYPE: DNA
<213> ORGANISM: Escherichia coli

<400> SEQUENCE: 126
gtcgagaaga ccattagcgt tacggcgagt gttgacccga ctgttgacct tctgcaatct      60
gatggctctg cgctgccgaa ctctgtcgca ttaacctatt ctccggctgt agggggtttt     120
gaagctcaca ccatcaacac cgttgttcat acaaatgacc cagctaaagg tgttattgtg     180
aagctgtcag cagaaccagt cctgtccaat gtactgaatc caaccctgca aattcctgtt     240
tctgtgaatt tcgcaggaaa aaaactgacc acaacaggca ctaccatcga atccaataaa     300
```

```
ctgaactttg cttcgagtgg tgttgataaa gtttcttcta cgcagaaact ttcaatccat    360
gcagatacta ctcaggtaac tggcggacta acagctggtc aatatcaggg gctcgtatca    420
attatcctga ctcagtcaac gtaa                                           444
```

<210> SEQ ID NO 127
<211> LENGTH: 1038
<212> TYPE: DNA
<213> ORGANISM: Escherichia coli

<400> SEQUENCE: 127

```
gggcgatacc cggaaactac agtaggtaat ctgacgaaga gttttcaagc ccctcgtcag     60
gatagaagcg tacaatcacc aatatataac atctttacga atcatgtggc tggatatagt    120
ttgagtcata acttatatga caggattgtt tttttatgta catcctcgtc gaatccggtt    180
aatggtgctt gcccaaccat tggaacatct ggagttcaat acggtactac aaccataacc    240
ttgcagttta cagaaaaaag aagtctgata aaagaaata ttaatcttgc aggtaataag    300
aaaccaatat gggagaatca gagttgcgac actagcaatc taatggtgtt gaattcgaag    360
tcttggtcct gtggggctta cggaaatgct aacggaacac ttctaaatct gtatatccct    420
gcaggagaaa tcaacaaatt gccttttgga gggatatggg aggcaactct gatcttacgc    480
ttatcaagat atggcgaagt cagtagcacc cattacggca attataccgt aaatattacg    540
gttgatttaa ctgataaagg taatattcag gtatggcttc cagggtttca cagcaacccg    600
cgtgtagacc tgaatctgca ccctatcggt aattataaat atagtggtag taattcactc    660
gacatgtgtt tctatgatgg atatagtaca acagtgata gcatggtaat aaagttccag    720
gatgataatc ctacctattc atctgaatat aatctttata agatagggg cactgaaaaa    780 ttaccatatg ctgtttcact gcttatggga gaaaaaatat tttatccagt gaatggtcaa    840
tcatttacta tcaatgacag tagtgtactc gaaacaaact ggaatcgagt aaccgcagtt    900
gctatgccgg aagttaatgt tccagtatta tgctggccag caagattgct attaaatgct    960
gatgtaaatg ctcccgatgc aggacagtat tcaggacaga tatatataac atttacaccc   1020
agtgtcgaaa atttatga                                                 1038
```

<210> SEQ ID NO 128
<211> LENGTH: 438
<212> TYPE: DNA
<213> ORGANISM: Escherichia coli

<400> SEQUENCE: 128

```
gtcgaaaaaa atattactgt gagggcaagt gttgacccta aacttgatct tctgcaagca     60
gatggaactt cactgccgga ctctatcgca ttaacctatt cttcggcttc aaataatttt    120
gaagtttact ctcttaatac tgctattcat acaaatgaca aaagcaaggg agttgtagtg    180
aagctgtcag cttcaccagt tctgtccaat attatgaagc caaactcgca aattccgatg    240
aaagtgactt tggggggaa gacgctgaat acaactgata ctgagtttac tgttgatact    300
ctgaactttg gtacatctgg tgttgaaaac gtttcttcca ctcaacagct tacgattcat    360
gcagacacac aaggaactgc gcctgaggca ggcaattacc aaggtattat ttctcttatc    420
atgactcaaa aaacttaa                                                 438
```

<210> SEQ ID NO 129
<211> LENGTH: 1041
<212> TYPE: DNA
<213> ORGANISM: Escherichia coli

<400> SEQUENCE: 129

```
caatcatggc atacgaacgt agaggctggt tcaataaata aaacagagtc gataggcccc      60
atagaccgaa gtgctgctgc atcgtatcct gctcattata tatttcatga acatgttgct     120
ggttacaata aagatcactc tcttttttgac aggatgacgt ttttatgtat gtcatcaaca    180
gatgcatcta aaggtgcatg tccgacagga gaaaactcca atcctctca aggggagact      240
aatattaagc taatatttac tgaaaagaaa agtctggcca gaaaaacatt aaacttaaaa     300
ggatataaga gattttttata tgaatcagat agatgcattc attatgtcga taaaatgaat    360
ctcaattctc atactgttaa atgtgtaggt tcattcacaa gaggagtaga tttcacttta     420
tatatcccac aaggtgaaat tgatgggctt ctaactggag gtatatggga ggcaacacta    480
gagttacgag tcaaaaggca ttacgactat aatcatggta cttacaaagt taatatcaca    540
gttgatttga cagacaaagg aaatattcag gtctggacac caaagtttca tagcgatcct    600
agaattgatc tgaatttacg tcctgaaggt aatggtaaat attctggtag taacgtgctt    660
gagatgtgtc tctatgatgg ctatagtaca catagtcaaa gtatagaaat gaggtttcag    720
gatgactcac aaacaggaaa taatgaatat aatcttataa aaactggaga gccattaaaa     780
aaattgccat ataaacttttc tcttctttta ggaggacgag agttttatcc aaataatgga    840
gaggctttta ctattaatga tacttcgtca ttgtttataa actggaatcg tattaagtct    900
gtatccttac cacagattag tattccagta ctatgctggc cagcaaaactt gacatttatg    960
tcagagctaa ataatccaga gcgggtgag tattcaggaa tacttaacgt aacatttact    1020
cctagtagtt caagtctgta a                                             1041
```

<210> SEQ ID NO 130
<211> LENGTH: 444
<212> TYPE: DNA
<213> ORGANISM: Escherichia coli

<400> SEQUENCE: 130

```
gccgagaaaa atatcactgt aactgctagc gttgatccaa ctatcgatct gatgcaatct      60
gatggcacag cgttaccaag tgcagttaat attgcatatc ttccaggaga gaaaagattt     120
gaatctgctc gtatcaatac ccaagttcat accaataata aaactaaggg tattcagata    180
aagcttacta atgataatgt ggtaatgact aacttatctg atccaagcaa gactattcct     240
ttagaggttt cattcgctgg cactaagctg agcacagctg caacatctat tactgccgat    300
caattaaatt ttggcgcagc tggtgtagag acagttctg caactaagga actcgttatt    360
aatgcaggaa gcacccagca aactaatatt gtagctggta actatcaagg attggtgtca    420
attgtgctta ctcaagaacc ttaa                                            444
```

<210> SEQ ID NO 131
<211> LENGTH: 441
<212> TYPE: DNA
<213> ORGANISM: Escherichia coli

<400> SEQUENCE: 131

```
gcagcggggc ccactctaac caaagaactg gcattaaatg tgctttctcc tgcagctctg      60
gatgcaactt gggctcctca ggataattta acattatcca atactggcgt ttctaatact    120
ttggtgggtg ttttgactct ttcaaatacc agtattgata cagttagcat tgcgagtaca    180
aatgtttctg atacatctaa gaatggtaca gtaacttttg cacatgagac aaataactct    240
```

```
gctagctttg ccaccaccat ttcaacagat aatgccaaca ttacgttgga taaaaatgct      300
ggaaatacga ttgttaaaac tacaaatggg agtcagttgc caactaattt accacttaag      360
tttattacca ctgaaggtaa cgaacattta gtttcaggta attaccgtgc aaatataaca      420
attacttcga caattaaata a                                                441
```

```
<210> SEQ ID NO 132
<211> LENGTH: 432
<212> TYPE: DNA
<213> ORGANISM: Escherichia coli

<400> SEQUENCE: 132
gcagtgggcc caacgaaaga tatgagttta ggtgcaaatt taacttcaga gcctacatta       60
gctattgatt ttacgcctat tgaaaatatt tatgtaggtg ccaattatgg taaagatatt      120
ggaacccttg ttttcacaac aaatgattta acagatatta cattgatgtc atctcgcagc      180
gttgttgatg gtcgccagac tggttttttt accttcatgg actcatcagc cacttacaaa      240
attagtacaa aactgggatc atcgaatgat gtaaacatta agaaattac tcaaggagct       300 aaaattactc ctgttagtgg agagaaaact ttgcctaaaa aattcactct taagctacat      360
gcacacagga gtagcagtac agttccaggt acgtatactg ttggtcttaa cgtaaccagt      420
aatgttattt aa                                                          432
```

```
<210> SEQ ID NO 133
<211> LENGTH: 1038
<212> TYPE: DNA
<213> ORGANISM: Escherichia coli

<400> SEQUENCE: 133
gggcgatacc cggaaactac agtaggtaat ctgacgaaga gttttcaagc ccctcgtctg       60
gatagaagcg tacaatcacc aatatataac atctttacga atcatgtggc tggatatagt      120
ttgagtcata gattatatga caggattgtt tttgtatgta catcctcgtc gaatccggtt      180
aatggtgctt gcccaaccat tggaacatct ggagttgaat acggtactac aaccataacc      240
ttgcagttta cagaaaaaag aagtctgata aaaagaaata ttaatcttgc aggtaataag      300
aaaccaatat gggagaatca gagttgcgac tttagcaatc taatggtgtt gaattcgaag      360
tcttggtcct gtggggctca aggaaatgct aacggaacac ttctaaatct gtatatccct      420
gcaggagaaa tcaacaaatt gccttttgga gggatatggg aggcaactct gatcttacgc      480
ttatcaagat atggcgaagt cagtagcacc cattacggca attataccgt aaatattacg      540
gttgatttaa ctgataaagg taatattcag gtatggcttc cagggtttca cagcaacccg      600
cgtgtagacc tgaatctgca ccctatcggt aattataaat atagtggtag taattcactc      660
gacatgtgtt tctatgatgg atatagtaca aacagtgata gcatggtaat aaagttccag      720
gatgataatc ctaccaattc atctgaatat aatctttata agagaggggg cactgaaaaa      780
ttaccatatg ctgtttcact gcttatggga ggaaaaatat tttatccagt gaatggtcaa      840
tcatttacta tcaatgacag tagtgtactc gaaacaaact ggaatcgagt aaccgcagtt      900
gctatgccgg aagttaatgt tccagtatta tgctggccag caagattgct attaaatgct      960
gatgtaaatg ctcccgatgc aggacagtat tcaggacaga tatatataac atttacacccc     1020 agtgtcgaaa atttatga                                                   1038
```

```
<210> SEQ ID NO 134
<211> LENGTH: 465
```

<212> TYPE: DNA
<213> ORGANISM: Escherichia coli

<400> SEQUENCE: 134

```
atgaagaaaa caattggttt aattctaatt cttgcttcat tcggcagcca tgccagaaca    60
gaaatagcga ctaaaaactt cccagtatca acgactattt caaaaagttt ttttgcgcct   120
gaaccacaaa tccagccttc ttttggtaaa aatgttggaa aggaaggaga tttattattt   180
agtgtgagct taattgttcc tgaaaatgta tcccaggtaa cggtctaccc tgtttatgat   240
gaagattatg gattaggacg actcgtaaat accgctgatg attcccaatc aataatctac   300
cagattgttg atgataaagg gaaaaaaatg ttaaaagatc atggtacaga ggttacgcct   360
aatcaacaaa taacttttaa agcgctgaat tatactagcg gagataaaga aatacctcct   420
gggatatata acgatcaggt tatggttggt tactatgtaa actaa              465
```

<210> SEQ ID NO 135
<211> LENGTH: 154
<212> TYPE: PRT
<213> ORGANISM: Escherichia coli

<400> SEQUENCE: 135

```
Met Lys Lys Thr Ile Gly Leu Ile Leu Ile Leu Ala Ser Phe Gly Ser
1               5                   10                  15

His Ala Arg Thr Glu Ile Ala Thr Lys Asn Phe Pro Val Ser Thr Thr
            20                  25                  30

Ile Ser Lys Ser Phe Phe Ala Pro Glu Pro Gln Ile Gln Pro Ser Phe
        35                  40                  45

Gly Lys Asn Val Gly Lys Glu Gly Asp Leu Leu Phe Ser Val Ser Leu
    50                  55                  60

Ile Val Pro Glu Asn Val Ser Gln Val Thr Val Tyr Pro Val Tyr Asp
65                  70                  75                  80

Glu Asp Tyr Gly Leu Gly Arg Leu Val Asn Thr Ala Asp Asp Ser Gln
                85                  90                  95

Ser Ile Ile Tyr Gln Ile Val Asp Asp Lys Gly Lys Lys Met Leu Lys
            100                 105                 110

Asp His Gly Thr Glu Val Thr Pro Asn Gln Gln Ile Thr Phe Lys Ala
        115                 120                 125

Leu Asn Tyr Thr Ser Gly Asp Lys Glu Ile Pro Pro Gly Ile Tyr Asn
    130                 135                 140

Asp Gln Val Met Val Gly Tyr Tyr Val Asn
145                 150
```

<210> SEQ ID NO 136
<211> LENGTH: 504
<212> TYPE: DNA
<213> ORGANISM: Escherichia coli

<400> SEQUENCE: 136

```
atgttgaaaa aaattattcc ggctattgca ttaattgcag gaacttccgg agtggtaaat    60
gcaggaaact ggcaatataa atctctggat gtaaatgtaa atattgagca aaattttatt   120
ccagatattg attccgctgt tcgtataata cctgttaatt acgattcgga tccgaaactg   180
aattcacagt tatatacggt tgagatgacg atccctgcag gtgtaagcgc agttaaaatc   240
gtaccaacag atagtctgac atcttctgga cagcagatcg aaagctggt taatgtaaac   300
aatccagatc aaaatatgaa ttattatatc agaaaggatt ctggcgctgg taagtttatg   360
```

-continued

```
gcagggcaaa aaggatcctt ttctgtcaaa gagaatacgt catacacatt ctcagcaatt    420
tatactggtg gcgaataccc taatagcgga tattcgtctg gtacttatgc aggacatttg    480
actgtatcat tttacagcaa ttaa                                          504
```

<210> SEQ ID NO 137
<211> LENGTH: 167
<212> TYPE: PRT
<213> ORGANISM: Escherichia coli

<400> SEQUENCE: 137

```
Met Leu Lys Lys Ile Ile Pro Ala Ile Ala Leu Ile Ala Gly Thr Ser
1               5                   10                  15

Gly Val Val Asn Ala Gly Asn Trp Gln Tyr Lys Ser Leu Asp Val Asn
            20                  25                  30

Val Asn Ile Glu Gln Asn Phe Ile Pro Asp Ile Asp Ser Ala Val Arg
        35                  40                  45

Ile Ile Pro Val Asn Tyr Asp Ser Asp Pro Lys Leu Asn Ser Gln Leu
    50                  55                  60

Tyr Thr Val Glu Met Thr Ile Pro Ala Gly Val Ser Ala Val Lys Ile
65                  70                  75                  80

Val Pro Thr Asp Ser Leu Thr Ser Ser Gly Gln Gln Ile Gly Lys Leu
                85                  90                  95

Val Asn Val Asn Asn Pro Asp Gln Asn Met Asn Tyr Tyr Ile Arg Lys
            100                 105                 110

Asp Ser Gly Ala Gly Lys Phe Met Ala Gly Gln Lys Gly Ser Phe Ser
        115                 120                 125

Val Lys Glu Asn Thr Ser Tyr Thr Phe Ser Ala Ile Tyr Thr Gly Gly
    130                 135                 140

Glu Tyr Pro Asn Ser Gly Tyr Ser Ser Gly Thr Tyr Ala Gly His Leu
145                 150                 155                 160

Thr Val Ser Phe Tyr Ser Asn
                165
```